United States Patent
Albers et al.

(10) Patent No.: US 6,677,360 B2
(45) Date of Patent: *Jan. 13, 2004

(54) BIPHENYL AND BIPHENYL-ANALOGOUS COMPOUNDS AS INTEGRIN ANTAGONISTS

(75) Inventors: Markus Albers, Leverkusen (DE); Klaus Urbahns, Wuppertal (DE); Andrea Vaupel, Wuppertal (DE); Michael Härter, Leverkusen (DE); Delf Schmidt, Wuppertal (DE); Beatrix Stelte-Ludwig, Wulfrath (DE); Christoph Gerdes, Leverkusen (DE); Elke Stahl, Bergisch Gladbach (DE); Jörg Keldenich, Wuppertal (DE); Ulf Brueggemeier, Leverkusen (DE); Klemens Lustig, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/828,514

(22) Filed: Apr. 6, 2001

(65) Prior Publication Data

US 2002/0016461 A1 Feb. 7, 2002

Related U.S. Application Data

(62) Division of application No. 09/464,237, filed on Dec. 15, 1999, now Pat. No. 6,420,396.
(60) Provisional application No. 60/172,217, filed on Oct. 16, 1998.

(51) Int. Cl.[7] .................. C07C 311/19; C07C 311/47; C07D 213/40; C07D 213/75; C07D 235/30; A01N 43/40
(52) U.S. Cl. .............. 514/352; 514/357; 514/362; 514/263; 514/371; 514/377; 514/380; 514/398; 514/400; 514/445; 514/471; 514/539; 514/562; 514/563; 514/567; 546/308; 546/309; 546/337; 548/126; 548/134; 548/136; 548/198; 548/199; 548/233; 548/243; 548/246; 548/308.7; 548/332.1; 548/335.5; 549/65; 549/487; 560/13; 560/19; 560/34; 560/37; 560/38; 560/41; 562/430; 562/442; 562/457
(58) Field of Search ................... 514/352, 353, 514/357, 362, 363, 371, 377, 380, 398, 400, 445, 471, 539, 562, 563, 567; 546/308, 309, 337; 548/126, 134, 136, 198, 199, 233, 243, 246, 308.7, 332.1, 333.5; 549/65, 487; 560/13, 19, 34, 37, 38, 41; 562/430, 442, 457

(56) References Cited

U.S. PATENT DOCUMENTS

| 5,238,923 A | 8/1993 | Connely et al. |
| 5,393,875 A | 2/1995 | Branca et al. |
| 5,475,013 A | 12/1995 | Talley et al. |
| 5,624,956 A | 4/1997 | Tjoeng et al. |
| 5,736,559 A | 4/1998 | Himmelsbach et al. |
| 5,756,545 A | 5/1998 | O'Brien ..................... 514/562 |
| 5,773,646 A | 6/1998 | Chandrakumar et al. |
| 5,852,210 A | 12/1998 | Chen et al. |
| 5,891,912 A | 4/1999 | Kawashima et al. |
| 5,914,348 A | 6/1999 | Kitano et al. |

FOREIGN PATENT DOCUMENTS

| DE | 2112840 | * 10/1972 |
| DE | 195 48 709 A | 7/1997 |
| EP | 877018 A1 | 11/1998 |
| GB | 2276161 A | 9/1994 |
| WO | WO 94/12181 | 6/1994 |
| WO | WO 97/36859 A | 10/1997 |
| WO | WO 98 00395 A | 1/1998 |
| WO | WO 98/118461 | 5/1998 |
| WO | 98/26773 A1 | 6/1998 |
| WO | 98/35982 A1 | 8/1998 |
| WO | WO 99/36393 A | 7/1999 |
| WO | wo 99/36393 | * 7/1999 |

OTHER PUBLICATIONS

Draetta, G. and Pagano, M. in "Annual Reports in Medicinal Chemistry, vol. 31", 1996, Academic Press, San Diego, p241–246.*
Bolton, G.L. et al, in "Annual Reports in Medicinal Chemistry, vol. 29", 1994, Academic Press, San Diego, p165–174.*
Neustadt, Bernard, et al.; "Construction of a Family of Biphenyl Combinatoial Libraries: Structure–Activity Studies Utilizing Libratries of Mixtures"; Bioorganic & Medicinal Chemistry Letters 8 (1998) 2395–2398.
Brown, Steven L., et al.; "Stimulation of Migration of Human Aortic Smooth Muscle Cells by Vitronectin: Implications for Atherosclerosis"; Cardiovascular Research 1994: 28; 1815–1820.

(List continued on next page.)

Primary Examiner—Mukund J. Shah
Assistant Examiner—Tom McKenzie
(74) Attorney, Agent, or Firm—Norris McLaughlin & Marcus

(57) ABSTRACT

The present invention relates to biphenyl and biphenyl-analogous compounds, their preparation and use as pharmaceutical compositions, as integrin antagonists and in particular for the production of pharmaceutical compositions for the treatment and prophylaxis of cancer, arteriosclerosis, restenosis, osteolytic disorders such as osteoporosis and ophthalmic diseases. The compounds according to the invention have the formula (1)

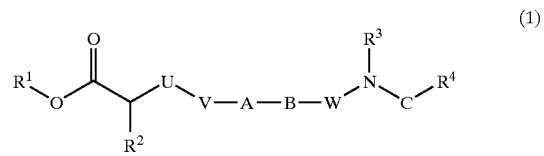

(1)

wherein
$R^1$, $R^2$, U, V, A, B, W, $R^3$, C and $R^4$ have the meaning as defined in the claims.

26 Claims, No Drawings

OTHER PUBLICATIONS

Brooks, Peter C., et al.; "Antiintegrin αvβ3 Blocks Human Breast Cancer Growth and Angiogenesis in Human Skin", J. Clin. Invest. ©The American Society for Clinical Investigation, Inc.; vol. 90, Oct. 1995, 1815–1822.

Brooks, Peter C., et al.; "Integrin $\alpha_v\beta_3$ Antagonists Promote Tumor Regression by Inducing Apoptosis of Angiogenic Blood Vessels"; Cell, vol. 79, Dec. 30, 1994; 1157–1164.

* cited by examiner

BIPHENYL AND BIPHENYL-ANALOGOUS COMPOUNDS AS INTEGRIN ANTAGONISTS

This application is a divisional of U.S. Ser. No. 09/464,237, which was filed on Dec. 15, 1999, now U.S. Pat. No. 6,420,396, which claims benefit under 35 U.S.C. §120 of U.S. Provisional Application No. 60/172,217, filed on Dec. 16, 1998, which was converted from U.S. application Ser. No. 09/213,381, filed on Dec. 16, 1998.

FIELD OF THE INVENTION

The present invention relates to new biphenyl and biphenyl-analogous compounds, their preparation and use as pharmaceutical compositions, as integrin antagonists and in particular for the production of pharmaceutical compositions for the treatment and prophylaxis of cancer, arteriosclerosis, restenosis, osteolytic disorders such as osteoporosis, rheumatoid arthritis and ophthalmic diseases.

BACKGROUND OF THE INVENTION

Integrins are heterodimeric transmembrane proteins found on the surface of cells, which play an important part in the adhesion of the cells to an extracellular matrix. They recognize extracellular glycoproteins such as fibronectin or vitronectin on the extracellular matrix by means of the RGD sequence occurring in these proteins (RGD is the single letter code for the amino acid sequence arginine-glycine-aspartate).

In general, integrins such as, for example, the vitronectin receptor, which is also called the $\alpha_v\beta_3$ receptor, or alternatively the $\alpha_v\beta_5$ receptor or the GpIIb/IIIa receptor play an important part in biological processes such as cell migration and cell-matrix adhesion and thus in diseases in which these processes are crucial steps. Cancer, osteoporosis, arteriosclerosis, restenosis (reoccurrence of stenosis after percutaneous transluminal angioplasty) and opthalmia may be mentioned by way of example.

The $\alpha_v\beta_3$ receptor occurs, for example, in large amounts on growing endothelial cells and makes possible their adhesion to an extracellular matrix. Thus the $\alpha_v\beta_3$ receptor plays an important part in angiogenesis, i.e. the formation of new blood vessels, which is a crucial prerequisite for tumor growth and metastasis formation in carcinoses. Furthermore, it is also responsible for the interaction between osteoclasts, i.e. cells resorbing mineralized tissue, and the bone structure. The first step in the degradation of bone tissue consists in the adhesion of osteoclasts to the bone. This cell-matrix interaction takes place via the $\alpha_v\beta_3$ receptor, which is why the corresponding integrin plays an important part in this process. Osteolytic diseases such as osteoporosis are induced by an inequilibrium between bone formation and bone destruction, i.e. the resorption of bone material caused by accumulation of osteoclasts predominates.

It was possible to show that the blockage of the abovementioned receptors is an important starting point for the treatment of disorders of this type. If the adhesion of growing endothelial cells to an extracellular matrix is suppressed by blocking their appropriate integrin receptors, for example, by a cyclic peptide or a monoclonal antibody, the endothelial cells die. Therefore angiogenesis does not occur, which leads to a cessation or resolution of the tumor growth (cf., for example, Brooks et al., Cell, Volume 79, 1157–1164, 1994).

Moreover, the invasive properties of tumor cells and thus their capability for metastasis formation are markedly decreased if their $\alpha_v\beta_3$ receptor is blocked by an antibody (Brooks et al., J. Clin. Invest., Volume 96, 1815, 1995).

The degradation of bone tissue can be suppressed by blockage of the $\alpha_v\beta_3$ receptors of the osteoclasts, since these are then unable to accumulate on the bone in order to absorb its substance (WO 98/18461, p. 1, 1.24 to p. 2, 1.13).

By means of the blockage of the $\alpha_v\beta_3$ receptor on cells of the smooth aorta vascular musculature with the aid of integrin receptor antagonists, the migration of these cells into the neointima and thus angioplasty leading to arteriosclerosis and restenosis can be suppressed (Brown et al., Cardiovascular Res., Volume 28, 1815, 1994).

In recent years, compounds have therefore been sought which act as antagonists of integrin receptors. For example, WO 98/00395 discloses the para-substituted phenylalanine derivative (I), which shows an $IC_{50}$ value of 0.13 nM in an $\alpha_v\beta_3$ receptor assay and an $IC_{50}$ value of 0.16 nM in an $\alpha_v\beta_5$ receptor assay:

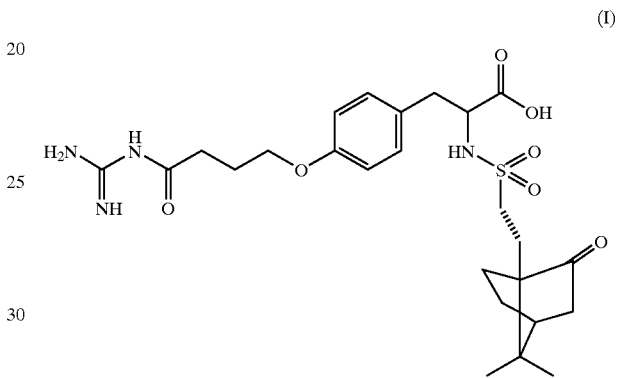

(I)

The abovementioned compound (I) has a guanidine unit, by means of which the oral availability is limited on account of the relatively rapid clearance rate of the compound in the digestive tract. Thus the compound (II), for example, is preferably administered parenterally (cf. WO 98/00395, p. 25, 1. 31–32).

Furthermore, WO 98/18461, for example, discloses naphthyl compounds such as (II), which have an $IC_{50}$ value in the range from 0.4 to 110 nM against the $\alpha_v\beta_3$ receptor in an SPA assay:

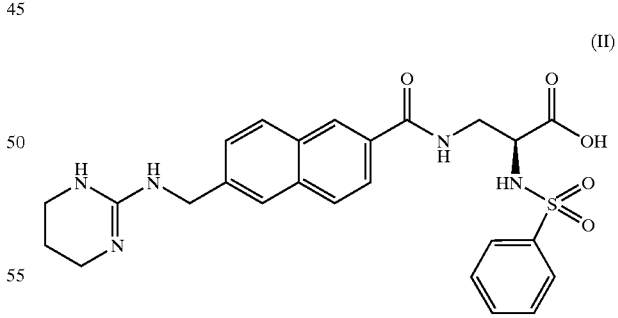

(II)

Biphenyl nuclei are present in numerous pharmaceutical compositions. Experiments carried out until now to establish integrin antagonists having a biphenyl nucleus only led, however, to compounds having relatively poor activity. Thus, in addition to numerous substances included by a general formula, WO 94/12181 actually describes the biphenyl compounds (III) as antagonists of the GpIIb/IIIa receptor. The use of these compounds as $\alpha_v\beta_3$ or $\alpha_v\beta_5$ receptor antagonists is not described:

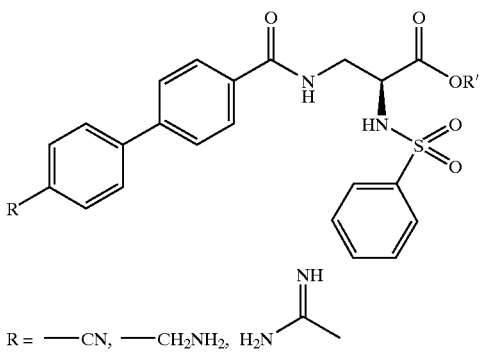

(III)

R = —CN, —CH₂NH₂, H₂N
R' = H, Me

The biphenyl compounds such as (IV) prepared by B. R. Neustadt et al. exhibit activity as $\alpha_v\beta_3$ receptor antagonists which is far below that of known integrin antagonists, which is why they are not suitable lead structures according to this document (Bioorg. Med. Chem. Lett. 8, 2395, 1998, in particular p. 2398, second paragraph):

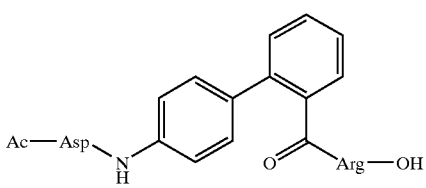

(IV)

It was the object of the present invention to develop compounds which exhibit a high activity as integrin antagonists and in particular against the $\alpha_v\beta_3$ and/or the $\alpha_v\beta_5$ receptor.

SUMMARY OF THE INVENTION

The present object is achieved according to the invention by the substituted biphenyl compounds defined below. In particular, it has emerged that the biphenyl compounds according to the invention have a very high activity as integrin antagonists, especially against the $\alpha_v\beta_3$ and/or the $\alpha_v\beta_5$ receptor.

The present invention relates to compounds of the general formula (1)

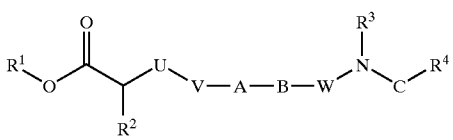

(1)

wherein
- $R^1$ is hydrogen, a substituted or unsubstituted alkyl or cycloalkyl residue, a substituted or unsubstituted aryl residue or a saturated or unsaturated, optionally substituted heterocyclic residue;
- $R^2$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, $—NR^{2'}SO_2R^{2''}$, $—NR^{2'}COOR^{2'}$, $—NR^{2'}COR^{2'}$, $—NR^{2'}CONR^{2'}{}_2$, or $—NR^{2'}CSNR^{2'}{}_2$;
- $R^{2'}$ is hydrogen, a substituted or unsubstituted alkyl or cycloalkyl residue, a substituted or unsubstituted aryl residue or a saturated or unsaturated, optionally substituted heterocyclic residue;
- $R^{2''}$ is a substituted or unsubstituted alkyl, alkenyl or cycloalkyl residue, a substituted or unsubstituted aryl residue or a saturated or unsaturated, optionally substituted heterocyclic residue;
- U is a direct bond or a substituted or unsubstituted alkylene group;
- V is a substituted or unsubstituted alkylene group, $—NR^{2'}CO—$ or $—NR^{2'}SO_2—$;
- A and B are each independently of one another a 1,3- or 1,4-bridging phenylene group or a 2,4- or 2,5-bridging thienylene group each of which may optionally have additional substituents,
- W is a direct bond or a substituted or unsubstituted alkylene group;
- C is a direct bond or

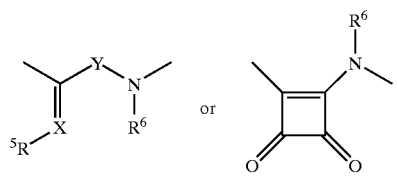

or

- $R^3$ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of $R^4$, Y, $R^5$ or $R^6$, if present, with formation of an optionally substituted heterocyclic ring system which includes the nitrogen atom to which $R^3$ is bonded, and can be saturated or unsaturated and/or can contain further heteroatoms;
- $R^4$ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of $R^3$, Y, $R^5$ or $R^6$, if present, with formation of an optionally substituted heterocyclic ring system which includes the nitrogen atom to which $R^4$ is bonded and can be saturated or unsaturated and/or can contain further heteroatoms;
- X is $CHNO_2$, CHCN, O, N or S;
- Y is a direct bond or an optionally substituted alkylene or alkine group;
- $R^5$ is absent, or is hydrogen, a substituted or unsubstituted alkyl or cycloalkyl residue, $—NO_2$, $—CN$, $—COR^{5'}$, $—COOR^{5'}$, or is connected to one of $R^3$, Y, $R^4$ or $R^6$, if present, with formation of an optionally substituted carbocyclic or heterocyclic ring system which includes X and can be saturated or unsaturated and/or can contain further heteroatoms;
- $R^{5'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

R⁶ is hydrogen, a substituted or unsubstituted alkyl or cycloalkyl residue, a substituted or unsubstituted aryl or arylcarbonyl residue, a saturated or unsaturated, optionally substituted heterocyclic residue, an alkylamine residue, an alkylamide residue or is connected to one of R³, R⁴, Y or R⁵, if present, with formation of an optionally substituted heterocyclic ring system which includes the nitrogen atom to which R⁶ is bonded and can be saturated or unsaturated and/or can contain further heteroatoms;

with the proviso that if A is a phenylene group and V is —NR²'CO— or —NR²'SO₂—, C is not a direct bond and X is not N; and their physiologically acceptable salts and stereoisomers.

If a certain variable substituent is present more than once in a general formula (e.g. R²' in —NR²'COOR²') the meaning for each substituent may be chosen independently from the others out of the list given in the respective definition.

According to a preferred embodiment, the present invention relates to compounds of the general formula (1), where R¹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl or a substituted derivative thereof;

R² is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, —NR²'SO₂R²", —NR²'COOR²', —NR²'COR²', —NR²'CONR²'₂ or —NR²'CSNR²'₂;

R²' is hydrogen, methyl, ethyl, propyl, isopropyl, butyl, isobutyl, t-butyl, pentyl, isopentyl, neopentyl, hexyl, cyclopropyl, cyclobutyl, cyclpentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

R²" is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl or a substituted derivative thereof, 4-ethylphenyl, —C₆H₂(CH₃)₃, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluoro-phenyl, 2-trifluoromethoxy-4-bromo-phenyl, 2-fluoro-4-trifluoromethylphenyl, 8-quinolinyl or a group of the formula

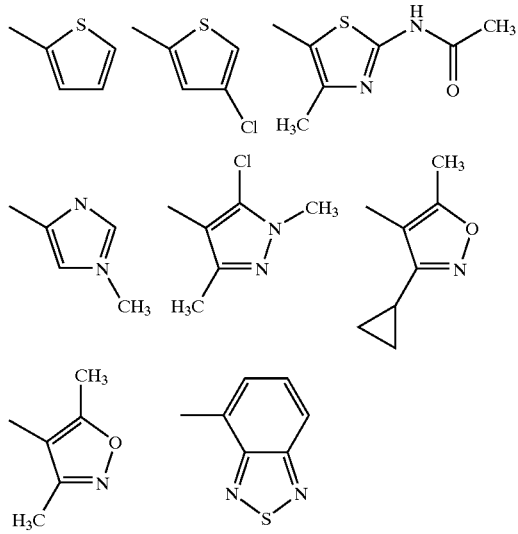

U is a direct bond,

V is an optionally substituted $C_{1-5}$-alkylene group;

A is a 1,3- or 1,4-bridging phenylene group which is unsubstituted or carries at least one alkoxy or halogeno residue;

B is a 1,3- or 1,4-bridging phenylene group which is unsubstituted or carries at least one alkyl residue;

W is a direct bond or an optionally substituted $C_{1-4}$-alkylene group;

C is a direct bond or

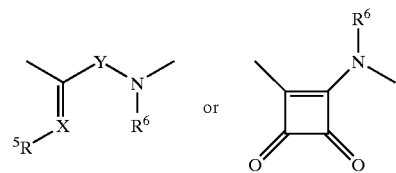

R³ is hydrogen, methyl, ethyl, propyl, isopropyl, butyl, 1-methylpropyl, isobutyl, t-butyl, pentyl, 2-methylbutyl, isopentyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-akylamino-$C_{1-4}$-alkyl, $C_{1-4}$-dialkylarino-$C_{1-4}$-alkyl, amino-$C_{1-4}$-alkyl, $C_{1-4}$-alkyloxy-$C_{1-4}$-alkyl, dialkylamino-$C_{1-4}$-alkyl, amino-$C_{1-4}$-alkyl, $C_{1-4}$-alkyloxy-$C_{1-4}$-alkyl, $C_{1-2}$-perafluoroalkyl-$C_{1-4}$-alkyl, (a1)

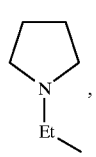

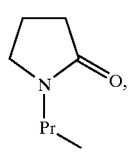 (a2)
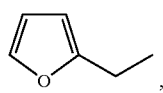 (a3)
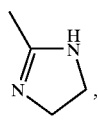 (a4)
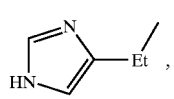 (a5)
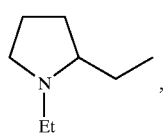 (a6)
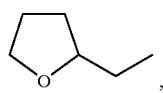 (a7)
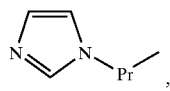 (a8)
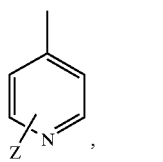 (a9)
 (a10)
 (a11)
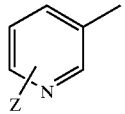 (a12)
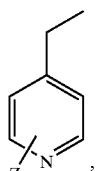 (a13)
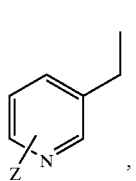
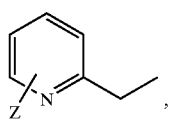 (a14)
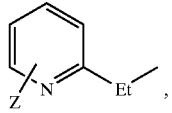 (a15)
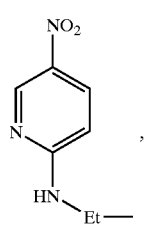 (a16)
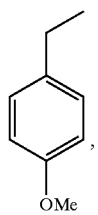 (a17)
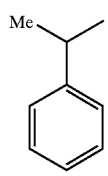 (a18)
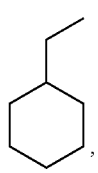 (a19)
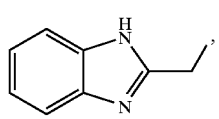 (a20)
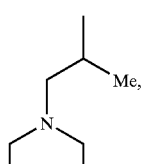 (a21)
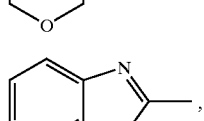 (a22)
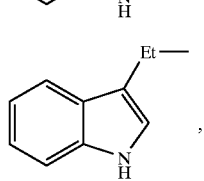 (a23)

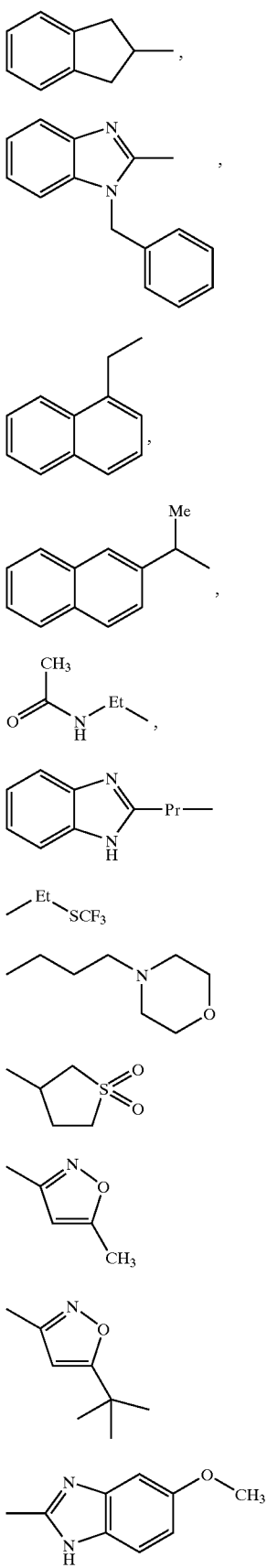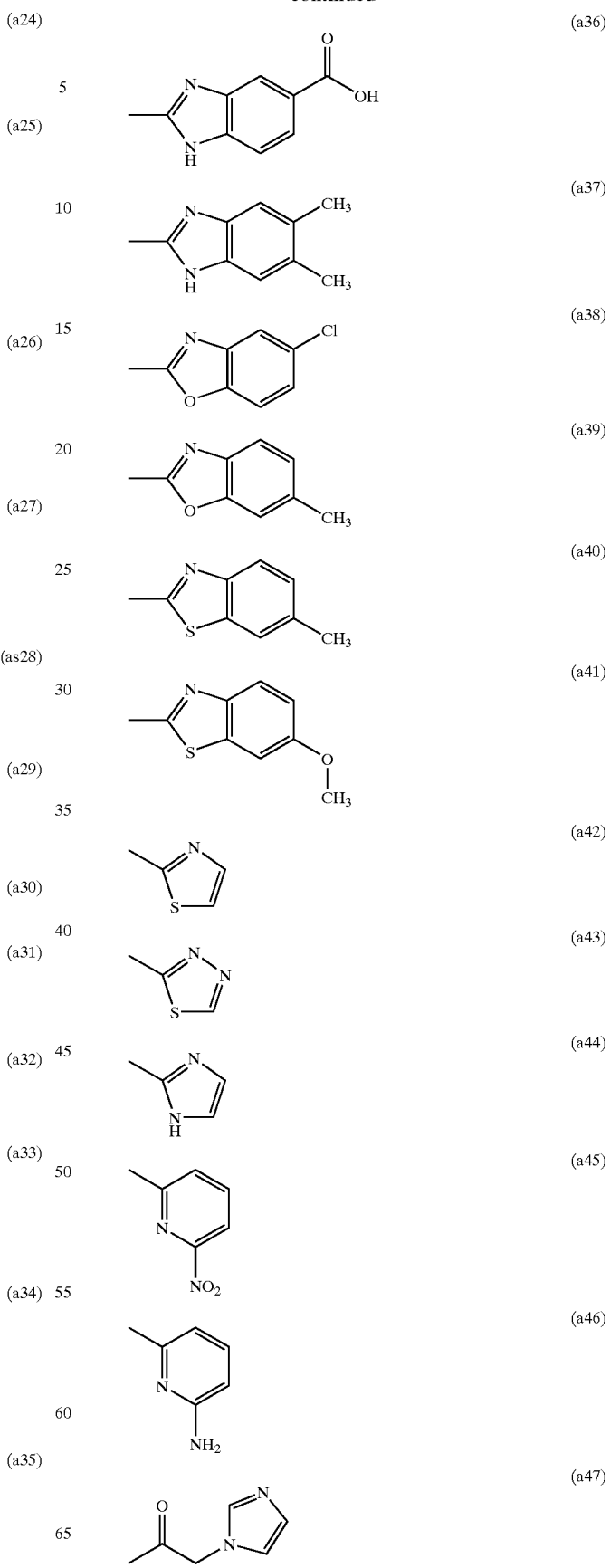

-continued (a48)
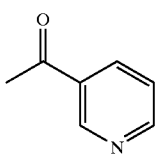

(a49)
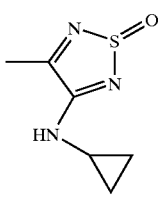

(a50)
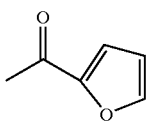

(a51)
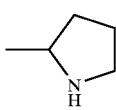

wherein Z is hydrogen, $CH_3$, $-NO_2$ or $-NH_2$, or $R^3$ is connected to one of $R^4$, Y, $R^5$ or $R^6$, if present, with formation of an optionally substituted heterocyclic 4- to 6-membered ring system which includes the nitrogen atom to which $R^3$ is bonded and can be saturated or unsaturated and/or can contain further heteroatoms;

$R^4$ is hydrogen, methyl, ethyl, propyl, isopropyl, butyl, 1-methyl-propyl, isobutyl, t-butyl, pentyl, 2-methyl-butyl, isopentyl, neopentyl, hexyl, $C_{1-4}$-perfluoralkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-alkylainino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoralkyl-$C_{1-4}$-alkyl, one of the residues (a1) to (a51) or is connected to one of $R^3$, Y, $R^5$ or $R^6$, if present, with formation of an optionally substituted heterocyclic 4- to 6-membered ring system which includes the nitrogen atom to which $R^4$ is bonded and can be saturated or unsaturated and/or can contain further heteroatoms;

X is $CHNO_2$, CHCN, O, N or S;

Y is a direct bond or a substituted or unsubstituted methylene or methine group;

$R^5$ is absent, or is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, $-NO_2$, $-CN$, $-COR^{5'}$, $-COOR^{5'}$ or is connected to one of $R^3$, Y, $R^4$ or $R^6$, if present, with formation of an optionally substituted carbocyclic or heterocyclic 4- to 6-membered ring system which includes X and can be saturated or unsaturated and/or can contain trrther heteroatoms;

$R^{5'}$ is hydrogen, methyl, ethyl, propyl, isopropyl, butyl, isobutyl, t-butyl, pentyl, isopentyl, neopentyl, bexyl, cyclopropyl, cyclobutyl, cyclopentyl, cyclohexyl, phenyl, benzyl, tolyl or a substituted derivative thereof;

$R^6$ is hydrogen, methyl, ethyl, propyl, isopropyl, butyl, 1-methylpropyl, isobutyl, t-butyl, pentyl, isopentyl, 2-methylbutyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl, one of the residues (a1) to (a51) or is connected to one of $R^3$, Y, $R^4$ or $R^5$, if present, with formation of an optionally substituted heterocyclic 4- to 6-membered ring system which includes the nitrogen atom to which $R^6$ is bonded and can be saturated or unsaturated and/or can contain further heteroatoms.

Particularly preferred compounds of the general formula (I) according to this embodiment are those in which $R^2$ is $-NR^{2'}SO_2R^{2''}$, $-NR^{2'}COOR^{2'}$, $-NR^{2'}COR^{2'}$, $-NR^{2'}CONR^{2'}_2$ or $-NR^{2'}CSNR^{2'}_2$;

$R^{2'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{2''}$ is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl or a substituted derivative thereof, 4-ethylphenyl, $-C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluoro-phenyl, 2-trifluoromethoxy-4-bromo-phenyl, 2-fluoro-4-trifluoromethylphenyl, 8-quinolinyl or a group of the formula

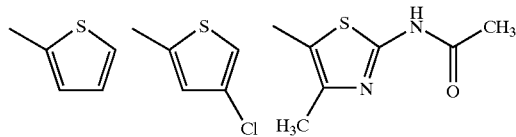

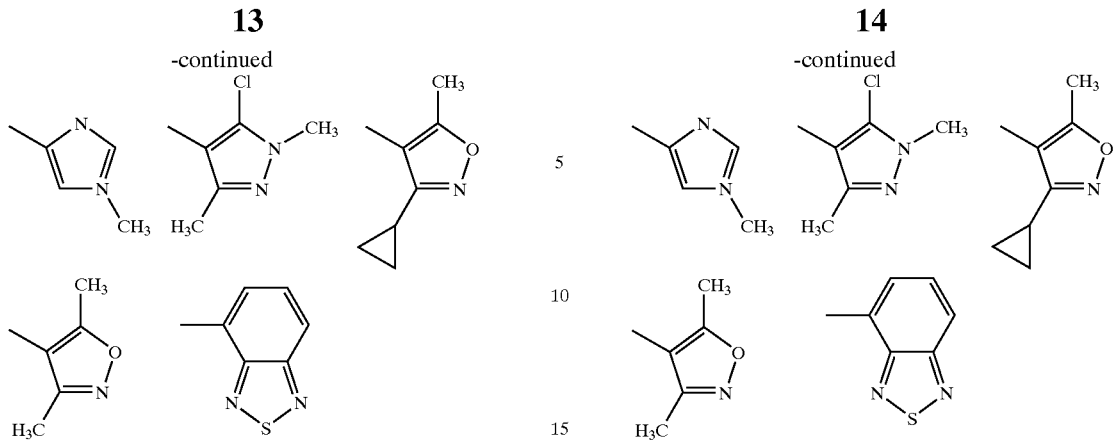
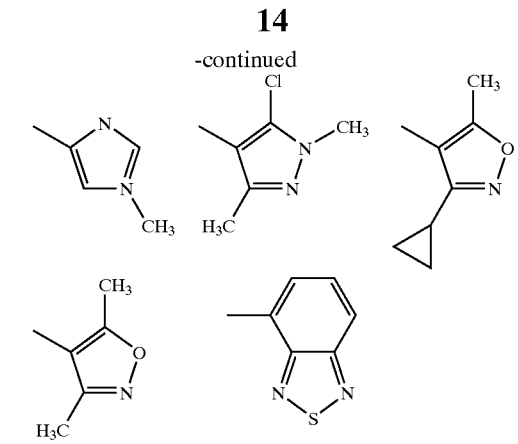

and the other substituents are as defined above.

Particularly preferred compounds of the formula (1) are in this case those in which $R^2$ is —$NR^{2'}SO_2R^{2''}$ or —$NR^{2'}COOR^{2'}$;

$R^{2'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example; 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{2''}$ is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl or a substituted derivative thereof, 4-ethylphenyl, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluorphenyl, 2-trifluoromethoxy-4-bromophenyl, 2-fluoro-4-trifluoromethylphenyl, 8-quinolinyl, a group of the formula

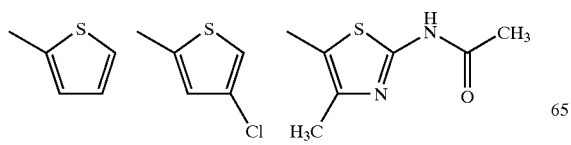

A is a 1,3- or 1,4-bridging phenylene group optionally substituted with a methoxy or up to 2 fluororesidues;

B is an optionally methyl-substituted 1,3- or 1,4-bridging phenylene group;

C is a direct bond or

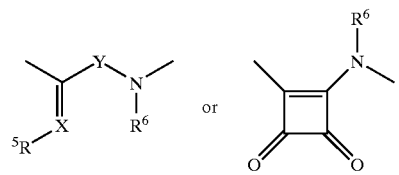

$R^5$ is absent, —$NO_2$, —CN, or is connected to one of $R^3$, Y, $R^4$ or $R^6$, if present, with formation of an optionally substituted carbocyclic or heterocyclic 4- to 6-membered ring system which includes X and can be saturated or unsaturated and/or can contain flirther heteroatoms;

and the other substituents are as defined above.

Additionally preferred compounds of the general formula (1) according to the present embodiment are those in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is —$CHR^7$— or —$CHR^7(CH_2)_{1-4}$—;

$R^7$ is —$NR^{7'}SO_2R^{7''}$, —$NR^{7'}COOR^{7'}$, —$NR^{7'}COR^{7'}$, —$NR^{7'}CONR^{7'}_2$ or —$NR^{7'}CSNR^{7'}_2$;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{7''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 2,6-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, and the other substituents are as defined above.

Particularly preferred compounds of the general formula (1) in this case are those in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond;

V is —CHR$^7$—;

$R^7$ is —NR$^{7'}$SO$_2$R$^{7''}$ or —NR$^{7'}$COOR$^{7''}$;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{7''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —C$_6$H$_2$(CH$_3$)$_3$, 2-chlorophenyl, 4-chlorophenyl, 2,5-dichlorophenyl, 4-trifluoromethylphenyl, campher-10-yl, 4-methoxyphenyl, 4-t-butyphenyl, 2,5-dimethylphenyl, 2,6-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, A is a 1,3- or 1,4-bridging phenylene group optionally substituted with a methoxy or up to 2 fluoro residnes;

B is an optionally methyl-substituted 1,3- or 1,4-bridging phenylene group;

C is a direct bond or

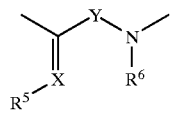

W is a direct bond or a —CH$_2$-group

X is O or S;

Y is a direct bond $R^5$ is absent and the other substituents are as defined above.

Additionally preferred compounds of the general formula (1) according to the present embodiment are those in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is a C$_{1-5}$-alkylene group which is optionally substituted by one or more residues $R^7$ which are selected from the group consisting of hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, a substituted derivative or a saturated or unsaturated, optionally substituted heterocyclic analog thereof, an optionally substituted alkenyl residue or an optionally substituted alkinyl residue;

and the other substituents are as defined above.

Particularly preferred compounds of the general formula (1) in this case are thosse in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is —CHR$^7$—;

$R^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, A is a 1,3- or 1,4-bridging phenylene group optionally substituted with a methoxy or up to 2 fluoro residues B is an optionally methyl-substituted 1,3- or 1,4-bridging phenylene group;

C is a direct bond or

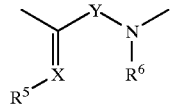

W is a direct bond or a —CH$_2$-group

X ist O or S;

Y is a direct bond $R^5$ is absent and the other substituents are as defined above.

According to yet another preferred embodiment, the present invention relates to compounds of the general formula (1), in which $R^1$ is hydrogen, methyl, ethyl, propyl, isopropyl, butyl, isobutyl, t-bputyl, pentyl, isopentyl, neopentyl, hexyl, cyclopropyl, cyclopropylmethyl, cyclobutyl, cyclopentyl, cyclohexyl, phenyl, benzyl, tolyl or a substituted derivative thereof;

$R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, phenylethyl, a substituted derivative or a saturated or unsaturated, optionally substituted heterocyclic analog thereof, an optionally substituted alkenyl residue, an optionally substituted alkinyl residue;

U is a direct bond or an optionally substituted $C_{1-3}$-alkylene group;

V is —$NR^8CO$— or —$NR^8SO_2$—;

$R^8$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl, phenylethyl, phenylpropyl, phenoxyethyl or a substituted derivative thereof;

A is a 1,3- or 1,4-bridging phenylene group or a 2,4- or 2,5-bridging thienylene group which are unsubstituted or have at least one alkoxy or halogeno residue;

B is a 1,3- or 1,4-bridging phenylene group which is unsubstituted or has at least one alkyl residue;

W is a direct bond or an optionally substituted $C_{1-3}$-alkylene group;

C is

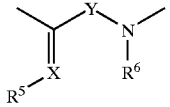

$R^3$ is hydrogen, methyl, ethyl, propyl, isopropyl, butyl, 1-methylpropyl, isobutyl, t-butyl, pentyl, 2-methylbutyl, isopentyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl, one of the residues (a1) to (a51) or is connected to one of $R^4$, Y or $R^6$, if present, with formation of an optionally substituted heterocyclic 4- to 6-membered ring system which includes the nitrogen atom to which $R^3$ is bonded and can be saturated or unsaturated and/or can contain further heteroatoms;

$R^4$ is hydrogen, methyl, ethyl, propyl, isopropyl, butyl, 1-methyl-propyl, isobutyl, t-butyl, pentyl, 2-methyl-butyl, isopentyl, neopentyl, hexyl, $C_{1-4}$-perfluoralkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoralkyl-$C_{1-4}$-alkyl, one of the residues (a1) to (a51) or is connected to one of $R^3$, Y or $R^6$, if present, with formation of an optionally substituted heterocyclic 4- to 6-membered ring system which includes the nitrogen atom to which $R^4$ is bonded and can be saturated or unsaturated and/or can contain further heteroatoms;

X is $CHNO_2$, CHCN, O or S;

Y is a direct bond or a substituted or unsubstituted methylene or methine group;

$R^5$ is absent;

$R^6$ is hydrogen, methyl, ethyl, propyl, isopropyl, butyl, 1-methylpropyl, isobutyl, t-butyl, pentyl, isopentyl, 2-methylbutyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl, one of the residues (a1) to (a51) or is connected to one of $R^3$, Y or $R^4$, if present, with formation of an optionally substituted heterocyclic 4- to 6-membered ring system which includes the nitrogen atom to which $R^6$ is bonded and can be saturated or unsaturated and/or can contain further heteroatoms.

Particularly preferred compounds of the general formula (1) according to this embodiment are those in which U is a direct bond or —$CHR^7$—;

$R^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue or pyridyl;

A is a 1,3- or 1,4-bridging phenylene group optionally substituted with a methoxy group or up to 2 fluoro residues;

B is an optionally methyl-substituted 1,3- or 1,4-bridging phenylene group;

W is a direct bond or a —$CH_2$-group;

C is

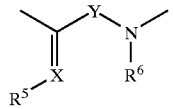

X ist O or S;

Y is a direct bond $R^5$ is absent and the other substituents are as defined above.

Another group of particularly preferred coumpounds of the general formula (1) according to this embodiment are those in which A is a 2,4- or 2,5-bridging thienylene group which ist unsubstituted or has at least one alkoxy residue and the other substituents are as defined above.

Further embodiments of the invention are described below.

The present invention furthermnore relates to compounds of the general formula (1)

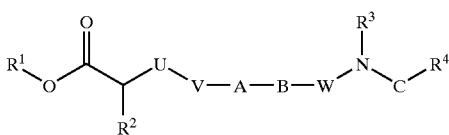

(1)

wherein
- R¹ is hydrogen, a substituted or unsubstituted alkyl or cycloalkyl residue, a substituted or unsubstituted aryl residue or a saturated or unsaturated, optionally substituted heterocyclic residue;
- R² is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, —NR²'SO₂R²", —NR²'COOR²", —NR²'COR²', —NR²'CONR²'₂ or —NR²'CSNR²'₂;
- R²' is hydrogen, a substituted or unsubstituted alkyl or cycloalkyl residue, a substituted or unsubstituted aryl residue or a saturated or unsaturated, optionally substituted heterocyclic residue;
- R²" is a substituted or unsubstituted alkyl or cycloalkyl residue, a substituted or unsubstituted aryl residue or a saturated or unsaturated, optionally substituted heterocyclic residue;
- U is a direct bond or a substituted or unsubstituted alkylene group;
- V is a substituted or unsubstituted alkylene group, —NR²'CO— or —NR²'SO₂—;
- A and B are each independently of one another a 1,3- or 1,4-bridging, optionally additionally substituted phenylene group;
- W is a direct bond or a substituted or unsubstituted alkylene group;
- C is a direct bond or

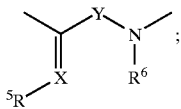

- R³ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of R⁴, Y, R⁵ or R⁶, if present, with formation of an optionally substituted heterocyclic ring system which includes the nitrogen atom to which R³ is bonded, and can be saturated or unsaturated and/or can contain further heteroatoms;
- R⁴ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of R³, Y, R⁵ or R⁶, if present, with formation of an optionally substituted heterocyclic ring system which includes the nitrogen atom to which R⁴ is bonded and can be saturated or unsaturated and/or can contain further heteroatoms;
- X is CHNO₂, CHCN, O, N or S;
- Y is a direct bond or an optionally substituted alkylene or alkine group;
- R⁵ is absent, or is hydrogen, a substituted or unsubstituted alkyl or cycloalkyl residue, —NO₂, —CN, —COR⁵', —COOR⁵', or is connected to one of R³, Y, R⁴ or R⁶, if present, with formation of an optionally substituted carbocyclic or heterocyclic ring system which includes X and can be saturated or unsaturated and/or can contain further heteroatoms;
- R⁵' is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;
- R⁶ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of R³, R⁴, Y or R⁵, if present, with formation of an optionally substituted heterocyclic ring system which includes the nitrogen atom to which R⁶ is bonded and can be saturated or unsaturated and/or can contain further heteroatoms;

with the proviso that if V is —NR²'CO— or —NR²'SO₂—, C is not a direct bond and X is not N; and their physiologically acceptable salts and stereoisomers.

According to a preferred embodiment, the present invention relates to compounds of the general formula (1), where
- R¹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl or a substituted derivative thereof;
- R² is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, —NR²'SO₂R²", —NR²'COOR²", —NR²'COR²', —NR²'CONR²'₂ or —NR²'CSNR²'₂;
- R²' is hydrogen, methyl, ethyl, propyl, isopropyl, butyl, isobutyl, t-butyl, pentyl, isopentyl, neopentyl, hexyl, cyclopropyl, cyclobutyl, cyclpentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;
- R²" is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —C₆H₂(CH₃)₃, 2-chlorophenyl, 4-chlorophenyl, 2,5-dichlorophesnyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorphenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, U is a direct bond, V is an optionally substituted $C_{1-5}$-alkylene group;

A is a 1,3- or 1,4-bridging phenylene group which is unsubstituted or carries at least one alkoxy residue;

B is a 1,3- or 1,4-bridging phenylene group which is unsubstituted or carries at least one alkyl residue;

W is a direct bond or an optionally substituted $C_{1-4}$-alkylene group;

C is a direct bond or

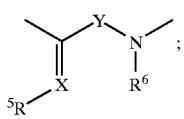

$R^3$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, dialkylamino-$C_{1-4}$-alkyl, amino-$C_{1-4}$-alkyl, $C_{1-4}$-alkyloxy-$C_{1-4}$-alkyl,

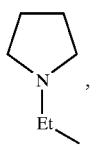 (a1)

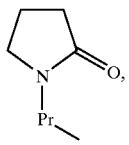 (a2)

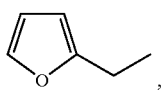 (a3)

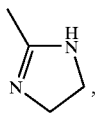 (a4)

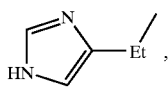 (a5)

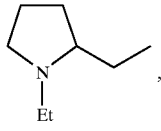 (a6)

-continued

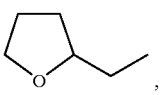 (a7)

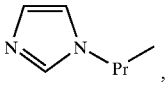 (a8)

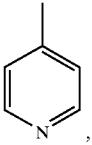 (a9)

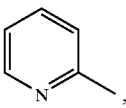 (a10)

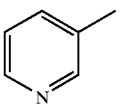 (a11)

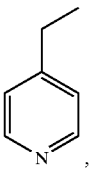 (a12)

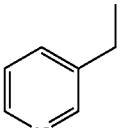 (a13)

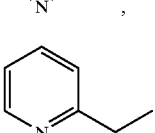 (a14)

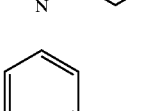 (a15)

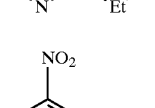 (a16)

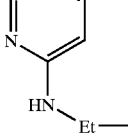 (a17)

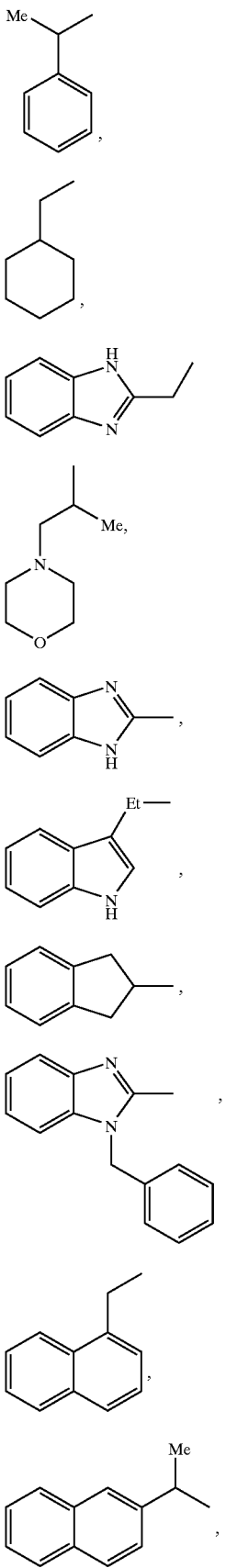

or is connected to one of $R^4$, Y, $R^5$ or $R^6$, if present, with formation of an optionally substituted heterocyclic 4- to 6-membered ring system which includes the nitrogen atom to which $R^3$ is bonded and can be saturated or unsaturated and/or can contain further heteroatoms;

$R^4$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a29) or is connected to one of $R^3$, Y, $R^5$ or $R^6$, if present, with formation of an optionally substituted heterocyclic 4- to 6-membered ring system which includes the nitrogen atom to which $R^4$ is bonded and can be saturated or unsaturated and/or can contain further heteroatoms;

X is $CHNO_2$, CHCN, O, N or S;

Y is a direct bond or a substituted or unsubstituted methylene or methine group;

$R^5$ is absent, or is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, $-NO_2$, $-CN$, $-COR^{5'}$, $-COOR^{5'}$ or is connected to one of $R^3$, Y, $R^4$ or $R^6$, if present, with formation of an optionally substituted carbocyclic or heterocyclic 4- to 6-membered ring system which includes X and can be saturated or unsaturated and/or can contain further heteroatoms;

$R^{5'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof;

$R^6$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a29) or is connected to one of $R^3$, Y, $R^4$ or $R^5$, if present, with formation of an optionally substituted heterocyclic 4- to 6-membered ring system which includes the nitrogen atom to which $R^6$ is bonded and can be saturated or unsaturated and/or can contain further heteroatoms.

Particularly preferred compounds of the general formula (I) according to this embodiment are those in which $R^2$ is $-NR^{2'}SO_2R^{2''}$, $-NR^{2'COOR2''}$, $-NR^{2'}COR^{2'}$, $-NR^{2'}CONR^{2'}_2$ or $-NR^{2'}CSNR^{2'}_2$;

$R^{2'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{2''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, and the other substituents are as defined above.

Particularly preferred compounds of the formula (1) are in this case those in which $R^2$ is —$NR^{2'}SO_2R^{2''}$ or —$NR^{2'}COOR^{2''}$;

$R^{2'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{2''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, A is an optionally methoxy-substituted 1,3- or 1,4-bridging phenylene group;

B is an optionally methyl-substituted 1,3- or 1,4-bridging phenylene group;

C is

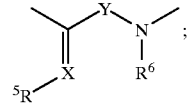

W is a direct bond;

X is O or S;

Y is a direct bond;

$R^5$ is absent;

and the other substituents are as defined above.

Additionally preferred compounds of the general formula (1) according to the present embodiment are those in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is —$CHR^7$— or —$CHR^7(CH_2)_{1-4}$—;

$R^7$ is —$NR^{7'}SO_2R^{7''}$, —$NR^{7'}COOR^{7'}$, —$NR^{7'}COR^{7'}$, —$NR^{7'}CONR^{7'}_2$ or —$NR^{7'}CSNR^{7'}_2$;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

$R^{7''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, and the other substituents are as defined above.

Particularly preferred compounds of the general formula (1) in this case are those in which $R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond;

V is —CHR$^7$—;

R$^7$ is —NR$^{7'}$SO$_2$R$^{7''}$ or —NR$^{7'}$COOR$^{7''}$;

R$^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl;

R$^{7''}$ is methyl, ethyl, propyl, isopropyl, butyl, isobutyl, t-butyl, pepntyl, isopentyl, neopentyl, hexyl, cyclopropyl, cyclobutyl, cyclopentyl, cyclohexyl, phenyl, benzyl, tolyl or a substituted derivative thereof, —C$_6$H$_2$(CH$_3$)$_3$, 2-chlorophenyl, 4-chlorophenyl, 2,5-dichlorophenyl, 4-trifluoromethylphenyl, campher-10-yl, 4-methoxyphenyl, 4-t-butyphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonyl phenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, A is an optionally methoxy-substituted 1,3- or 1,4-bridging phenylene group;

B is an optionally methyl-substituted 1,3- or 1,4-bridging phenylene group;

C is

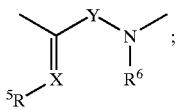

W is a direct bond;

X is O or S;

Y is a direct bond;

R$^5$ is absent;

and the other substituents are as defined above.

Additionally preferred compounds of the general formula (1) according to the present embodiment are those in which R$^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is a C$_{1-5}$-alkylene group which is optionally substituted by one or more residues R$^7$ which are selected from the group consisting of hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, a substituted derivative or a saturated or unsaturated, optionally substituted heterocyclic analog thereof, an optionally substituted alkenyl residue or an optionally substituted alkinyl residue;

and the other substituents are as defined above.

Particularly preferred compounds of the general formula (1) in this case are those in which R$^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is —CHR$^7$—;

R$^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, A is an optionally methoxy-substituted 1,3- or 1,4-bridging phenylene group;

B is an optionally methyl-substituted 1,3- or 1,4-bridging phenylene group;

C is

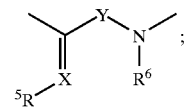

W is a direct bond;

X is O or S;

Y is a direct bond;

R$^5$ is absent;

and the other substituents are as defined above.

According to yet another preferred embodiment, the present invention relates to compounds of the general formula (1), in which R$^1$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl or a substituted derivative thereof;

R$^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, phenylethyl, a substituted derivative or a saturated or unsaturated, optionally substituted heterocyclic analog thereof, an optionally substituted alkenyl residue, an optionally substituted alkinyl residue;

U is a direct bond or an optionally substituted C$_{1-3}$-alkylene group;

V is —NR$^8$CO— or —NR$^8$SO$_2$—;

R$^8$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl, phenylethyl, phenylpropyl, phenoxyethyl or a substituted derivative thereof;

A is a 1,3- or 1,4-bridging phenylene group which is unsubstituted or has at least one alkoxy residue;

B is a 1,3- or 1,4-bridging phenylene group which is unsubstituted or has at least one alkyl residue;

W is a direct bond or an optionally substituted $C_{1-3}$-alkylene group;

C is

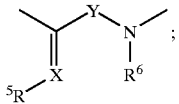

$R^3$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a29) or is connected to one of $R^4$, Y or $R^6$, if present, with formation of an optionally substituted heterocyclic 4- to 6-membered ring system which includes the nitrogen atom to which $R^3$ is bonded and can be saturated or unsaturated and/or can contain further heteroatoms;

$R^4$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a29) or is connected to one of $R^3$, Y or $R^6$, if present, with formation of an optionally substituted heterocyclic 4- to 6-membered ring system which includes the nitrogen atom to which $R^4$ is bonded and can be saturated or unsaturated and/or can contain further heteroatoms;

X is $CHNO_2$, CHCN, O or S;

Y is a direct bond or a substituted or unsubstituted methylene or methine group;

$R^5$ is absent;

$R^6$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a29) or is connected to one of $R^3$, Y or $R^4$, if present, with formation of an optionally substituted heterocyclic 4- to 6-membered ring system which includes the nitrogen atom to which $R^6$ is bonded, and can be saturated or unsaturated and/or can contain further heteroatoms.

Particularly preferred compounds of the general formula (1) according to this embodiment are those in which U is a direct bond or —$CHR^7$—;

$R^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue;

A is an optionally methoxy-substituted 1,3- or 1,4-bridging phenylene group;

B is an optionally methyl-substituted 1,3- or 1,4-bridging phenylene group;

W is a direct bond;

Y is a direct bond;

and the other substituents are as defined above.

The present invention fairthermore relates to a process for the preparation of the above-mentioned compounds having the general formula (1),

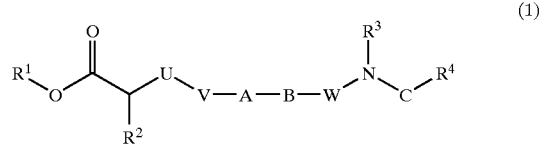

(1)

which comprises the steps a) reaction of a carboxylic acid derivative of the formula (2)

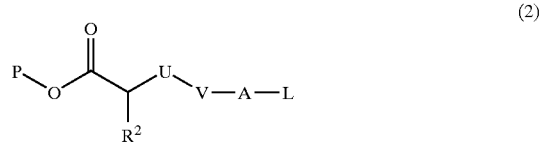

(2)

wherein

P is a conventional protective group, a solid phase used for carrying out a solid-phase reaction or $R^1$ is as defined in claim 1;

A is a phenylene group which is 1,3- or 1,4-substituted or a thienylene group which is 2,4- or 2,5-substituted with respect to V and L and optionally has additional residues;

L is —H, —F, —Cl, —Br, —I, —SCN, —$N_2^+$ or an organometallic residue; and the other residues are as defined above;

with a phenyl compound of the formula (3)

M—B—W—D (3)

wherein

M is —H, —I, —$N_2^+$, —$COOCOBNO_2$ or an organometallic residue;

B is a phenylene group which is 1,3- or 1,4-substituted with respect to M and W—D and optionally has additional residues;

W is as defined in claim 1;

D is —$NO_2$, —$NH_2$ or —CHO;

to give a biphenyl or thienyl-phenyl compound of the formula (4)

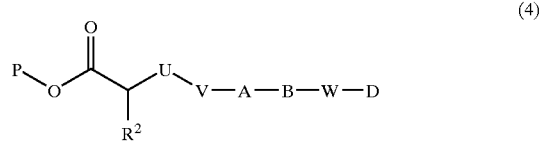

(4)

where the residues are as defined above;

b) conversion of the residue D into the corresponding amino group, if D is not —$NH_2$; and c) if appropriate, derivatization of nitrogen atoms present at preferred times within the preparation process and/or the conversion of the compound obtained into the free acid and/or the conversion of the compound obtained into one of its physiologically acceptable salts by reaction with an inorganic or organic base or acid.

In the process according to the invention all steps can be carried out during the bonding of the carboxylic acid derivative of the formula (2) to a solid phase.

Furthermore, according to a preferred embodiment of the process according to the invention a carboxylic acid derivative of the formula (2), in which L is —F, —Cl, —Br or —I and the other residues are as defined above, is reacted with a phenyl compound of the formula (3), in which M is an organometallic residue;

and the other residues are as defined above, in the presence of a palladium compound and of a phosphane.

Preferably, in the above process according to the invention a carboxylic acid derivative of the formula (2) is employed which contains a sulfonamide or carbamate group which was formed by reaction of an amino group of the corresponding precursor of the carboxylic acid derivative of the formula (2) with a sulfonyl halide or a carbamoyl halide.

It is furthermore preferred that in the above process according to the invention, in the case in which D is —NO$_2$ in the compound of the formula (4), the conversion of D into an amino group is carried out in the presence of a tin(II) compound. It is furthermore preferred that in the above process according to the invention, in the case in which D is —CHO in the compound of the formula (4), the conversion of D into an amino group by reaction with an amine is carried out under reducing conditions.

It is moreover preferred that the compound of the formula (4) in which D is an amino group is converted into a urea or thiourea unit by a reaction of this amino group with a carbonic acid derivative or thiocarbonic acid derivative and a subsequent reaction with an amine of the formula NHR$^4$R$^6$, where R$^4$ and R$^6$ are as defined above.

The present invention furthermore relates to a pharmaceutical composition which contains at least one of the compounds defined above.

The present invention also relates to the use of the compounds described above for the production of pharmaceutical compositions having integrin-antagonistic action.

The present invention furthermore relates to the use of compounds of the general formula (1)

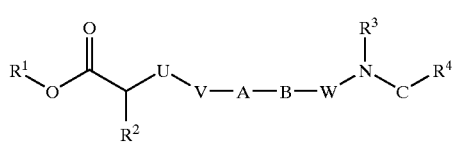

(1)

wherein

R$^1$ is hydrogen, a substituted or unsubstituted alkyl or cycloalkyl residue, a substituted or unsubstituted aryl residue or a saturated or unsaturated, optionally substituted heterocyclic residue;

R$^2$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, —NR$^{2'}$SO$_2$R$^{2''}$, —NR$^{2'}$COOR$^{2'}$, —NR$^{2'}$COR$^{2'}$, —NR$^{2'}$CONR$^{2'}{}_2$ or —NR$^{2'}$CSNR$^{2'}{}_2$;

R$^{2'}$ is hydrogen, a substituted or unsubstituted alkyl or cycloalkyl residue, a substituted or unsubstituted aryl residue or a saturated or unsaturated, optionally substituted heterocyclic residue;

R$^{2''}$ is a substituted or unsubstituted alkyl, alkenyl or cycloalkyl residue, a substituted or unsubstituted aryl residue or a saturated or unsaturated, optionally substituted heterocyclic residue;

U is a direct bond or a substituted or unsubstituted alkylene group;

V is a substituted or unsubstituted alkylene group, —NR$^{2'}$CO— or —NR$^{2'}$SO$_2$—;

A and B are each independently of one another a 1,3- or 1,4-bridging phenylene group or a 2,4- or 2,5-bridging thienylene group each of which may optionally have additional substituents, W is a direct bond or a substituted or unsubstituted alkylene group;

C is a direct bond or

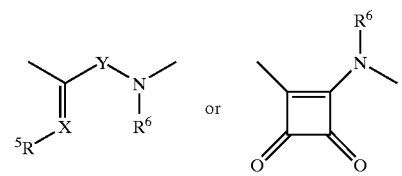

R$^3$ is hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or is connected to one of R$^4$, Y, R$^5$ or R$^6$, if present, with formation of an optionally substituted heterocyclic ring system which includes the nitrogen atom to which R$^3$ is bonded, and can be saturated or unsaturated and/or can contain further heteroatoms;

R$^4$ is hydrogen, a substituted or unsubstituted alkyl or cycloalkyl residue, a substituted or unsubstituted aryl residue, a saturated or unsaturated, optionally substituted heterocyclic residue, an alkylarnine residue, an alkylamide residue or is connected to one of R$^3$, Y, R$^5$ or R$^6$, if present, with formation of an optionally substituted heterocyclic ring system which includes the nitrogen atom to which R$^4$ is bonded and can be saturated or unsaturated and/or can contain further heteroatoms;

X is CHNO$_2$, CHCN, O, N or S;

Y is a direct bond or an optionally substituted alkylene or alkine group;

R$^5$ is absent, or is hydrogen, a substituted or unsubstituted alkyl or cycloalkyl residue, —NO$_2$, —CN, —COR$^{5'}$, —COOR$^{5'}$, or is connected to one of R$^3$, Y, R$^4$ or R$^6$, if present, with formation of an optionally substituted carbocyclic or heterocyclic ring system which includes X and can be saturated or unsaturated and/or can contain further heteroatoms;

R$^{5'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

R$^6$ is hydrogen, a substituted or unsubstituted alkyl or cycloalkyl residue, a substituted or unsubstituted aryl or arylcarbonyl residue, a saturated or unsaturated, optionally substituted heterocyclic residue, an alkylamine residue, an alkylamide residue or is connected to one of $R^3$, $R^4$, Y or $R^5$, if present, with formation of an optionally substituted heterocyclic ring system which includes the nitrogen atom to which $R^6$ is bonded and can be saturated or unsaturated and/or can contain further heteroatoms;

and their physiologically acceptable salts and stereoisomers, for the production of a pharmaceutical composition for the inhibition of angiogenesis and/or for the therapy and prophylaxis of cancer, osteolytic diseases such as osteoporosis, arteriosclerosis, restenosis, rheumatoid arthritis and ophthalmic disorders. It is particularly preferred in this case that, for the production of the pharmaceutical composition, compounds are employed such as are defined in one of the attached claims 1 to 11.

DETAILED DESCRIPTION OF THE PREFERRED EMBODIMENTS

The invention is illustrated more in detail below with reference to preferred embodiments, to which, however, it is not restricted in any way. In the description below, bivalent substituents are indicated such that their respective left end is connected to the indicated group left of the corresponding substituent in formula (1) and their respective right end is connected to the indicated group right of the corresponding substituent in formula (1). If in formula (1), for example, the residue V is —$NR^8SO_2$—, the nitrogen atom is connected to the residue U and the sulfur atom to the residue A.

The compounds according to the invention comprise, as a main structural element, a biphenyl nucleus which bridges a residue having a terminal carboxyl group with a residue including at least one nitrogen atom in the main chain, which is a constituent of an amino group, amide group, urea group, thioamide group, thiourea group, amidine group, enamine group or guanidine group which is optionally incorporated into a cyclic ring system. In the biphenyl nucleus the phenyl ring A which is located nearer to the terminal carboxyl group may optionally be replaced by a thiophene ring. In addition to one of the abovementioned residues, the biphenyl nucleus can moreover carry further substituents.

The terminal carboxyl unit can be present as a free carboxylic acid or as an ester. In the case in which the terminal carboxyl unit is esterified, in principle all carboxylic acid esters which are obtainable according to conventional processes and can be metabolized in the human body into the free carboxylic acid, such as the corresponding alkyl esters, cycloalkyl esters, aryl esters and heterocyclic analogs thereof, can be used according to the invention, wherein alkyl esters, cycloalkyl esters and aryl esters are preferred and the alcoholic residue can carry further substituents. $C_{1-6}$-Alkyl esters such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

The abovementioned esters can be employed as prodrugs for the inhibition of angiogenesis and/or the treatment of the diseases mentioned at the beginning, such as cancer, osteoporosis, arteriosclerosis, restenosis, rheumatoid arthritis or ophthalmia, since they are easily converted into the corresponding carboxylic acid in animals and humans. However, for the treatment of the abovementioned disorders the compounds of the general formula (1) according to the invention are preferably used in a form in which the terminal carboxyl unit is present as a free carboxylic acid.

For medicinal use, the compounds of the general formula (1) according to the invention can also be employed in the form of their physiologically acceptable salts. According to the invention, physiologically acceptable salts are understood as meaning nontoxic salts which in general are accessible by reaction of the compounds of the general formula (1) according to the invention with an inorganic or organic base or acid conventionally used for this purpose. Examples of preferred salts of the compounds of the general formula (1) according to the invention are the corresponding alkali metal salt, e.g. lithium, potassium or sodium salt, the corresponding alkaline earth metal salt such as the magnesium or calcium salt, a quaternary ammonium salt such as, for example, the triethylammonium salt, acetate, benzenesulfonate, benzoate, dicarbonate, disulfate, ditartrate, borate, bromide, carbonate, chloride, citrate, dihydrochloride, fumarate, gluconate, glutamate, hexylresorcinate, hydrobromide, hydrochloride, hydroxynaphthoate, iodide, isothionate, lactate, laurate, malate, maleate, mandelate, mesylate, methylbromide, methylnitrate, methylsulfate, nitrate, oleate, oxalate, palmitate, pantothenate, phosphate, diphosphate, polygalacturonate, salicylate, stearate, sulfate, succinate, tartrate, tosylate and valerate, and other salts used for medicinal purposes.

The terminal carboxyl unit is connected to the biphenyl nucleus or thiophene-phenyl-nucleus by means of an alkylene chain which can optionally carry further substituents. Within certain limits, it is possible to control the biological activity of the compounds according to the invention against integrin receptors such as, in particular, the $\alpha_v\beta_3$ or $\alpha_v\beta_5$, receptor, by means of the distance between the terminal carboxyl unit and the nitrogen atom of an amino group, amide group, urea group, thioamide group, thiourea group, amidine group, enamine group or guanidine group which is located in the main chain of the residue linked to the phenyl ring B of the biphenyl nucleus or thiophene-phenyl-nucleus, where in the case in which more than one nitrogen atom is present in the main chain of the respective residue, the nitrogen atom located nearer to the phenyl ring B of the nucleus is decisive. In addition to the biphenyl nucleus or thiophene-phenyl-nucleus, preferably not more than 6 atoms should be located in the main chain between these two structural elements. However, compounds in which, additionally to the biphenyl nucleus or thiophene-phenyl-nucleus, less than 6 additional atoms are located in the main chain between the terminal carboxyl unit and the nitrogen atom of the amino group, amide group, urea group, thioamide group, thiourea group, amidine group, enamine group or guanidine group which is located in the main chain of the residue linked to the phenyl ring B of the biphenyl nucleus or thiophene-phenyl-nucleus, are more preferred. According to the present invention, particularly preferred compounds are those in which the abovementioned nitrogen atom of the amino group, amide group, urea group, thioamide group, thiourea group, amidine group, enamine group or guanidine group is bonded directly or via a —$CH_2$-group to the phenyl ring B of the biphenyl nucleus or thiophene-phenyl-nucleus and, at the same time, the terminal carboxyl unit is separated from the phenyl ring A of the biphenyl nucleus or thiophene-phenyl-nucleus by two to four atoms in the main chain.

The alkylene chain which connects the terminal carboxyl group to the phenyl ring A of the biphenyl nucleus or thiophene-phenyl-nucleus can alternatively carry additional substituents on any of the carbon atoms forming the alkylene chain. These substituents can be selected from the group which consists of hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, —NR$^{2'}$SO$_2$R$^{2"}$, —NR$^{2'}$COOR$^{2'}$, —NR$^{2'}$COR$^{2'}$, —NR$^{2'}$CONR$^{2'}_2$ or —NR$^{2'}$CSNR$^{2'}_2$, wherein R$^{2'}$ can be hydrogen, a substituted or unsubstituted alkyl, alkenyl or cycloalkyl residue, a substituted or unsubstituted aryl residue or a saturated or unsaturated, optionally substituted heterocyclic residue and R$^{2"}$ can be a substituted or unsubstituted alkyl, alkenyl or cycloalkyl residue, a substituted or unsubstituted aryl residue or a saturated or unsaturated, optionally substituted heterocyclic residue. The alkyl residue can preferably be a $C_{1-6}$-alkyl such as, for example, methyl, ethyl, propyl, isopropyl, butyl, isobutyl, t-butyl, pentyl, isopentyl, neopentyl or hexyl. The alkenyl residue can preferably be a $C_2$–$C_6$-alkenyl having one or two double bonds such as, for example vinyl, allyl, prop-1-en-yl, isopropenyl, but-1-enyl, buta-1,3-dienyl. The cycloalkyl residue can preferably be a $C_{3-7}$-cycloalkyl such as, for example, cyclopropyl, cyclopropylmethyl, cyclobutyl, cyclopentyl or cyclohexyl. The aryl residue can preferably be phenyl, benzyl or tolyl. As an example for substituted aryl p-fluorobenzyl may be mentioned. The heterocyclic residue can preferably be pyrrole, pyridine, tetrahydrofuran, furan, thiophene, tetrahydrothiophene, thiooxazole, benzofuran, quinoline, isoquinoline, pyrimidine, imidazole, thiazole, pyrazole, isoxazole and benzothiadiazole. The alkenyl residue can be a terminal or internal E- or Z-alkene unit. The abovementioned residues can alternatively carry one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl, cyclohexyl or cycloheptyl, aryl residues such as phenyl, benzyl, tolyl, naphthyl, heterocyclic residues such as pyrrole, pyridine, tetrahydrofuran, furan, thiophene, tetrahydrothiophene, oxazole, thiazole, thiooxazole, benzofuran, benzoxazole, benzothiazole, quinoline, isoquinoline, or functional groups such as a double bond to a heteroatom such as oxygen, sulfur or nitrogen, an optionally substituted amino group, a nitro group, a halogeno group, a trifluoromethyl group, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, benzofuranyl, benzoxazolyl, benzothiazolyl, quinolinyl or isoquinolinyl unit or a partially or completely hydrogenated analog thereof.

Preferred substituents among those optionally located at the alkylene chain connecting the terminal carboxyl group to the phenyl ring A of the biphenyl nucleus or thiophene-phenyl-nucleus are —NR$^{2'}$SO$_2$R$^{2"}$, —NR$^{2'}$COOR$^{2'}$, —NR$^{2'}$COR$^{2'}$, —NR$^{2'}$CONR$^{2'}_2$ or —NR$^{2'}$CSNR$^{2'}_2$, wherein R$^{2'}$ can be hydrogen, a substituted or unsubstituted alkyl, alkenyl or cycloalkyl residue, a substituted or unsubstituted aryl residue or a saturated or unsaturated, optionally substituted heterocyclic residue and R$^{2"}$ can be a substituted or unsubstituted alkyl, alkenyl or cycloalkyl residue, a substituted or unsubstituted aryl residue or a saturated or unsaturated, optionally substituted heterocyclic residue. R$^{2'}$ is preferably selected from the group which consists of hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl, while R$^{2"}$ is preferably selected from the group which consists of a $C_{1-6}$-alkyl such as, for example, methyl, ethyl, propyl, isopropyl, butyl, isobutyl, t-butyl, pentyl, isopentyl, neopentyl, hexyl, a substituted $C_{1-6}$-alkyl such as for example 1,1,1-trifluoro-n-but-4-yl, a $C_{2-6}$-alkenyl having one double bond such as, for example allyl, a $C_{3-7}$-cycloalkyl such as, for example, cyclopropyl, cyclobutyl, cyclopentyl, cyclohexyl, phenyl, benzyl, tolyl or a substituted derivative thereof, such as p-fluorobenzyl, 4-ethylphenyl, —C$_6$H$_2$(CH$_3$)$_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluorophenyl, 2-trifluoromethoxy-4-bromophenyl, 2-fluoro-4-trifluoromethylphenyl, 8-quinolinyl, a group of the formula

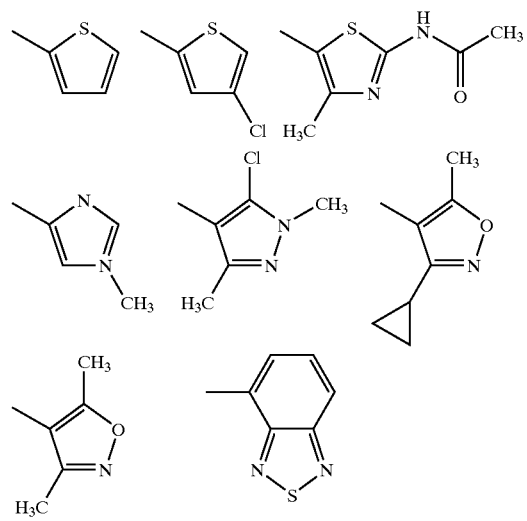

According to the invention, particularly preferred compounds of the general formula (1) are those in which a sulfonamide or carbamate group is located at the alkylene chain which connects the terminal carboxyl group to the phenyl ring A of the biphenyl nucleus or thiophene-phenyl-nucleus. The sulfonamide or carbamate group is preferably located in the α- or β-position to the terminal carboxyl group. However, more than 2 carbon atoms can also be located between the carboxyl carbon of the terminal carboxyl group and the nitrogen atom of the sulfonamide or carbamate unit. According to the present invention, the sulfonamide group, if present, particularly preferably carries a residue R²" on the sulfur atom, which is selected from the group consisting of phenyl, benzyl, tolyl or a substituted derivative thereof, such as p-fluorobenzyl, —C₆H₂(CH₃)₃, 2-chlorophenyl, 4-chlorophenyl, 2,4-dichlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 8-quinolinyl or a group of the formula

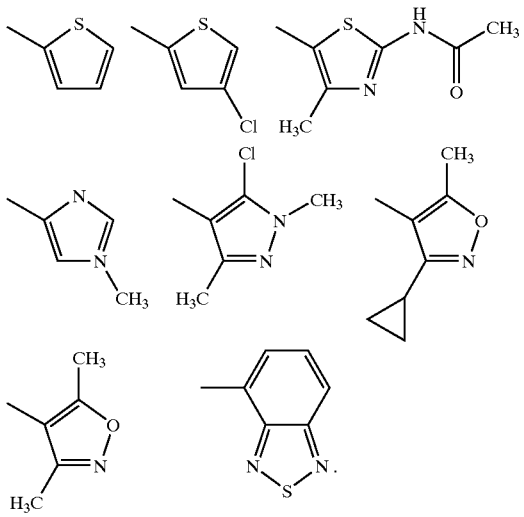

If present, the carbamate group particularly preferably carries a residue R²' as an alcoholic component which is selected from the group consisting of a C₁₋₆-alkyl residue such as methyl, ethyl, propyl, isopropyl, butyl, isobutyl, t-butyl, pentyl, isopentyl, neopentyl or hexyl, a C₃₋₇-cycloalkyl residue such as cyclopropyl, cyclopropylmethyl, cyclobutyl, cyclopentyl, cyclohexyl or cycloheptyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl, and which is particularly preferably a benzyl residue.

According to a flirther aspect, the present invention relates to compounds of the general formula (1) in which the terminal carboxyl group is bonded to the phenyl/thienyl ring A of the biphenyl nucleus or thienyl-phenyl nucleus by means of an alkylenesulfonamide unit or an alkylenamide unit, i.e. an —NRSO₂— or —NR—CO— group is inserted between the alkylene chain and the phenyl/thienyl ring A of the nucleus, the phenyl/thienyl ring A of the nucleus being bonded to the sulfur atom of the sulfonamide unit or the carboxyl carbon atom of the amide unit. In accordance with the above details, the alkylene chain between the terminal carboxyl group and the sulfonamide or amide unit can in this case optionally carry further substituents, where a C₁₋₆-alkyl such as, for example, methyl, ethyl, propyl, isopropyl, butyl, isobutyl, t-butyl, pentyl, isopentyl, neopentyl or hexyl, a C₃₋₇-cycloalkyl such as, for example, cyclopropyl, cyclopropylmethyl, cyclobutyl, cyclopentyl or cyclohexyl, an aryl such as, for example, phenyl, benzyl, phenylethyl or tolyl, a heterocyclic residue such as pyrrole, pyridine, tetrahydrofuran, furan, thiophene, tetrahydrothiophene, thiooxazole, benzofuran, quinoline, isoquinoline or pyrimidine, or a terminal or internal E- or Z-alkene unit are preferred, which can alternatively carry one or more C₁₋₆-alkyl residues such as methyl, ethyl, propyl, isopropyl, butyl, isobutyl, t-butyl, pentyl, isopentyl, neopentyl or hexyl, C₃₋₇-cycloalkyl residues such as cyclopropyl, cyclopropylmethyl, cyclobutyl, cyclopentyl or cyclohexyl, aryl residues such as phenyl, benzyl, tolyl, naphthyl, heterocyclic residues such as pyrrole, pyridine, tetrahydrofuran, furan, thiophene, tetrahydrothiophene, thiooxazole, benzofuran, quinoline, isoquinoline or pyrimidine, or functional groups such as a double bond to a heteroatom such as oxygen, sulfur or nitrogen, an optionally substituted amino group, a nitro group, a halogeno, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, benzofuranyl, benzoxazolyl, benzothiazolyl, quinolinyl or isoquinolinyl unit or a partially or completely hydrogenated analog thereof.

Particularly preferred compounds according to this embodiment are those in which the alkylene chain which connects the terminal carboxyl group and the bridging sulfonamide or amide unit has a phenyl, aminophenyl, benzyl or pyridyl residue in the α- or β-position to the terminal carboxyl unit.

In the compounds of this aspect in which a sulfonamide or amide unit is inserted between the corresonding alkylene chain and the phenyl/thienyl ring A of the nucleus, the alkylene chain between the terminal carboxyl group and the bridging sulfonamide or amide unit should preferably comprise not more than two carbon atoms in its main chain in order that, as mentioned above, in addition to the biphenyl nucleus or thiophene-phenyl-nucleus preferably not more than 6 atoms are present between the terminal carboxyl group and the nitrogen atom of the amino group, amide group, urea group, thioamide group, thiourea group, amidine group, enarnine group or guanidine group which is nearest to the phenyl ring B in the main chain of the residue linked to the phenyl ring B of the biphenyl or thienyl-phenyl nucleus.

The nitrogen atom of the bridging sulfonamide or amide unit can optionally carry a residue which is selected from the group consisting of hydrogen, a C₁₋₆-alkyl such as, for example, methyl, ethyl, propyl, isopropyl, butyl, isobutyl, t-butyl, pentyl, isopentyl, neopentyl, hexyl, a C₃₋₇-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof such as, for example, phenylethyl, phenylpropyl or phenoxyethyl.

The biphenyl or thienyl-phenyl nucleus is the central structural element of the compounds according to the invention. It bridges the residue at the phenyl/thienyl ring A including the terminal carboxyl group with the residue at the phenyl ring B which comprises at least one nitrogen atom of an amino group, amide group, urea group, thioamide group, thiourea group, amidine group, enamine group or guanidine group in its main chain. Preferably, it moreover carries no firther substituents. Each of the two phenyl/thienyl rings, however, can carry additional substituents. Preferably the phenyl/thienyl ring A, i.e. the ring connected directly to the residue including the terminal carboxyl group, carries one or more additional $C_{1-6}$-alkyl residues such as, for example, methyl or ethyl, halogeno residues such as, for example fluoro, chloro, bromo, iodo, preferably one or two fluoro residues, alkoxy residues, preferably a $C_{1-6}$-alkoxy residue such as methoxy, ethoxy, propoxy, butoxy, pentoxy or hexoxy, particularly preferably one or more methoxy residues, and the phenyl ring B, i.e. the ring to which the residue including at least one nitrogen atom of an amino group, amide group, urea group, thioamide group, thiourea group, amidine group , enamine group or guanidine group in its main chain is bonded, carries one or more alkyl residues, preferably a $C_{1-6}$alkyl residue such as methyl, ethyl, propyl, isopropyl, butyl, isobutyl, t-butyl, pentyl, isopentyl, neopentyl, hexyl, a $C_{3-7}$-cycloalkyl residue such as cyclopropyl, cyclobutyl, cyclopentyl, cyclohexyl, and particularly preferably one or more methyl groups. In this case, the rings A and B can independently of one another carry one or more of the abovementioned additional substituents.

The two phenyl rings can be linked 1,3 or 1,4 to one another and to the residue including the terminal carboxyl group and to the residue including at least one nitrogen atom of an amino group, amide group, urea group, thioamide group, thiourea group, amidine group, enamine group or guanidine group in its main chain, i.e. the residue including the terminal carboxyl group and the phenyl ring B can be substituted in the meta- or para-position to one another at the phenyl ring A, and at the same time the phenyl ring A and the residue including at least one nitrogen atom of an amino group, amide group, urea group, thioamide group, thiourea group, amidine group, enamine group or guanidine group in its main chain can be substituted in the meta- or para-position to one another at the phenyl ring B, each combination of the abovementioned substitution patterns being possible for the biphenyl nucleus of the compounds according to the invention. In case A is a thiophene ring it can accordingly be linked 2,5 or 2,4 to ring B and to the residue including to terminal carboxy group. According to the present invention, compounds are particularly preferred whose biphenyl nucleus according to the above definition consists of a p-substituted phenyl ring A and a p-substituted phenyl ring B, a p-substituted phenyl ring A and an m-substituted phenyl ring B, an m-substituted phenyl ring A and a p-substituted phenyl ring B, or an m-substituted phenyl ring A and an m-substituted phenyl ring B. According to the present invention, compounds are particularly preferred whose biphenyl nucleus according to the above definition consists of a p-substituted phenyl ring A and an m-substituted phenyl ring B. According to another particularly preferred embodiment the nucleus consists of a 2,5-substituted thienyl ring A and a m-substituted or p-substituted phenyl ring B.

As a third structural element, in addition to the biphenyl or thienyl-phenyl nucleus and the residue including a terminal carboxyl group, the compounds according to the invention have a group which in its main chain comprises at least one nitrogen atom of an amino group, amide group, urea group, thioamide group, thiourea group, amidine group, enamine group or guanidine group. This nitrogen atom can be bonded to the phenyl ring B of the biphenyl or thienyl-phenyl nucleus directly or via an alkylene chain. This alkylene chain preferably consists of at most 4 carbon atoms in the main chain, wherein from the abovementioned considerations, in addition to the biphenyl nucleus between the terminal carboxyl group and the nitrogen atom of the amino group, amide group, urea group, thioamide group, thiourea group, amidine group, enamine group or guanidine group which is located nearest to the phenyl ring B, not more than 6 further atoms should be present. As preferred example ring B and the nitrogen atom of the amino, amide, urea, thioamide, thiourea, amidine, enamine or guanidine group are connected via a —$CH_2$-group or via a direct bond. Alternatively, this alkylene chain can carry futher substituents which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic residue such as pyrrole, pyrrolidine, pyridine, tetrahydrofuran, furan, thiophene, tetrahydrothiophene, thiooxazole, benzofuran, quinoline, isoquinoline or pyrimidine, or a terminal or internal E- or Z-alkene unit, and can alternatively carry one or more $C_{1-6}$alkyl residues such as methyl, ethyl, propyl, isopropyl, butyl, isobutyl, t-butyl, pentyl, isopentyl, neopentyl or hexyl, cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrole, pyrrolidine, pyridine, tetrahydrofuran, furan, thiophene, tetrahydrothiophene, thiooxazole, benzofuran, quinoline, isoquinoline or pyrimidine, or functional groups such as a double bond to a heteroatom such as oxygen, sulfur or nitrogen, an optionally substituted amino group, a nitro group, a halogeno, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analog thereof.

The nitrogen atom located in the main chain of the residue bonded to the phenyl ring B of the biphenyl or thienyl-phenyl nucleus, which lies nearest to the phenyl ring B, can either be a constituent of an optionally substituted amino group or can be located in direct vicinity to a —C=O unit —$CONR_2$ unit, —C=S unit, —$CSNR_2$ unit, —C=NR unit, —C=$CHNO_2$ unit, C=CHCN unit or a —$CNRNR_2$ unit and can thus be a constituent of an amide group, urea group, thioamide group, thiourea group, amidine group, enamine group or guanidine group.

In the case in which the nitrogen atom. located in the main chain of the residue bonded to the phenyl ring B of the biphenyl nucleus, which lies nearest to the phenyl ring B, is a constituent of an amino group, it can be unsubstituted or can carry one or two substituents, i.e. can be a constituent of a primary, secondary or tertiary amino group. These substituents can be independent of one another or simultaneously hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or can be bonded to one another and thus, together with the nitrogen atom to which they are bonded, form a heterocyclic ring system. In this case, substituents are preferred which are selected from the group consisting of hydrogen, a $C_{1-6}$alkyl such as, for example, methyl, ethyl, propyl, isopropyl, butyl, 1-methylpropyl, isobutyl, t-butyl, pentyl, 2-methylbutyl, isopentyl, neopentyl or hexyl, a $C_{1-4}$-perfluoroalkyl such as, for example $CF_3$, a $C_{3-7}$-cycloalkyl such as, for example, cyclopropyl, cyclopropylmethyl, cyclobutyl, cyclopentyl, cyclohexyl or cycloheptyl, an aryl such as, for ,example, phenyl, benzyl or tolyl, an arylcarbonyl such as for example benzoyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively carry one or more $C_{1-6}$-alkyl residues such as methyl, ethyl, propyl, isopropyl, butyl, isobutyl, t-butyl, pentyl, isopentyl, neopentyl or hexyl, a $C_{1-4}$-perfluoroalkyl such as for example $CF_3$, $C_{3-7}$-cycloalkyl residues such as cyclopropyl, cyclopropylmethyl, cyclobutyl, cyclopentyl, cyclohexyl or cycloheptyl, aryl residues such as phenyl, benzyl, tolyl, naphthyl, indolyl, heterocyclic residues such as pyrrolidine, piperidine, piperazine, pyrrole, pyridine, tetrahydrofuiran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulfur or nitrogen, an optionally substituted amino group, a nitro group, a halogeno, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analog thereof. Particularly preferred substituents are those such as hydrogen, methyl, ethyl, propyl, isopropyl, 1-methylpropyl, butyl, isobutyl, t-butyl, 2-methylbutyl pentyl, isopentyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl, benzoyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl,

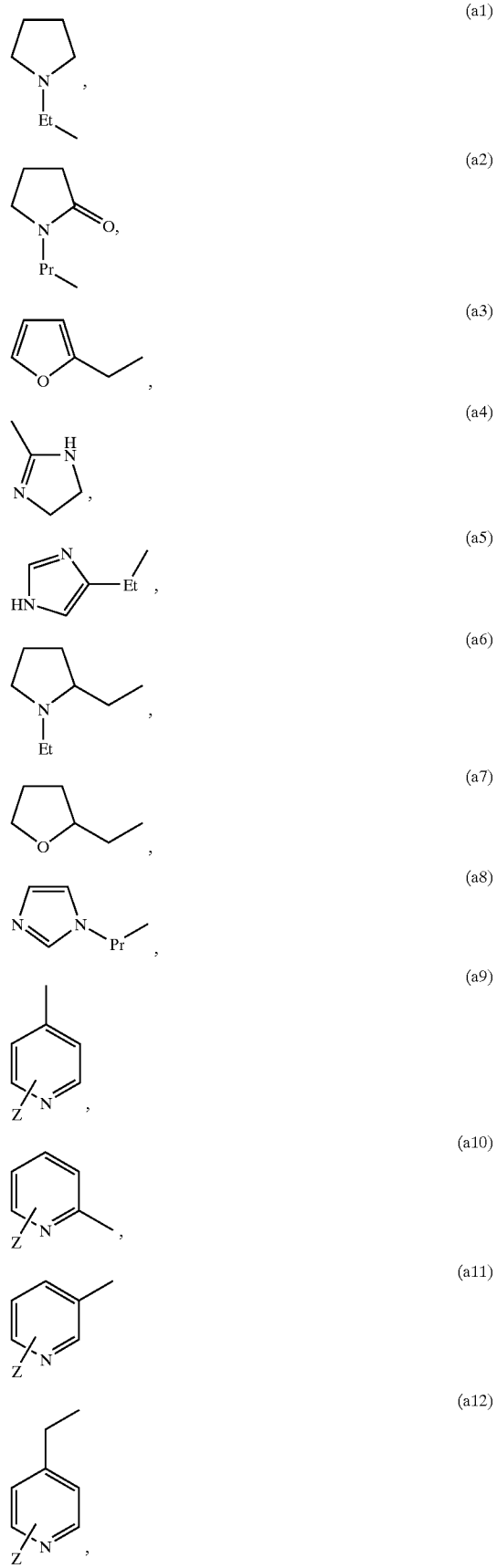

-continued
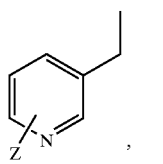 (a13)
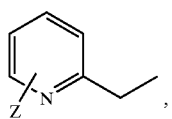 (a14)
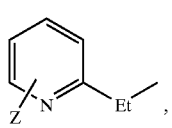 (a15)
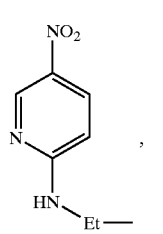 (a16)
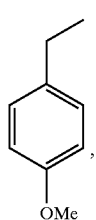 (a17)
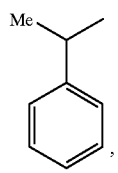 (a18)
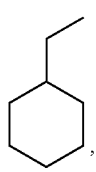 (a19)
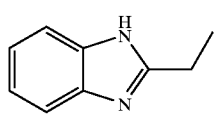 (a20)
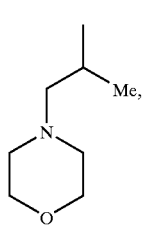 (a21)
-continued
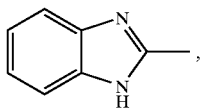 (a22)
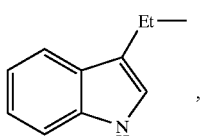 (a23)
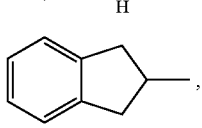 (a24)
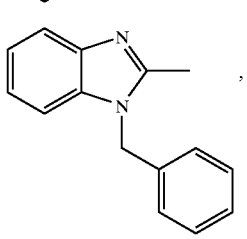 (a25)
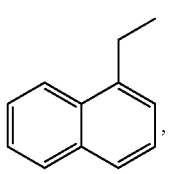 (a26)
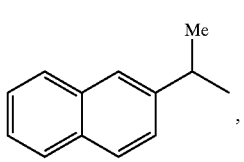 (a27)
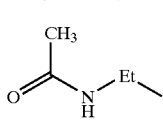 (a28)
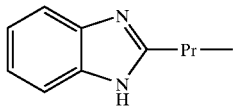 (a29)
 (a30)
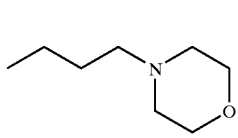 (a31)
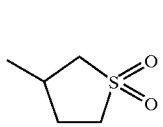 (a32)
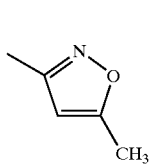 (a33)

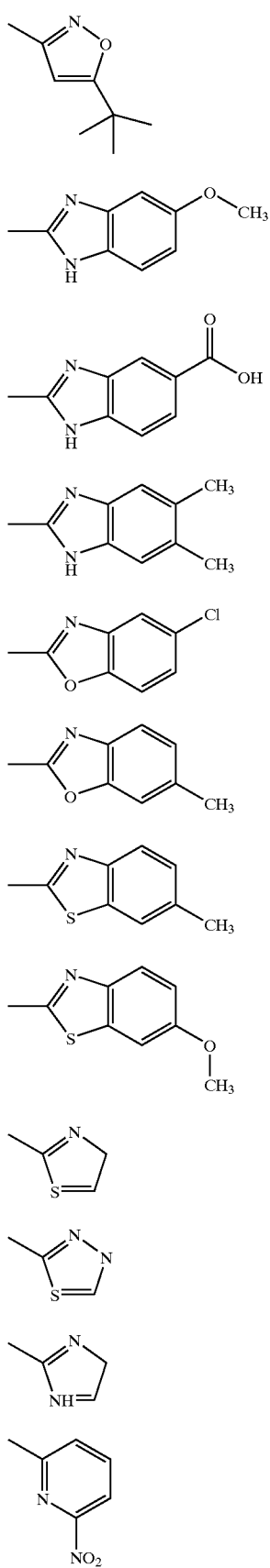
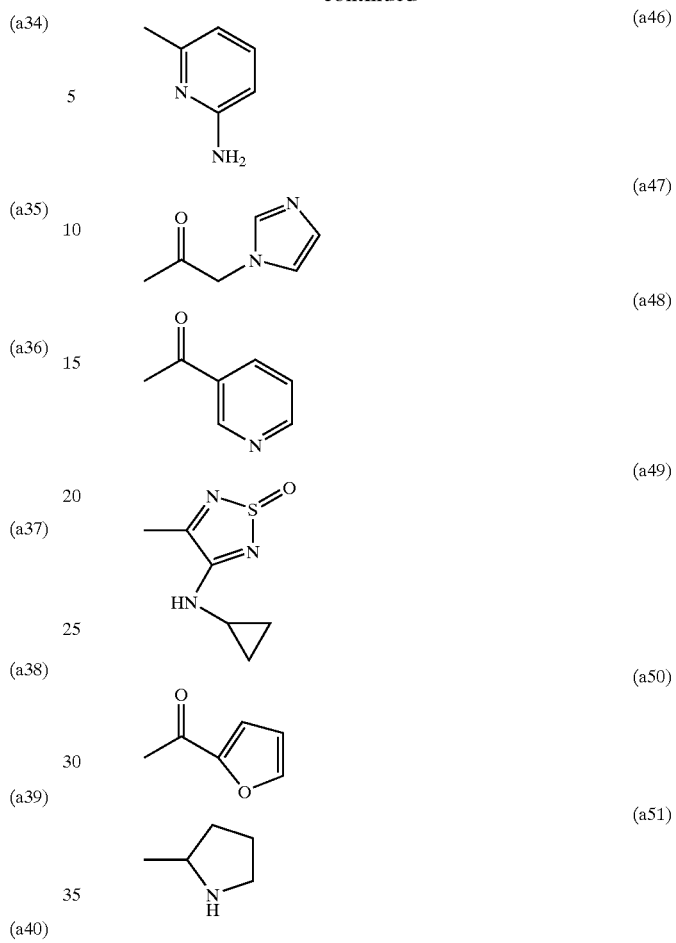

wherein Z is hydrogen, $CH_3$, $-NO_2$ or $-NH_2$.

In the case in which the two substituents at the nitrogen atom which lies nearest to the phenyl ring B are connected to one another and thus form a heterocyclic system with the nitrogen atom, the heterocyclic system formed can be selected, for example, from the following, nonexclusive list:

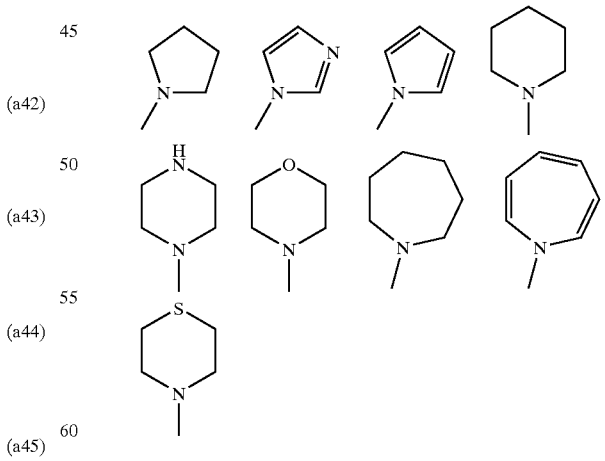

where the ring systems shown can carry one or more residues which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively carry one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuiran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulfur or nitrogen, an optionally substituted amino group, a nitro group, a halogeno, a hydroxyl group, an ether group in particular a C1–6-alkoxy group such as for example, a methoxy gruop, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, indolyl, benzofuranyl, benzoxazolyl, benzothiazolyl, benziridazolyl, quinolinyl or isoquinolinyl unit or a partially or completely hydrogenated analog thereof Of the ring systems shown above, the four- to six-membered ring systems are preferred.

As mentioned above, the nitrogen atom in the main chain of the residue bonded to the phenyl ring B of the biphenyl or thienyl-phenyl nucleus, which lies nearest to the phenyl ring B, can also be a constituent of one of the following preferred functional units:

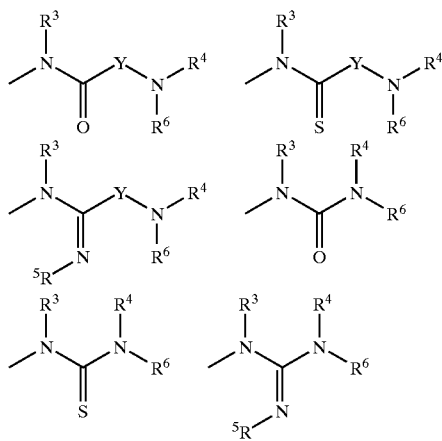

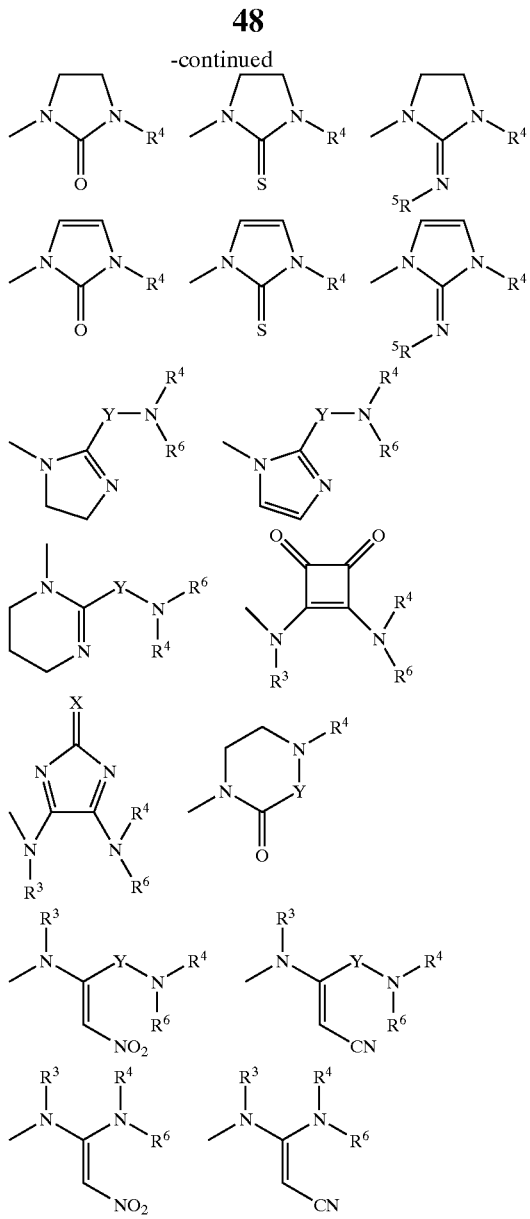

where the above list is not a conclusive enumeration of all possible structural units.

According to the invention, additionally to the abovementioned preferred structural units, analogs thereof are also included in which one or more 4- to 6-membered ring systems are fused to the heterocycle, such as, for example, the corresponding benzo-fused analogs of the above structural units.

In the structural units shown above, $R^3$, $R^4$ and $R^6$ can each be hydrogen, a $C_{1-6}$-alkyl such as, for example, methyl, ethyl, propyl, isopropyl, butyl, 1-methylpropyl, isobutyl, t-butyl, pentyl, 2-methylbutyl, isopentyl, neopentyl or hexyl, a $C_{1-4}$-perfluoroalkyl such as, for example $CF_3$, a $C_{3-7}$-cycloalkyl such as, for example, cyclopropyl, cyclopropylmethyl, cyclobutyl, cyclopentyl or cyclohexyl or cycloheptyl, an aryl such as, for example, phenyl, benzyl or tolyl, a $C_{6-10}$-arylcarbonyl such as, for example, benzoyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrzole, pyrimidine, purine, cytosine, thymine, uracil, adenine, guanine or xanthine, or a terminal or internal E- or Z-alkene unit and can alternatively carry one or more $C_{1-6}$-alkyl residues such as methyl, ethyl, propyl, isopropyl, butyl, isobutyl, t-butyl, pentyl, isopentyl, neopentyl or hexyl, a $C_{1-4}$-perfluoroalkyl such as for example, $CF_3$, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, tlhymine, uracil, adenine, guanine or xanthine, or functional groups such as a double bond to a heteroatom such as oxygen, sulfur or nitrogen, an optionally substituted amino group, a nitro group, a halogeno, a hydroxyl group, an ether group in particular a $C_{1-6}$-alkoxy group such as for example, a methoxy group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Particularly preferred substituents are those such as hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, or one of the abovementioned residues (a1) to (a51).

In the above structural units, $R^4$ and $R^6$, however, can also be bonded to one anqther and can form a heterocyclic ring system with the nitrogen atom to which they are bonded. Examples of these rings which can be mentioned are:

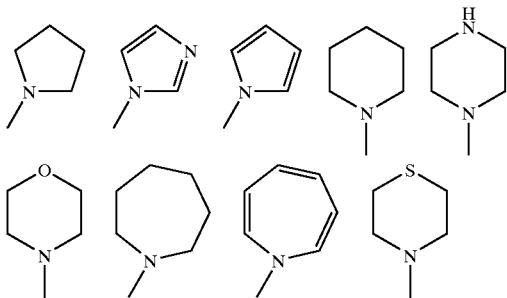

wherein the above enumeration is nonconclusive and the ring systems formed from the connection of $R^4$ and $R^6$ can carry one or more residues which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively carry one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, an aryl residue such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulfur or nitrogen, an optionally substituted amino group, a nitro group, a halogeno, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, indolyl, benzofuranyl, benzoxazolyl, benzothiazolyl, benzimidazolyl, quinolinyl, isoquinolinyl unit or a partially or completely hydrogenated analog thereof. Of the ring systems formed from the connection of $R^4$ and $R^6$, the four- to six-membered ring systems are preferred. According to the invention, compounds wherein at least one of the residues $R^3$, $R^4$ or $R^6$ is H are particularly preferred.

Furthermore, in the above structural units $R^5$ can be hydrogen, a $C_{1-6}$-alkyl residue such as methyl, ethyl, propyl, isopropyl, butyl, isobutyl, t-butyl, pentyl, isopentyl, neopentyl or hexyl, a $C_{3-7}$-cycloalkyl residue such as cyclopropyl, cyclopropylmethyl, cyclobutyl, cyclopentyl or cyclohexyl, —$NO_2$, —CN, —$COR^{5'}$ or —$COOR^{5'}$, wherein $R^{5'}$ can be a substituted or unsubstituted alkyl or cycloalkyl residue, a substituted or unsubstituted aryl residue or a saturated or unsaturated, optionally substituted heterocyclic residue, which can be saturated or unsaturated and/or can contain further heteroatoms, and is preferably a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl, tolyl or a substituted derivative thereof. Moreover, $R^5$ can be connected to one of $R^3$, Y, $R^4$ or $R^6$, if present, with formation of an optionally substituted carbocyclic or heterocyclic 4- to 6-membered ring system which includes the atom X to which $R^5$ is bonded and can be saturated or unsaturated and/or can contain furter heteroatoms.

Furthermore, in the above structural units Y can be absent or can be an alkylene or alkine unit which carries 1 to 5 carbon atoms in its main chain. According to the invention, Y, if present, preferably has a main chain consisting of one carbon atom. Y can moreover carry one or more residues which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively carry one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulfur or nitrogen, an optionally substituted amino group, a nitro group, a halogeno, a hydroxyl group, an ether group, a sulfide group, a mercaptan group, a cyano group, an isonitrile group, an alkenyl group, an alkinyl group, an aldehyde group, a keto group, a carboxyl group, an ester group, an amide group, a sulfoxide group or a sulfone group. Furthermore, one or more saturated or unsaturated additional rings can be fused to the abovementioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analog thereof. Moreover Y can be connected to one of $R^3$, $R^4$, $R^5$ or $R^6$, if present, with formation of an optionally substituted carbocyclic or heterocyclic 4- to 6-membered ring system which can be saturated or unsaturated and/or can contain further hetero atoms.

According to the invention, particularly preferred compounds of the general formula (1) are those in which the nitrogen atom located in the main chain of the residue bonded to the phenyl ring B, which lies nearest to the phenyl ring B, is a constituent of a urea or thiourea unit. In this case, particularly preferred compounds of the general formula (1) are those in which a urea or thiourea unit is bonded directly to the phenyl ring B of the biphenyl nucleus.

Furthermore particularly preferred compounds of the general formula (1) are those in which the nitrogen atom located in the main chain of the residue bonded to the phenyl ring B, which lies nearest to the phenyl ring B is a constituent of an amino group which is bonded via a methylene group to ring B. The amino group can preferably be substituted by one of the residues (a1) to (a5 1).

The present invention comprises both the individual enantiomers or diastereomers and the corresponding racemates, diastereomer mixtures and salts of the compounds defined in claim 1. In addition, all possible tautomeric forms of the compounds described above are also included according to the present invention. The present invention furthermore comprises both the pure E and Z isomers of the compounds of the general formula (1) and their E/Z mixtures in all ratios. The diastereomer mixtures or E/Z mixtures can be separated into the individual isomers by chromatographic procedures. The racemates can be separated into the respective enantiomers by chromatographic procedures on chiral phases or by resolution of racemates.

The compounds described above can be prepared from commercially available starting compounds. The essential steps of the preparation process according to the invention are the reaction of a carboxylic acid, whose carboxyl group is protected and which has at least one aryl or thienyl group provided with a residue accessible to an aryl-aryl coupling reaction, with a phenyl compound having at least one residue accessible to an aryl-aryl coupling reaction, which furthermore has a residue D which is an amino group or can be converted into an amino group in a simple manner, and the conversion of the residue D into the corresponding amino group if it is not already an amino group. The derivatization of nitrogen atoms present in the molecule at preferred times within the preparation process and/or the conversion of the compound obtained into the free acid and/or the conversion of the compound obtained into one of its physiologically acceptable salts by reaction with an inorganic or organic acid or base can be included as further process steps.

The carboxylic acids to be employed as starting compounds are either commercially available or are easily accessible by standard chemical processes, such as are known to any person skilled in the art and are described in standard textbooks such as Houben-Weyl, Methoden der organischen Chemie [Methods of Organic Chemistry], Georg Thieme-Verlag, Stuttgart.

According to a preferred embodiment, starting materials used in the process according to the invention for the preparation of compounds of the general formula (1) are the following carboxylic acid derivatives:

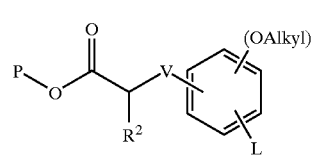

(2a)

Analogously for the thienyl-phenyl compounds, the corresponding thienyl-derivative ist used.

For the preparation process according to the invention, the carboxyl group is in this case blocked by a conventional protective group P. Protective groups of this type are known to the person skilled in the art and do not have to be expressly mentioned here. The carboxyl group is particularly preferably esterified, P being a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof. The preparation process according to the invention for the compounds of the general formula (1) can be carried out on a solid phase in order to achieve a process implementation which is as economical as possible. In this case, the carboxyl residue can be bonded to any solid phase conventionally used for reactions of this type. According to the invention, the solid phase used is particularly preferably a polystyrene resin and in particular a commercially available Wang polystyrene resin. According to the present preferred embodiment, $R^2$ can be as described above and V can be an optionally substituted $C_{1-5}$-alkylene group.

Thus the starting compounds of this preferred embodiment can be interpreted as derivatives of propanoic acid, butanoic acid, pentanoic acid, hexanoic acid or heptanoic acid. In the α-position to the carboxyl group, these carboxylic acid derivatives can have a substituent such as, for example, hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl, tolyl or a substituted derivative thereof, an optionally substituted alkenyl residue, an optionally substituted alkinyl residue, $—NR^{2'}SO_2R^{2''}$, $—NR^{2'}COOR^{2''}$, $—NR^{2'}COR^{2'}$, $—NR^{2'}CONR^{2''}{}_2$ or $—NR^{2'}CSNR^{2''}{}_2$. The alkyl and cycloalkyl residues and the benzyl residue can be introduced by reaction of the ester of the starting compounds with the appropriate alkyl, cycloalkyl or benzyl halides in basic medium, if the corresponding derivatives are not commercially available. The alkinyl residue can be introduced, for example, by reaction of the α-bromo ester of the present starting compound with an appropriate acetylide anion. In the case of the phenyl residue, of the alkenyl residue and of the nitrogen-containing substituents, the starting materials used are preferably the corresponding α-phenyl- or α-amino-carboxylic acid derivatives and, if necessary, the other substituents at the α-C atom to the terminal carboxyl group are introduced via the appropriate alkyl halide. The above reactions and their implementation are well known to the person skilled in the art and are described in detail in standard textbooks such as, for example, Houben-Weyl, Methoden der organischen Chemie [Methods of Organic Chemistry], Georg Thieme Verlag, Stuttgart.

For the introduction of a substituent into the β-position relative to the carboxyl group, the possibility that suggests itself, for example, is to start from the corresponding α,β-unsaturated carboxylic acid derivatives and to react these with the respective alkyl or cycloalkyl cuprates in the sense of a Michael addition. β-substituted derivatives are also accesible via the condensation of a derivative of malonic acid with an aldehyde or a keton. Subsequently, if desired, another substituent can be introduced into the α-position relative to the carboxyl group as described above. These reactions and their implementation are also well known to the person skilled in the art and are described in detail in standard textbooks such as, for example, Houben-Weyl, Methoden der organischen Chemie [Methods of Organic Chemistry], Georg Thieme Verlag, Stuttgart.

The residues $—NR^{2'}SO_2R^{2''}$, $—NR^{2'}COOR^{2'}$, $—NR^{2'}COR^{2'}$, $—NR^{2'}CONR^{2''}{}_2$ or $—NR^{2'}CSNR^{2''}{}_2$ preferably found in the α- or β-position relative to the carboxyl group are preferably prepared from the respective α- or β-amino acid. The α-amino acids used according to the invention are commercially available, for example, from Novabiochem or Bachem. The β-amino acids can in some cases likewise be obtained from these companies or can be prepared according to the procedures of T. B. Johnson, Journal of the American Chemical Society, 1936, 58, or of V. A. Soloshonok, Tetrahedron Assymetry, 1995, 1601. These amino acids can be converted into the desired carboxyl-protected amino acid derivative, for example, by protection of the amino group, subsequent protection of the carboxylic acid unit and subsequent deprotection of the amino group. Protective groups which can be used in this case for the amino group are all groups known for this purpose. According to the invention, the use of a 9-fluorenylmethoxycarbonyl group (FMOC) as a protective group for the amino unit is particularly preferred. The carboxylic acid group is protected or derivatized as described above. The carboxyl-protected α- or β-amino acids thus accessible are reacted with a suitable sulfonating, carbamoylating or acylating reagent in order to obtain the corresponding sulfonamide, carbamate or amide derivatives. The sulfonating reagent is preferably a sulfonyl chloride of the formula $R^{2''}—SO_2Cl$ or a chloroformiate of the formula $R^{2'}—OCOCl$, wherein $R^{2'}$ is preferably selected from the group which consists of hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, phenyl, benzyl, tolyl or a substituted derivative thereof as, for example, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, 4-trifluoromethyl phenyl, while $R^2$ is a $C_{1-10}$-alkyl such as methyl, ethyl, propyl, isopropyl, butyl, isobutyl, t-butyl, pentyl, isopentyl, neopentyl, hexyl, heptyl, octyl, nonyl, decyl, cyclopropyl, cyclobutyl, cyclopentyl, cyclohexyl or campher-10-yl, an aryl such as phenyl, benzyl, tolyl, mesityl or substituted derivatives of these such as 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, or a heterocyclic analog of the abovementioned cyclic residues. Particularly preferably, $R^{2''}$ is a mesityl residue, a benzyl residue, a 2-chlorophenyl residue, a 4-chlorophenyl residue, a 2,5-dichlorophenyl residue, a 2,6-dichlorophenyl residue, a 4-trifluoromethylphenyl residue, a campher-10-yl residue or a group of the formula

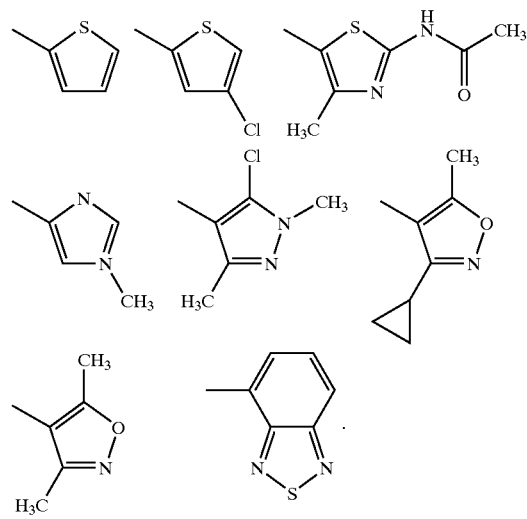

Instead of the abovementioned sulfonyl or carbamoyl chlorides, the corresponding fluorides, bromides or iodides can also be employed. As an acylating reagent, the appropriate carboxylic acid halides or carboxylic acid anhydrides are reacted with the amino group, the appropriate $C_{1-6}$-alkyl- such as methyl-, ethyl-, propyl-, isopropyl-, butyl-, isobutyl-, t-butyl-, pentyl-, isopentyl-, neopentyl-, hexyl-, $C_{3-7}$-cycloalkyl- such as cyclopropyl-, cyclobutyl-, cyclopentyl-, cyclohexyl-, aryl- such as phenyl-, benzyl- or tolylcarboxylic acid chlorides or substituted derivatives thereof being preferred according to the invention. For the preparation of the urea or thiourea residues, the amino group is preferably first reacted with a carbonic acid or thiocarbonic acid derivative such as a chloroformnic acid ester or thiophosgene and then with a suitable amine $NHR^{2'}_2$. The above reactions and their implementation are well known to the person skilled in the art and are described in detail in standard textbooks such as, for example, Houben-Weyl, Methoden der organischen Chemie [Methods of Organic Chemistry], Georg Thieme Verlag, Stuttgart.

The starting compounds to be employed according to the above preferred embodiment have a terminal phenyl unit which must carry at least one substituent L. This substituent L must be substitutable by another phenyl group by means of one of the known aryl-aryl coupling procedures. According to the present invention, L can be —H, —F, —Cl, —Br, —I, —SCN, —$N_2^+$ or an organometalllic residue. Preferred organometallic residues which may be mentioned are, for example, a magnesium, copper, boron, tin, lithium or lithium cuprate residue.

Additionally to the residues V and L, the terminal phenyl unit can have one or more further substituents, preferably one or more alkoxy residues, particularly preferably one or more methoxy residues.

If the corresponding starting compounds are not commercially available, the terminal phenyl unit can be connected to the appropriate carboxylic acid derivative by standard processes such as, for example, a Friedel-Crafts alkylation, Friedel-Crafts acylation or by organometallic synthesis procedures such as, for example, a palladium-assisted coupling, after which, if appropriate, further derivatization steps follow which are known to the person skilled in the art and described in detail in standard textbooks such as, for example, Houben-Weyl, Methoden der organischen Chemie [Methods of Organic Chemistry], Georg Thieme Verlag, Stuttgart.

The terminal phenyl unit can be 1,3- or 1,4-substituted with respect to the residues V and L. Each of these isomers, if not commercially available, is accessible in a manner known to the person skilled in the art.

According to a further preferred embodiment, starting materials used in the process according to the invention for the preparation of compounds of the general formula (1) are the following carboxylic acid derivatives:

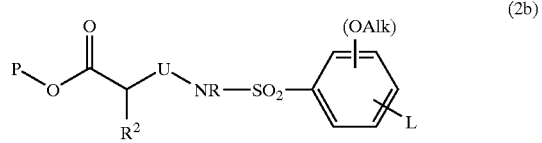

(2b)

For the preparation of the thienyl-phenyl-compounds the corresponding thienyl-derivatives are used as stating materials.

In this case, P and $R^2$ are as described above and can be introduced in the manner explained above if they are not already contained in the commercial starting compound. U represents an optionally substituted alkylene group and preferably an optionally substituted $C_{1-3}$-alkylene group.

With respect to the possible substituents at U, reference is made to the above explanations for the compounds according to the invention.

For example, in the case in which U is an optionally substituted methylene group, the optionally additionally substituted 3-aminopropanoic acid is used as a starting material for the preparation of the compound shown above and this is reacted with an arylsulfonyl halide, preferably an arylsulfonyl chloride. The arylsulfonyl chloride is selected in accordance with the desired presence and position of the residues L and OAlk, L having the same meaning as described above and OAlk representing one or more alkoxy residues, preferably one or more methoxy residues. The arylsulfonyl halides preferred according to the invention are commercially available or can be prepared by standard reactions familiar to the person skilled in the art. The above reactions and their implementation are well known to the person skilled in the art and are described in detail in standard textbooks such as, for example, Houben-Weyl, Methoden der organischen Chemie [Methods of Organic Chemistry], Georg Thieme Verlag, Stuttgart.

In all embodiments according to the invention, the biphenyl or thienyl-phenyl nucleus is generated by means of an aryl-aryl coupling. Formally, in this case the residue L at the terminal phenyl/thienyl group of the carboxylic acid derivative serving as a starting compound is replaced by a phenyl compound of the following formula

 (3)

wherein

M is —H, —I, —$N_2^+$, —COOCOBNO$_2$ or an organometallic residue;

B is a phenylene group which is 1,3- or 1,4-substituted with respect to M and W—D and optionally has additional residues;

W is as defined in claim 1;

D is —$NO_2$, —$NH_2$ or —CHO;

Possible coupling reactions are, for example, the reaction of two unsubstituted phenyl groups (i.e. L and M are hydrogen) in the presence of $AlCl_3$ and an acid (Scholl reaction), the coupling of the two phenyl iodides in the presence of copper (Ullmann reaction), the reaction of the unsubstituted carboxylic acid derivative with a phenyldiazonium compound under basic conditions (Gomberg-Bachmann reaction) or coupling with participation of organometallic reagents. In this connection, the coupling of two phenyl Grignard compounds in the presence of thallium bromide, the coupling of two organoboron compounds in the presence of silver nitrate and sodium hydroxide, the reaction of a diphenyllithium cuprate in the presence of oxygen and palladium-assisted couplings of a phenyl halide with an organometallic phenyl compound deserve mention. The implementation of these reactions is described in detail in standard textbooks such as Houben-Weyl, Methoden der organischen Chemie [Methods of Organic Chemistry], Georg Thieme Verlag, Stuttgart. The choice of the coupling reaction depends on the presence of possibly interfering or sensitive substituents in the reactants. For the preferred compounds according to the invention, however, it has proven particularly advantageous to generate the biphenyl nucleus by coupling of a phenyl halide with an organometallic phenyl compound in the presence of a palladium compound, for example a Pd(0), a Pd(II) or a Pd(IV) compound, and of a phosphane such as triphenylphosphane.

The thienyl-phenyl compounds can be prepared in analogous manner according to the methods described above.

The phenyl/thienyl halide used in this case can be the corresponding phenyl/thienyl fluoride, chloride, bromide or iodide, the corresponding bromide being particularly preferred. The organometallic phenyl compound used is preferably a substance in which a metallic element such as, for example, zinc, magnesium, boron, lithium, copper, tin or another element conventionally used for this purpose is bonded directly to the aryl ring. According to the invention, organoboron compounds are particularly preferred. Further substituents can be bonded to the aryl ring additionally to the residue —W—D and the metallic element. Preferably, these substituents are one or more alkyl residues, preferably a $C_{1-6}$-alkyl residue such as methyl, ethyl, propyl, isopropyl, butyl, isobutyl, t-butyl, pentyl, isopentyl, neopentyl, hexyl, a $C_{3-7}$-cycloalkyl residue such as cyclopropyl, cyclobutyl, cyclopentyl, cyclohexyl, and particularly preferably one or more methyl groups. If W is present, i.e. the residue D is bonded to the phenyl ring B via an optionally substituted alkylene group, the length of the main chain of this alkylene group must be selected for reasons described above such that no more than 6 atoms additionally to the biphenyl or thienyl-phenyl nucleus are present in the resulting compound of the formula (4) between the terminal carboxyl unit and the residue D.

Particularly preferred aryl reagents according to the invention are 3-nitrobenzeneboronic acid, 3-formylbenzeneboronic acid or 3-aminobenzeneboronic acid.

The residue D thus introduced into the compound, if it is not already an amino group, is converted into an amino group. In the case in which D is a nitro group, this is reduced to the corresponding amino group by conventional reductants such as, for example, tin chloride. In the case in which D is an aldehyde group, the conversion into the amino group is carried out by reaction with an amine under reducing conditions, for example in the presence of an ortho ester and of a reductant such as a metal hydride, for example a boron hydride. The amino group thus formed can subsequently be derivatized, for example by reaction with, for example, alkyl or cycloalkyl halides. With respect to the preferred substituents on the nitrogen atom which can be introduced in this way, reference is made to the above description of the compounds according to the invention.

The amines can be converted into the squaric acid monoamides which in turn can be functionalised to the corresponding squaric acid diamides by treating with amines. The amines can further be converted into the 1,1-diaminonitroethylenes by treatment with an appropriate alkylating agent, preferrabyl 1,1-dithiomethyl-2-nitroethylene and subsequent conversion with another amine. The amines can further be converted into the 2,3-diaminothiadiazoles by treatment with an appropriate alkylating agent, preferrabyl 3,4-bismethythio-1,2,5 thiadiazole-1oxide and subsequent conversion with another amine. Finally the amines can be transformed into the diaminocyanoguanidines by treatment with an appropriate alkylating agent, preferrably cyanimidodithiocarbonate dimethyl ester and subsequent conversion with another amine The thioureas can be converted to heterocycles such as benzimidazoles by cyclisation of a suited thiourea with a desulflrizing agent such as HgO. Thiazoles can be generated by alkylation with suitable alkylating agents preferrably 1,2-dichloroethylethylether, or 2-chloro-1,1-bisethoxyethane. The imidazoles can be obtained from the thioureas by alkylating with methyl iodide, followed by treatment with 1,1-diethoxy-2aminoethane and subsequent acid-mediated ring closure.

According to a preferred embodiment of the present invention, the synthesis of the compounds according to the invention is carried out on a solid phase such as a polystyrene resin, particularly preferably, a commercially available Wang polystyrene resin. In this case, the resin is first swollen in a solvent such as dimethylformamide (D)MF). The carboxylic acid serving as a starting compound is then bonded to the resin by standard procedures. For example, the bonding of the carboxylic acid to the resin can be carried out in the presence of a base such as pyridine and a reagent activating the carboxyl unit, such as an acid halide, for example dichlorobenzoyl chloride, in a solvent such as dimethylformamide (DMF). However, other reagents conventionally used for this purpose can also be employed. The reaction mixture is stirred at room temperature and normal pressure for at least 2 hours, preferably 12 hours, particularly preferably approximately 24 hours, the carboxylic acid being employed in an excess, preferably in a two- to three-fold excess, with respect to the, loading of the solid phase.

After removal of possibly unreacted reagents, if desired, a derivatization of the carboxylic acid bonded to the resin can be carried out without this needing to be separated from the resin beforehand. According to a preferred embodiment according to the invention, an amino acid whose amino group is protected is bonded to the solid phase, for example as described above, and after liberation of the amino group a substituent is then introduced onto the latter. Preferably, the amino group is sulfonylated or carbamoylated. For this purpose, the amino acid bonded to the solid phase is treated with an excess of a solution of the appropriate sulfonylating or carbamoylating agent, preferably a two- to four-fold excess, particularly preferably an approximately three-fold excess, in a solvent such as, for example, tetrahydrofuran (THF) in the presence of an auxiliary base such as diisopropylethylamine and the reaction mixture is stirred at room temperature and normal pressure for at least 2 hours, preferably 12 hours, particularly preferably approximately 24 hours. The sulfonamide or carbamate obtained does not have to be removed from the resin, but can be immediately reacted further after removal of unreacted reactants which may possibly be present.

The aryl-aryl coupling is preferably carried out according to the invention by treating the carboxylic acid bonded to the solid, phase, which is optionally derivatized, for example sulfonylated or carbamoylated as described above, in aqueous medium in the presence of a base such as sodium carbonate with the appropriate aryl coupling reagent of the formula (3) and a catalyst conventionally used for this purpose, for example a palladium(II) salt, preferably bis-(triphenylphosphane)-palladium(II) chloride in combination with triphenylphosphane. An approximately 3- to 8-fold, preferably an approximately 4- to 6-fold, excess of the aryl coupling agent, which according to the invention is in particular 3-nitrobenzeneboronic acid, 3-formylbenzeneboronic acid or 3-aminobenzenboronic acid, and catalytically active amounts of the palladium compound, for example approximately 10 times lower than the amount of the carboxylic acid, is preferably employed in this case and, after stirring briefly at room temperature, for example for 5 to 10 minutes, the reaction mixture is heated for approximately 2–24 hours, preferably 6–24 hours and particularly preferably 12–24 hours, to a temperature in the range from 40 to 110° C., preferably 50 to 100° C. and particularly preferably 60 to 90° C. The biphenyl compound obtained can immediately be reacted further without purification after unreacted reactants which may be present are removed by washing with an acidic solution, for example a hydrochloric acid solution.

If the residue D is a nitro group, its conversion into an amino group is preferably carried out according to the invention by addition of a customary reductant such as tin(II) chloride to the intermediate bonded to the solid phase and obtained as above, if appropriate in the presence of solvents such as N-methylpyrrolidone (NMP), by stirring the reaction mixture at room temperature and normal pressure for at least 2 hours, preferably 12 hours, particularly preferably approximately 24 hours.

If the residue D is an aldehyde group, its conversion into an amino group is carried out by reductive amination. For this purpose, the intermediate bonded to the solid phase and obtained as above is treated with an approximately 3- to 6-fold, preferably approximately 4- to 5-fold, excess of an amine, optionally in the presence of diisopropylethylamine, and of an approximately 6- to 10-fold excess of ortho ester. After stirring at room temperature for several hours, preferably 1 to 3 hours, an approximately 3- to 6-fold, preferably 4- to 5-fold, excess of an acetic acid solution of a metal hydride such as, for example, tetrabutylammonium borohydride is added to the reaction mixture and it is stirred again for several hours, preferably 12–24 hours, at room temperature.

The product obtained above can optionally be reacted further by derivatization of the residue D of the compound of the formula (4) representing an amino group or an introduction of further substituents onto nitrogen atoms present in the molecule or directly removed from the resin. Removal from the resin is carried out in a conventional manner in acidic medium. After removal of solvent which may be present, the product separated off from the resin can be purified by known purification procedures such as, for example, chromatographic procedures.

The residue D of the compound of the formula (4) representing an amino group can furthermore be converted into an amide group, urea group, thioamide group, thiourea group, amidine group, enamine group or guanidine group. These structural units can be prepared by the standard reactions familiar to the person skilled in the art, such as are described, for example, in Houben-Weyl, Methoden der organischen Chemie [Methods of Organic Chemistry], Georg Thieme Verlag, Stuttgart.

It is particularly preferred according to the invention to convert the residue D of the compound of the formula (4) representing an amino group into a urea or thiourea unit. For this purpose, the above amino group of the carboxylic acid bonded to the solid phase is first preferably reacted with a 2- to 5-fold, preferably 3- to 4-fold, excess of a carbonic acid ester or thiocarbonic acid ester derivative in an inert solvent such as tetrahydrofuran (THF), dichloromethane or a mixture of the two (preferably a 1:1 mixture) at room temperature and with stirring for approximately 1 hour, preferably approximately 45 minutes. The carbonic acid ester or thiocarbonic acid ester derivative employed is preferably phosgene, triphosgene, thiophosgene or chloroformic acid esters, commercially obtainable chloroformic acid esters being preferred for the preparation of the urea derivatives and thiophosgene for, the preparation of the thiourea derivatives.

The carbamates or isothiocyanates formed in this way are convertible into the corresponding urea and thiourea derivatives by reaction with suitable amines. Amines which can be used are substances of the formula HNRR', wherein R and R' independently of one another or simultaneously are hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or are connected to one another and together with the nitrogen atom can form an optionally substituted heterocyclic ring system which can be saturated or unsaturated and/or can contain further heteroatoms. With respect to the preferred residues at the amine, reference is made to the above description of the compounds according to the invention. According to the invention, the carbamate or isothiocyanate bonded to a solid phase is preferably reacted with a distinct excess of amine, preferably a 3- to 10-fold excess and particularly preferably a 5- to 10-fold excess, at room temperature with stirring for approximately 1 to 5 hours, preferably aproximately 2 to 3 hours, in the presence of an auxiliary base such as diisopropylethylamine in an inert solvent such as dimethylformamide (DMF).

According to another preferred embodiment of the present invention, the synthesis of the compounds according to the invention is carried out with a commercially available amino functionalized ester serving as a protected carboxylic starting compound. Preferably, the amino group is sulfonylated or carbamoylated. For this purpose, the amino ester and the appropriate sulfonylating or carbamoylating agent are dissolved in a solvent such as, for example, dichloromethane and an auxilliary base such as pyridine or triethylamin is added at 0° C. The mixture is stirred at 0° C. for 1 hour and then at room temperature overnight. The reaction mixture is washed with an aqueous acid such as, for example, aq 1N HCl, brine and water and dried. The concentrated organic solutions are recrystallized in a solvent such as, for example, acetic acid ethyl ester/petroleum ether or if necessary are purified by chromatography over silica, using cyclohexane/ ethyl acetate as the solvent.

The aryl-aryl coupling is preferably carried out according to the invention by treating the ester, wich is optionally derivatized, for example sulfonylated or carbamoylated as described above, in an appropriate solvent such as, for example, 1,2 dimethoxyethane in the present of a base such as aqueous sodium carbonate with the appropriate aryl coupling reagent of the formula (3) such as, for example, 3-aminobenzeneboronic acid or 3-formylbenzeneboronic acid and a catalyst conventionally used for this purpose, for example a palladium(II) salt, preferably bis (triphenylphosphane)-palladium(II) chloride. The mixture is heated to reflux for 3 hours and then cooled to room temperature. After dilution with ethyl acetate, the mixture is successiveley washed with 5% aqueous sodium dihydrogenphosphate, water and brine and dried. After removal of the solvent the crude product is purified over silica, using cyclohexane/ethyl acetate as the solvent.

If the residue D is an aldehyde group, its conversion into an amino group is carried out by reductive amination. For this purpose, the intermediate obtained as above is treated with an amine in the presence of acetic acid and methanol. After stirring at room temperature for 5 hours a metal hydride such as, for example, sodium cyanoborohydride is added. The mixture is stirred overnight and then treated with aqueous 2M hydrochloric acid. After removal of most of the solvent the residue is neutralized with 2M aqueous sodium hydroxide and extracted with ethyl acetate. The organic layer is washed with brine and dried. The solvent is removed and the crude product is purified over silica with dichloromethane/ethyl acetate as the solvent.

According to another preferred embodiment of the present invention the residue D of the compound of the formula (4) representing an amino group is converted into the squaric acid monoamide which in turn can be functionalised to the corresponding squaric acid diamides by treating with amines. The amino group can further be converted into the 1,1-diaminonitroethylenes by treatment with an appropriate alkylating agent, preferrabyl 1,1-dithiomethyl-2-nitroethylene and subsequent conversion with another amine. The amino group can further be converted into the 2,3-diaminothiadiazoles by treatment with an appropriate alkylating agent, preferrabyl 3,4-bismethythio-1,2,5-thiadiazole-1-oxide and subsequent conversion with another amine. The amino group can be transformed into the diaminocyanoguanidines by treatment with an appropriate alkylating agent, preferably cyanimidodithiocarbonate dimethyl ester and subsequent conversion with another amine. The thioureas can be converted into heterocycles such as benzimidazoles by cyclisation of a suited thiourea with a desulfurizing agent such as HgO. Thiazoles can be generated by alkylation with suitable alkylating agents preferrably 1,2-dichloroethylethylether, or 2-chloro-1,1-bisethoxyethane. The imidazoles can be obtained from the thioureas by alkylating with iodomethane, followed by treatment with 1,1-diethoxy-2-aminoethane and subsequent acid mediated ring closure.

The compounds obtained according to the procedures explained above can furthermore be derivatized by continuing substitution of nitrogen atoms present at preferred positions in the preparation procedure and/or conversion of the compound obtained into the free acid and/or its physiologically acceptable salts. Suitable alkylating agents in this step are reagents conventionally used for this purpose, with which, for example, a substituted or unsubstituted alkyl or cycloalkyl residue, a substituted or unsubstituted aryl residue or a saturated or unsaturated, optionally substituted heterocyclic residue can be bonded to the appropriate nitrogen atom. With respect to the substituents preferably bonded to the respective nitrogen atoms, reference is made to the above description of the compounds according to the invention. The above reactions and their implementation are well known to the person skilled in the art and are described in detail in standard textbooks such as, for example, Houben-Weyl, Methoden der organischen Chemie [Methods of Organic Chemistry], Georg Thieme Verlag, Stuttgart.

The ester derivatives according to the invention can be converted into the corresponding free carboxylic acids in a conventional manner, such as, for example, by basic hydrolysis with a solution of aqueous sodium hydroxide or lithium hydroxide in tetrahydrofuran (THF) or dimethoxyethane and following acidification with acetic acid or aqueous HCl.

If desired, the compounds according to the invention can be converted into their physiologically acceptable salts. This can be carried out either by reaction with an organic or inorganic base such as, for example, an alkali metal hydroxide or alkaline earth metal hydroxide such as KOH, NaOH, LiOH, $Mg(OH)_2$ or $Ca(OH)_2$, by means of which the terminal carboxyl group is deprotonated and the corresponding carboxylate is formed, or by reaction with an organic or inorganic acid such as, for example, hydrochloric acid, sulfuric acid, phosphoric acid, mandelic acid, oleic acid, linoleic acid or p-toluenesulfonic acid, by means of which one or more of the nitrogen atoms present are protonated.

The steps of the preparation process according to the invention described above can be carried out in a normal atmosphere, i.e. in air, and without the use of absolute, i.e. essentially anhydrous, solvents.

The compounds according to the invention exhibit a very good antagonistic action against integrin receptors, in particular the $\alpha_v\beta_3$ receptor or the $\alpha_v\beta_5$ receptor. This makes them suitable for use in pharmaceutical compositions, in particular for the treatment and prophylaxis of arteriosclerosis, restenosis, osteolytic disorders such as osteoporosis, cancer and ophthalmic diseases. Furthermore they are suitable for the reduction and inhibition of angiogenesis and consequently they are suitable for the prophylaxis and treatment of conditions and diseases such as cancer or rheumatoid arthritis.

The compounds according to the invention can be used as active compound components for the production of pharmaceutical compositions against the abovementioned diseases. For this purpose, they can be converted into the customary formulations such as tablets, coated tablets, aerosols, pills, granules, syrups, emulsions, suspensions and solutions using inert, nontoxic, pharmaceutically suitable excipients or solvents. Preferably, the compounds according to the invention are in this case used in such an amount that their concentration in the total mixture is approximately 0.5 to approximately 90% by weight, the concentration being dependent, inter alia, on the corresponding indication of the pharmaceutical composition.

The abovementioned formulations are prepared, for example, by extending the active compounds with solvents and/or excipients having the above properties, where, if appropriate, emulsifier or dispersant and, in the case of water as a solvent, alternatively an organic solvent additionally has to be added.

The pharmaceutical compositions according to the invention can be administered in a customary manner.

The present invention is illustrated below by means of nonrestrictive examples and comparison examples.

EXAMPLES

In the examples below, all quantitative data, if not stated otherwise, relate to percentages by weight.

All retention times are indicated in minutes and were determined by high-performance liquid chromatography (HPLC) on an RP column (Eurospher 100, C18, ID 4 mm) by means of UV absorption. An eluent mixture of 0.1% strength acetonitrile/water was used with the following method: 0 min=10% acetonitrile, 13 min=80% acetonitrile, 15 min=80% acetonitrile, 17 min=10% acetonitrile.

The mass determinations were carried out by high-performance liquid chromatography-mass spectrometry (HPLC-MS) using the electron spray ionization (ESI) method.

Example 1

General synthesis scheme for method 1:

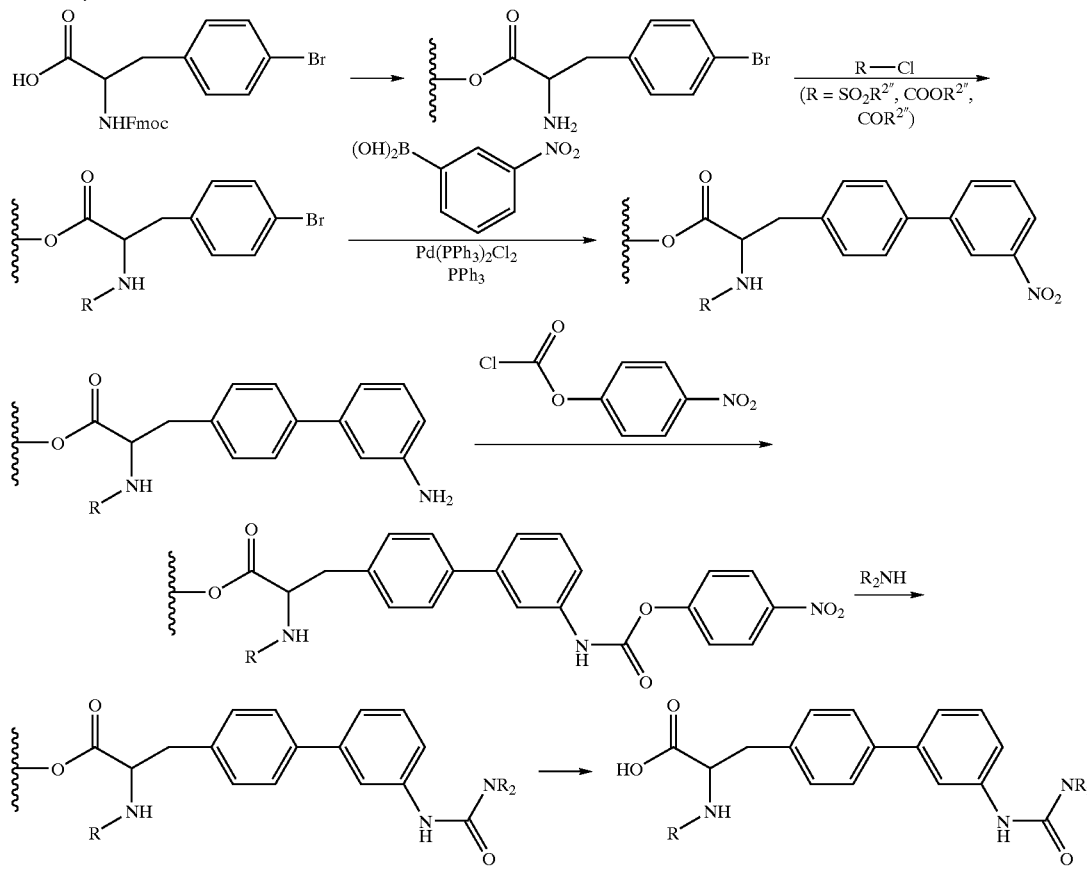

Example 1.1

(2R,S)-3-[3'-(3-Propylureido)-biphenyl-4-yl]-2-[2,4,6-trimethylbenzenesulfonylamino]-propanoic acid

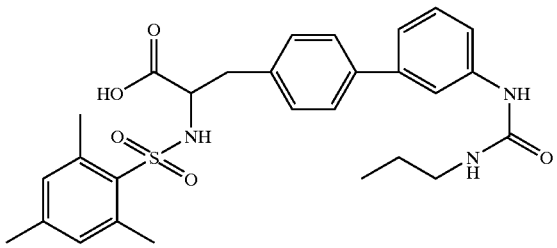

1.2 g of Wang polystyrene resin (Rapp-Polymere, Tuibingen; loading 1.08 mmol/g) are swollen in dimethylformamide (DMF). The solvent is filtered off with suction and a solution of 1.088 g of (2R,S)-3-(4-bromophenyl)-2-(9-fluorenylmethoxycarbonylamino)-propanoic acid (acid reagent) in 20 ml of dimethylformamide (DMF) is added. After shaking at room temperature for 15 minutes, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% piperidine solution in dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 1.2 ml of diisopropylethylamine in 10 ml of tetrahydrofliran (THF) and a solution of 1.53 g of 2,4,6-trimethylbenzenesulfonyl chloride (sulfonylating reagent) in 10 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid (boronic acid reagent) and a solution of 1.37 g of sodium carbonate in 6 ml of water and shaken for 5 min at room temperature. 227 mg of bis(triphenylphosphane)-palladium(II) chloride and 170 mg of triphenylphosphane are then added and the mixture is stirred overnight at 85° C. The resin is then washed with tetrahydrofuran (THF)/water 1:1, 0.25M aqueous hydrochloric acid, water, dimethylformamid (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is then treated with a solution of 564 µl of diisopropylethylamine in 13 ml of tetrahydrofuran (THF)/dichloromethane (1:1) and a solution of 3.13 g of 4-nitrophenylchloroformic acid ester in 13 ml of tetrahydrofuran (THF)/dichloromethane 1:1. After shaking at room temperature for 45 min, it is washed with tetrahydrofuran (THF) and dimethylformamide (DMF) and a solution of 1.07 g of propylamine (amine reagent) and 3.16 ml of diisopropylethylamine in 23 ml of dimethylformamide (DMF) is added. After shaking for 2 h, the resin is washed with dimethylformamide (DMF), methanol, tetrahydrofuran (THF) and dichloromethane. To remove the product, the resin is shaken with 10 ml of trifluoroacetic acid (TFA)/dichloromethane for 1 h, filtered off, and the filtrate is concentrated in vacuo and purified on silica gel. 210 mg of the title compound are obtained.

Mass spectrometry (ESI): 524.

Retention time (HPLC): $R_t$=10.4.

$^1$H-NMR (400 MHz, methanol) δ=7.67 (s, 1H), 7.32–7.22 (m, 4H), 7.17 (d, 1H), 7.04 (d, 2H), 6.77 (s, 2H), 3.93 (dd, 1H, J=4.6 Hz, J=10.0 Hz, H-2), 3.18 (t, 2H, J=7.0 Hz), 3.09 (dd, 1H, J=4.6 Hz, J=13.6 Hz, H-3a), 2.79 (dd, 1H, J=10.0 Hz, J=13.8 Hz, H-3b), 2.44 (s, 6H), 2.03 (s, 3H), 1.57 (tq, 2H, J=7.2 Hz), 0.97 (3H, J=7.2 Hz).

Example 1.2

(2R,S)-3-[3'-(3-Benzylureido)-biphenyl-4-yl]-2-[2,4,6-trimethylbenzenesulfonylamino]-propanoic acid

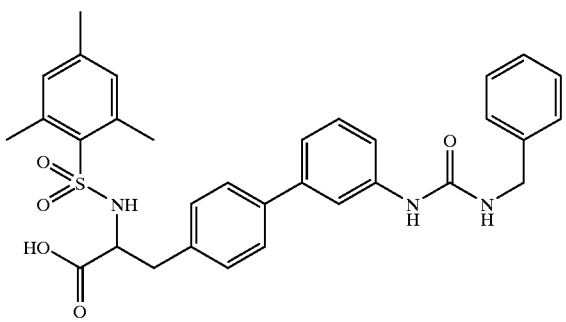

(2R,S)-3-[3'-(3-Benzylureido)-biphenyl-4-yl]-2-[2,4,6-trimethylbenzenesulfonylamino]-propanoic acid is prepared according to the procedure of example 1.1 with the exception that benzylamine is used as an amine reagent instead of propylamine.

Mass spectrometry (ESI): 572.

Retention time (HPLC): $R_t$=11.0.

Example 1.3

(2R,S)-3-[3'-(3-(2-Pyrrolidin-1-yl-ethyl)-ureido)-biphenyl-4-yl]-2-[2,4,6-trimethylbenzenesulfonylamino]-propanoic acid

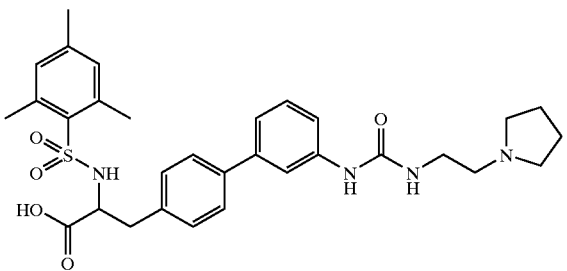

(2R,S)-3-[3'-(3-(2-Pyrrolidin-1-yl-ethyl)-ureido)-biphenyl-4-yl]-2-[2,4,6-trimethylbenzenesulfonylamino]-propanoic acid is prepared according to the procedure of example 1.1, with the exception that 2-pyrrolidin-1-yl-ethylamine is used as an amine reagent instead of propylamine.

Mass spectrometry (ESI): 579.

Retention time (HPLC): $R_t$=8.3.

Example 1.4

(2R,S)-3-[3'-(3-(Pyridin-2-yl-methylureido)-biphenyl-4-yl]-2-[2,4,6-trimethylbenzenesulfonylamino]-propanoic acid

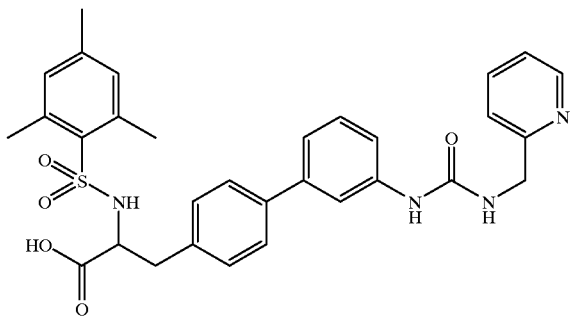

(2R,S)-3-[3'-(Pyridin-2-yl-methylureido)-biphenyl-4-yl]-2-[2,4,6-trimethylbenzenesulfonylamino]-propanoic acid is prepared according to the procedure of example 1.1, with the exception that 2-aminomethylpyridine is used as an amine reagent instead of propylamine.

Mass spectrometry (ESI): 573.

Retention time (HPLC): $R_t$=8.0.

Example 1.5

(2R,S)-3-[3'-(3-(Pyridin-3-yl-methylureido)-biphenyl-4-yl]-2-2,4,6-trimethylbenzenesulfonylamino]-propanoic acid

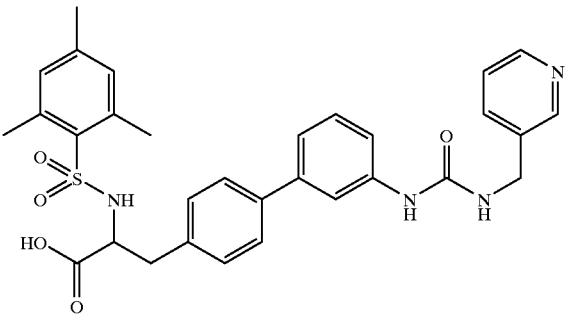

(2R,S)-3-[3'-(3-(Pyridin-3-yl-methylureido)-biphenyl-4-yl]-2-[2,4,6-trimethylbenzenesulfonylamino]-propanoic acid is prepared according to the procedure of example 1.1, with the exception that 3-aminomethylpyridine is used as an amine reagent instead of propylamine.

Mass spectrometry (ESI): 573.

Retention time (HPLC): $R_t$=7.9.

$^1$H-NMR (400 MHz, methanol) δ=8.75 (s, 1H), 8.65 (s, 1H), 8.37 (d, 1H), 7.84 (m 1H), 7.71 (s, 1H), 7.38–7.25 (m, 4H), 7.22 (d, 1H), 7.06 (d, 2H), 6.77 (s, 2H), 4.57 (s, 2H), 3.92 (dd, 1H, J=4.6 Hz, J=10.2 Hz, H-2), 3.09 (dd, 1H, J=4.6

Hz, J=13.8 Hz, H-3a), 2.79 (dd, 1H, J=10.2 Hz, J=13.8 Hz, H-3b), 2.43 (s, 6H), 2.02 (s, 3H).

Example 1.6

(2R,S)-3-[3'-(3-Methylureido)-biphenyl-4-yl]-2-[2,4,6-trimethylbenzenesulfonylamino]-propanoic acid

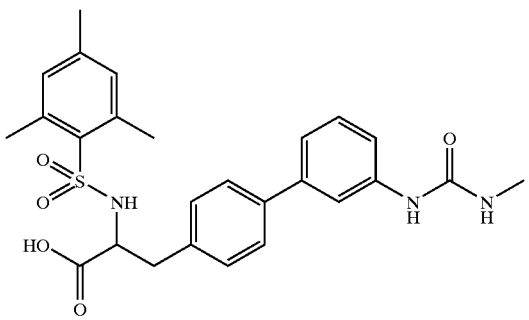

(2R,S)-3-[3'-(3-Methylureido)-biphenyl-4-yl]-2-[2,4,6-trimethylbenzenesulfonylamino]-propanoic acid is prepared according to the procedure of example 1.1, with the exception that methylamine is used as an amine reagent instead of propylamine.

Mass spectrometry (ESI): 496.

Retention time (HPLC): $R_t$=9.4.

Example 1.7

(2R,S)-3-[3'-(3-(2-Methyl-butyl)ureido)-biphenyl-4-yl]-2-[2,4,6-trimethylbenzenesulfonylamino]-propanoic acid

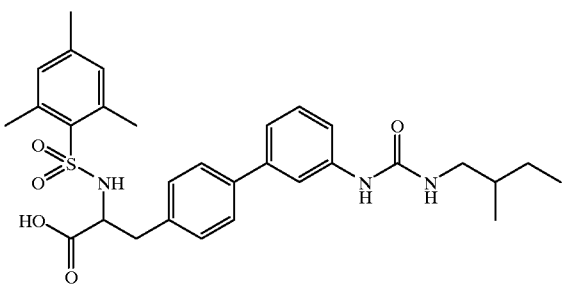

(2R,S)-3-[3'-(3-(2-Methyl-butyl)ureido)-biphenyl-4-yl]-2-[2,4,6-trimethylbenzenesulfonylamino]-propanoic acid is prepared according to the procedure of example 1.1, with the exception that 2-methylbutylamine is used as an amine reagent instead of propylamine.

Mass spectrometry (ESI): 552.

Retention time (HPLC): $R_t$=11.5.

Example 1.8

(2R,S)-3-[3'-(3-sec-Butylureido)-biphenyl-4-yl]-2-[2,4,6-trimethylbenzenesulfonylamino]-propanoic acid

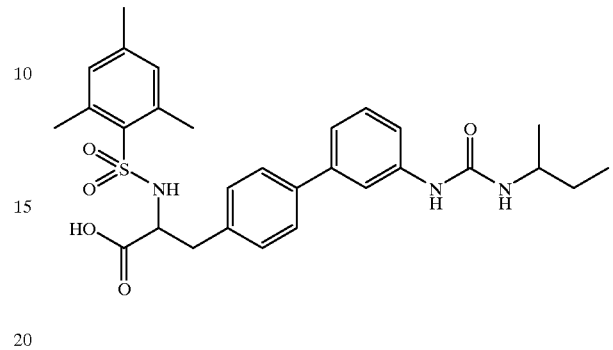

(2R,S)-3-[3'-(3-sec-Butylureido)-biphenyl-4-yl]-2-[2,4,6-trimethylbenzenesulfonylamino]-propanoic acid is prepared according to the procedure of example 1.1, with the exception that sec-butylamine is used as an amine reagent instead of propylamine.

Mass spectrometry (ESI): 538.

Retention time (HPLC): $R_t$=10.9.

$^1$H-NMR (400 MHz, MeOH) δ=7,68 (s, 1H), 7,31 (d, 3H), 7,25 (d, 1H), 7,18 (d, 1H), 7,04 (d, 2H), 6,77 (s, 2H), 3,92 (dd, 1H, J=4,6 Hz, J=10,4 Hz, H-2), 3,74 (dq, 1H, J=6,6 Hz), 3,09 (dd, 1H, J=4,6 Hz, J=13,6 Hz, H-3a), 2,79 (dd, 1H, J=10,2 Hz, J=13,8 Hz, H-3b), 2,42 (s, 6H), 2,03 (s, 3H), 1,52 (m, 2H), 1,17 (d, 3H, J=6,6 Hz), 0,97 (t, 3H, J=7,4 Hz).

Example 1.9

(2R,S)-3-[3'-(3-iso-Butyl-ureido)-biphenyl-4-yl]-2-(2,4,6-trimethylbenzenesulfonylamino)-propanoic acid

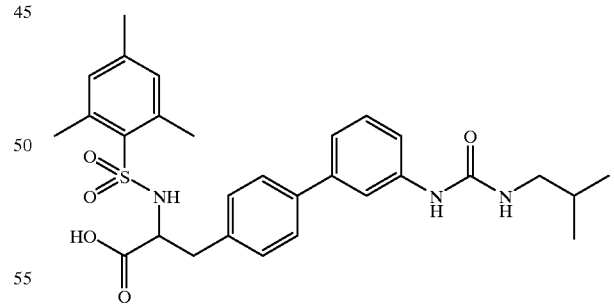

(2R,S)-3-[3'-(3-iso-Butyl-ureido)-biphenyl-4-yl]-2-(2,4,6-trimethylbenzenesulfonylamino)-proanoic acid is prepared according to the procedure of example 1.1, with the exception that isobutylamine is used as an amine reagent instead of propylamine.

Mass spectrometry (ESI): 538.

Retention time (HPLC): $R_t$=11.0.

Example 1.10

(2R,S)-3-[3'-(3-Pyridin-4-yl-ureido)-biphenyl-4-yl]-2-(2,4,6-trimethylbenzenesulfonylamino)-propanoic acid

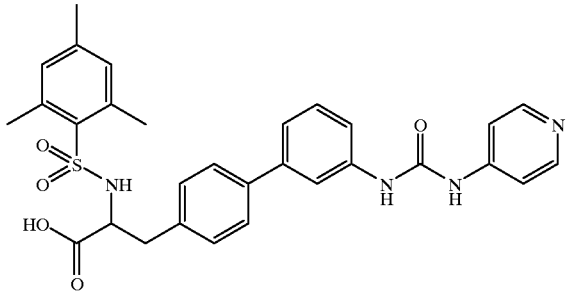

(2R,S)-3-[3'-(3-Pyridin-4-yl-ureido)-biphenyl-4-yl]-2-(2,4,6-trimethylbenzenesulfonylamino)-propanoic acid is prepared according to the procedure of example 1.1, with the exception that 4-aminopyridine is used as an amnine reagent instead of propylamine.

Mass spectrometry (ESI): 559.

Retention time (HPLC): $R_t$=8.6.

$^1$H-NMR (400 MHz, methanol) δ=8.48 (d, 2H), 7.98 (d, 2H), 7.82 (s, 1H), 7.42 (d, 2H), 7.33 (d, 3H), 7.09 (d, 2H), 6.79 (s, 2H), 3.93 (dd, 1H, J=4.6 Hz, J=10.0 Hz, H-2), 3.11 (dd, 1H, J=4.6 Hz, J=13.6 Hz, H-3a), 2.81 (dd, 1H, J=10.0 Hz, J=13.8 Hz, H-3b), 2.44 (s, 6H), 2.04 (s, 3H).

Example 1.11

(2R,S)-3-[3'-(3-Pyridin-3-yl-ureido)-biphenyl-4-yl]-2-(2,4,6-trimethylbenzenesulfonylamino)-propanoic acid

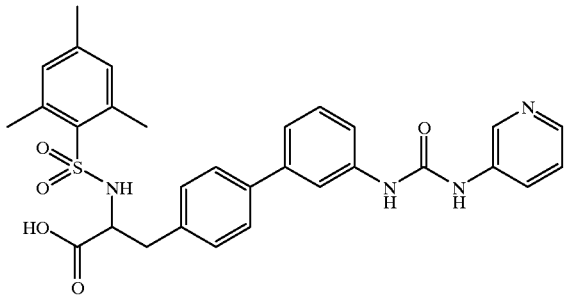

(2R,S)-3-[3'-(3-Pyridin-3-yl-ureido)-biphenyl-4-yl]-2-(2,4,6-trimethylbenzenesulfonylamino)-propanoic acid is prepared according to the procedure of example 1.1, with the exception that 3-aminopyridine is used as an amine reagent instead of propylamine.

Mass spectrometry (ESI): 559.

Retention time (HPLC): $R_t$=8.4.

$^1$H-NMR (400 MHz, methanol) δ=8.37 (m, 2H), 7.83 (m, 2H), 7.42–7.26 (m, 6H), 7.07 (d, 2H), 6.78 (s, 2H), 3.94 (dd, 1H, J=4.6 Hz, J=10.2 Hz, H-2), 3.11 (dd, 1H, J=4.6 Hz, J=13.6 Hz, H-3a), 2.80 (dd, 1H, J=10.2 Hz, J=13.6 Hz, H-3b), 2.43 (s, 6H), 2.03 (s, 3H).

Example 1.12

(2R,S)-3-[3'-(3-Pyridin-2-yl-ureido)-biphenyl-4-yl]-2-(2,4,6-trimethylbenzenesulfonylamino)-propanoic acid

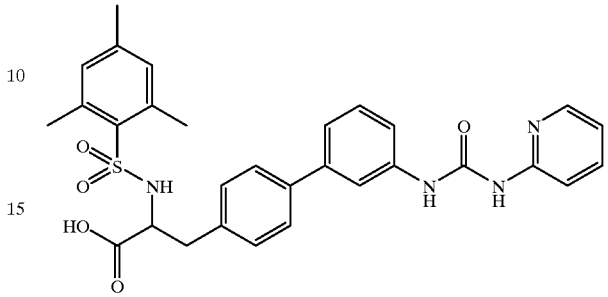

(2R,S)-3-[3'-(3-Pyridin-2-yl-ureido)-biphenyl-4-yl]-2-(2,4,6-trimethylbenzenesulfonylamino)-propanoic acid is prepared according to the procedure of example 1.1, with the exception that 2-aminopyridine is used as an amine reagent instead of propylamine.

Mass spectrometry (ESI): 559.

Retention time (HPLC): $R_t$=9.4.

$^1$H-NMR (400 MHz, methanol) δ=8.31 (d, 1H), 8.05 (dd, 1H), 7.86 (s, 1H), 7.43 (m, 2H), 7.33 (m, 4H), 7.26 (m, 1H), 7.07 (d, 2H), 6.68 (s, 2H), 3.94 (dd, 1H, J=4.8 Hz, J=10.4 Hz, H-2), 3.11 (dd, 1H, J=4.8 Hz, J=14.0 Hz, H-3a), 2.81 (dd, 1H, J=10.2 Hz, J=14.0 Hz, H-3b), 2.43 (s, 6H), 2.02 (s, 3H).

Example 1.13

(2S)-3-[3'-(3-Cyclopropyl-ureido)-biphenyl-4-yl]-2-(2,4,6-trimethylbenzenesulfonylamino)-propanoic acid

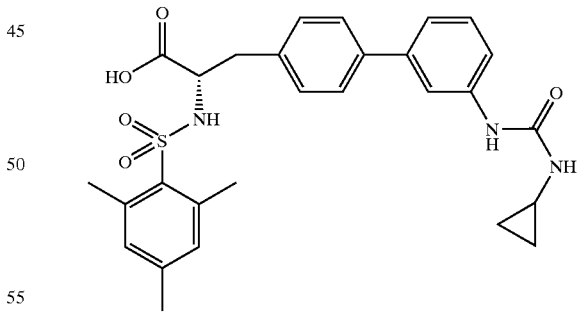

(2S)-3-[3'-(3-Cyclopropyl-ureido)-biphenyl-4-yl]-2-(2,4,6-trimethylbenzenesulfonylamino)-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid and cyclopropylamine is used as an amine reagent instead of propylamine.

Mass spectrometry (ESI): 522.

Retention time (HPLC): $R_t$=10.4.

$^1$H-NMR (400 MHz, methanol) δ=7.72 (s, 1H), 7.30 (m, 4H), 7.19 (d, 1H), 7.06 (d, 2H), 6.78 (s, 2H), 3.92 (dd, 1H, J=4.8 Hz. J=10.0 Hz, H-2), 3.10 (dd, 1H, J=4.6 Hz, J=14.0 Hz, H-3a), 2.80 (dd, 1H, J=10.0 Hz, J=14.0 Hz, H-3b), 2.62 (m, 1H), 2.47 (s, 6H), 2.04 (s, 3H), 0.76 (m, 2H), 0.54 (m, 2H).

Example 1.14

(2R,S)-3-(3'-{3-[2-(1H-Imidazol-4-yl)-ethyl]-ureido}-biphenyl-4-yl)-2-(2chloro-benzenesulfonylamino)-propanoic acid

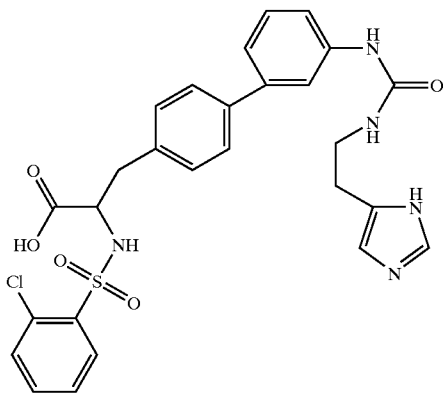

(2R,S)-3-(3'-{3-[2-(1H-Imidazol-4-yl)-ethyl]-ureido}-biphenyl-4-yl)-2-(2-chloro-benzenesulfonylamino)-propanoic acid acid is prepared according to the procedure of example 1.1, with the exception that 2-chlorobenzenesulfonyl chloride is used as a sulfonylating reagent instead of 2,4,6-trimethylbenzenesulfonyl chloride and 2-(imidazol-4-yl)-ethylamine is used as an amine reagent instead of propylamine.

Mass spectrometry (ESI): 569.
Retention time (HPLC): $R_t$=7.0.

Example 1.15

(2R,S)-3-[3'-(3-Pyridin-4-ylmethyl-ureido)-biphenyl-4-yl]-2-(2-chloro-benzenesulfonylamino)-propanoic acid

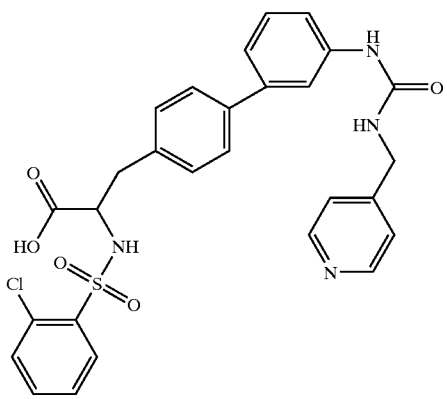

(2R,S)-3-[3'-(3-Pyridin-4-ylmethyl-ureido)-biphenyl-4-yl]-2-(2-chloro-benzenesulfonylamino)-propanoic acid is prepared according to the procedure of example 1.1, with the exception that 2-chlorobenzenesulfonyl chloride is used as a sulfonylating reagent instead of 2,4,6-trimethylbenzenesulfonyl chloride and 4-aminomethylpyridine is used as an amine reagent instead of propylamine.

Mass spectrometry (ESI): 566.

Retention time (HPLC): $R_t$=7.0.

Example 1.16

(2R,S)-3-[3'-(3-Pyridin-2-ylmethyl-ureido)-biphenyl-4-yl]-2-(2-chloro-benzenesulfonylamino)-propanoic acid

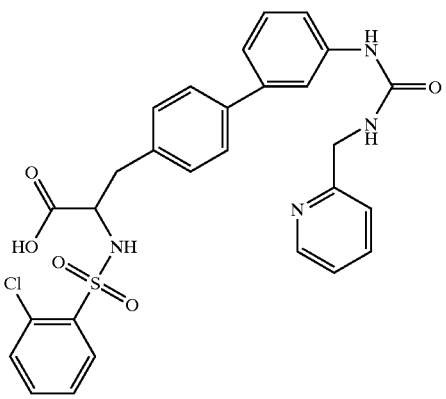

(2R,S)-3-[3'-(3-Pyridin-2-ylmethyl-ureido)-biphenyl-4-yl]-2-(2-chloro-benzenesulfonylamino)-propanoic acid is prepared according to the procedure of example 1.1, with the exception that 2-chlorobenzenesulfonyl chloride is used as a sulfonylating reagent instead of 2,4,6-trimethylbenzenesulfonyl chloride and 2-aminomethylpyridine is used as an amine reagent instead of propylamine.

Mass spectrometry (ESI): 566.

Retention time (HPLC): $R_t$=7.0.

$^1$H-NMR (400 MHz, methanol) δ=8.67 (d, 1H), 8.37 (dd, 1H), 7.92 (d, 1H), 7.82–7.74 (m, 2H), 7.70 (s, 1H), 7.37–7.23 (m, 7H), 7.20 (d, 1H), 7.14 (d, 2H), 4.70 (s, 2H), 4.10 (dd, 1H, J=4.6 Hz, J=10.0 Hz, H-2), 3.15 (dd, 1H, J=4.6 Hz, J=14.0 Hz, H-3a), 2.86 (dd, 1H, J=10.0 Hz, J=14.0 Hz, H-3b).

Example 1.17

(2R,S)-3-[3'-(3-Pyridin-4-yl-ureido)-biphenyl-4-yl]-2-(2-chloro-benzenesulfonylamino)-propanoic acid

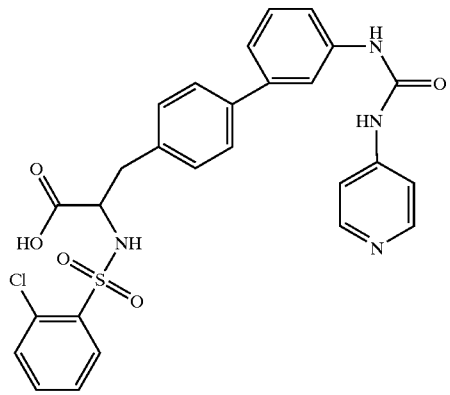

(2R,S)-3-[3'-(3-Pyridin-4-yl-ureido)-biphenyl-4-yl]-2-(2-chloro-benzenesulfonylamino)-propanoic acid is prepared according to the procedure of example 1.1, with the exception that 2-chlorobenzenesulfonyl chloride is used as a sulfonylating reagent instead of 2,4,6-trimethylbenzenesulfonyl chloride and 4-aminopyridine is used as an amine reagent instead of propylamine.

Mass spectrometry (ESI): 552.

Retention time (HPLC): $R_t$=7.7.

Example 1.18

(2R,S)-3-[3'-(3-Propyl-ureido)-biphenyl-4-yl]-2-(2-chloro-benzenesulfonylamino)-propanoic acid

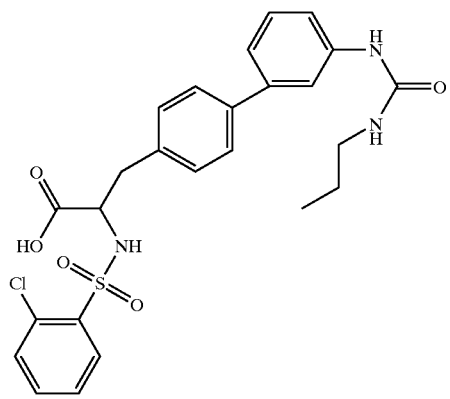

(2R,S)-3-[3'-(3-Propyl-ureido)-biphenyl-4-yl]-2-(2-chlorobenzenesulfonylamino)-propanoic acid is prepared according to the procedure of examnple 1.1, with the exception that 2-chlorobenzenesulfonyl chloride is used as a sulfonylating reagent instead of 2,4,6-trimethylbenzenesulfonyl chloride.

Mass spectrometry (ESI): 517.

Retention time (HPLC): $R_t$=9.5.

Example 1.19

(2R,S)-3-{3'-[3-(2-Dimethylamino-ethyl)-ureido]-biphenyl-4-yl}-2-(4-chloro-benezenesulfonylamino)-propanoic acid

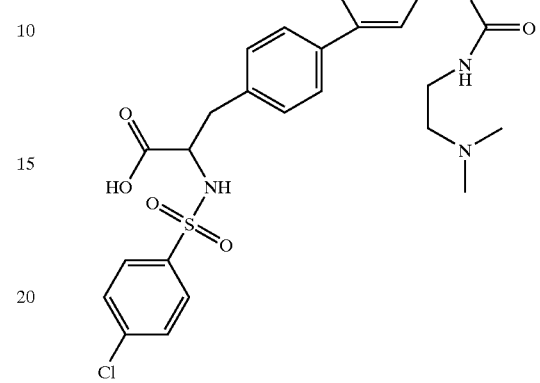

(2R,S)-3-{3'-[3-(2-Dimethylamino-ethyl)-ureido]-biphenyl-4-yl}-2-(4-chloro-benezenesulfonylamino)-propanoic acid is prepared according to the procedure of example 1.1, with the exception that 4-chlorobenzenesulfonyl chloride is used as a sulfonylating reagent instead of 2,4,6-trimethylbenzenesulfonyl chloride and N,N-dimethyl-ethylenediamine is used as an amine reagent instead of propylamnine.

Mass spectrometry (ESI): 546.

Retention time (HPLC): $R_t$=7.3.

Example 1.20

(2R,S)-3-{3-[3'-(2-Pyridin-2-yl-ethyl)-ureido]-biphenyl-4-yl}-2-(4-chloro-benezenesulfonylamino)-propanoic acid

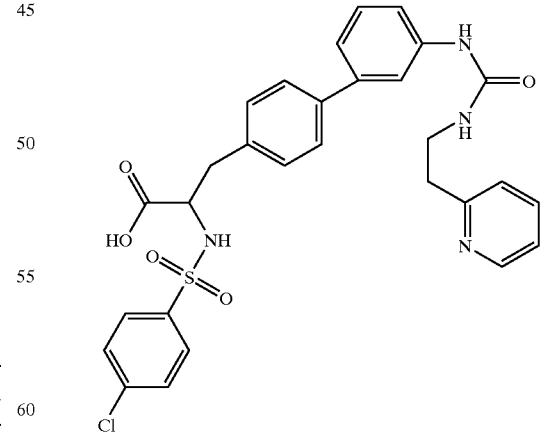

(2R,S)-3-{3-[3'-(2-Pyridin-2-yl-ethyl)-ureido]-biphenyl-4-yl}-2-(4-chloro-benezenesulfonylamino)-propanoic acid is prepared according to the procedure of example 1.1, with the exception that 4-chlorobenzenesulfonyl chloride is used as a sulfonylating reagent instead of 2,4,6-trimethylbenzenesulfonyl chloride and 2-(pyridin-4-yl)-ethylamine is used as an amine reagent instead of propylamine.

Mass spectrometry (ESI): 580.

Retention time (HPLC): $R_t$=7.3.

$^1$H-NMR (400 MHz, methanol) δ=8.70 (d, 1H), 8.41 (dd, 1H), 7.93 (d, 1H), 7.84 (dd, 1H), 7.58 (m, 3H), 7.41 (d, 2H), 7.33 (d, 2H), 7.29 (d, 1H), 7.22 (m, 4H), 4.08 (dd, 1H, J=5.0 Hz, J=9.6 Hz, H-2), 3.67 (t, 2H, J=6.8 Hz), 3.25 (t, 2H, J=6.8 Hz), 3.13 (dd, 1H, J=5.0 Hz, J=14.0 Hz, H-3a), 2.85 (dd, 1H, J=9.6 Hz, J=14.0 Hz, H-3b).

Example 1.21

(2R,S)-3-[3'-(3-Pyridin-4-ylmethyl-ureido)-biphenyl-4-yl]-2-(4-chloro-benzenesulfonylamino)-propanoic acid

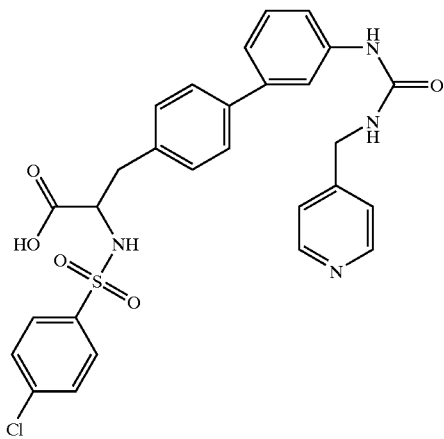

(2R,S)-3-[3'-(3-Pyridin-4-ylmethyl-ureido)-biphenyl-4-yl]-2-(4-chloro-benzenesulfonylamino)-propanoic acid is prepared according to the procedure of example 1.1, with the exception that 4-chlorobenzenesulfonyl chloride is used as a sulfonylating reagent instead of 2,4,6-trimethylbenzenesulfonyl chloride and 4-aminomethylpyridine is used as an amine reagent instead of propylamine.

Mass spectrometry (ESI): 566.

Retention time (HPLC): $R_t$=7.3.

Example 1.22

(2R,S)-3-[3'-(3-Pyridin-3-ylmethyl-ureido)-biphenyl-4-yl]-2-(4-chloro-benzenesulfonylamino)-propanoic acid

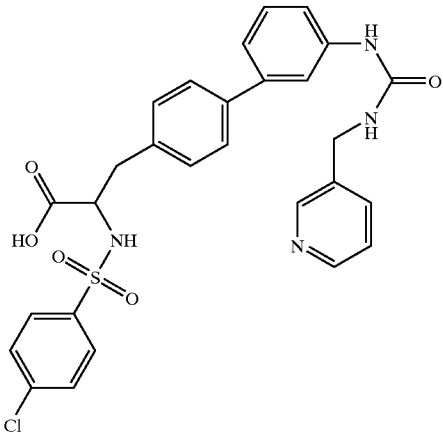

(2R,S)-3-[3'-(3-Pyridin-3-ylmethyl-ureido)-biphenyl-4-yl]-2-(4-chloro-benzenesulfonylamino)-propanoic acid is prepared according to the procedure of example 1.1, with the exception that 4-chlorobenzenesulfonyl chloride is used as a sulfonylating reagent instead of 2,4,6-trimethylbenzenesulfonyl chloride and 3-aminomethylpyridine is used as an amine reagent instead of propylamine.

Mass spectrometry (ESI): 566.

Retention time (HPLC): $R_t$=7.2.

Example 1.23

(2R,S)-3-[3'-(3-Benzyl-ureido)-biphenyl-4-yl]-2-(4-chloro-benzenesulfonylamino)-propanoic acid

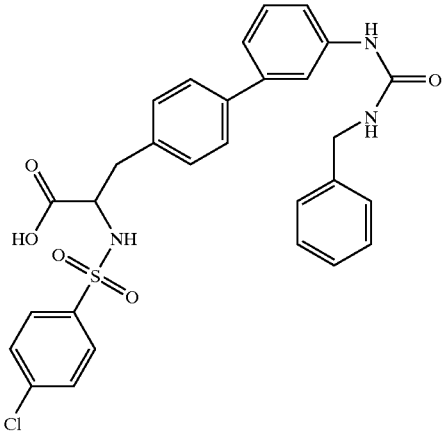

(2R,S)-3-[3'-(3-Benzyl-ureido)-biphenyl-4-yl]-2-(4-chloro-benzenesulfonylamino)-propanoic acid is prepared according to the procedure of example 1.1, with the exception that 4-chlorobenzenesulfonyl chloride is used as a sulfonylating reagent instead of 2,4,6- trimethylbenzenesulfonyl chloride and benzylamine is used as an amine reagent instead of propylamine.

Mass spectrometry (ESI): 565.
Retention time (HPLC): $R_t$=10.4.

Example 1.24

(2S)-3-[3'-(3-Propyl-ureido)-biphenyl-4-yl]-2-(2,5-dichloro-benzenesulfonylamino)-propanoic acid

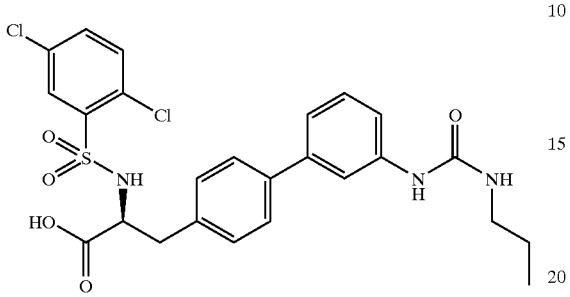

(2S)-3-[3'-(3-Propyl-ureido)-biphenyl-4-yl]-2-(2,5-dichloro-benzenesulfonylamino)-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid and 2,5-dichlorobenzenesulfonyl chloride is used as a sulfonylating reagent instead of 2,4,6-trimethylbenzenesulfonyl chloride.

Mass spectrometry (ESI): 551.
Retention time (HPLC): $R_t$=10.2.
$^1$H-NMR (400 MHz, methanol) δ=7.77 (s, 1H), 7.67 (s, 1H), 7.37–7.11 (m, 9H), 4.16 (dd, 1H, J=4.4 Hz, J=10.4 Hz, H-2), 3.19 (t, 2H, J=7.0 Hz), 3.18 (dd, 1H, J=4.4 Hz, J=13.4 Hz, H-3a), 2.84 (dd, 1H, J=10.6 Hz, J=14.0 Hz, H-3b), 1.58 (tq, 2H, J=7.2 Hz), 0.98 (t, 3H, J=7.6 Hz).

Example 1.25

(2R,S)-3-[3'-(3-Pyridin-2-ylmethyl-ureido)-biphenyl-4-yl]-2-benzyloxycarbonylamino-propanoic acid

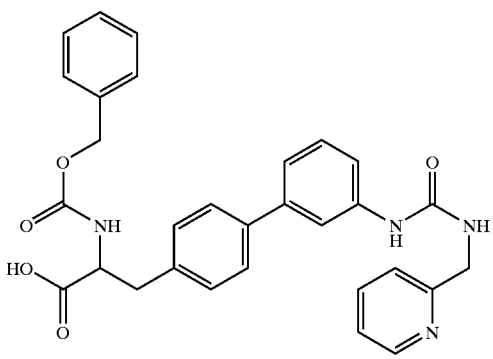

(2R,S)-3-[3'-(3-Pyridin-2-ylmethyl-ureido)-biphenyl-4-yl]-2-benzyloxycarbonylamino-propanoic acid is prepared according to the procedure of example 1.1, with the exception that benzyl chloroformate is used as a carbamoylating reagent instead of 2,4,6-trimethylbenzenesulfonyl chloride as a sulfonylating reagent and 2-aminomethylpyridine is used as an amine reagent instead of propylamine.

Mass spectrometry (ESI): 525.
Retention time (HPLC): $R_t$=7.6.

Example 1.26

(2R,S)-3-{3'-[3-(1H-Benzoimidazol-2-yl)-ureido]-biphenyl-4-yl}-2-benzyloxycarbonylamino-propanoic acid

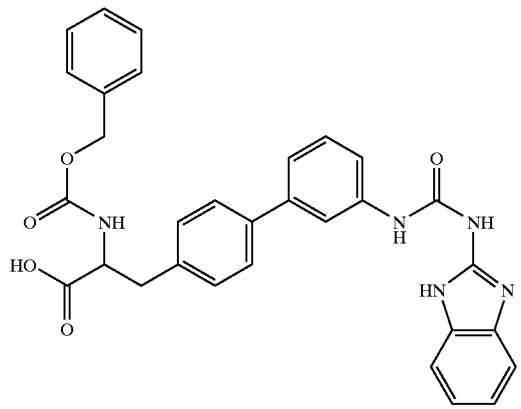

(2R,S)-3-{3'-[3-(1H-Benzoimidazol-2-yl)-ureido]-biphenyl-4-yl}-2-benzyloxycarbonylamino-propanoic acid is prepared according to the procedure of example 1.1, with the exception that benzyl chloroformate is used as a carbamoylating reagent instead of 2,4,6-trimethylbenzenesulfonyl chloride as a sulfonylating reagent and 2-aminobenzimidazole is used as an amine reagent instead of propylamine.

Mass spectrometry (ESI): 550.
Retention time (14PLC): $R_t$=9.3.

Example 1.27

(2R,S)-3-{3'-[3-(2-Acetylamino-ethyl)-ureido]-biphenyl-4-yl}-2-benzyloxycarbonylamino-propanoic acid

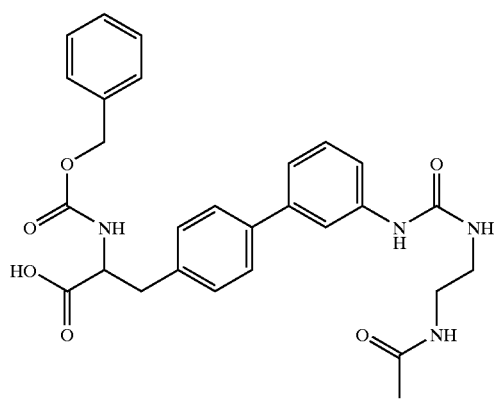

(2R,S)-3-{3'-[3-(2-Acetylamino-ethyl)-ureido]-biphenyl-4-yl}-2-benzyloxycarbonylamino-propanoic acid is prepared according to the procedure of example 1.1, with the exception that benzyl chloroformate is used as a carbamoylating reagent instead of 2,4,6-trimethylbenzenesulfonyl chloride as a sulfonylating reagent and N-acetylethylenediamine is used as an amine reagent instead of propylamine.

Example 1.28

(2S)-3-[3'-(3-Pyridin-4-yl-ureido)-biphenyl-4-yl]-2-benzyloxycarbonylamino-propanoic acid

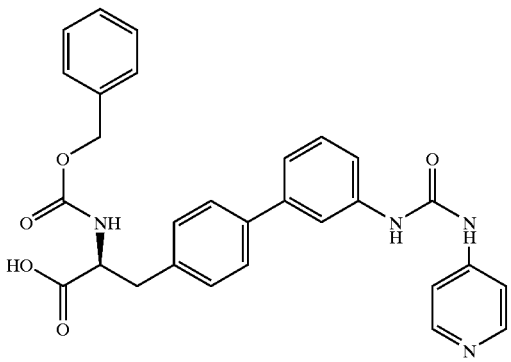

(2S)-3-[3'-(3-Pyridin-4-yl-ureido)-biphenyl-4-yl]-benzyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, benzyl chloroformate is used as a carbamoylating reagent instead of 2,4,6-trimethylbenzenesulfonyl chloride as a sulfonylating reagent and 4-aminopyridine is used as an amine reagent instead of propylamine.

Mass spectrometry (ESI): 511.

Retention time (HPLC): $R_t$=8.6.

$^1$H-NMR (400 MHz, methanol) δ=8.48 (d, 2H), 8.03 (d, 2H), 7.80 (s, 1H), 7.52 (d, 2H), 7.48–7.20 (m, 12H), 5.07 (d, 1H, J=12.6 Hz9, 5.01 (d, 1H, J=12.6 Hz), 4.46 (dd, 1H, J=4.8 Hz, J=9.4 Hz, H-2), 3.26 (dd, 1H, J=4.8 Hz, J=14.0 Hz, H-3a), 2.98 (dd, 1H, J=9.6 Hz, J=14.0 Hz, H-3b).

Example 1.29

(2S)-3-[3'-(3-Cyclopropyl-ureido)-biphenyl-4-yl]-2-[(S)-campher-10-yl-sulfonylamino]-propanoic acid

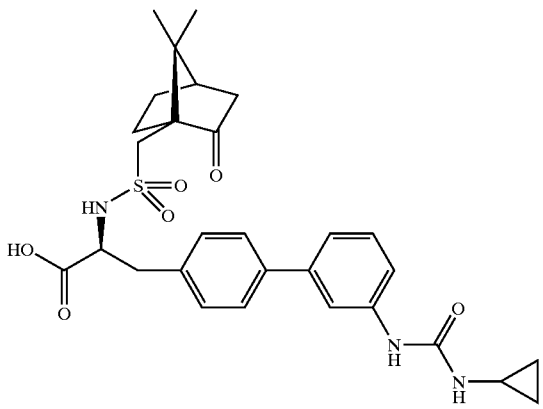

(2S)-3-[3'-(3-Cyclopropyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and cyclopropylamine is used as an amine reagent instead of propylamine.

Mass spectrometry (ESI): 554.

Retention time (HPLC): $R_t$=9.1.

$^1$H-NMR (400 MHz, methanol) δ=7.78–7.18 (m, 8H), 4.32 (dd, 1H, J=4.6 Hz, J=9.2 Hz, H-2), 3.24 (dd, 1H, J=4.8 Hz, J=14.0 Hz, H-3a), 3.03 (m, 1H, J=15.2 Hz), 2.94 (dd, 1H, J=9.6 Hz, J=14.0 Hz, H-3b), 2.65 (d, 1H, J=15.2 Hz), 2.59 (m, 1H), 2.28 (m, 1H, J=18.2 Hz), 2.20 (m, 1H, J=14.0 Hz), 2.03 (m, J=7.8 Hz, J=15.4 Hz), 1.97 (m, 1H), 1.84 (d, 1H, J=19.0 Hz), 1.58 (ddd, 1H, J=4.8 Hz, J=9.6 Hz, J=14.4 Hz), 1.37 (m, 1H), 0.91 (s, 3H), 0.74 (m, 2H), 0.66 (s, 3H), 0.52 (m, 2H).

Example 1.30

(2S)-3-[3'-(3-Propyl-ureido)-biphenyl-4-yl]-2-[(S)-campher-10-yl-sulfonylamino]-propanoic acid

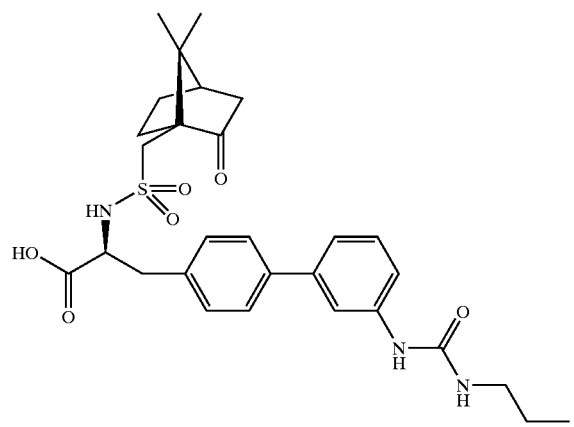

(2S)-3-[3'-(3-Propyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid and (S)-(+)-campher-10-sulfonyl chloride is used as a sulfonylating reagent instead of 2,4,6-trimethylbenzenesulfonyl chloride.

Mass spectrometry (ESI): 556.

Retention time (HPLC): $R_t$=9.6.

$^1$H-NMR (400 MHz, methanol) δ=7.63–7.18 (m, 8H), 4.31 (dd, 1H, J=4.6 Hz, J=9.2 Hz, H-2), 3.24 (dd, 1H, J=4.8 Hz, J=14.0 Hz, H-3a), 3.16 (t, 2H, J=7.0 Hz), 3.02 (m, 1H, J=15.2 Hz), 2.93 (dd, 1H, J=9.6 Hz, J=14.0 Hz, H-3b), 2.65 (d, 1H, J=15.2 Hz), 2.28 (m, 1H, J=18.2 Hz), 2.20 (m, 1H, J=14.0 Hz), 2.03 (m, J=7.8 Hz, J=15.4 Hz), 1.96 (m, 1H), 1.84 (d, 1H, J=19.0 Hz), 1.58 (ddd, 1H, J=4.8 Hz, J=9.6 Hz, J=14.4 Hz), 1.55 (tq, 2H, J=7.8 Hz, J=7.4 Hz), 1.37 (m, 1H), 0.95 (t, 3H, J=7.8 Hz), 0.91 (s, 3H), 0.67 (s, 3H).

Example 1.31

(2S)-3-[3'-(3-Pyridin-3-ylmethyl-ureido)-biphenyl-4-yl]-2-(2-chloro-benzensulfonylamino)-propanoic acid

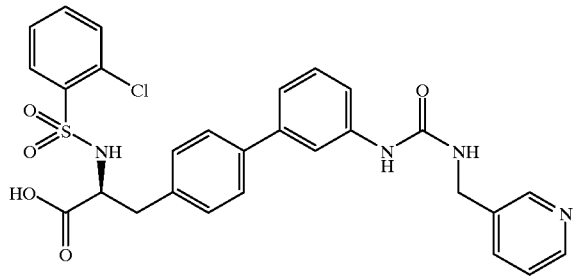

(2S)-3-[3'-(3-Pyridin-3-ylmethyl-ureido)-biphenyl-4-yl]-2-(2-chloro-benzensulfonylamino)-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, 2-chlorobenzenesulfonyl chloride is used as a sulfonylating reagent instead of 2,4,6-trimethylbenzenesulfonyl chloride and 3-aminomethylpyridine is used as an amine reagent instead of propylamine.

Mass spectrometry (ESI): 566.

Retention time (HPLC): $R_t$=7.6.

$^1$H-NMR (400 MHz, methanol) δ=8.72 (s, 1H), 8.63 (d, 1H), 8.31 (d, 1H), 7.80 (m, 2H), 7.70 (s, 1H), 7.39–7.26 (M, 7H), 7.19 (d, 1H), 7.16 (d, 2H), 4.56 (s, 2H), 4.10 (dd, 1H, J=5.0 Hz, J=10.0 Hz, H-2), 3.15 (dd, 1H, J=5.0 Hz, J=13.5 Hz, H-3a), 2.87 (dd, 1H, J=10.0 Hz, J=13.6 Hz, H-3b).

Example 1.32

(2R,S)-3-(3'-ureido-biphenyl-4-yl)-2-(2,4,6-trimethylbenzenesulfonylamino)-propanoic acid

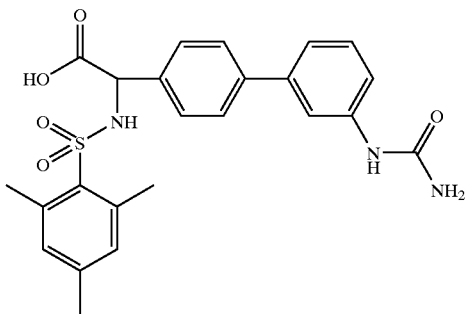

(2R,S)-3-(3'-ureido-biphenyl-4-yl)-2-(2-chloro-benzensulfonylamino)-propanoic acid is prepared according to the procedure of example 1.1, with the exception 2,4-dimethoxy-benzylamine is used as an amine reagent instead of propylamine.

Mass spectrometry (ESI): 482.

Retention time (HPLC): $R_t$=8.8.

$^1$H-NMR (400 Mhz, MeOH) δ=7,63 (s, 1H), 7,30 (m, 4H), 7,21 (m, 1H), 7,09 (d, 2H), 6,79 (s, 2H), 3,87 (dd, 1H, J=4,2 Hz, J=8,8 Hz, H-2), 3,09 (dd, 1H, J=4,4 Hz, J=13,8 Hz, H-3a), 2,83 (dd, 1H, J=13,8 Hz, J=8,8 Hz, H-3b), 2,47 (s, 6H), 2,06 (s, 3H).

Example 1.33

(3R,S)-3-[3'-(3-Pyridin-3-ylmethylureido)-biphenyl-3-yl]-3-(4-toluenesulfonylamino)-propanoic acid

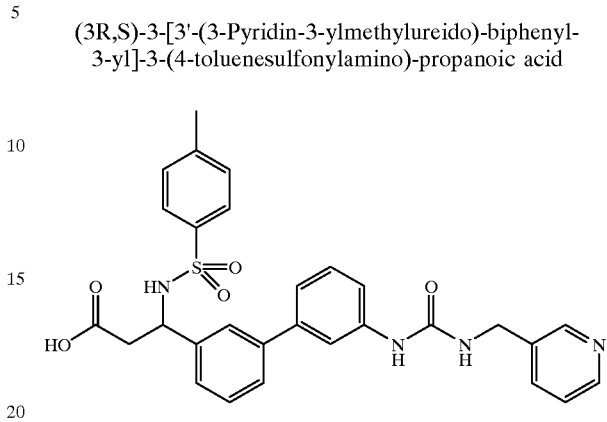

(3R,S)-3-[3'-(3-Pyridin-3-ylmethylureido)-biphenyl-3-yl]-3-(4-toluenesulfonylamino)-propanoic acid is prepared according to the procedure of example 1.1, with the exception that (3R,S)-3-(4-bromophenyl)-3-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, 4-toluenesulfonyl chloride is used as a sulfonylating reagent instead of 2,4,6-trimethylbenzenesulfonyl chloride and 3-aminomethylpyridine is used as an amine reagent instead of propylamine.

Mass spectrometry (ESI): 545.

Retention time (HPLC): $R_t$=6.9.

$^1$H-NMR (400 Mhz, MeOH) δ=8,83 (s, 1H), 8,73 (s, 1H), 8,58 (d, 1H), 8,02 (dd, 1H), 7,60 (s, 1H), 7,43 (d, 2H), 7,34 (d, 1H), 7,31 (d, 1H), 7,27 (d, 1H), 7,20 (m, 2H), 7,12 (d, 2H), 7,04 (d, 2H), 4,80 (dd, 1H, J=7,6 Hz, H-3), 4,60 (s, 2H), 2,79 (dd, 1H, J=7,6 Hz, J=15,8 Hz, H-2a), 2,70 (dd, 1H, J=7,6 Hz, J=15,6 Hz, H-2b), 2,18 (s, 3H).

Example 1.34

(2R,S)-3-[3'-(3-iso-Propyl-ureido)-biphenyl-3-yl]-2-(2,4,6-trimethylbenzenesulfonylamino)-propanoic acid

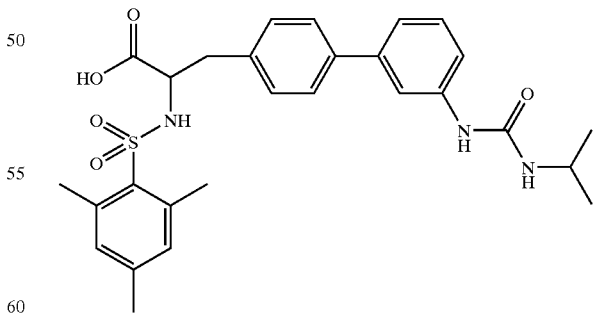

(2R,S)-3-[3'-(3-iso-Propyl-ureido)-biphenyl-3-yl]-2-(2,4,6-trimethylbenzenesulfonylamino)-propanoic acid is prepared according to the procedure of example 1.1, with the exception that iso-propylamine is used as an amine reagent instead of propylamine.

Mass spectrometry (ESI): 524.

Retention time (HPLC): $R_t$=10,5.

$^1$H-NMR (400 MHz, methanol) δ=7,68 (s, 1H), 7,30 (d, 3H), 7,23 (d, 1H), 7,18 (d, 1H), 7,05 (d, 2H), 6,78 (d, 2H), 3,92 (m, 2H), 3,10 (dd, 1H, J=4,8 Hz, J=14,0 Hz, H-3a), 2,79 (dd, 1H, J=10,4 Hz, J=14,0 Hz, H-3b), 2,44 (s, 6H), 2,04 (s, 3H), 1,20 (d, 6H).

Example 1.35

(2R,S)-3-[3'-(3-Ethylureido)-biphenyl-4-yl]-2-(2,4,6-trimethylbenzenesulfonylamino)-propanoic acid

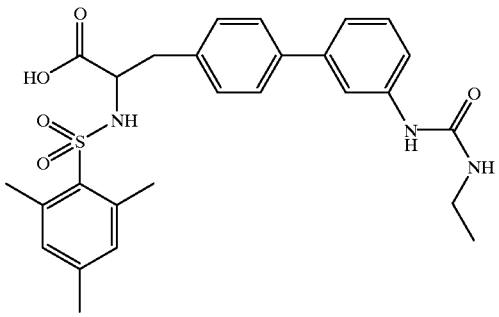

(2R,S)-3-[3'-(3-Ethylureido)-biphenyl-4-yl]-2-(2,4,6-trimethylbenzenesulfonylamino)-propanoic acid is prepared according to the procedure of example 1.1, with the exception that ethylamine is used as an amine reagent instead of propylamine.

Mass spectrometry (ESI): 510.

Retention time (HPLC): $R_t$=9,8.

$^1$H-NMR (400 MHz, methanol) δ=7,69 (s, 1H), 7,30 (m, 3H), 7,26 (d, 1H), 7,18 (d, 1H), 7,05 (d, 2H), 6,78 (s, 2H), 3,92 (dd, 1H, J=4,6 Hz, J=10,2 Hz, H-2), 3,25 (q, 2H, J=7,2 Hz), 3,09 (dd, 1H, J=4,6 Hz, J=14,0 Hz, H-3a), 2,79 (dd, 1H, J=10,2 Hz, J=14,0 Hz, H-3b), 2,42 (s, 6H), 2,04 (s, 3H), 1,17 (t, 3H, J=7,2 Hz).

Example 1.36

(2R,S)-3-[3'-(3-Cyclopropylureido)-4'-methyl-biphenyl-4-yl]-2-(2,4,6-trimethylbenzenesulfonylamino)-propanoic acid

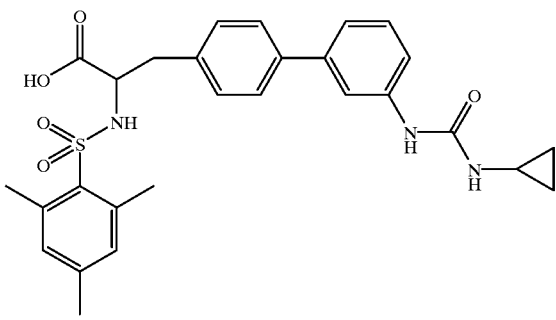

(2R,S)-3-[3'-(3-Cyclopropylureido)-4'-methyl-biphenyl-4-yl]-2-(2,4,6-trimethylbenzenesulfonylamino)-propanoic acid is prepared according to the procedure of example 1.1, with the exception that 4'-methyl-3-nitrobenzeneboronic acid is used as a boronic acid reagent instead of 3-nitrobenzeneboronic acid and ethylamine is used as an amine reagent instead of propylamine.

Mass spectrometry (ESI): 536.

Retention time (HPLC): $R_t$=10,3.

$^1$H-NMR (400 MHz, methanol) δ=7,79–7,20 (m, 5H), 7,03 (d, 2H), 6,78 (s, 2H), 3,92 (dd, 1H, H-2), 3,08 (dd, 1H, H-3a), 2,78 (dd, 1H, H-3b), 2,62 (m, 1H), 2,43 (s, 6H), 2,29 (s, 3H), 2,08 (s, 3H), 0,78 (m, 2H), 0,56 (m, 2H).

Example 1.37

(2R,S)-3-[3'-(3-Cyclopentylureido)-4'-methyl-biphenyl-4-yl]-2-(2,4,6-trimethylbenzenesulfonylamino)-propanoic acid

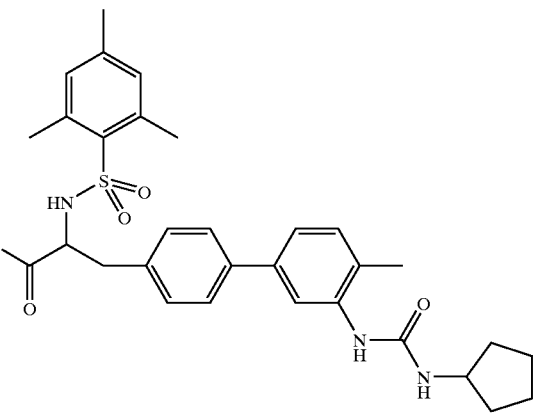

(2R,S)-3-[3'-(3-Cyclopentylureido)-4'-methyl-biphenyl-4-yl]-2-(2,4,6-trimethylbenzenesulfonylamino)-propanoic acid is prepared according to the procedure of example 1.1, with the exception that 4-methyl-3-nitrobenzeneboronic acid is used as a boronic acid reagent instead of 3-nitrobenzeneboronic acid and cyclopentylamine is used as an amine reagent instead of propylamine.

Mass spectrometry (ESI): 564.

Retention time (HPLC): $R_t$=11,3

$^1$H-NMR (400 MHz, methanol) δ=7,93 (s, 1H), 7,32 (d, 2H), 7,23 (d, 1H), 7,18 (d, 1H), 7,03 (d, 2H), 6,78 (s, 2H), 4,09 (m; 1H), 3,91 (dd, 1H, J=4,8 Hz, J=10,4 Hz, H-2), 3,08 (dd, 1H, J=4,8 Hz, J=14,0 Hz, H-3a), 2,78 (dd, 1H, J=10,4 Hz, J=14,0 Hz, H-3b), 2,42 (s, 6H), 2,28 (s, 3H), 2,07 (s, 3H), 1,99 (m, 2H), 1,75 (m, 2H), 1,64 (m, 2H), 1,49 (m, 2H).

Example 1.38

(2R,S)-3-[3'-(3-Propylureido)-4'-methyl-biphenyl-4-yl]-2-(2,4,6-trimethylbenzenesulfonylamino)-propanoic acid

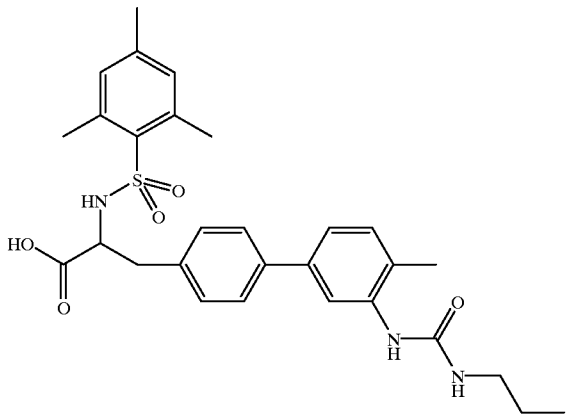

(2R,S)-3-[3'-(3-Propylureido)-4'-methyl-biphenyl-4-yl]-2-(2,4,6-trimethylbenzenesulfonylamino)-propanoic acid is prepared according to the procedure of example 1.1, with the exception that 4-methyl-3-nitrobenzeneboronic acid is used as a boronic acid reagent instead of 3-nitrobenzeneboronic acid.

Mass spectrometry (ESI): 538.

Retention time (HPLC): $R_t$=10,6

$^1$H-NMR (400 MHz, methanol) δ=7,87 (s, 1H), 7,32 (d, 2H), 7,23 (d, 1H), 7,21 (d, 1H), 7,03 (d, 2H), 6,78 (s, 2H), 3,91 (dd, 1H, J=4,6 Hz, J=10,0 Hz, H-2), 3,19 (t, 2H, J=7,2 Hz), 3,08 (dd, 1H, J=4,6 Hz, J=14,0 Hz, H-3a), 2,78 (dd, 1H, J=10,2 Hz, J=14,0 Hz, H-3b), 2,42 (s, 6H), 2,29 (s, 3H), 2,07 (s, 3H), 1,58 (dq, 2H, J=7,2 Hz), 0,99 (t, 3H, J=7,6 Hz, J=7,6 Hz).

Example 1.39

(2R,S)-3-[3'-(3-iso-Propyl-ureido)-biphenyl-3-yl]-2-(4-ethyl-benzenesulfonylamino)-propanoic acid

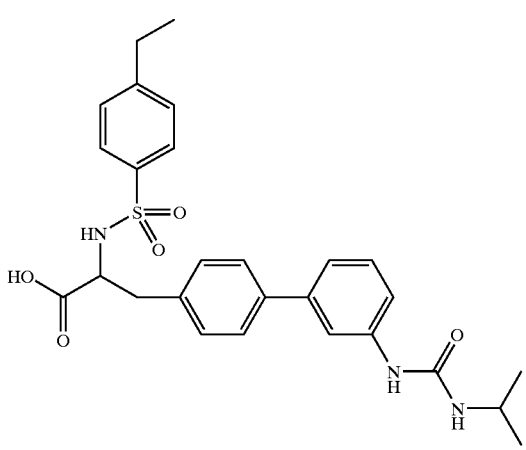

(2R,S)-3-[3'-(3-iso-Propyl-ureido)-biphenyl-3-yl]-2-(4-ethyl-benzenesulfonylamino)-propanoic acid is prepared according to the procedure of example 1.1, with the exception that 4-methylbenzenesulfonyl chloride is used as a sulfonylating reagent instead of 2,4,6-trimethylbenzenesulfonyl chloride and isopropylamine is used as an amine reagent instead of propylamine.

Mass spectrometry (ESI): 510.

Retention time (HPLC): $R_t$=10,1

$^1$H-NMR (400 MHz, methanol) δ=7,97–7,12 (m, 12H), 4,03 (dd, 1H, J=5,2 Hz, J=9,2 Hz, H-2), 3,91 (m, 1H, J=6,8 Hz), 3,09 (dd, 1H, J=5,0 Hz, J=13,8 Hz, H-3a), 2,85 (dd, 1H, J=9,2 Hz, J=13,8 Hz, H-3b), 2,54 (q, 2H, J=7,8 Hz), 1,19 (d, 6H, J=6,6 Hz), 1,12 (t, 3H, J=7,8 Hz).

Example 1.40

(2R,S)-3-[3'-(3-Pyridin-4-yl-ureido)-4'-methyl-biphenyl-4-yl]-2-(2-chloro-benzenesulfonylamino)-propanoic acid

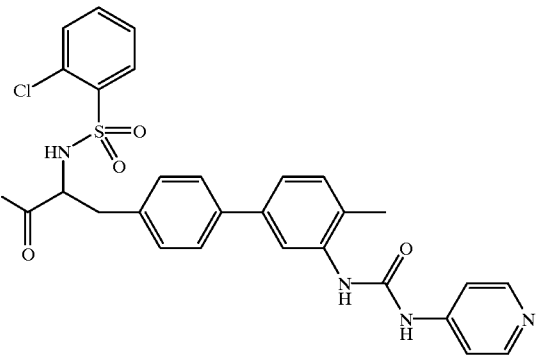

(2R,S)-3-[3'-(3-Pyridin-4-yl-ureido)-4'-methyl-biphenyl-4-yl]-2-(2-chloro-benzenesulfonylamino)-propanoic acid is prepared according to the procedure of example 1.1, with the exception that 2-chlorobenzenesulfonyl chloride is used as a sulfonylating reagent instead of 2,4,6-trimethylbenzenesulfonyl chloride, 4-methyl-3-nitrobenzeneboronic acid is used as a boronic acid reagent instead of 3-nitrobenzeneboronic acid and 4-aminopyridine is used as an amine reagent instead of propylamine.

Mass spectrometry (ESI): 566.

Retention time (HPLC): $R_t$=7,9

$^1$H-NMR (400 MHz, methanol) δ=8,48 (d, 2H), 7,96 (m, 3H), 7,82 (d, 1H), 7,33–7,27 (m, 7H), 7,17 (d, 2H), 4,09 (dd, 1H, J=4,6 Hz, J=9,8 Hz, H-2), 3,15 (dd, 1H, J=4,6 Hz, J=14,0 Hz, H-3a), 2,87 (dd, 1H, J=9,8 Hz, J=14,0 Hz, H-3b), 2,38 (s, 3H).

Example 1.41

(2R,S)-3-[3'-(3-Pyridin-3-yl-ureido)-4'-methyl-biphenyl-4-yl]-2-(2,4,6-trimethyl-benzenesulfonylamino)-propanoic acid

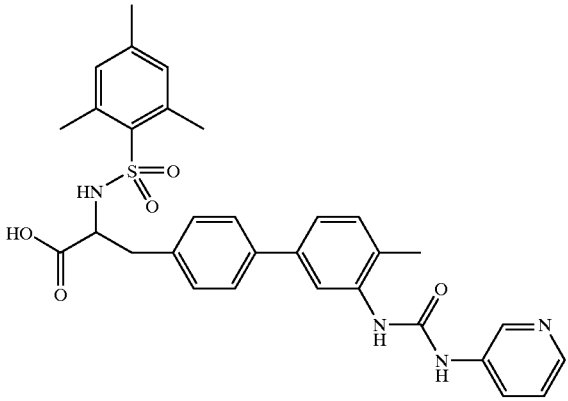

(2R,S)-3-[3'-(3-Pyridin-3-yl-ureido)-4'-methyl-biphenyl-4-yl]-2-(2,4,6-trimethyl-benzenesulfonylamino)-propanoic acid is prepared according to the procedure of example 1.1, with the exception that 4-methyl-3-nitrobenzeneboronic acid is used as a boronic acid reagent instead of 3-nitrobenzeneboronic acid and 3-aminopyridine is used as an amine reagent instead of propylamine.

Mass spectrometry (ESI): 573.

Retention time (HPLC): $R_t$=8,6

$^1$H-NMR (400 MHz, methanol) δ=9,22 (s, 1H), 8,41 (s, 1H), 8,30 (d, 1H), 7,97 (s, 1H), 7,84 (m, 1H), 7,32 (m, 4H), 7,06 (d, 2H), 6,80 (s, 2H), 3,92 (dd, 1H, J=4,6 Hz, J=10,2 Hz, H-2), 3,10 (dd, 1H, J=4,6 Hz, J=14,0 Hz, H-3a), 2,79 (dd, 1H, J=10,2 Hz, J=14,0 Hz, H-3b), 2,42 (s, 6H), 2,37 (s, 3H), 2,07 (s, 3H).

Example 1.42

(2R,S)-3-[3'-(3-Pyridin-3-ylmethylureido)-4'-methyl-biphenyl-4-yl]-2-(2-chloro-benzenesulfonylamino)-propanoic acid

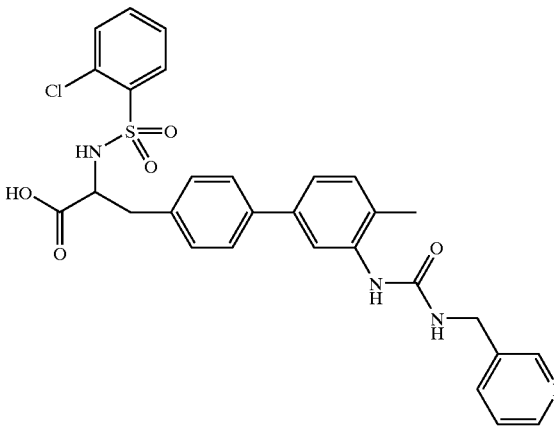

(2R,S)-3-[3'-(3-Pyridin-3-ylmethylureido)-4'-methyl-biphenyl-4-yl]-2-(2-chloro-benzenesulfonylamino)-propanoic acid is prepared according to the procedure of example 1.1, with the exception that 2-chlorobenzenesulfonyl chloride is used as a sulfonylating reagent instead of 2,4,6-trimethylbenzenesulfonyl chloride, 4-methyl-3-nitrobenzeneboronic acid is used as a boronic acid reagent instead of 3-nitrobenzeneboronic acid and 3-aminomethylpyridine is used as an amine reagent instead of propylamine.

Mass spectrometry (ESI): 580.

Retention time (HPLC): $R_t$=7,4

$^1$H-NMR (400 MHz, methanol) δ=8,73 (s, 1H), 8,62 (s, 1H), 8,37 (d, 1H), 7,87 (m, 1H), 7,82 (m, 2H), 7,38–7,22 (m, 7H), 7,13 (d, 2H), 4,58 (s, 2H), 4,09 (dd, 1H, J=4,6 Hz, J=9,8 Hz, H-2), 3,14 (dd, 1H, J=4,6 Hz, J=14,0 Hz, H-3a), 2,86 (dd, 1H, J=9,8 Hz, J=14,0 Hz, H-3b), 2,29 (s, 3H).

Example 1.43

(2R,S)-3-[3'-(3-Ethyl-ureido)-biphenyl-3-yl]-2-(2,5-dimethyl-benzenesulfonylamino)-propanoic acid

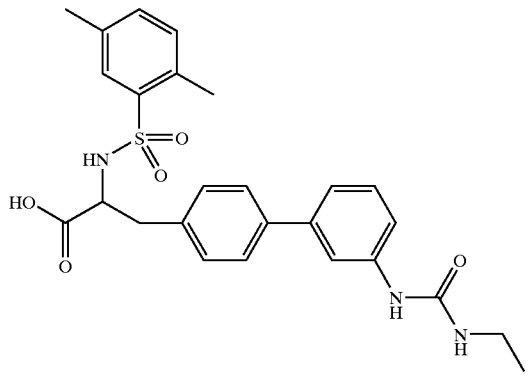

(2R,S)-3-[3'-(3-Ethyl-ureido)-biphenyl-3-yl]-2-(2,5-dimethyl-benzenesulfonylamino)-propanoic acid is prepared according to the procedure of example 1.1, with the exception that 2,5-dimethylbenzenesulfonyl chloride is used as a sulfonylating reagent instead of 2,4,6-trimethylbenzenesulfonyl chloride and ethylamine is used as an amine reagent instead of propylamine.

Mass spectrometry (ESI): 496.

Retention time (HPLC): $R_t$=9,4

$^1$H-NMR (400 MHz, methanol) δ7,70–6,95 (m, 11H), 3,95 (dd, 1H, J=4,8 Hz, J=10,0 Hz, H-2), 3,25 (q, 2H, J=7,4 Hz), 3,09 (dd, 1H, J=4,8 Hz, J=14,0 Hz, H-3a), 2,82 (dd, 1H, J=10,0 Hz, J=13,8 Hz, H-3b), 2,30 (s, 3H), 2,29 (s, 3H), 1,17 (t, 3H, J=7,4 Hz).

Example 1.44

(2R,S)-3-[3'-(3-Benzyl-ureido)-biphenyl-3-yl]-2-(2,6-dichloro-benzenesulfonylamino)-propanoic acid

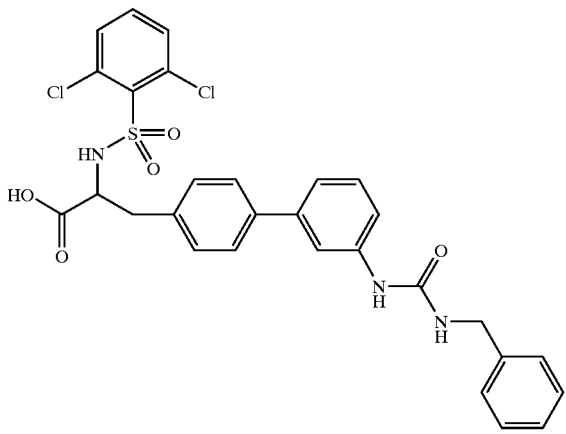

(2R,S)-3-[3'-(3-Benzylureido)-biphenyl-3-yl]-2-(2,6-dichloro-benzenesulfonylamino)-propanoic acid is prepared according to the procedure of example 1.1, with the exception that 2,6-dichlorobenzenesulfonyl chloride is used as a sulfonylating reagent instead of 2,4,6-trimethylbenzenesulfonyl chloride and benzylamine is used as an amine reagent instead of propylamine.

Mass spectrometry (ESI): 599.

Retention time (HPLC): $R_t$=10,5

$^1$H-NMR (400 MHz, methanol) δ=7,69–7,07 (m, 16H), 4,42 (s, 2H), 4,28 (dd, 1H, J=4,2 Hz, J=10,8 Hz, H-2), 3,20 (dd, 1H, J=4,2 Hz, J=14,0 Hz, H-3a), 2,83 (dd, 1H, J=10,8 Hz, J=14,9 Hz, H-3b).

Example 1.45

(2R,S)-3-[3'-(3-Ethyl-ureido)-biphenyl-3-yl]-2-methylsulfonylamino-propanoic acid

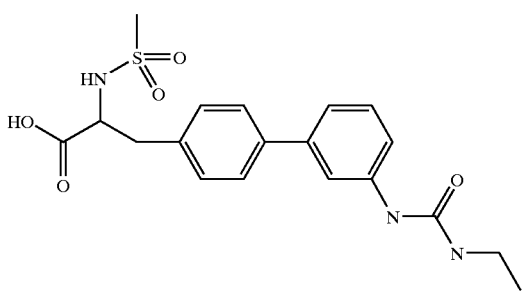

(2R,S)-3-[3'-(3-Ethyl-ureido)-biphenyl-3-yl]-2-methylsulfonylamino-propanoic acid is prepared according to the procedure of example 1.1, with the exception that methylsulfonyl chloride is used as a sulfonylating reagent instead of 2,4,6-trimethylbenzenesulfonyl chloride and ethylamine is used as an amine reagent instead of propylamine.

Mass spectrometry (ESI): 406.

Retention time (HPLC): $R_t$=6,8

$^1$H-NMR (400 MHz, methanol) δ7,67 (s, 1H), 7,56 (d, 2H), 7,35 (d, 2H), 7,28 (m, 2H), 7,20 (d, 1H), 4,27 (dd, 1H, J=5,0 Hz, J=8,8 Hz, H-2), 3,23 (q, 2H, J=7,4 Hz), 3,21 (dd, 1H, J=5,0 Hz, J=14,0 Hz, H-3a), 2,96 (dd, 1H, J=9,0 Hz, J=14,0 z, H-3b), 1,16 (t, 3H, J=7,0 Hz).

Example 1.46

(2R,S)-3-{3'-[3-(2-Methyl-butyl)-ureido]-biphenyl-4-yl}-2-(2,6-dichloro-benzenesulfonylamino)-propanoic acid

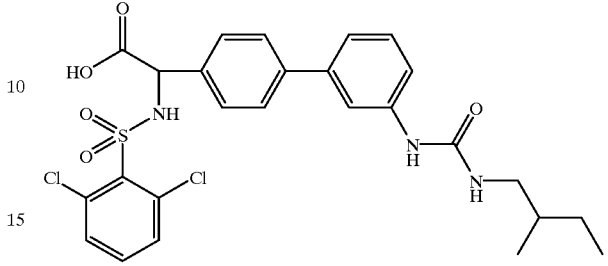

(2R,S)-3-{3'-[3-(2-Methyl-butyl)-ureido]-biphenyl-4-yl}-2-(2,6-dichloro-benzenesulfonylamino)-propanoic acid is prepared according to the procedure of example 1.1, with the exception that 2,6-dichlorobenzenesulfonyl chloride is used as a sulfonylating reagent instead of 2,4,6-trimethylbenzenesulfonyl chloride and 2-methylbutylamine is used as an amine reagent instead of propylamine.

Mass spectrometry (ESI):

Retention time (HPLC): $R_t$=10,9

$^1$H-NMR (400 MHz, methanol) δ=7,64 (s, 1H), 7,35–7,09 (m, 10H), 4,29 (dd, 1H, J=4,2 Hz, J=10,8 Hz, H-2), 3,20 (dd, 1H, J=4,4 Hz, J=14,0 Hz, H-3a), 3,18 (dd, 1H, J=6,2 Hz, J=15,4 Hz), 3,05 (dd, 1H, J=7,0 Hz, J=15,4 Hz), 2,84 (dd, 1H, J=10,8 Hz, J=14,0 Hz, H-3b), 1,58 (m, 1H), 1,48 (m, 1H), 1,21 (m, 1H), 0,96 (t, 3H, J=7,4 Hz), 0,96 (d, 3H, J=6,8 Hz).

Example 1.47

(2S)-3-[3'-(3-Pyridin-4-yl-ureido)-biphenyl-4-yl]-2-[(S)-campher-10-yl-sulfonylamino]-propanoic acid

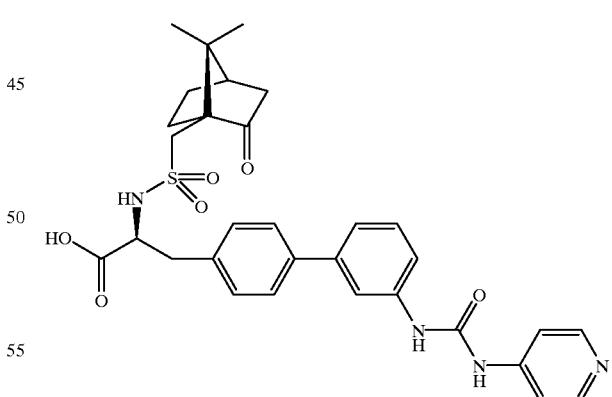

(2S)-3-[3'-(3-Pyridin-4-yl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 4-aminopyridine is used as an amine reagent instead of propylamine.

Mass spectrometry (ESI): 577.

Retention time (HPLC): $R_t$=7,9

$^1$H-NMR (400 MHz, methanol) δ=7,49 (d, 2H), 8,03 (d, 2H), 7,81 (s, 1H), 7,59 (d, 2H), 7,48–7,32 (m, 5H), 4,33 (dd, 1H, J=4,8 Hz, J=9,4 Hz, H-2), 3,26 (dd, 1H, J=4,8 Hz, H-3a), 3,06 (d, 1H, J=15,2 Hz), 2,95 (dd, 1H, J=9,4 Hz, J=14,0 Hz, H-3b), 2,68 (d, 1H, J=15,2 Hz), 2,29 (m, 1H), 2,22 (m, 1H), 1,98 (m, 2H), 1,85 (d, 1H, J=18,8 Hz), 1,60 (m, 1H), 1,36 (m, 1H), 0,93 (s, 3H), 0,68 (s, 3H).

Example 1.48

(2S)-3-[3'-(3-iso-Butyl-ureido)-biphenyl-4-yl]-2-[(S)-campher-10-yl-sulfonylamino]-propanoic acid

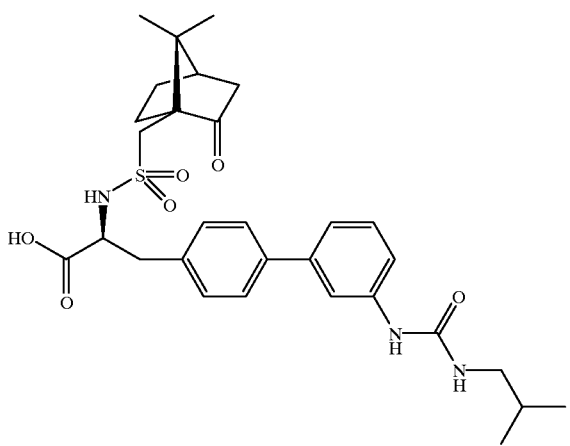

(2S)-3-[3'-(3-iso-Butyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and iso-butylamine is used as an amine reagent instead of propylamine.

Mass spectrometry (ESI): 570.

Retention time (HPLC): $R_t$=10,0

$^1$H-NMR (400 MHz, methanol) δ=7,64 (s, 1H,1H'), 7,56 (d, 2H, 2H'), 7,38 (d, 2H, 2H'), 7,29 (m, 2H, 2H'), 7,20 (m, 1H, 1H'), 4,33 (dd, 1H'), 4,30 (dd, 1H,'), 3,24 (d, 1H), 3,23 (d, 1H'), 3,15 (d, 1H), 3,05 (d, 1H'), 3,03 (d, 2H, 2H'), 2,95 (dd, 1H), 2,93 (dd, 1H'), 2,66 (d, 1H), 2,46 (d, 1H'), 2,25 (m, 2H, 2H'), 1,97 (m, 2H, 2H'), 1,84 (d, 1H), 1,83 (d, 1H'), 1,78 (m, 1H, 1H'), 1,59 (m, 1H), 1,50 (m, 1H'), 1,35 (m, 2H, 2H'), 0,95 (d, 6H, 6H'), 0,94 (s, 3H), 0,92 (s, 3H'), 0,67 (s, 3H), 0,64 (s, 3H').

Example 1.49

(2R,S)-3-[3'-(3-Ethyl-ureido)-biphenyl-4-yl]-2-[(S)-campher-10-yl-sulfonylamino]-propanoic acid

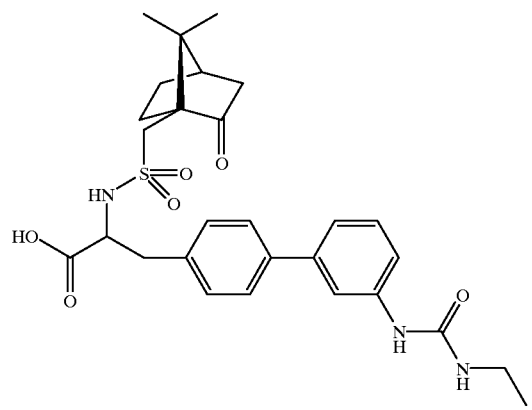

(2R,S)-3-[3'-(3-Ethyl-ureido)-biphenyl-4-yl]-2-[(S)-campher-10-yl-sulfonylamino]-propanoic acid is prepared according to the procedure of example 1.1, with the exception that (S)-(+)-campher-10-sulfonyl chloride is used as a sulfonylating reagent instead of 2,4,6-trimethylbenzenesulfonyl chloride and ethylamine is used as an amine reagent instead of propylamine.

Mass spectrometry (ESI): 542.

Retention time (HPLC): $R_t$=8,9

$^1$H-NMR (400 MHz, methanol) δ=7,64 (s, 1H, 1H'), 7,56 (d, 2H, 2H'), 7,38 (d, 2H, 2H'), 7,29 (d, 2H, 2H'), 7,20 (m, 1H, 1H'), 4,32 (dd, 1H), 4,31 (dd, 1H'), 3,23 (m, 3H, 3H'), 3,15 (d, 1H), 3,04 (d, 1H'), 2,95 (dd, 1H), 2,92 (d, 1H'), 2,66 (d, 1H), 2,47 (d, 1H'), 2,25 (m, 2H, 2H'), 1,97 (m, 2H, 2H'), 1,84 (d, 1H), 1,83 (d, 1H'), 1,60 (m, 1H), 1,50 (m, 1H'), 1,34 (m, 1H, 1H'), 1,15 (t, 3H, 3H'), 0,94 (s, 3H), 0,92 (s, 3H'), 0,67 (s, 3H), 0,64 (s, 3H').

Example 1.50

(2R,S)-3-[3'-(3-Pyridin-4-yl-ureido)-biphenyl-4-yl]-2-ethyloxycarbonylamino-propanoic acid

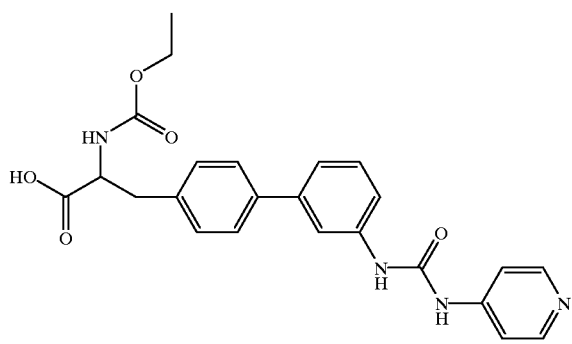

(2R,S)-3-[3'-(3-Pyridin-4-yl-ureido)-biphenyl-4-yl]-2-ethyloxycarbonylamino-propanoic acid is prepared according to the procedure of example 1.1, with the exception that ethyl chloroformate is used as a carbamoylating reagent instead of 2,4,6-trimethylbenzenesulfonyl chloride as a sulfonylating reagent and 4-aminopyridine is used as an amine reagent instead of propylamine.

Mass spectrometry (ESI): 449. $R_t$=6,4

$^1$H-NMR (400 MHz, methanol) δ=8,47 (d, 2H), 7,92 (d, 2H), 7,77 (s, 1H), 7,55 (d, 2H), 7,45 (m, 1H), 7,40 (dd, 1H), 7,35 (m, 1H), 7,33 (d, 2H), 4,43 (dd, 1H, J=4,8 Hz, J=9,0 Hz, H-2), 4,03 (q, 2H, J=7,0 Hz), 3,24 (dd, 1H, J=4,8 Hz, J=14,0 Hz H-3a), 2,98 (dd, 1H, J=9,0 Hz, J=14,0 Hz, H-3b), 1,19 (t, 3H, J=7,0 Hz).

Example 1.51

(2S)-3-[3'-(3-Propyl-ureido)-biphenyl-4-yl]-2-ureido-propanoic acid

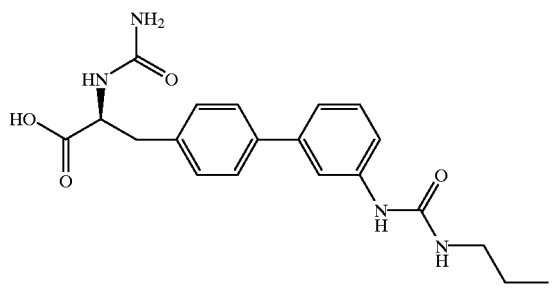

(2S)-3-[3'-(3-Propyl-ureido)-biphenyl-4-yl]-2-ureido-propanoic acid is prepared according to the procedure of example 1.1, with the exception that 4-nitrophenyl chloroformate and 2,4-dimethoxybenzylamine were used as urea forming reagent instead of 2,4,6-trimethylbenzenesulfonyl chloride as a sulfonylating reagent.

Mass spectrometry (ESI): 385.

Retention time (HPLC): $R_t$=6,4

$^1$H-NMR (400 MHz, methanol) δ7,63 (s, 1H), 7,53 (d, 2H), 7,30 (m, 4H), 7,21 (m, 1H), 4,54 (m, 1H, H-2), 3,19 (t, 2H, J=7,2 Hz), 3,16 (m, 1H, H-3a), 3,06 (dd, 1H, J=7,0 Hz, J=13,8 Hz, H-3b), 1,58 (m, 2H), 0,98 (t, 3H, 7,0 Hz).

Example 1.52

(2R,S)-3-[3'-(3-Cyclohexyl-ureido)-biphenyl-4-yl]-2-(3-cyclohexyl-ureido)-propanoic acid

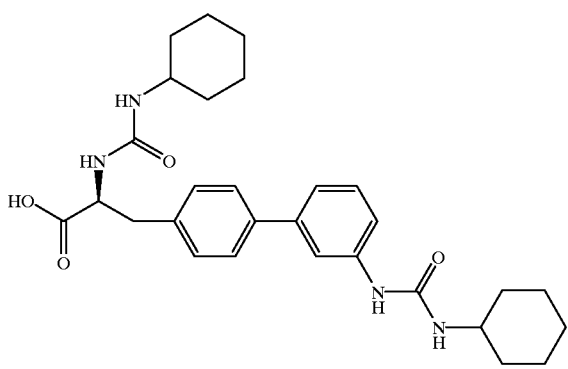

(2R,S)-3-[3'-(3-Cyclohexyl-ureido)-biphenyl-4-yl]-2-(3-cyclohexyl-ureido)-propanoic acid is prepared according to the procedure of example 1.1, with the exception that 4-nitrophenyl chloroformate and cylohexylamine were used as urea forming reagent instead of 2,4,6-trimethylbenzenesulfonyl chloride as a sulfonylating reagent and cyclohexylamine is used as an amine reagent instead of propylamine.

Mass spectrometry (ESI): 507.

Retention time (HPLC): $R_t$=10,6

$^1$H-NMR (400 MHz, methanol) δ=7,65 (s, 1H), 7,52 (d, 2H), 7,27 (m, 4H), 7,19 (m, 1H), 4,58 (dd, 1H, J=5,0 Hz, J=7,4 Hz, H-2), 3,58 (m, 1H), 3,42 (m, 1H), 3,17 (dd, 1H, J=5,0 Hz, J=14,0 Hz, H-3a), 3,02 (dd, 1H, J=7,4 Hz, J=14,0 Hz, H-3b), 2,02–1,05 (m, 20H).

Example 1.53

(2S)-3-[3'-(3-Pyridin-4-ylmethyl-ureido)-biphenyl-4-yl]-2-[(S)-campher-10-yl-sulfonylamino]-propanoic acid

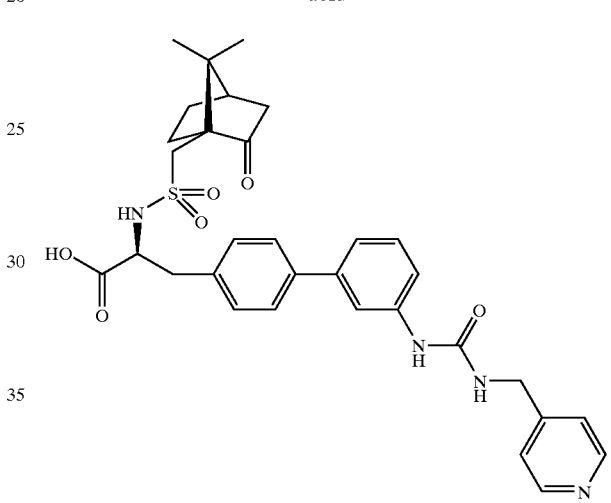

(2S)-3-[3'-(3-Pyridin-4-ylmethyl-ureido)-biphenyl-4-yl]-2-[(S)-campher-10-ylsulfonylamino]-propanioc acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 4-aminomethylpyridine is used as an amine reagent instead of propylamine.

Mass spectrometry (ESI): 605.

Retention time (HPLC): $R_t$=7,0

$^1$H-NMR (400 MHz, methanol) δ=8,74 (d, 2H), 8,02 (d, 2H), 7,69 (s, 1H), 7,57 (d, 2H), 7,39 (d, 2H), 7,31 (m, 2H), 7,25 (m, 1H), 4,68 (s, 2H), 4,32 (dd, 1H, H-2), 3,22 (dd, 1H, H-3a), 3,06 (d, 1H), 2,93 (dd, 1H, H-3b), 2,69 (d, 1H), 2,28 (m, 1H), 2,20 (m, 1H), 2,01 (m, 1H), 1,95 (m, 1H), 1,83 (d, 1H), 1,59 (ddd, 1H), 1,39 (m, 1H), 0.92 (s, 3H), 0,68 (s, 3H).

Example 1.54

(2S)-3-[3'-(3-Pyridin-2-yl-ureido)-biphenyl-4-yl]-2-[(S)-campher-10-yl-sulfonylamino]-propanoic acid

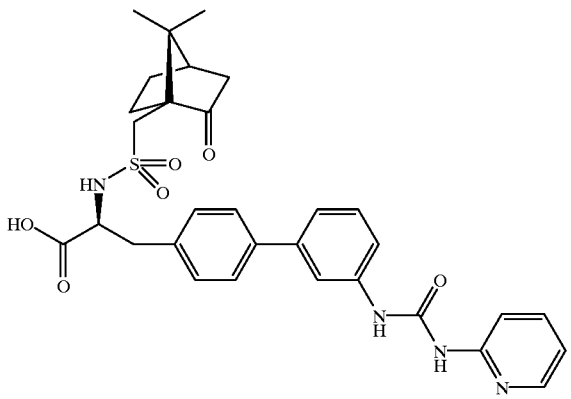

(2S)-3-[3'-(3-Pyridin-2-yl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 2-aminopyridine is used as an amine reagent instead of propylamine.

Mass spectrometry (ESI): 591.

Retention time (HPLC): $R_t$=8,2

$^1$H-NMR (400 MHz, methanol) δ=8,29 (d, 1H), 8,03 (dd, 1H), 7,82 (s, 1H), 7,61 (d, 2H), 7,49 (m, 1H), 7,42–7,29 (m, 5H), 7,22 (dd, 1H), 4,32 (dd, 1H, H-2), 3,26 (dd, 1H, H-3a), 3,06 (d, 1H), 2,93 (dd, 1H, H-3b), 2,68 (d, 1H), 2,28 (m, 1H), 2,22 (m, 1H), 2,01 (m, 1H), 1,94 (m, 1H), 1,83 (d, 1H), 1,59 (ddd, 1H), 1,36 (m, 1H), 0,93 (s, 3H), 0,68 (s, 3H).

Example 1.55

(2S)-3-[3'-(3-Methyl-ureido)-biphenyl-4-yl]-2-[(S)-campher-10-yl-sulfonylamino]-propanoic acid

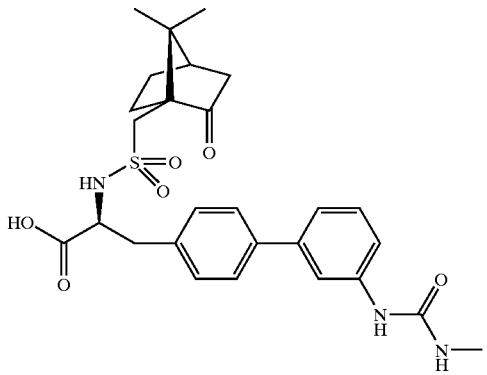

(2S)-3-[3'-(3-Methyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and methylamine is used as an amine reagent instead of propylamine.

Mass spectrometry (ESI): 528.

Retention time (HPLC): $R_t$=8,3

$^1$H-NMR(400 MHz, methanol) δ=7,63 (s, 1H), 7,57 (d, 2H), 7,38 (d, 2H), 7,29 (m, 2H), 7,20 (m, 1H), 4,32 (dd, 1H, H-2), 3,23 (dd, 1H, H-3a), 3,06 (d, 1H), 2,93 (dd, 1H, H-3b), 2,77 (s, 3H), 2,67 (d, 1H), 2,29 (m, 1H), 2,21 (m, 1H), 2,02 (m, 1H), 1,95 (m, 1H), 1,85 (d, 1H), 1,60 (ddd, 1H), 1,35 (m, 1H), 0,92 (s, 3H), 0,67 (s, 3H).

Example 1.56

(2R,S)-3-[3'-(3-Phenyl-ureido)-biphenyl-4-yl]-2-[(S)-campher-10-yl-sulfonylamino]-propanoic acid

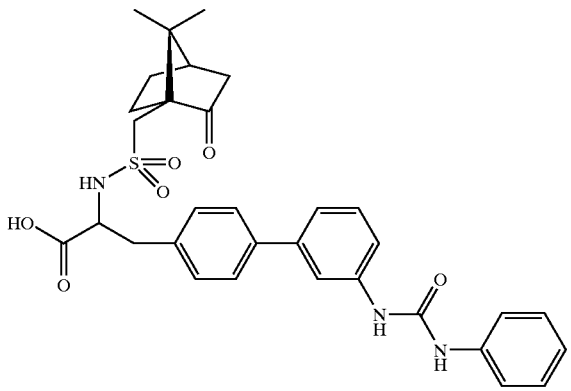

(2R,S)-3-[3'-(3-Phenyl-ureido)-biphenyl-4-yl]-2-[(S)-campher-10-yl-sulfonylamino]-propanoic acid is prepared according to the procedure of example 1.1, with the exception that (S)-(+)-campher-10-sulfonyl chloride is used as a sulfonylating reagent instead of 2,4,6-trimethylbenzenesulfonyl chloride and anilin is used as an amine reagent instead of propylamine.

Mass spectrometry (ESI): 590.

Retention time (HPLC): $R_t$=10,5

$^1$H-NMR (400 MHz, methanol) δ=7,72 (s, 1H, 1H'), 7,59 (d, 2H, 2H'), 7,47–7,22(m, 9H, 9H'), 7,01 (m, 1H, 1H'), 4,33 (dd, 1H, H-2), 4,32 (dd, 1H', H'-2), 3,23 (dd, 1H, H-3a), 3,22 (dd, 1H', H'-3a), 3,16 (d, 1H), 3,05 (d, 1H'), 2,97 (dd, 1H, H-3b), 1,94 (dd, 1H', H'-3b), 2,67 (d, 1H), 2,48 (d, 1H'), 2,29 (m, 1H, 1H'), 2,21 (m, 1H, 1H'), 2,00 (m, 1H, 1H'), 1,94 (m, 1H, 1H'), 1,85 (d, 1H), 1,84 (d, 1H'), 1,60 (ddd, 1H), 1,50 (ddd, 1H'), 1,37 (m, 1H, 1H'), 0,93 (s, 3H), 0,91 (s, 3H'), 0,68 (s, 3H), 0,66 (s, 3H').

Example 1.57

(2S)-3-[3'-(3-Methyl-ureido)-biphenyl-4-yl]-2-methylsulfonylamino-propanoic acid

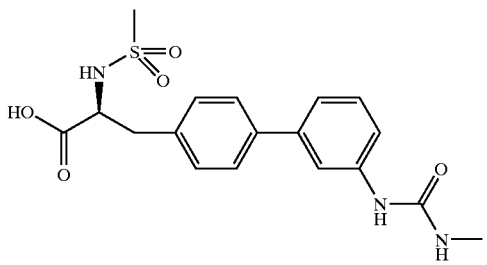

(2S)-3-[3'-(3-Methyl-ureido)-biphenyl-4-yl]-2-methylsulfonylamino-propanoic acid is prepared according to the procedure of example 1.1, with the exception that (2S)-3-(4-bromophenyl)-2-(9-acid is used as an acid reagent instead of (2R,S)-3-(4-bromophenyl)-2-(9-fluorenylmethoxycarbonylamino)-propanoic acid, methylsulfonyl chloride is used as a sulfonylating reagent instead of 2,4,6-trimethylbenzenesulfonyl chloride and methylamine is used as an amine reagent instead of propylamine.

Mass spectrometry (ESI): 392.

Retention time (HPLC): $R_t$=5,8

$^1$H-NMR (400 MHz, methanol) δ=7,68 (s, 1H), 7,57 (d, 2H), 7,36 (d, 2H), 7,28 (m, 2H), 7,20 (m, 1H), 4,28 (dd, 1H, H-2), 3,21 (dd, 1H, H-3a), 2,97 (dd, 1H, H-3b), 2,78 (s, 3H), 2,68 (s, 3H).

Example 1.58

(2S)-3-[3'-(3-Propyl-ureido)-biphenyl-4-yl]-2-methylsulfonylamino-propanoic acid

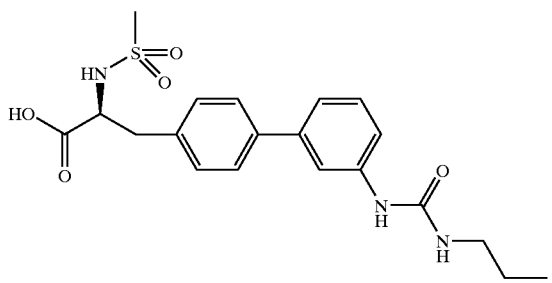

(2S)-3-[3'-(3-Propyl-ureido)-biphenyl-4-yl]-2-methylsulfonylamino-propanoic acid is prepared according to the procedure of example 1.1, with the exception that (2S)-3-(4-bromophenyl)-2-(9-acid is used as an acid reagent instead of (2R,S)-3-(4-bromophenyl)-2-(9-fluorenylmethoxycarbonylamino)-propanoic acid, methylsulfonyl chloride is used as a sulfonylating reagent instead of 2,4,6-trimethylbenzenesulfonyl chloride.

Mass spectrometry (ESI): 420.

Retention time (HPLC): $R_t$=7,1

$^1$H-NMR (400 MHz, methanol) δ=7,68 (s, 1H), 7,57 (d, 2H), 7,36 (d, 2H), 7,28 (m, 2H), 7,20 (m, 1H), 4,28 (dd, 1H, H-2), 3,21 (dd, 1H, H-3a), 3,17 (t, 2H), 2,97 (dd, 1H, H-3b), 2,68 (s, 3H), 1,56 (m, 2H), 0,97 (t, 3H).

Example 1.59

(2S)-3-[3'-(3-Pyridin-3-ylmethyl-ureido)-biphenyl-4-yl]-2-ethyloxycarbonylamino-propanoic acid

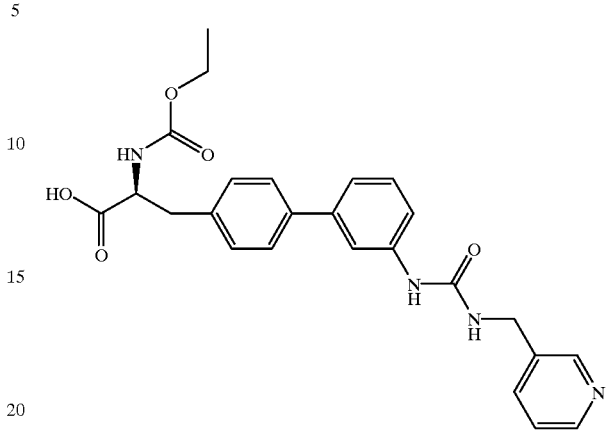

(2S)-3-[3'-(3-Pyridin-3-ylmethyl-ureido)-biphenyl-4-yl]-2-ethyloxycarbonylamino-propanoic acid is prepared according to the procedure of example 1.1, with the propanoic acid is used as an acid reagent instead of (2R,S)-3-(4-bromophenyl)-2-(9-fluorenylmethoxycarbonylamnino)-propanoic acid, ethyl chloroformate is used as a carbamoylating reagent instead of 2,4,6-trimethylbenzenesulfonyl chloride as a sulfonylating reagent and 3-aminomethylpyridine is used as an amine reagent instead of propylamine.

Mass spectrometry (ESI): 449.

Retention time (HPLC): $R_t$=6,0

$^1$H-NMR (400 MHz, methanol) δ=8,78 (s, 1H), 8,67 (s, 1H), 8,48 (d, 1H), 7,96 (m, 1H), 7,68 (s, 1H), 7,52 (d, 2H), 7,30 (m, 4H), 7,23 (m, 1H), 4,57 (s, 2H), 4,41 (dd, 1H, H-2), 4,02 (q, 2H), 3,31 (dd, 1H, H-3a), 2,96 (dd, 1H, H-3b), 1,18 (t, 3).

Example 1.60

(2S)-3-[3'-(3-Pyridin-4-ylmethyl-ureido)-biphenyl-4-yl]-2-ethyloxycarbonylamino-propanoic acid

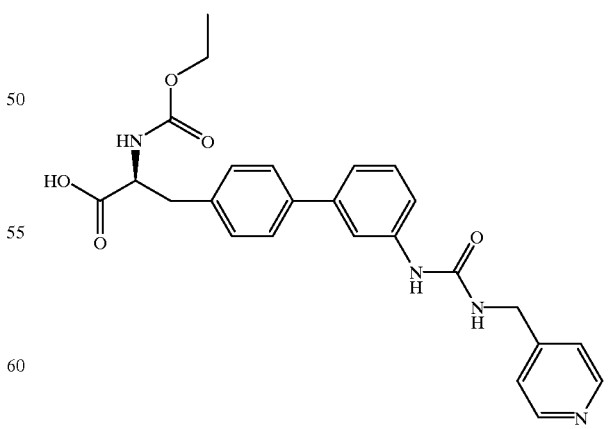

(2S)-3-[3'-(3-Pyridin-4-ylmethyl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and 4-amninomethylpyridine is used as an amine reagent instead of propylamine.

Mass spectrometry (ESI): 449.

Retention time (HPLC): $R_t$=5,3

$^1$H-NMR (400 MHz, methanol) δ=8,72 (d, 2H), 7,95 (d, 2H), 7,67 (s, 1H), 7,50 (d, 2H), 7,34–7,21 (m, 5H), 4,64 (s, 2H), 4,42 (dd, 1H, H-2), 4,02 (q, 2H), 3,21 (dd, 1H, H-3a), 2,96 (dd, 1H, H-3b), 1,20 (t, 3H).

Example 1.61

(2S)-3-[3'-(3-Propyl-ureido)-biphenyl-4-yl]-2-ethyloxycarbonylamino-propanoic acid

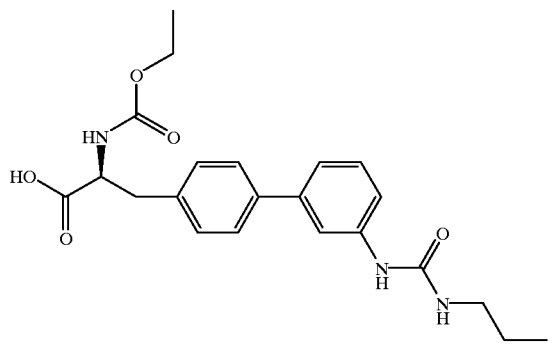

(2S)-3-[3'-(3-Propyl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid and ethyl chloroformate is used as a carbamoylating reagent instead of 2,4,6-trimethylbenzenesulfonyl chloride as a sulfonylating reagent.

Mass spectrometry (ESI): 414.

Retention time (HPLC): $R_t$=8,5

$^1$H-NMR (400 MHz, methanol) δ=7,65 (s, 1H), 7,54 (d, 2H), 7,31 (m, 4H), 7,20 (m, 1H), 4,42 (dd, 1H, H-2), 4,03 (q, 2H), 3,21 (dd, 1H, H-3a), 3,17 (t, 2H), 2,97 (dd, 1H, H-3b), 2,57 (m, 2H), 1,18 (t, 3H), 0,96 (t, 3H).

Example 1.62

(2S)-3-[3'-(3-Methyl-ureido)-biphenyl-4-yl]-2-ethyloxycarbonylamino-propanoic acid

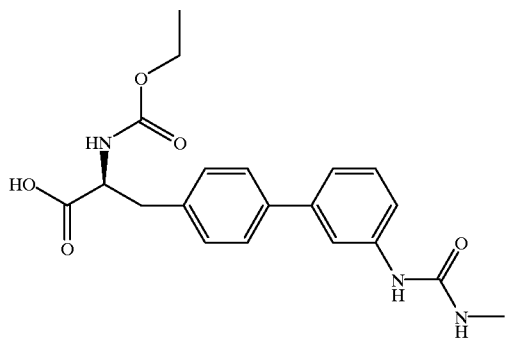

(2S)-3-[3'-(3-Methyl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and methylamine is used as an amine reagent instead of propylamnine.

Mass spectrometry (ESI): 386.

Retention time (HPLC): $R_t$=6,7

$^1$H-NMR (400 MHz, methanol) δ=7,65 (s, 1H), 7,52 (d, 2H), 7,30 (m, 4H), 7,21 (m, 1H), 4,42 (dd, 1H, H-2), 4,02 (q, 2H), 3,21 (dd, 1H, H-3a), 3,17 (t, 2H), 2,96 (dd, 1H, H-3b), 2,78 (s, 3H), 1,18 (t, 3H).

Example 1.63

(2S)-3-[3'-(3-Pyridin-2-yl-methyl-ureido)-biphenyl-4-yl]-2-[(S)-campher-10-yl-sulfonylamino]-propanoic acid

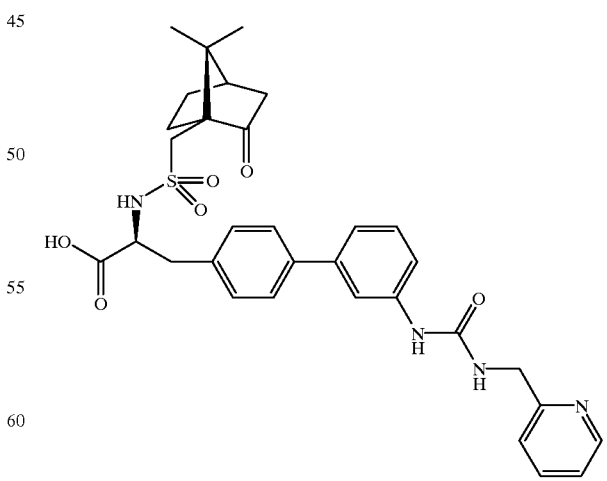

(2S)-3-[3'-(3-Pyridin-2-yl-methyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 2-aminomethylpyridine is used as an amine reagent instead of propylamine.

Mass spectrometry (ESI): 605.

Retention time (HPLC): $R_t$=6,9

$^1$H-NMR (400 MHz, methanol) δ=8,78 (s, 1H), 8,69 (s, 1H), 8,45 (d, 1H), 7,92 (dd, 1H), 7,67 (s, 1H), 7,54 (d, 2H), 7,38 (d, 2H), 7,29 (m, 2H), 7,23 (m, 1H), 4,58 (s, 2H), 4,32 (dd, 1H, H-2), 3,23 (dd, 1H, H-3a), 3,08 (d, 1H), 2,94 (dd, 1H, H-3b), 2,68 (d, 1H), 2,28 (m, 1H), 2,21 (m, 1H), 2,01 (m, 1H), 1,95 (m, 1H), 1,83 (d, 1H), 1,59 (ddd, 1H), 1,38 (m, 1H), 0,93 (s, 3H), 0,67 (s, 3H).

Example 1.64

(2S)-3-[3'-(3-Pyridin-3-yl-methyl-ureido)-biphenyl-4-yl]-2-[(S)-campher-10-yl-sulfonylamino]-propanoic acid

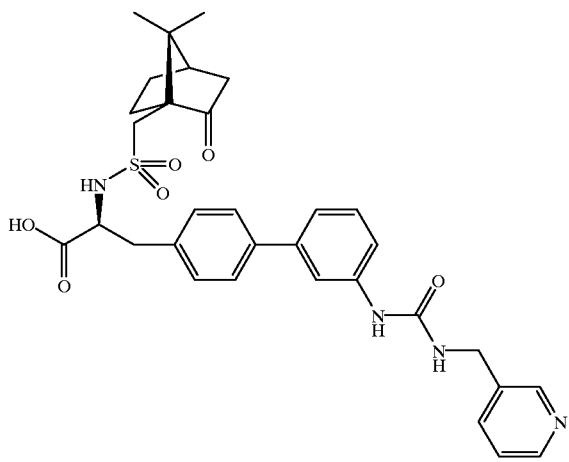

(2S)-3-[3'-(3-Pyridin-3-yl-methyl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 3-aminomethylpyridine is used as an amine reagent instead of propylamine.

Mass spectrometry (ESI): 605.

Retention time (HPLC): $R_t$=6,7

$^1$H-NMR (400 MHz, methanol) δ=8,67 (d, 1H), 8,38 (d, 1H), 7,90 (d, 1H), 7,78 (dd, 1H), 7,69 (s, 1H), 7,54 (d, 2H), 7,38 (d, 2H), 7,31 (m, 2H), 7,23 (m, 1H), 4,69 (s, 2H), 4,32 (dd, 1H, H-2), 3,23 (dd, 1H, H-3a), 3,08 (d, 1H), 2,94 (dd, 1H, H-3b), 2,68 (d, 1H), 2,28 (m, 1H), 2,21 (m, 1H), 2,01 (m, 1H), 1,95 (m, 1H), 1,83 (d, 1H), 1,59 (ddd, 1H), 1,38 (ddd, 1H), 0,93 (s, 3H), 0,67 (s, 3H).

Example 1.65

(2S)-3-[3'-(3-Pyridin-4-yl-ureido)-biphenyl-4-yl]-2-ethyloxycarbonylamino-propanoic acid

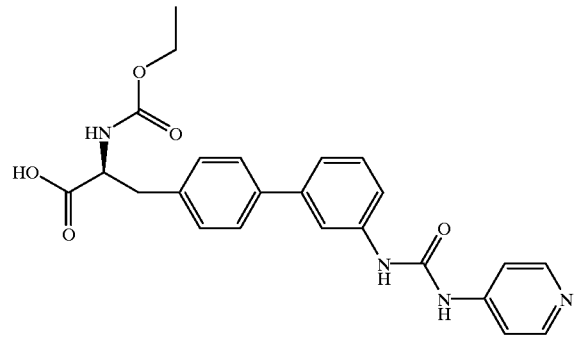

(2S)-3-[3'-(3-Pyridin-4-yl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and 4-aminopyridine is used as an amine reagent instead of propylamine.

Mass spectrometry (ESI): 449.

Retention time (HPLC): $R_t$=6,0

$^1$H-NMR (400 MHz, methanol) δ32 8,49 (d, 2H), 8,00 (d, 2H), 7,79 (s, 1H), 7,55 (d, 2H), 7,48–7,31 (m, 5H), 4,43 (dd, 1H, H-2), 4,01 (q, 2H), 3,23 (dd, 1H, H-3a), 2,95 (dd, 1H, H-3b), 1,19 (t, 3H).

Example 1.66

(2S)-3-[3'-(3-Pyridin-3-yl-ureido)-biphenyl-4-yl]-2-ethyloxycarbonylamino-propanoic acid

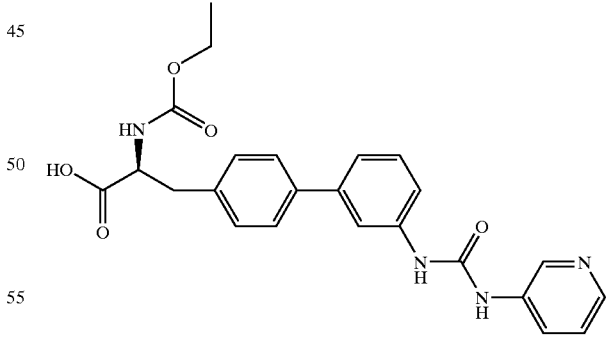

(2S)-3-[3'-(3-Pyridin-3-yl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and 3-aminopyridine is used as an amine reagent instead of propylamine.

Mass spectrometry (ESI): 449.

Retention time (HPLC): $R_t$=6,0

¹H-NMR (400 MHz, methanol) δ=9,18 (s, 1H), 8,39 (m, 1H), 8,30 (d, 1H), 7,85 (m, 1H), 7,77 (s, 1H), 7,57 (d, 2H), 7,45–7,29 (m, 5H), 4,42 (dd, 1H, H-2), 4,03 (q, 2H), 3,26 (dd, 1H, H-3a), 2,97 (dd, 1H, H-3b), 1,18 (t, 3H).

Example 1.67

(2S)-3-[3'-(3-Pyridin-2-yl-ureido)-biphenyl-4-yl]-2-ethyloxycarbonylamino-propanoic acid

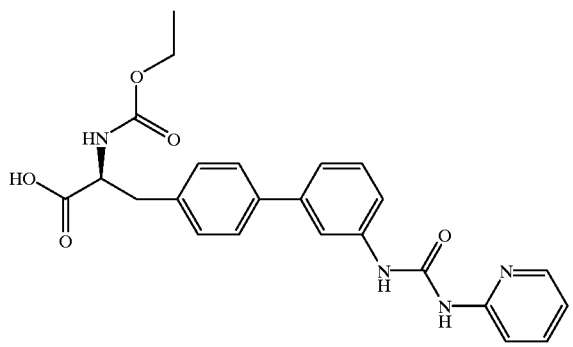

(2S)-3-[3'-(3-Pyridin-2-yl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and 2-aminopyridine is used as an amine reagent instead of propylamine.

Mass spectrometry (ESI): 449.

Retention time (HPLC): $R_t$=6,6

¹H-NMR (400 MHz, methanol) δ=8,31 (d, 1H), 8,06 (dd, 1H), 7,82 (s, 1H), 7,57 (d, 2H), 7,48 (d, 1H), 7,43–7,28 (m, 5H), 7,25 (dd, 1H), 4,42 (dd, 1H, H-2), 4,02 (q, 2H), 3,24 (dd, 1H, H-3a), 2,97 (dd, 1H, H-3b), 1,19 (t, 3H).

Example 1.68

(2S)-3-[3'-(3-Pyridin-2-yl-methyl-ureido)-biphenyl-4-yl]-2-ethyloxycarbonylamino-propanoic acid

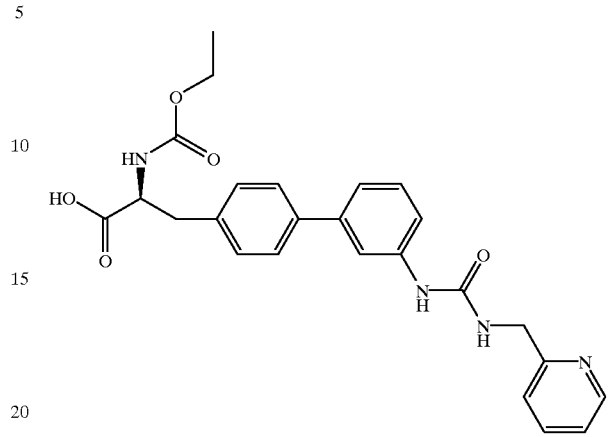

(2S)-3-[3'-(3-Pyridin-2-yl-methyl-ureido)-biphenyl-4-yl]-2-ethyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, ethyl chloroformate is used as a carbamoylating reagent instead of 2,4,6-trimethylbenzenesulfonyl chloride as a sulfonylating reagent and 2-aminomethylpyridine is used as an amine reagent instead of propylamine.

Mass spectrometry (ESI):

Retention time (HPLC): $R_t$=6,1

¹H-NMR (400 MHz, methanol) δ=8,68 (d, 1H), 8,40 (dd, 1H), 7,92 (d, 1H), 7,78 (dd, 1H), 7,68 (s, 1H), 7,52 (d, 2H), 7,33–7,22 (m, 5H), 4,70 (s, 2H), 4,41 (dd, 1H, H-2), 4,02 (q, 2H), 3,23 (dd, 1H, H-3a), 2,95 (dd, 1H, H-3b), 1,19 (t, 3H).

Example 1.69

(2S)-3-[3'-(3-Pyridin-3-yl-methyl-ureido)-biphenyl-4-yl]-2-methylsulfonylamino-propanoic acid

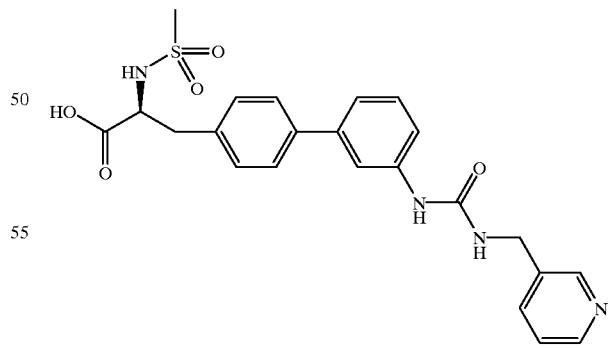

(2S)-3-[3'-(3-Pyridin-3-yl-methyl-ureido)-biphenyl-4-yl]-2-methylsulfonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9- fluorenylmethoxycarbonylamino)-propanoic acid, methylsulfonyl chloride is used as a sulfonylating reagent instead of 2,4,6-trimethylbenzenesulfonyl chloride and 3-aminomethylpyridine is used as an amine reagent instead of propylamine.

Mass spectrometry (ESI): 469.

Retention time (HPLC): $R_t$=4,5

$^1$H-NMR (400 MHz, methanol) δ=8,79(s, 1H), 8,70 (s, 1H), 8,50 (d, 1H), 7,96 (dd, 1H), 7,68 (s, 1H), 7,54 (d, 2H), 7,38–7,22 (m, 5H), 4,58 (s, 2H), 4,27 (dd, 1H, H-2), 3,22 (dd, 1H, H-3a), 2,96 (dd, 1H, H-3b), 2,70 (s, 3H).

Example 1.70

(2S)-3-[3'-(3-Pyridin-2-yl-methylureido)-biphenyl-4-yl]-2-methylsulfonylamino-propanoic acid

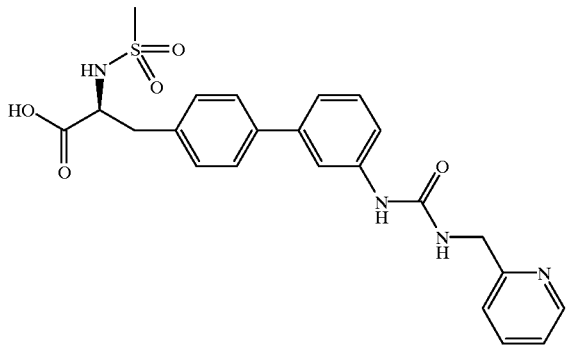

(2S)-3-[3'-(3-Pyridin-2-yl-methyl-ureido)-biphenyl-4-yl]-2-methylsulfonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, methylsulfonyl chloride is used as a sulfonylating reagent instead of 2,4,6-trimethylbenzenesulfonyl chloride and 2-aminomethylpyridine is used as an amine reagent instead of propylamine.

Mass spectrometry (ESI): 469.

Retention time (HPLC): $R_t$=4,6

$^1$H-NMR (400 MHz, methanol) δ=8,69 (d, 1H), 8,42 (dd, 1H), 7,93 (d, 1H), 7,81 (dd, 1H), 7,69 (s, 1H), 7,53 (d, 2H), 7,37–7,22 (m, 5H), 4,70 (s, 2H), 4,26 (dd, 1H, H-2), 3,21 (dd, 1H, H-3a), 2,95 (dd, 1H, H-3b), 2,69 (s, 3H).

Example 1.71

(2S)-3-[3'-(3-Pyridin-3-yl-ureido)-biphenyl-4-yl]-2-methylsulfonylamino-propanoic acid

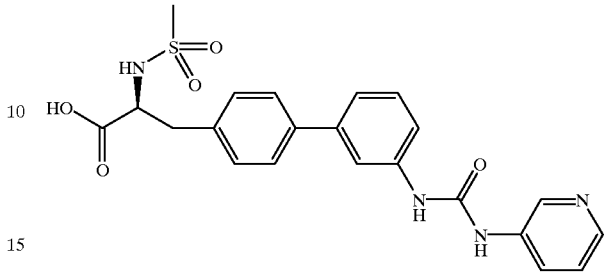

(2S)-3-[3'-(3-Pyridin-3-yl-ureido)-biphenyl-4-yl]-2-methylsulfonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, methylsulfonyl chloride is used as a sulfonylating reagent instead of 2,4,6-trimethylbenzenesulfonyl chloride and 3-aminopyridine is used as an amine reagent instead of propylamine.

Mass spectrometry (ESI): 455.

Retention time (HPLC): $R_t$=5,0

$^1$H-NMR (400 MHz, methanol) δ=9,08 (s, 1H), 8,37 (s, 1H), 8,23 (d, 1H), 7,78 (s, 2H), 7,58 (d, 2H), 7,42–7,30 (m, 5H), 4,29 (dd, 1H, H-2), 3,23 (dd, 1H, H-3a), 2,98 (dd, 1H, H-3b), 2,70 (s, 3H).

Example 1.72

(2S)-3-[3'-(3-Pyridin-2-yl-ureido)-biphenyl-4-yl]-2-methylsulfonylamino-propanoic acid

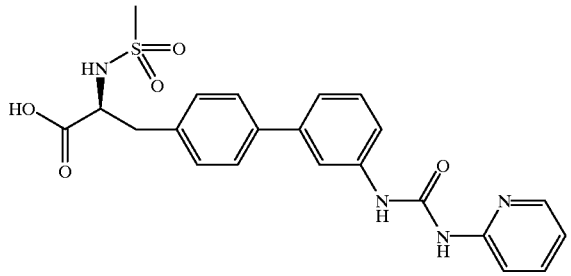

(2S)-3-[3'-(3-Pyridin-2-yl-ureido)-biphenyl-4-yl]-2-methylsulfonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, methylsulfonyl chloride is used as a sulfonylating reagent instead of 2,4,6-trimethylbenzenesulfonyl chloride and 2-aminopyridine is used as an amine reagent instead of propylamine.

Mass spectrometry (ESI): 455.

Retention time (HPLC): R$_t$=5,9

$^1$H-NMR (400 MHz, methanol) δ=8,31 (d, 1H), 7,85 (s, 1H), 7,60 (d, 2H), 7,47 (d, 1H), 7,42–7,23 (m, 6H), 7,12 (s, 1H), 4,28 (dd, 1H, H-2), 3,23 (dd, 1H, H-3a), 2,98 (dd, 1H, H-3b), 2,70 (s, 3H).

Example 1.73

(2S)-3-[3'-(3-Pyridin-3-yl-ureido)-biphenyl-4-yl]-2-[(S)-campher-10-yl-sulfonylamino]-propanoic acid

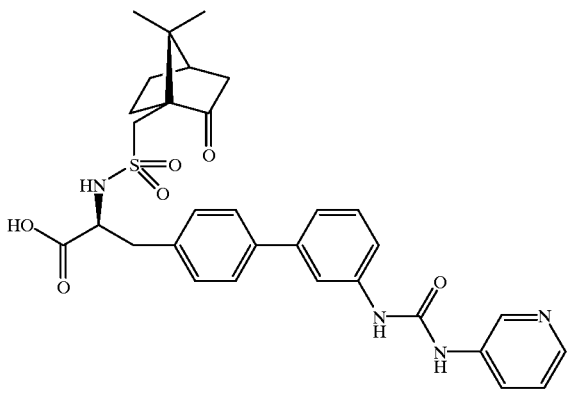

(2S)-3-[3'-(3-Pyridin-3-yl-ureido)-biphenyl-4-yl]-2-[(S)-campher-10-yl-sulfonylamino]-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, (S)-(+)-campher-10-sulfonyl chloride is used as a sulfonylating reagent instead of 2,4,6-trimethylbenzenesulfonyl chloride and 3-aminopyridine is used as an amine reagent instead of propylamine.

Mass spectrometry (ESI): 591.

Retention time (HPLC): R$_t$=7,1

$^1$H-NMR (400 MHz, methanol) δ=9,21 (s, 1H), 8,40 (d, 1H), 8,30 (d, 1H), 7,87 (dd, 1H), 7,78 (s, 1H), 7,59 (d, 2H), 7,42–7,31 (m, 5H), 4,33 (dd, 1H, H-2), 3,26 (dd, 1H, H-3a), 3,07 (d, 1H), 2,96 (dd, 1H, H-3b), 2,69 (d, 1H), 2,29 (m, 1H), 2,22 (m, 1H), 2,00 (m, 1H), 1,96 (m, 1H), 1,84 (d, 1H), 1,60 (ddd, 1H), 1,39 (m, 1H), 0,93 (s, 3H), 0,69 (s, 3H).

Example 1.74

(2S)-3-[3'-(3-sec-Butyl-ureido)-biphenyl-4-yl]-2-(2,4,6-trimethylbenzensulfonylamino)-propanoic acid

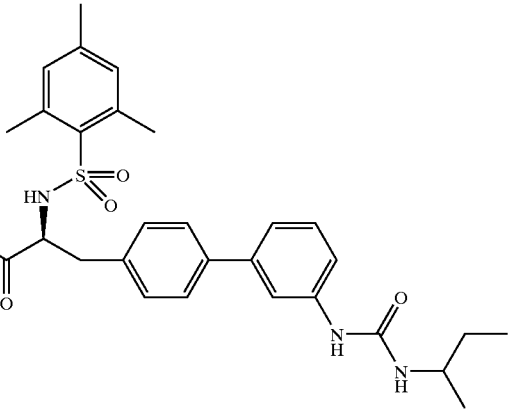

(2S)-3-[3'-(3-iso-Butyl-ureido)-biphenyl-4-yl]-2-(2,4,6-trimethylbenzensulfonylamino)-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid and sec-butylamine is used as an amine reagent instead of propylamine.

Mass spectrometry (ESI): 538.

Retention time (HPLC): R$_t$=10,6

$^1$H-NMR (400 MHz, methanol) δ=7,67 (s, 1H), 7,32 (m, 3H), 7,25 (d, 1H), 7,18 (d, 1H), 7,05 (d, 2H); 6,77 (s, 2H), 3,92 (dd, 1H, H-2), 3,74 (m, 1H), 3,08 (dd, 1H, H-3a), 2,79 (dd, 1H, H-3b), 2,43 (s, 6H), 2,05 (s, 3H), 1,52 (m, 2H), 1,17 (d, 3H), 0,97 (s, 3H).

Example 1.75

(2S)-3-[3'-(3-Pyridin-2-yl-methyl-ureido)-biphenyl-4-yl]-2-benzyloxycarbonylamino-propanoic acid

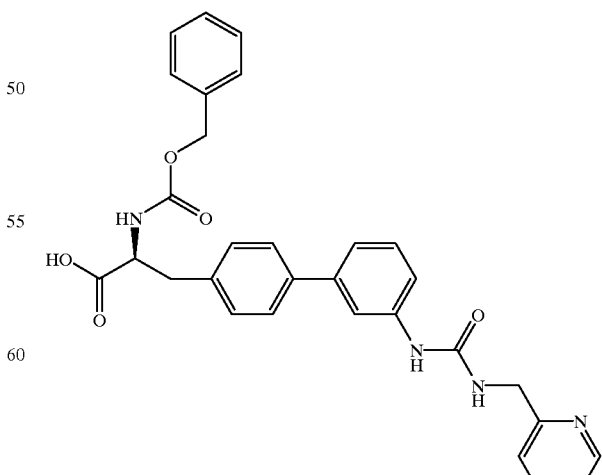

109

(2S)-3-[3'-(3-Pyridin-2-yl-methyl-ureido)-biphenyl-4-yl]-2-benzyloxycarbonylamino-propanoic acid is prepared according to the procedure of example 1.1, with the exception that (2S)-3-(4-bromophenyl)-2-(9-fluorenylmethoxycarbonylamino)-propanoic acid is used as an acid reagent instead of (2R,S)-3-(4-bromophenyl)-2-(9-fluorenylmethoxycarbonylamino)-propanoic acid, benzyl chloroformate is used as a carbamoylating reagent instead of 2,4,6-trimethylbenzenesulfonyl chloride as a sulfonylating reagent and 2-aminomethylpyridine is used as an amine reagent instead of propylamine.

Mass spectrometry (ESI): 525.

Retention time (HPLC): $R_t$=6,9

¹H-NMR (400 MHz, methanol) δ=8,49 (d, 1H), 7,84–7,18 (m, 16H), 5,07 (d, 1H), 4,99 (d, 1H), 4,53 (s, 2H), 4,32 (m, 1H, H-2), 3,25 (dd, 1H, H-3a), 2,96 (dd, 1H, H-3b).

Example 2

General synthesis scheme:

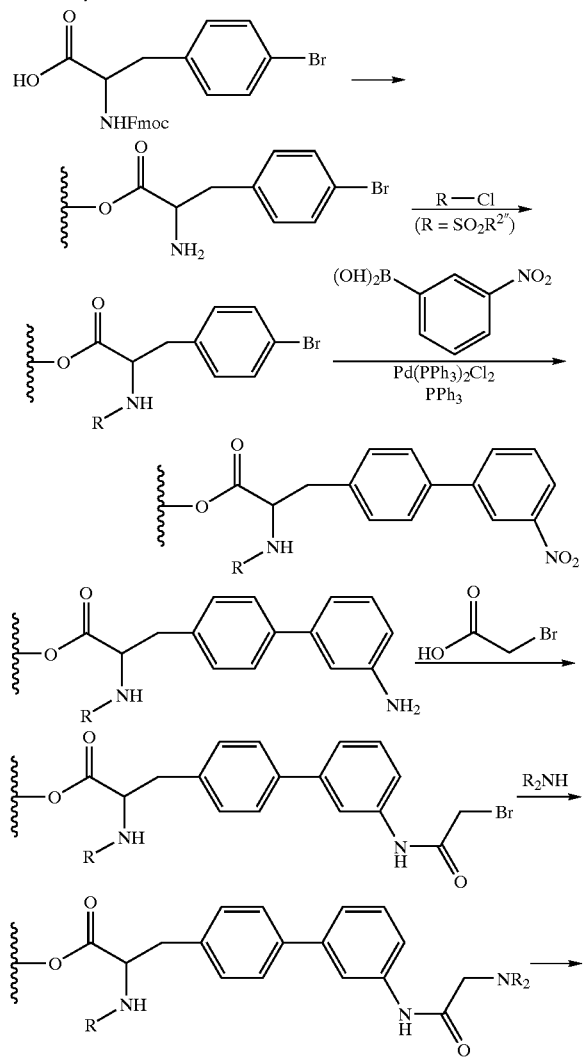

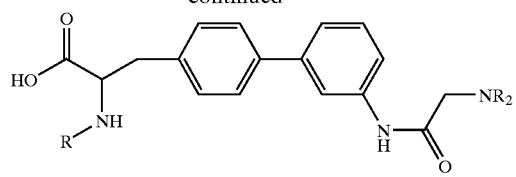

Example 2.1

(2R,S)-3-(3'-{2-[2-(1H-Imidazol-4-yl)-ethylamino]-acetylamino}-biphenyl-4-yl)-2-(2-chloro-benzenesulfonylamino)-propanoic acid

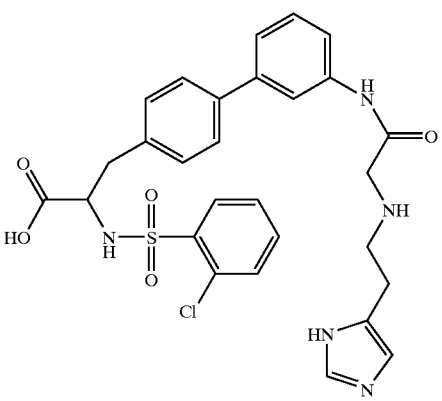

1.2 g of Wang polystyrene resin (Rapp-Polymere, Tübingen; loading 1.08 mmol/g) are swollen in dimethylformamide (DMF). The solvent is filtered off with suction and a solution of 1.088 g of (2R,S)-3-(4-bromophenyl)-2-(9-fluorenylmethoxycarbonylamino)-propanoic acid (acid reagent) in 20 ml of dimethylformamide (DMF) is added. After shaking at room temperature for 15 min, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution in dimethylformamide (DMF) and shaken at room temperature for 10 min. It is then washed 3 times with dimethylformamide (DMF) and a farther 15 ml of a 20% strength piperidine solution in dimethylformamide (DMF) are added. After shaking for 20 min it is washed with dimethylformamide (DMF) and tetrahydrofuran (THF). The resin is treated with a solution of 1.2 ml of diisopropylethylamine in 10 ml of tetrahydrofuran (THF) and a solution of 1.48 g of 2-chlorobenzenesulfonyl chloride (sulfonylation/carbamoylating reagent) in 10 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 1.80 g of bromoacetic acid in 20 ml of dimethylformamide (DMF) and a solution of 2.12 g of diisopropylcarbodiimide (DIC) in 5 ml of dimethylformamide (DMF). It is shaken at room temperature for 3 h and then filtered off with suction and washed with dimethylformamide (DMF). The resin is again treated with a solution of 1.80 g of bromoacetic acid in 20 ml of dimethylformamide (DMF) and a solution of 2.12 g of diisopropylcarbodiimide (DIC) in 5 ml of dimethylformamide (DMF) and shaken at room temperature for 3 h. It is then filtered off with suction and washed with dimethylformamide (DMF), methanol and dichloromethane. The resin is then treated with a solution of 2.02 g of 2-(imidazol-5-yl)-ethylamine (amine reagent) and 1.13 ml of diisopropylethylamine in 18 ml of dimethylformamide (DMF). It is stirred overnight and then washed with dimethylformamide (DMF), methanol and dichloromethane. For removal of the product, the resin is shaken with 10 ml of trifluoroacetic acid (TFA)/dichloromethane 1:1 for 1 h, filtered off, and the filtrate is concentrated in vacuo and purified on silica gel. 210 mg of the title compound are obtained.

Mass spectrometry (ESI): 583.
Retention time (HPLC): $R_t$=6.1.

Example 2.2

(2R,S)-3-{3'-[2-(2-Pyridin-2-yl-ethylamino)-acetylamino]-biphenyl-4-yl}-2-(4-trifluormethyl-benzenesulfonylamino)-propanoic acid

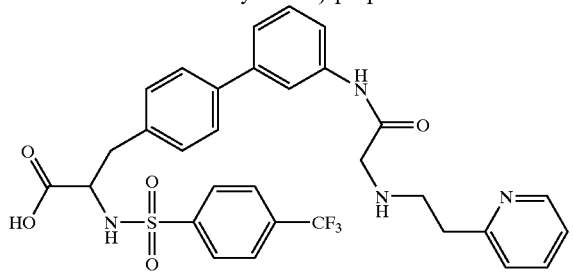

(2R,S)-3-{3'-[2-(2-Pyridin-2-yl-ethylamino)-acetylamino]-biphenyl-4-yl}-2-(4-trifluormethyl-benzenesulfonylamino)-propanoic acid is prepared according to the procedure of example 2.1, with the exception that 4-trifluoromethylbenzenesulfonyl chloride is used as a sulfonylating reagent instead of 2-chlorobenzenesulfonyl chloride and 2-(pyridin-2-yl)-ethylamine is used as an amine reagent instead of 2-(imidazol-5-yl)-ethylamine.

Mass spectrometry (ESI): 627.
Retention time (HPLC): $R_t$=7.3.

Example 2.3

(2R,S)-3-[3'-(2-Propylamino-acetylamino)-biphenyl-4-yl]-2-(4-trifluormethyl-benzenesulfonylamino)-propanoic acid

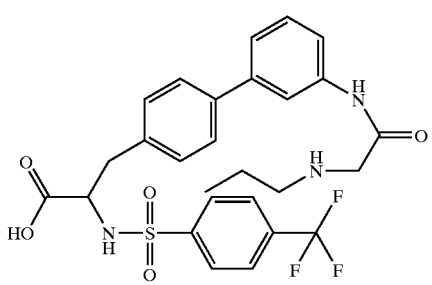

(2R,S)-3-[3'-(2-Propylamino-acetylamino)-biphenyl-4-yl]-2-(4-trifluormethylbenzenesulfonylamino)-propanoic acid is prepared according to the procedure of example 2.1, with the exception that 4-trifluoromethylbenzenesulfonyl chloride is used as a sulfonylating agent instead of 2-chlorobenzenesulfonyl chloride.

Mass spectrometry (ESI): 564.
Retention time (HPLC): $R_t$=8.2.
$^1$H-NMR (400 MHz, methanol) δ=7.88 (s,1H), 7.80 (d, 2H), 7.65 (d, 2H), 7.52 (d, 1H), 7.48–7.35 (m, 4H), 7.22 (d, 2H), 4.14 (dd, 1H, J=4.8 Hz, J=9.6 Hz, H-2), 4.00 (s, 2H), 3.16 (dd, 1H, J=5.0 Hz, J=14.0 Hz, H-3a), 3.08 (t, 2H, J=7.8 Hz), 2.87 (dd, 1H, J=9.6 Hz, J=14.0 Hz, H-3b), 1.78 (tq, 2H, J=7.8 Hz), 1.06 (t, 3H. J=7.6 Hz).

Example 2.4

(2R,S)-3-[3'-(2-Cyclopropylamino-acetylamino)-biphenyl-4-yl]-2-benzyloxycarbonylamino-propanoic acid

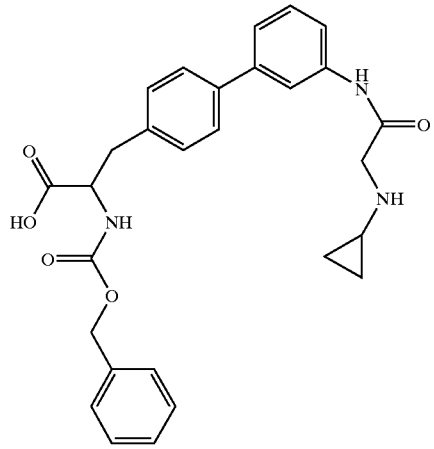

(2R,S)-3-[3'-(2-Cyclopropylamino-acetylamino)-biphenyl-4-yl]-2-benzyloxycarbonylamino-propanoic acid is prepared according to the procedure of example 2.1, with the exception that benzyl chloroformate is used as a carbamoylating reagent instead of 2-chlorobenzenesulfonyl chloride as a sulfonylating reagent and cyclopropylamine is used as an amine reagent instead of 2-(imidazol-5-yl)-ethylamine.

Mass spectrometry (ESI): 488.
Retention time (HPLC): $R_t$=7.6

Example 2.5

(2R,S)-3-[3'-(2-Pyrrolidin-1-yl-acetylamino)-biphenyl-4-yl]-2-benzyloxycarbonylamino-propanoic acid

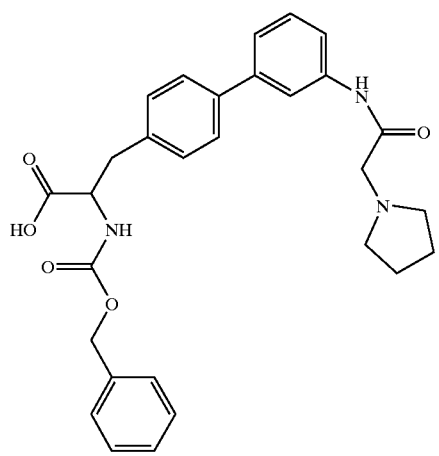

(2R,S)-3-[3'-(2-Pyrrolidin-1-yl-acetylamino)-biphenyl-4-yl]-2-benzyloxycarbonylamino-propanoic acid is prepared according to the procedure of example 2.1, with the exception that benzyl chloroformate is used as a carbamoylating reagent instead of 2-chlorobenzenesulfonyl chloride as a sulfonylating reagent and pyrrolidine is used as an amine reagent instead of 2-(imidazol-5-yl)-ethylamine.

Mass spectrometry (ESI): 502.
Retention time (HPLC): $R_t$=7.7.

Example 3

General synthesis scheme:

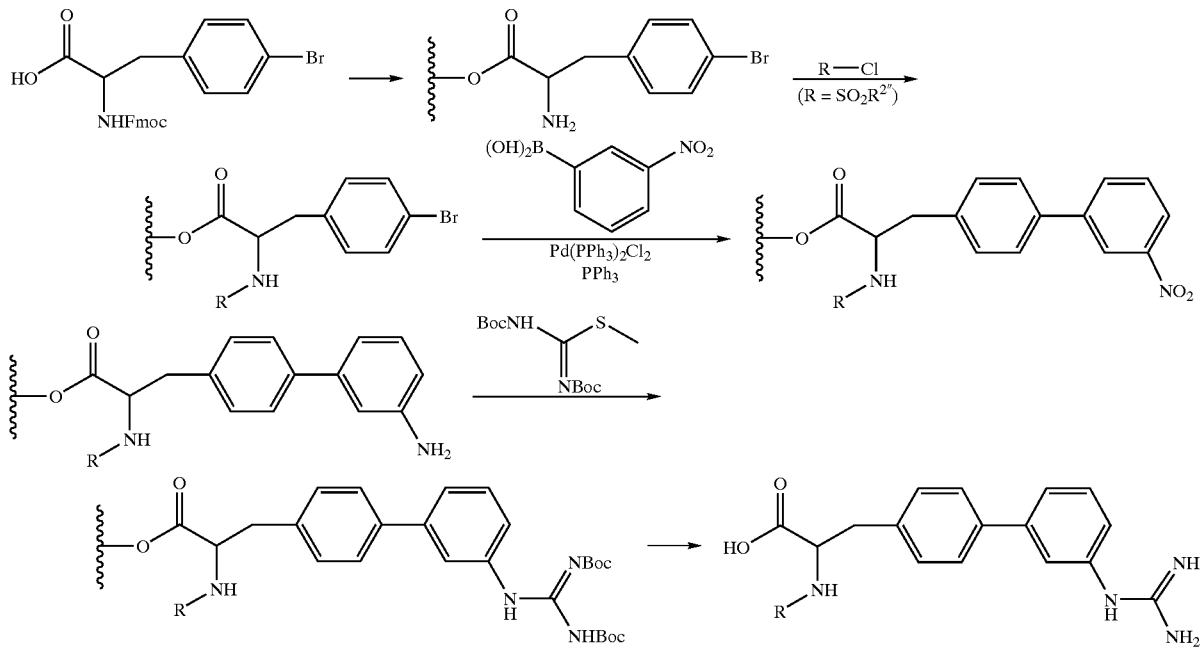

Example 3.1

(2R,S)-3-(3-Guanidino-biphenyl-4-yl)-2-(2,4,6-trimethylbenzenesulfonylamino)-propanoic acid

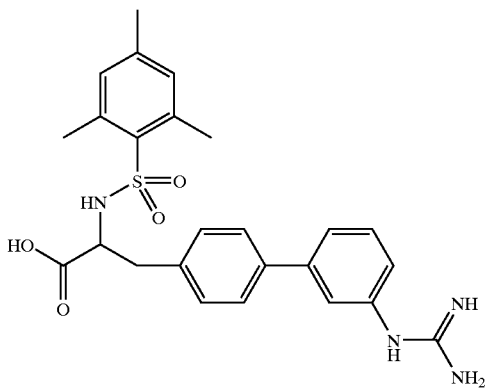

1.2 g of Wang polystyrene resin (Rapp-Polymere, Tübingen; loading 1.08 mmol/g) are swollen in dimethylformamide (DMF). The solvent is filtered off with suction and a solution of 1.088 g of (2R,S)-3-(4-bromophenyl)-2-(9-fluorenylmethoxycarbonylamino)-propanoic acid in 20 ml of dimethylformamide (DMF) is added. After shaking at room temperature for 15 min, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution in dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 1.2 ml of diisopropylethylamine in 10 ml of tetrahydrofuran (THF) and a solution of 1.53 g of 2,4,6-trimethylbenzenesulfonyl chloride (sulfonylation/carbamoylating reagent) in 10 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 900 μl of diisopropylethylamine in 9 ml of dimethylformamide (DMF), 1.5 g of 1,3-bis-(tert-butoxycarbonyl)-2-methyl-2-thiopseudourea in 15 ml of dimethylformamide (DMF) and 1.77 g of mercury(II) chloride. The mixture is shaken overnight and the resin is then washed with dimethylformamide (DMF), methanol, tetrahydrofuran (THF) and dichloromethane. For removal of the product, the resin is shaken with 10 ml of trifluoroacetic acid (TFA)/dichloromethane for 1 h, filtered off, and thed filtrate is concentrated in vacuo and purified on silica gel. 52 mg of the title compound are obtained.

Mass spectrometry (ESI): 481.
Retention time (HPLC): $R_t$=7.6.

Example 4

Example 4.1
[3'-(3-Pyridin-2-ylmethyl-ureido)-biphenyl-3-sulfonylamino]-acetic acid

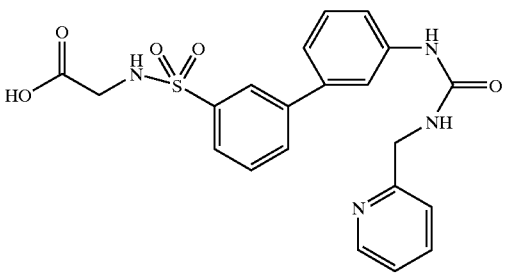

1.2 g of Wang polystyrene resin (Rapp-Polymere, Tübingen; loading 1.08 mmol/g) are swollen in dimethylformamide (DMF). The solvent is filtered off with suction and a solution of 771 mg of Fmoc-glycine (amino acid reagent) in 10 ml of dimethylformamide (DMF) is added. After shaking at room temperature for 15 min, the suspension is General synthesis scheme for method 4:

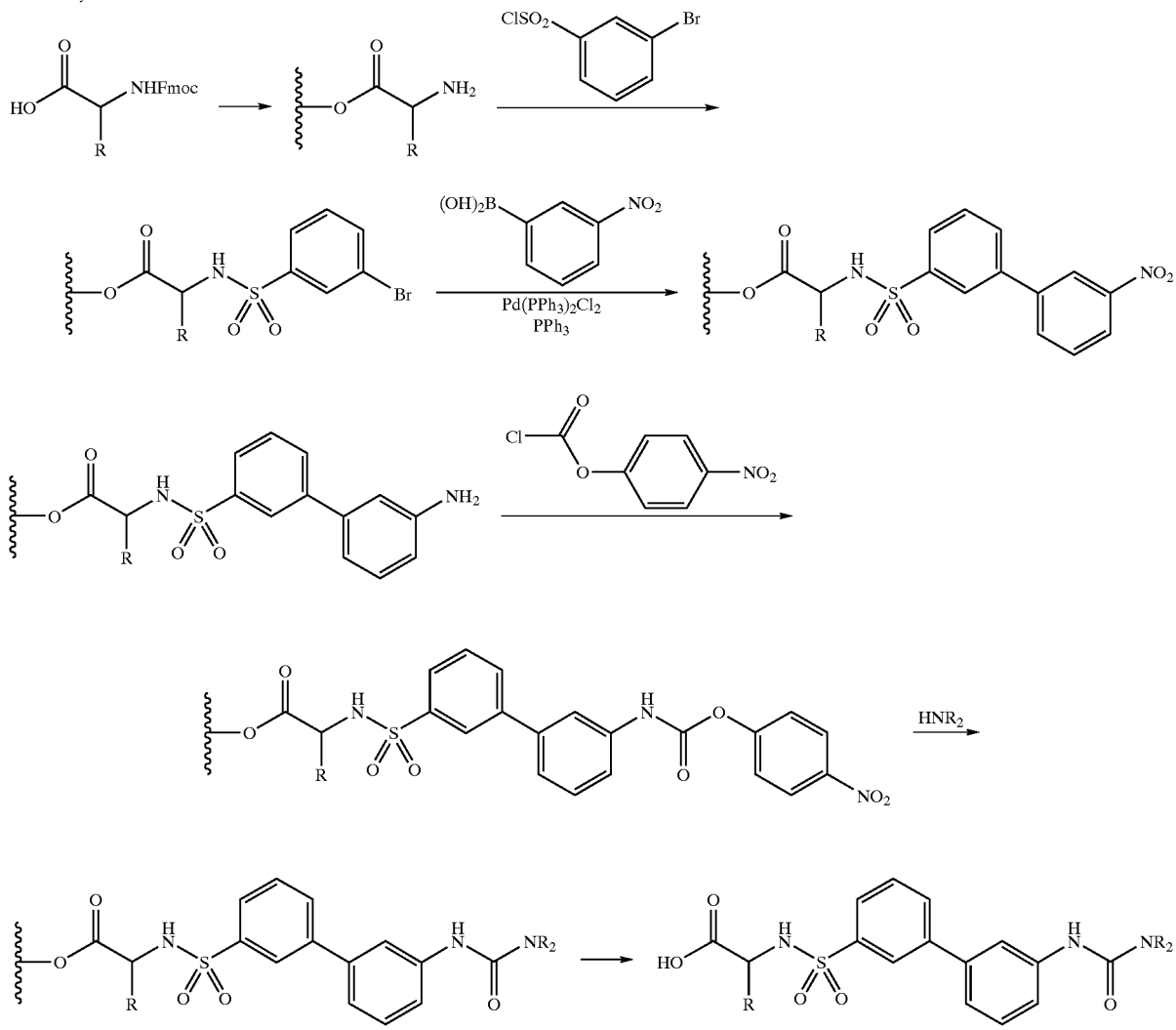

Compounds wherein A is a thienyl ring can be prepared in analogy to the above synthesis scheme for method 4 but with 5-bromothienyl-2-sulfonylchloride instead of 3-bromobenzenesulfonylchloride as starting material.

treated with 345 μl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 452 ml of diisopropylethylamine in 5 ml of tetrahydrofuran (THF) and a solution of 431 mg of 3-bromobenzenesulfonyl chloride in 5 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 564 μl of diisopropylethylamine in 13 ml of tetrahydrofuran (THF)/dichloromethane 1:1 and a solution of 3.13 g of 4-nitrophenyl chloroformate in 13 ml of tetrahydrofuran (THF)/dichloromethane 1:1. After shaking at room temperature for 45 min, it is washed with tetrahydrofuran (THF) and dimethylformamide (DMF) and a solution of 1.96 g of 2-aminomethylpyridine (amine reagent) and 3.16 ml of diisopropylethylamine in 23 ml of dimethylformamide (DMF) is added. After shaking for 2 h, the resin is washed with dimethylformamide (DMF), methanol, tetrahydrofuran (THF) and dichloromethane. For removal of the product, the resin is shaken with 10 ml of trifluoroacetic acid (TFA)/dichloromethane for 1 h, filtered off, and the filtrate is concentrated in vacuo and purified on silica gel. 210 mg of the title compound are obtained.

Mass spectrometry (ESI): 441.

Retention time (HPLC): R$_t$=5.3.

$^1$H-NMR (400 MHz, methanol) δ=8.59 (s, 1H), 8.14 (dd, 1H); 8.08 (s, 1H), 7.84 (m, 2H), 7.78 (s, 1H), 7.72 (d, 1H), 7.61 (d, 1H), 7.59 (m, 1H), 7.41 (m, 2H), 7.32 (m, 1H), 4.62 (s, 2H), 3.74 (s, 2H).

Example 4.2

[3'-(3-Pyridin-3-ylmethyl-ureido)-biphenyl-3-sulfonylamino]-acetic acid

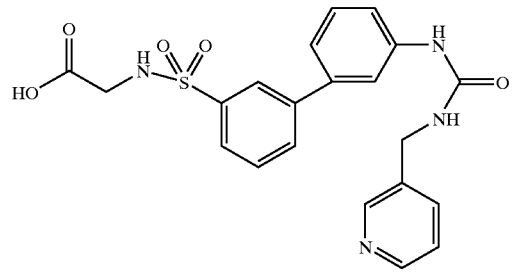

[3'-(3-Pyridin-3-ylmethyl-ureido)-biphenyl-3-sulfonylamino]-acetic acid is prepared according to the procedure of example 4.1, with the exception that 3-aminomethylpyridine is used as an amine reagent instead of 3-aminomethylpyridine.

Mass spectrometly (ESI): 441.

Retention time (HPLC): R$_t$=5.3

$^1$H-NMR (400 Mhz, methanol) δ=8.65 (s, 1H), 8.54 (d, 1H), 8.08 (m, 2H), 7.84 (m, 2H), 7.77 (s, 1H), 7.62 (m, 2H), 7.37 (m, 2H), 7.32 (m, 1H), 4.50 (s, 2H), 3.74 (s, 2H).

Example 4.3

(2R,S)-2-{3'-[3-(1H-Benzoimidazol-2-yl)-ureido]-biphenyl-3-sulfonylamino}-3-phenyl-propanoic acid

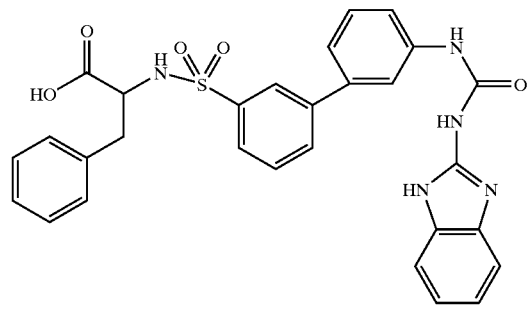

(2R,S)-2-{3'-[3-(1 H-Benzoimidazol-2-yl)-ureido]-biphenyl-3-sulfonylamino}-3-phenyl-propanoic acid is prepared according to the procedure of example 4.1, with the exception that D,L-Fmoc-phenylalanine is used as an amino acid reagent instead of Fmoc-glycine and 2-aminobenzimidazole is used as an amine reagent instead of 2-aminomethylpyridine.

Mass spectrometry (ESI): 556.

Retention time (HPLC): R$_t$=8.9.

Example 4.4

(3R,S)-3-[4-Methoxy-3'-(3-propyl-ureido)-biphenyl-3-sulfonylamino]-3-phenyl-propanoic acid

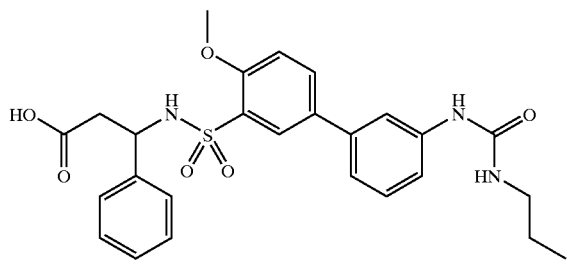

(3R,S)-3-[4-Methoxy-3'-(3-propyl-ureido)-biphenyl-3-sulfonylamino]-3-phenyl-propanoic acid is prepared according to the procedure of example 4.1, with the exception that D,L-Fmoc-phenylalanine is used as an amino acid reagent instead of Fmoc-glycine, 5-bromo-2-methoxy-benzenesulfonylchloride is used as sulfonylation reagent instead of 3-bromobenzenesulfonyl chloride and propylamine is used as an amine reagent instead of 2-aminomethylpyridine.

Mass spectrometry (ESI): 512.

Retention time (HPLC): $R_t$=8.7.

$^1$H-NMR (400 Mhz, MeOH) δ=7,83 (s, 1H), 7,59 (m, 2H), 7,32 (d, 2H), 7,13 (m, 1H), 7,03 (m, 5H), 6,84 (d, 1H), 4,72 (dd, 1H, J=7,4 Hz, J=7,4 Hz, H-3), 3,78 (s, 3H), 3,18 (t, 2H, J=7,0 Hz), 2,89 (dd, 1H, J=7,2 Hz, J=15,8 Hz, H-2a), 2,73 (dd, 1H, J=7,6 Hz, J=15,8 Hz, H-2b), 1,57 (dq, 2H, J=7,2 Hz), 0,97 (t, 3H, J=7,6 Hz).

Example 4.5

(3R,S)-3-{3'-[3-(1H-Benzoimidazol-2-yl-ureido]-biphenyl-3-sulfonylamino}-3-phenyl-propanoic acid

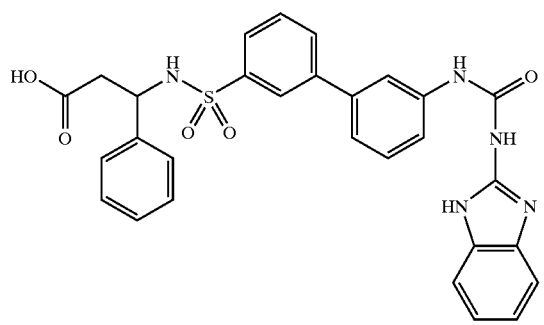

(3R,S)-3-{3'-[3-(1H-Benzoimidazol-2-yl)-ureido]-biphenyl-3-sulfonylamino}-3-phenyl-propanoic acid is prepared according to the procedure of example 4.1, with the exception that D,L-Fmoc-β-phenylalanine is used as an amino acid reagent instead of Fmoc-glycine and 1H-Benzoimidazol-2-yl-amine is used as an amine reagent instead of 2-aminomethylpyridine.

Mass spectrometry (ESI): 556.

Retention time (HPLC): $R_t$=8.4.

$^1$H-NMR (400 Mhz, MeOH) δ=7,88–7,00 (m, 17H), 4,83 (dd, 1H, J=7,6 Hz, H-3), 2,79 (dd, 1H, J=7,4 Hz, J=15,6 Hz, H-2a), 2,68 (dd, 1H, J=7,6 Hz, J=15,6 Hz, H-2b).

Example 4.6

(3R,S)-3-{3'-[3-(1H-Benzoimidazol-2-yl)-ureido]-biphenyl-4-sulfonylamino}-3-phenyl-propanoic acid

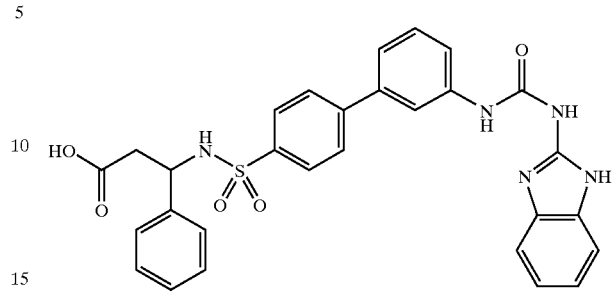

(3R,S)-3-{3'-[3-(1H-Benzoimidazol-2-yl)-ureido]-biphenyl-4-sulfonylamino}-3-phenyl-propanoic acid is prepared according to the procedure of example 4.1, with the exception that D,L-Fmoc-β-phenylalanine is used as an amino acid reagent instead of Fmoc-glycine, 4-bromobenzenesulfonyl chloride is used as sulfonylation reagent instead of 3-bromobenzenesulfonyl chloride and 1H-Benzoimidazol-2-yl-amine is used as an amine reagent instead of 2-aminomethylpyridine.

Mass spectrometry (ESI): 556.

Retention time (HPLC): $R_t$=8.4.

$^1$H-NMR (400 Mhz, MeOH) δ=7,78–7,06 (m, 17H), 4,81 (dd, 1H, J=7,4 Hz, H-3), 2,80 (dd, 1H, J=7,4 Hz, J=15,6 Hz, H-2a), 2,69 (dd, 1H, J=7,6 Hz, J=15,6 Hz, H-2b).

Example 4.7

(3R,S)-3-[3'-(3-propyl-ureido)-biphenyl-4-sulfonylamino]-3-phenyl-propanoic acid

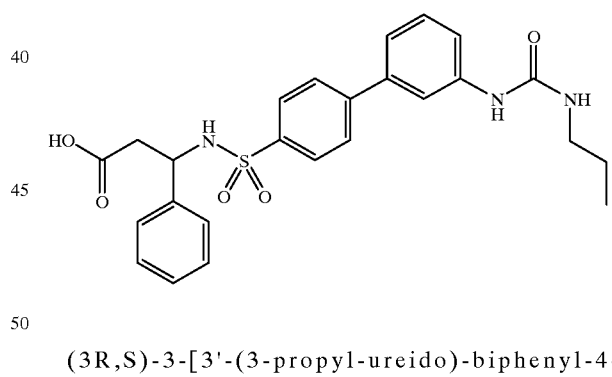

(3R,S)-3-[3'-(3-propyl-ureido)-biphenyl-4-sulfonylamino]-3-phenyl-propanoic acid is prepared according to the procedure of example 4.1, with the exception that D,L-Fmoc-β-phenylalanine is used as an amino acid reagent instead of Fmoc-glycine, 4-bromobenzenesulfonyl chloride is used as sulfonylation reagent instead of 3-bromobenzenesulfonyl chloride and propylamine is used as an amine reagent instead of 2-aminomethylpyridine.

Mass spectrometry (ESI): 482.

Retention time (HPLC): $R_t$=8.7.

$^1$H-NMR (400 Mhz, MeOH) δ=7,68 (s, 1H), 7,62 (d, 2H), 7,50 (d, 2H), 7,32 (m, 2H), 7,19 (d, 1H), 7,09 (s, 5H), 4,79 (dd, 1H, J=7,4 Hz, H-3), 3,18 (t, 2H, J=7,0 Hz), 2,79 (dd, 1H, J=7,4 Hz, J=15,4 Hz, H-2a), 2,67 (dd, 1H, J=7,6 Hz, J=15,4 Hz, H-2b), 1,57 (tq, 2H, J=7,2 Hz), 0,97 (t, 3H, J=7,6 Hz).

Example 4.8

(2R,S)-2-{4-Methoxy-3-[3'-(1H-Benzoimidazol-2-yl)-ureido]-biphenyl-3-sulfonylamino}-3-phenyl-propanoic acid

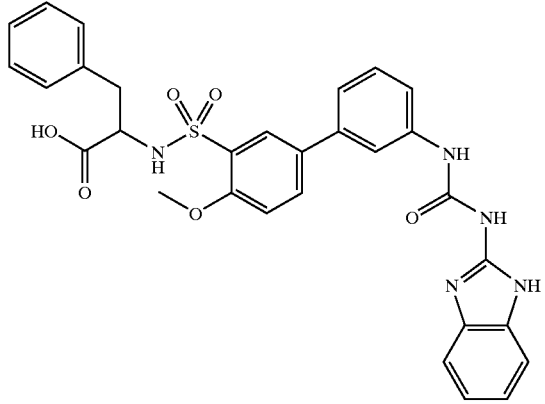

(2R,S)-2-{4-Methoxy-3-[3'-(1H-Benzoimidazol-2-yl)-ureido]-biphenyl-3-sulfonylamino}-3-phenyl-propanoic acid is prepared according to the procedure of example 4.1, with the exception that D,L-Fmoc-phenylalanine is used as an amino acid reagent instead of Fmoc-glycine, 5-bromo-2-methoxy-benzenesulfonyl chloride is used as sulfonylation reagent instead of 3-bromobenzenesulfonyl chloride and 1H-Benzoimidazol-2-yl-amine is used as an amine reagent instead of 2-aminomethylpyridine.

Mass spectrometry (ESI): 586.

Retention time (HPLC): $R_t$=8.6.

$^1$H-NMR (400 Mhz, MeOH) δ=8,00–7,10 (m, 16H), 4,19 (dd, 1H, J=5,6 Hz, J=8,0 Hz, H-2), 3,10 (dd, 1H, J=5,8 Hz, J=14,0 Hz, H-3a), 2,96 (dd, 1H, J=8,0 Hz, J=15,0 Hz, H-3b).

Example 4.9

(2R,S)-2-[4-Methoxy-3'-(3-Pyridin-3-ylmethyl-ureido)-biphenyl-3-sulfonylamino]-3-phenyl-propanoic acid

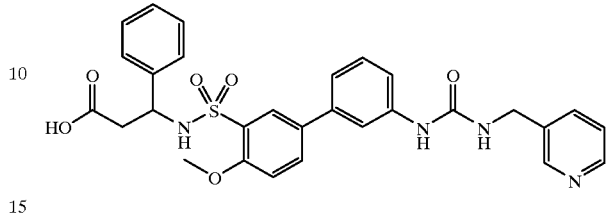

(2R,S)-2-[4-Methoxy-3'-(3-Pyridin-3-ylmethyl-ureido)-biphenyl-3-sulfonylamino]-3-phenyl-propanoic acid is prepared according to the procedure of example 4.1, with the exception that D,L-Fmoc-β-phenylalanine is used as an amino acid reagent instead of Fmoc-glycine, 4-bromobenzenesulfonyl chloride is used as sulfonylation reagent instead of 5-bromo-2-methoxybenzenesulfonyl chloride and 3-aminomethylpyridine is used as an amine reagent instead of 2-aminomethylpyridine.

Mass spectrometry (ESI): 561.

Retention time (HPLC): $R_t$=6,5.

$^1$H-NMR (400 MHz, methanol) δ=8,74 (s, 1H), 8,64 (s, 1H), 8,37(d, 1H), 7,84 (s, 2H), 7,61 (m, 2H), 7,33 (m, 2H), 7,18 (m, 1H), 7,03 (s, 5H), 6,86 (d, 1H), 4,71 (dd, 1H, J=7,4 Hz, J=7,4 Hz, H-3), 4,56 (s, 2H), 3,78 (s, 3H), 2,89 (dd, 1H, J=7,2 Hz, J=16,0 Hz, H-2a), 2,73 (dd, 1H, J=7,6 Hz, J=16,0 Hz, H-2b).

Example 5

General synthesis scheme:

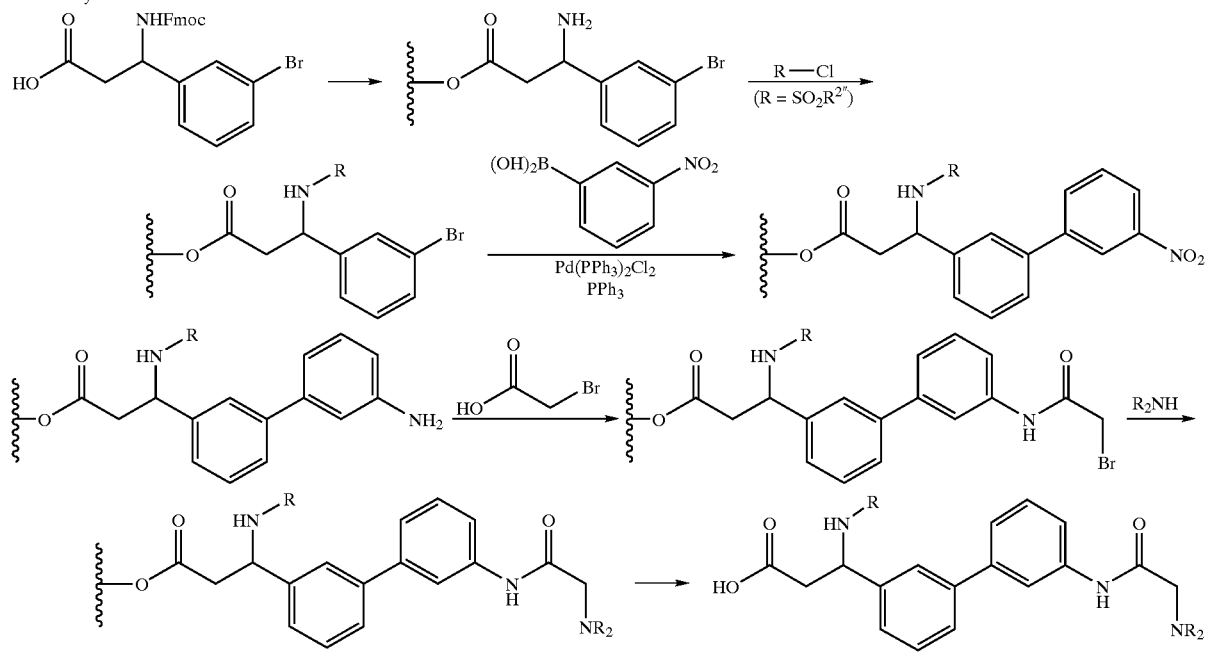

Example 5.1

(3R,S)-3-[3'-(2-Imidazol-3-yl-acetylamino)-biphenyl-3-yl]-3-(2,4,6-trimethylbenzenesulfonylamino)-propanoic acid

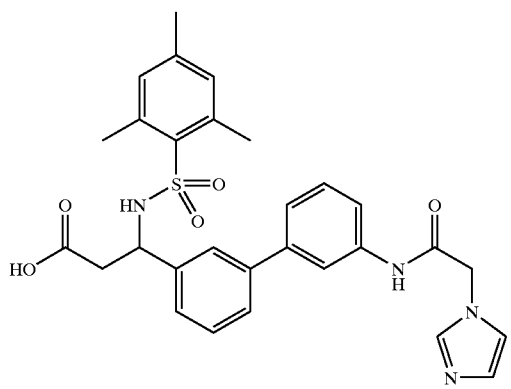

1.2 g of Wang polystyrene resin (Rapp-Polymere, Tübingen; loading 1.08 mmol/g) are swollen in dimethylformamide (DMF). The solvent is filtered off with suction and a solution of 1.088 g of (3R,S)-3-(4-bromophenyl)-3-(9-fluorenylmethoxycarbonylamino)-propanoic acid in 20 ml of dimethylformamide (DMF) is added. After shaking at room temperature for 15 minutes, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution in dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 1.2 ml of diisopropylethylamine in 10 ml of tetrahydrofuran (THF) and a solution of 1.53 g of 2,4,6-trimethylbenzenesulfonyl chloride (sulfonylating/carbamoylating reagent) in 10 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 1.80 g of bromoacetic acid in 20 ml of dimethylformamide (DMF) and a solution of 2.12 g of diisopropylcarbodiimide in 5 ml of dimethylformamide (DMF). It is shaken at room temperature for 3 h and then filtered off with suction and washed with dimethylformamide (DMF). The resin is again treated with a solution of 1.80 g of bromoacetic acid in 20 ml of dimethylformamide (DMF) and a solution of 2.12 g of diisopropylcarbodiimide in 5 ml of dimethylformamide (DMF) and shaken at room temperature for 3 h. It is then filtered off with suction and washed with dimethylformamide (DMF), methanol and dichloromethane. The resin is then treated with a solution of 1.24 g of imidazole and 1.13 ml of diisopropylethylamine in 18 ml of dimethylformamide (DMF). It is stirred overnight and then washed with dimethylformamide (DMF), methanol and dichloromethane. For removal of the product, the resin is shaken with 10 ml of trifluoroacetic acid (TFA)/dichloromethane 1:1 for 1 h, filtered off, and the filtrate is concentrated in vacuo and purified on silica gel. 210 mg of the title compound are obtained.

Mass spectrometry(ESI): 547.

Retention time (HPLC): $R_t$=7.8.

Example 6

General synthesis scheme for method 6:

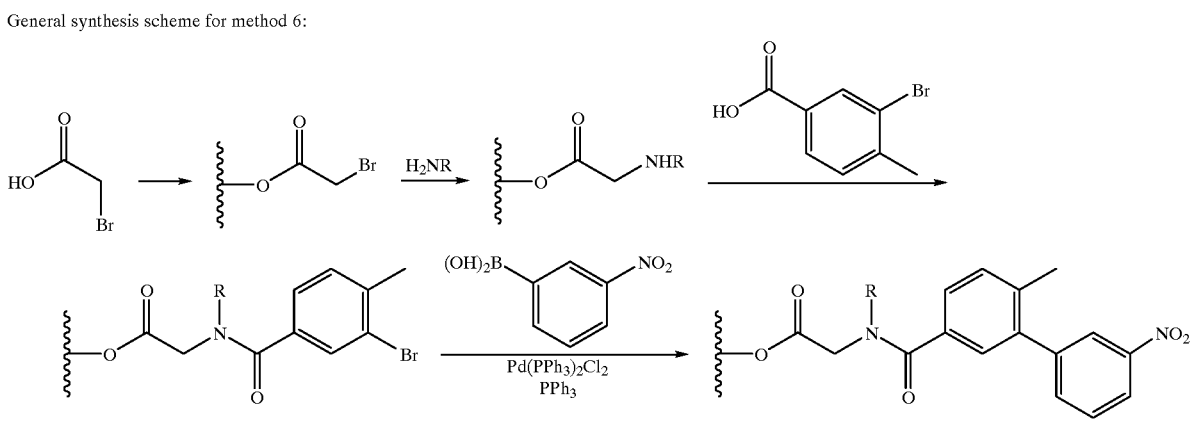

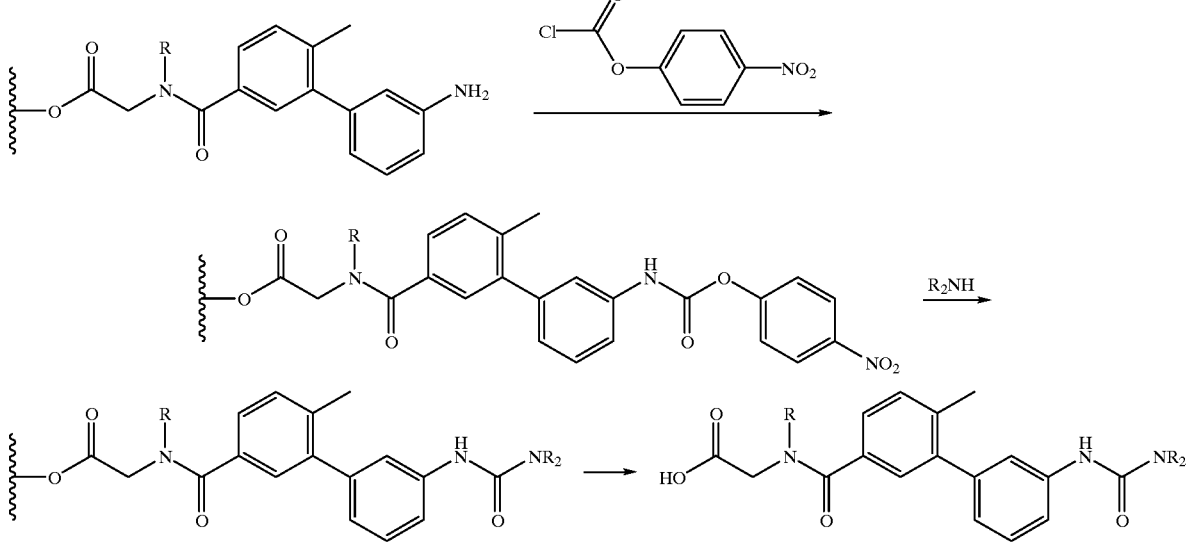

Example 6.1

N-(1-methyl-3-phenyl-propyl)-3'-{3-(2-Methoxy-ethyl)-ureido]-biphenyl-1-methyl-3-carbonylamino}-acetic acid

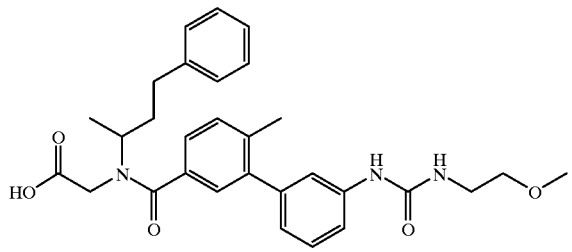

1.2 g of Wang polystyrene resin (Rapp-Polymere, Tübingen; loading 1.08 mmol/g) are swollen in dimethylformamide (DMF). The solvent is filtered off with suction and a solution of 360 mg of bromoacetic acid (acid reagent) in 8 ml of dimethylformamide (DMF) is added. After shaking at room temperature for 15 min, the suspension is treated with 345 µl of pyridine and 543 mg of 2,6-dichlorobenzoyl chloride. It is shaken at room temperature for 2 h. It is then filtered off with suction and the resin is washed with dimethylformamide (DMF). A further 360 mg of bromoacetic acid (acid reagent) in 8 ml of dimethylformamide (DMF) are added, the mixture is shaken for 15 min, and the suspension is treated with 345 µl of pyridine and 543 mg of 2,6-dichlorobenzoyl chloride and shaken overnight at room temperature. The resin is then washed with dimethylformnamide (DMF), methanol and dichloromethane.

The resin is treated with a solution of 2.24 g of 1-phenyl-3-butylamine (amine reagent) in 7.5 ml of dimethyl sulfoxide (DMSO) and shaken overnight. The resin is then washed with dimethylformamide (DMF), methanol, tetrahydrofuran (THF) and dichloromethane.

The resin is treated with a solution of 2.6 ml of diisopropylcarbodiimide in 5 ml of dimethylformamide (DMF) and a solution of 2.79 g of 3-bromo-4-methylbenzoic acid (acylating/sulfonylating reagent) in 18 ml of dimethylformamide (DMF). It is shaken at room temperature for 3 h. The resin is then filtered off with suction, washed with dimethylformamide (DMF) and again treated with a solution of 2.6 ml of diisopropylcarbodiimide in 5 ml of dimethylformarnide (DMF) and a solution of 2.79 g of 3-bromo-4-methylbenzoic acid in 18 ml of dimethylformamide (DMF). After shaking at room temperature for 3 h, the resin is washed with dimethylformamide (DMF), methanol and dichloromethane.

The resin is suspended in 8 ml xylene, treated with 1.73 g of 3-nitrobenzeneboronic acid (boronic acid reagent) and a solution of 2.2 g of sodium carbonate in 9 ml of water and shaken for 5 min at room temperature. 227 mg of bis(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 564 µl of diisopropylethylamine in 13 ml of tetrahydrofuran (THF)/dichloromethane 1:1 and a solution of 3.13 g of 4-nitrophenyl chloroformate in 13 ml of tetrahydrofuran (THF)/dichloromethane 1:1. After shaking at room temperature for 45 min, it is washed with tetrahydrofuran (THF) and dimethylformamide (DMF) and a solution of 1.17 g of 2-methoxyethylamine (amine reagent for urea formation) and 2.7 ml of diisopropylethylamine in 20 ml of dimethylformamide (DMF) are added. After shaking for 2 h, the resin is washed with dimethylformamide (DMF), methanol, tetrahydrofuran (THF) and dichloromethane. For removal of the product, the resin is shaken with 10 ml of trifluoroacetic acid (TFA)/dichloromethane for 1 h, filtered off, and the filtrate is concentrated in vacuo and purified on silica gel. 200 mg of the title compound are obtained.

Mass spectrometry (ESI): 518.
Retention time (HPLC): $R_t$=7.8.

Example 7

General synthesis scheme for method 7:

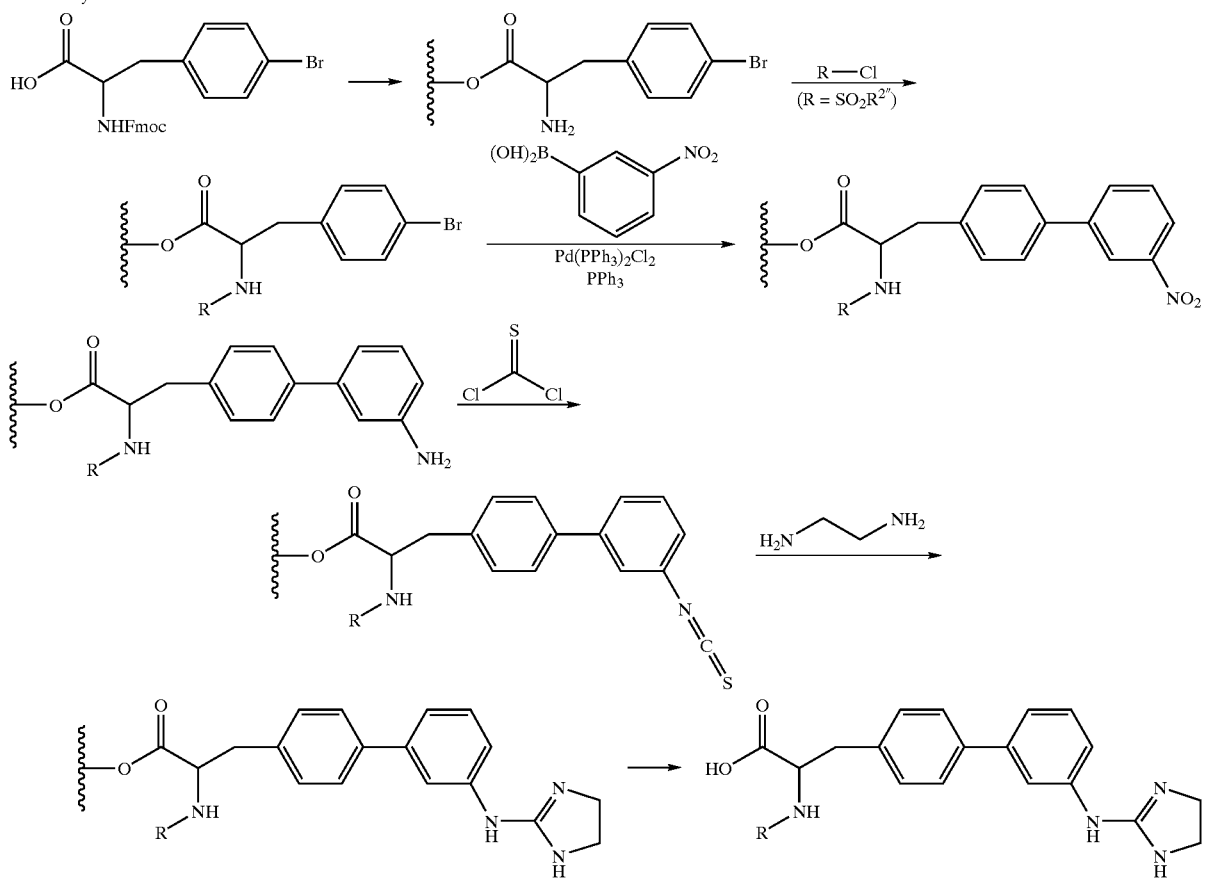

Example 7.1

(2R,S)-3-[3'-(4,5-Dihydro-1H-Imidazol-2-ylamino)-biphenyl-4-yl]-2-(2,4,6-trimethyl-benzenesulfonylamino)-propanoic acid

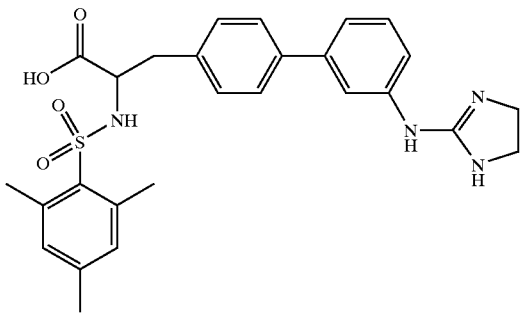

1.2 g of Wang polystyrene resin (Rapp-Polymere, Tübingen; loading 1.08 mmol/g) are swollen in dimethylformamide (DMF). The solvent is filtered off with suction and a solution of 1.088 g of (2R,S)-3-(4-bromophenyl)-2-(9-fluorenylmethoxycarbonylamino)-propanoic acid (acid reagent) in 20 ml of dimethylformamide (DMF) is added. After shaking at room temperature for 15 min, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution in dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 1.2 ml of diisopropylethylamine in 10 ml of tetrahydrofuran (THF) and a solution of 1.53 g of 2,4,6-trimethylbenzenesulfonyl chloride (sulfonylating/carbamoylating reagent) in 10 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water (1:1), 0.25 M aqueous hydrochloric acid. water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 1.13 ml of diisopropylethylamine in 10 ml of tetrahydrofuran (THF) and a solution of 400 µl of thiophosgene in 10 ml of tetrahydrofuran (THF) and shaken at room temperature for 2 h. The resin is then filtered off with suction, washed with tetrahydrofuran (THF), a solution of 1.5 ml of ethanol in 14 ml of dioxane is added and the mixture is stirred for 4 h at 70° C. The resin is then filtered off with suction, washed with dimethylformamide (DMF) and treated with a solution of 1.17 g of ethylenediamine in 20 ml of dimethylformamide (DMF). The suspension is stirred overnight at 70° C. The resin is then washed with dimethylformamide (DMF), methanol, tetrahydrofuran (THF) and dichloromethane. For removal of the product, the resin is shaken with 10 ml of trifluoroacetic acid (TFA)/dichloromethane for 1 h, filtered off, and the filtrate is concentrated in vacuo and purified on silica gel. 70 mg of the title compound are obtained.

Mass spectrometry (ESI): 507.
Retention time (HPLC): $R_t$=8.0.

Example 8

Example 8.1

(3R,S)-3-(3'-{[(1H-Benzoimidazol-2-ylmethyl)-amino]-methyl}-biphenyl-3-sulfonylamino)-3-phenyl-propanoic acid

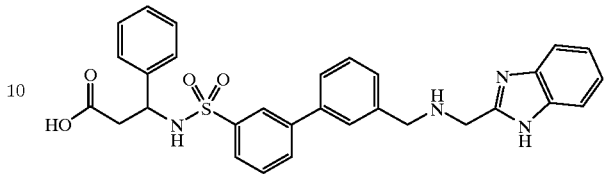

1.2 g of polystyrene Wang resin (Rapp-Polymere, Tübingen; loading 1.08 mmol/g) are swollen in dimethylformamide (DMF). The solvent is filtered off with suction and a solution of 904 mg of (3R,S)-3-(9-fluorenylmethoxycarbonylamino)-3-phenyl-propanoic acid (amino acid reagent) in 9 ml of dimethylformamide (DMF) is added. After shaking at room temperature for 15 min, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

General synthesis scheme for method 8:

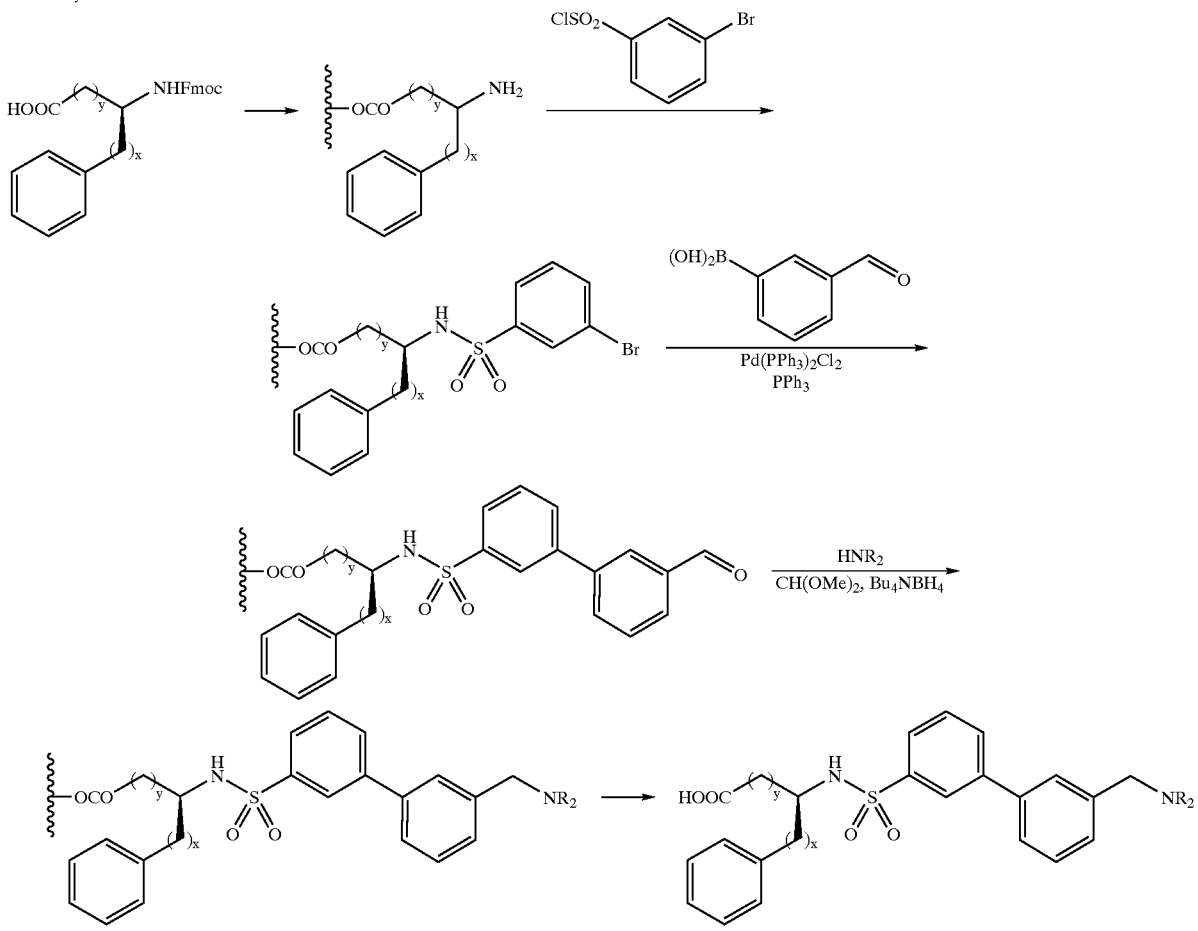

x = 0, 1
y = 0, 1

The resin is treated with 15 ml of a 20% strength piperidine solution in dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (TFF). The resin is treated with a solution of 452 ml of diisopropylethylamine in 5 ml of tetrahydrofuran (THF) and a solution of 431 mg of 3-bromobenzenesulfonyl chloride in 5 ml of tetrahydrofuran (THF). It is shaken overnight at room temperature. The resin is then washed with dimethylformamide (DMF), methanol and tetrahydrofuran (THF).

The resin is suspended in 9 ml of xylene, treated with 1.55 g of 3-formylbenzeneboronic acid (boronic acid reagent) and a solution of 2.2 g of sodium carbonate in 9 ml of water and shaken for 5 min at room temperature. 227 mg of bis(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, is then washed with water, dimethylformamide (DMF), methanol, tetrahydrofuran (THF) and dichloromethane.

The resin is treated with a solution of 2.16 g of 2-aminomethylbenzimidazole dihydrochloride (amine reagent), 5.1 ml of diisopropylethylamine (for neutralization) and 2.68 ml of trimethyl orthoformate in 8 ml of dimethylformamide (DMF). After shaking at room temperature for 2 h, a solution of 3.14 g of tetrabutylammonium borohydride and 2.8 ml of acetic acid in 18 ml of dimethylformamide (DMF) is added. The mixture is shaken at room temperature overnight. The resin is then filtered off with suction and washed with dimethylformamide (DMF), methanol, tetrahydrofuran (THF) and dichloromethane. For removal of the product, the resin is shaken with 10 ml of trifluoroacetic acid (TFA)/dichloromethane for 1 h, filtered off, and the filtrate is concentrated in vacuo and purified on silica gel. 190 mg of the title compound are obtained.

Mass spectrometry (ESI): 541.

Retention time (HPLC): R$_t$=7.1.

Example 8.2

(3R,S)-3-(3'-{[(Tetrahydro-furan-2-ylmethyl)-amino]-methyl}-biphenyl-3-sulfonylamino)-3-phenyl-propanoic acid

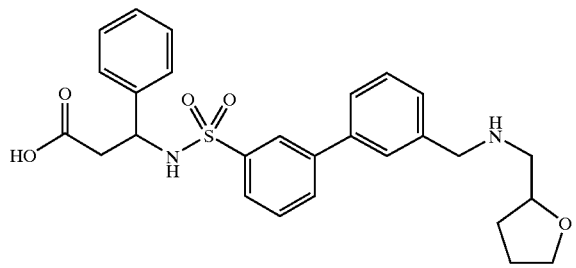

(3R,S)-3-(3'-{[(Tetrahydro-furan-2-ylmethyl)-amino]-methyl}-biphenyl-3-sulfonylamino)-3-phenyl-propanoic acid is prepared according to the procedure of example 8.1, with the exception that 2-aminomethyltetrahydrofuran is used as amine reagent instead of 2-aminomethylbenzimidazole dihydrochloride.

Mass spectrometry (ESI): 495.

Retention time (HPLC): R$_t$=7.0.

Example 8.3

(3R,S)-3-(4'-{[(1H-Benzoimidazol-2-ylmethyl)-amino]-methyl}-biphenyl-3-sulfonylamino)-3-phenyl-propanoic acid

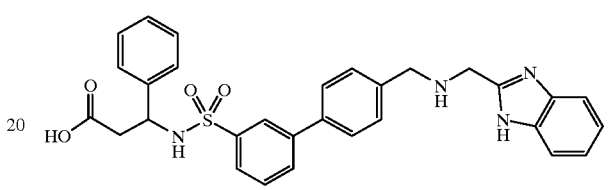

(3R,S)-3-(4'-{[(1H-Benzoimidazol-2-ylmethyl)-amino]-methyl}-biphenyl-3-sulfonylamino)-3-phenyl-propanoic acid is prepared according to the procedure of example 8.1, with the exception that 4-formylbenzeneboronic acid is used as a boronic acid reagent instead of 3-formylbenzeneboronic acid.

Mass spectrometry (ESI): 451.

Retention time (HPLC): R$_t$=6.9.

Example 8.4

(3R,S)-3-[4'-({[2-(1H-Imidazol-4-yl)-ethyl]-amino}-methyl)-biphenyl-3sulfonylamino]-3-phenyl-propanoic acid

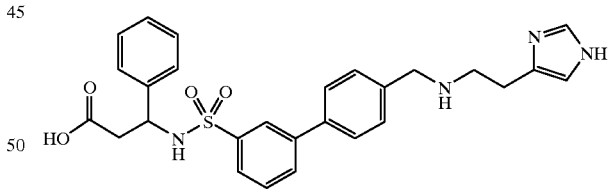

(3R,S)-3-[4'-({[2-(1H-Imidazol-4-yl)-ethyl]-amino}-methyl)-biphenyl-3-sulfonylamino]-phenyl-propanoic acid is prepared according to the procedure of example 8.1, with the exception that 4-formylbenzeneboronic acid is used as a boronic acid reagent instead of 3-formylbenzeneboronic acid and 2-(imidazol-5-yl)-ethylamine is used as an amine reagent instead of 2-aminomethylbenzimidazole dihydrochloride.

Mass spectrometry (ESI): 505.

Retention time (HPLC): R$_t$=5.4.

Example 8.5

(3R,S)-3-(4'-{[(1-methyl-2-morpholin-4-yl-ethyl)-amino]-methyl}-biphenyl-3-sulfonylamino)-3-phenyl-propanoic acid

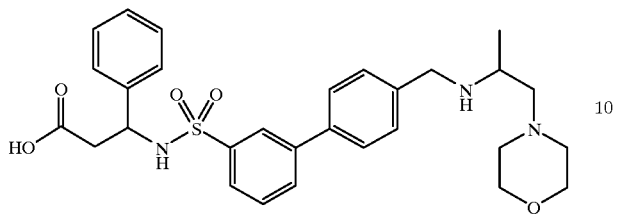

(3R,S)-3-(4'-{[(1-methyl-2-morpholin-4-yl-ethyl)-amino]-methyl}-biphenyl-3-sulfonylamino)-3phenyl-propanoic acid is prepared according to the procedure of example 8.1, with the exception that 4-formylbenzeneboronic acid is used as a boronic acid reagent instead of 3-formylbenzeneboronic acid and 1-morpholino-2-propylamine is used as an amine reagent instead of 2-aminomethylbenzimidazole dihydrochloride.

Mass spectrometry (ESI): 538.
Retention time (HPLC): $R_t$=5.9.

Example 8.6

(2R,S)-2-(3'-Propylaminomethyl-biphenyl-3-sulfonylamino)-3-phenyl-propanoic acid

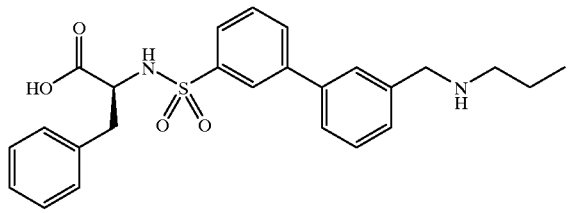

(2R,S)-2-(3'-Propylaminomethyl-biphenyl-3-sulfonylamino)-3-phenyl-propanoic acid is prepared according to the procedure of example 8.1, with the exception that Fmoc-phenylalanine is used as an amino acid reagent instead of (3R,S)-3-(9-fluorenylmethoxycarbonylamino)-3-phenyl-propanoic acid and propylamine is used as an amine reagent instead of 2-aminomethylbenzimidazole dihydrochloride.

Mass spectrometry (ESI): 453.
Retention time (HPLC): $R_t$=7,6.

$^1$H-NMR (400 MHz, methanol) δ=8,04 (s, 1H), 7,89 (s, 1H), 7,80 (m, 2H), 7,74 (d, 1H), 7,57 (m, 2H), 7,45 (d, 1H), 7,28–7,13 (m, 5H), 3,97 (dd, 1H, H-2), 3,03 (m, 4H), 1,74 (m, 2H), 1,02 (t, 3H).

Example 8.7

(2R,S)-2-(3'-{[(Tetrahydrofuran-2-yl-methyl)-amino]-methyl}-biphenyl-3-sulfonylamino)-3-phenyl-propanoic acid

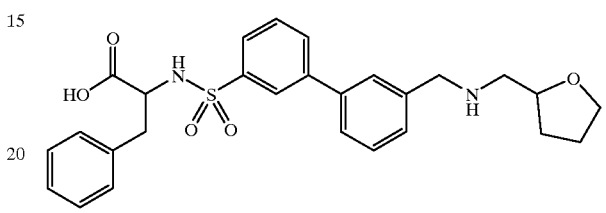

(2R,S)-2-(3'-{[(Tetrahydrofuran-2-yl-methyl)-amino]-methyl}-biphenyl-3-sulfonylamino)-3-phenyl-propanoic acid is prepared according to the procedure of example 8.1, with the exception that D,L-Fmoc-phenylalanine is used as an amino acid reagent instead of (3R,S)-3-(9-fluorenylmethoxycarbonylamino)-3-phenyl-propanoic acid and 2-aminomethyltetrahydrofuran is used as an amine reagent instead of 2-aminomethylbenzimidazole dihydrochloride.

Mass spectrometry (ESI): 495.
Retention time (HPLC): $R_t$=7,6.

$^1$H-NMR (400 MHz, methanol) δ=7,97 (s, 1H), 7,83 (d, 1H), 7,77 (s, 1H), 7,73 (d, 1H), 7,68 (d, 1H), 7,60 (dd, 1H), 7,52 (m, 2H), 7,12 (m, 5H), 4,35 (d, 1H, J=13,0 Hz), 4,31 (d, 1H, J=13,0 Hz), 4,18 (dddd, 1H, J=2,8 Hz, J=7,0 Hz, J=7,0 Hz, J=10,0 Hz), 4,10 (dd, 1H, J=5,6 Hz, J=8,4 Hz, H-2), 3,92 (dd, 1H, J=7,0 Hz, J=15,2 Hz), 3,83 (dd, 1H, J=7,0 Hz, J=15,2 Hz), 3,20 (dd, 1H, J=4,8 Hz, 12,8 Hz), 3,06 (dd, 1H, J=5,6 Hz, J=14,0 Hz, H-3a), 3,01 (dd, 1H, J=10,0 Hz, J=12,8 Hz), 2,87 (dd, 1H, J=8,6 Hz, J=14,0 Hz, H-3b), 2,12 (m, 1H), 1,96 (m, 2H), 1,61 (m, 1H).

Example 9

General synthesis scheme:

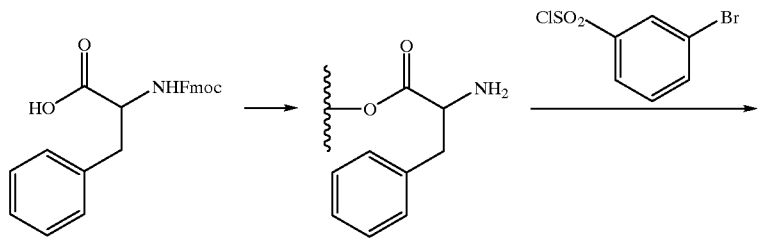

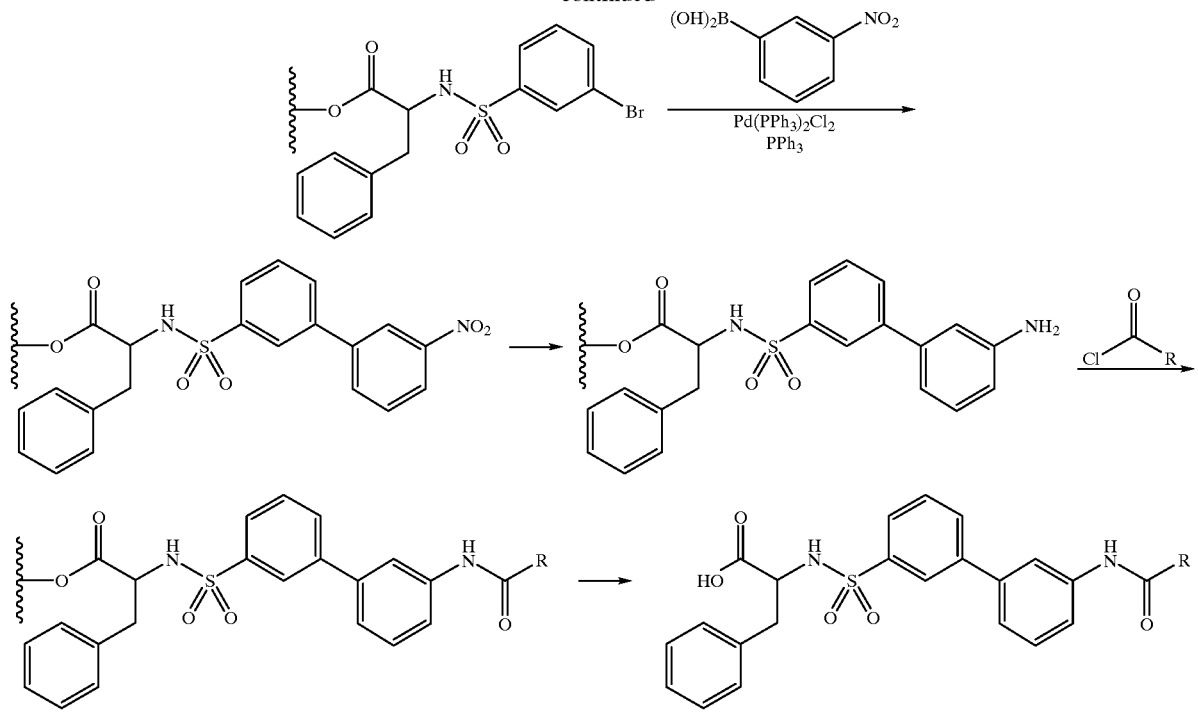

Example 9.1

(2R,S)-2-[3'-(Furan-2-yl-carbonylamino)-biphenyl-3-sulfonylamino]-3-phenyl-propanoic acid

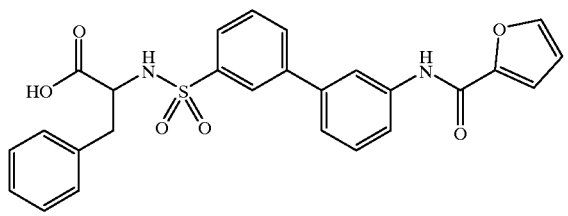

1.2 g of Wang polystyrene resin (Rapp-Polymere, Tübingen; loading 1.08 mmol/g) are swollen in dimethylformamide (DMF). The solvent is filtered off with suction and a solution of 1005 mg of Fmoc-phenylalanine (amino acid reagent) in 10 ml of dimethylformamide (DMF) is added. After shaking at room temperature for 15 min, the suspension is treated with 345 µl of pyridine and 543 mg of 2,6-dichlorobenzoyl chloride. It is shaken overnight at room temperature. The resin is then washed with dimethylformamide (DMF), methanol and dichloromethane.

The resin is treated with 15 ml of a 20% strength piperidine solution dimethylformamide (DMF) and shaken at room temperature for 10 min. It is then washed 3 times with dimethylformamide (DMF) and a further 15 ml of a 20% strength piperidine solution in dimethylformamide (DMF) are added. After shaking for 20 min, it is washed with dimethylformamide (DMF) and tetrahydrofuran (THF). The resin is treated with a solution of 452 ml of diisopropylethylamine in 5 ml of tetrahydrofuran (THF) and a solution of 431 mg of 3-bromobenzenesulfonyl chloride in 5 ml of tetrahydrofuran (THF). It is shaken overnight at room temperature. The resin is then washed with dimethylformamide (DMF), methanol and tetrahydrofuran (THF).

The resin is suspended in 7 ml of xylene, treated with 1.08 g of 3-nitrobenzeneboronic acid and a solution of 1.37 g of sodium carbonate in 6 ml of water and shaken for 5 min at room temperature. 227 mg of bis-(triphenylphosphane)-palladium(II) chloride and 170 mg of triphenylphosphane are then added and the mixture is stirred overnight at 85° C. The resin is then washed with tetrahydrofuran (THF)/water 1:1, 0.25 M aqueous hydrochloric acid, water, dimethylformamide (DMF), methanol, tetrahydrofuran (THF) and dichloromethane. The resin is treated with a solution of 5.4 g of tin(II) chloride dihydrate in 12 ml of N-methylpyrrolidone (NMP) and shaken overnight at room temperature. The resin is then washed with N-methylpyrrolidone (NMP), methanol, tetrahydrofuran (THF) and dichloromethane.

The resin is treated with a solution of 1.45 g 2-furanyl-carboxylic acid (acid reagent) in 20 ml dimethylformamide (DMF). After shaking for 1 minute a solution of 2.64 ml diisopropylcarbodiimide in 5 ml dimethylformamide (DMF) is added and the mixture is shaken for 3 hours at room temperature. The resin is then washed with dimethylformamide (DMF) and is treated with 1.45 g 2-furanyl-carboxylic acid in 20 ml dimethylformamide (DMF) and 2.64 ml diisopropylcarbodiimide in 5 ml dimethylformnamide (DMF) again. After shaking for 3 hours the resin is washed with dimethylformamide (DMF), methanol, tetrahydrofurane (THF) and dichloromethane. For removal of the product, the resin is shaken with 10 ml of trifluoroacetic acid (TFA)/dichloromethane 1:1 for 1 hour, filtered off. The filtrate is concentrated in vacuo and purified on silica gel. 201 mg of the title compound are obtained.

Mass spectrometry (ESI): 491.

Retention time (HPLC): $R_t$=9,6.

$^1$H-NMR (400 MHz, methanol) δ=7,99 (s, 1H), 7,91 (s, 1H), 7,81 (d, 1H), 7,75 (m, 2H), 7,66 (m, 1H), 7,52–7,43 (m, 2H), 7,41 (d, 1H), 7,29 (d, 1H), 7,11 (s, 5H), 7,68 (m, 1H), 4,10 (dd, 1H, J=5,6 Hz, J=10,8 Hz, H-2), 3,06 (dd, 1H, J=5,6 Hz, J=13,8 Hz, H-3a), 2,85 (dd, 1H, J=10,8 Hz, J=13,8 Hz, H-3b).

Example 9.2

(3R,S)-3-[3'-(2-Benzamido-acetylamino)-4-methoxy-biphenyl-3-sulfonylamino]-3-phenyl-propanoic acid

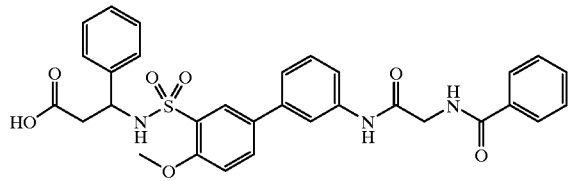

(3R,S)-3-[3'-(2-Benzamido-acetylamino)-4-methoxy-biphenyl-3-sulfonylamino]-3-phenyl-propanoic acid is prepared according to the procedure of example 9.1, with the exception that D,L-Fmoc-β-phenylalanine is used as an amino acid reagent instead of Fmoc-phenylalanine and benzoic acid is used as an acid reagent instead of 2-furanyl-carboxylic acid.

Mass spectrometry (ESI): 588.

Retention time (HPLC): $R_t$=8,6.

$^1$H-NMR (400 MHz, methanol) δ=7,91 (d, 2H), 7,85 (s, 1H), 7,80 (s, 1H), 7,63–7,53 (m, 3H), 7,49 (m, 2H), 7,40 (dd, 1H), 7,28 (d, 1H), 7,05 (s, 5H), 6,87 (d, 1H), 4,72 (dd, 1H, J=7,4 Hz, J=7,4 Hz, H-3), 4,23 (s, 2H), 3,78 (s, 3H), 2,89 (dd, 1H, J=7,2 Hz, J=15,6 Hz, H-2a), 2,73 (dd, 1H, J=7,6 Hz, J=15,6 Hz, H-2b).

Example 10

General synthesis scheme for method 10:

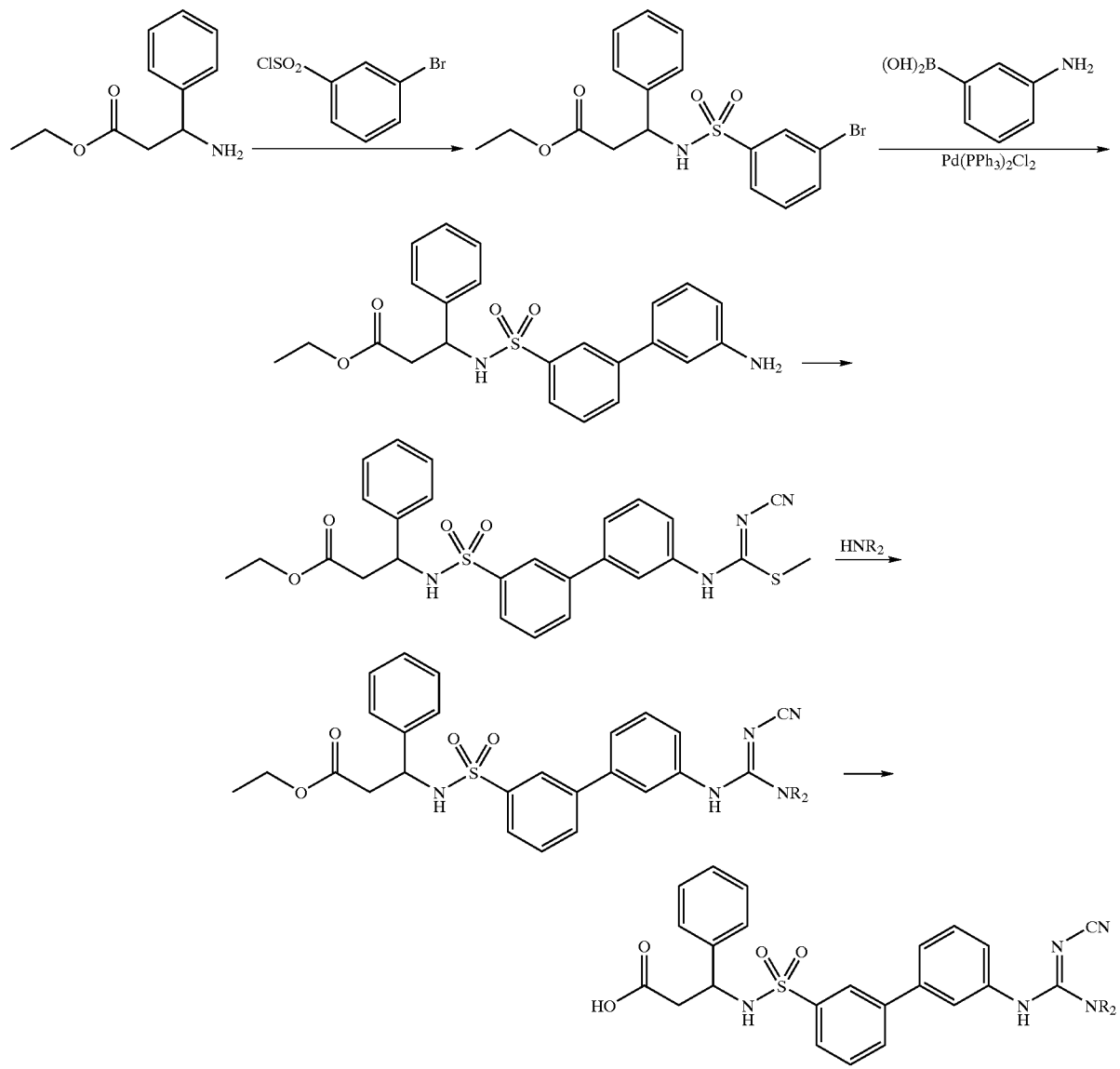

Example 10.1.1

Ethyl 3-{[(3-bromophenyl)sulfonyl]amino}-3-phenyl-propanoate

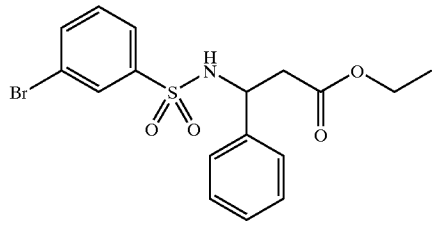

Ethyl 3-Amino-3-phenyl-propanoate (27g, 117 mmol) and 3-bromobenzensulfonylchloride (33 g,129 mmol) were dissolved in dichloromethane (660 ml) at 0° C. and 65 ml triethylamin were added. The mixture was stirred at 0° C. for 1 h and at room temperature overnight. The reaction mixture was washed with aq 1N HCl, brine and water and dried (MgSO$_4$). The concentrated organic solutions were recrystallized (acetic acid ethyl ester/petroleum ether) to yield 33 g (68%) of the title material.

Mass spectrometry (ESI): 412.

Retention time (TLC): Rf=0.6; (dichloromethane/methanol 10+1)

Example 10.1.2

Ethyl 3-{[(3'-amino[1,1'-biphenyl]-3-yl)sulfonyl]amino}-3-phenyl-propanoate

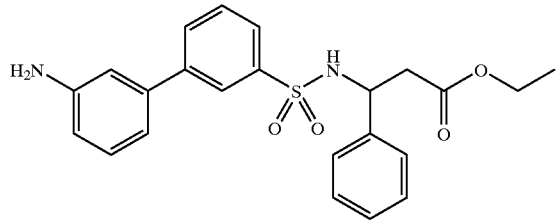

23.5 g (57 mmol) of ethyl 3-{[(3-bromophenyl)sulfonyl]amino}-3-phenyl-propanoate 10.1.1 were dissolved in 1,2 dimethoxyethane (270 ml) and 12.72 g (68 mmol) of 3-aminobenzeneboronic acid hemisulfate were added along with 63 ml of 2N sodium carbonate solution and 1.2 g of bis(triphenylphosphine)-palladiumdichloride. The mixture is refluxed for 2 h at room temperature. Diluted with acetic acid ethyl ester and washed with brine. The organic layer is dried, concentrated and purified via twofold flash chromatography (dichloromethane/acetic acid ethyl ester 10+1; petroleum ether/acetic acid ethyl ester 2+1).

Mass spectrometry (ESI): 424.

Retention time (HPLC): 7.46 min ((Kromasil C18; H$_3$PO$_4$ acetonitrile gradient)

Example 10.1.3

Ethyl 3-{[(3'-{[(cyanoimino)(methylsulfanyl)methyl]amino}-[1,1'-biphenyl]-3-yl)sulfonyl]amino}-3-phenyl-propanoate

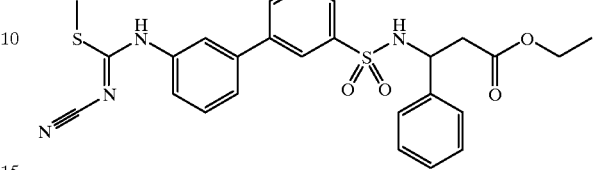

1.5 g of ethyl 3-{[(3'-amino[1,1'-biphenyl]-3-yl)sulfonyl]amino}-3-phenyl-propanoate 10.1.2 were dissolved in 20 ml ethanol and 5.17 g of cyanimidodithiocarbonate dimethyl ester were added. After 72 h of reflux, the reaction mixture was separated by flash chromatography (dichloromethane/methanol 50+1) and subsequently median pressure liquid chromatography (MPLC) (dichloromethane/acetic acid ethyl ester 2+1). 1 g (54.2%) of the title compound were obtained.

Retention time (TLC): Rf=0.6 (dichloromethane/methanol 10+1).

Example 10.1.4

Ethyl 3-[(3'-{[(benzylamino)(cyanoimino)methyl]amino}[1,1'-biphenyl]-3-yl)sulfonylamino]-3-phenyl-propanoate

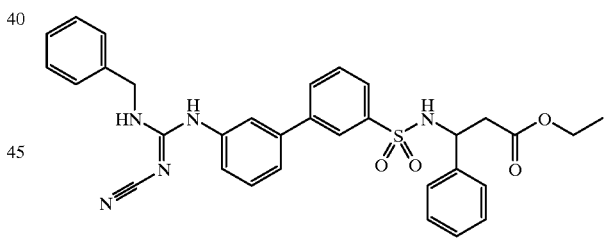

0.3 g (0.57 mmol) Ethyl 3-{[(3'-{[(cyanoimino)(methylsulfanyl)methyl]amnino}[1,1'-biphenyl]-3-yl)sulfonyl]amino}-3-phenyl-propanoate 10.1.3 were dissolved in 10 ml ethanol and 0.37 g (3.4 mmol) benzylamine (amine reagent) was added. The mixture was refluxed for 20 h, concentrated, and purified via flash chromatography (dichloromethane/acetic acid ethyl ester 5+1). 0.296 g (80%) were obtained.

Mass spectrometry (ESI): 582

Retention time (TL C): Rf=0.3 (dichloromethane/acetic acid ethyl ester 4+1).

m.p.: 80° C.

Example 10.1.5

3-[(3'-{[(benzylamino)(cyanoimino)methyl]amino}[1,1'-biphenyl]-3-yl)sulfonylamino]-3-phenyl-propanoic acid

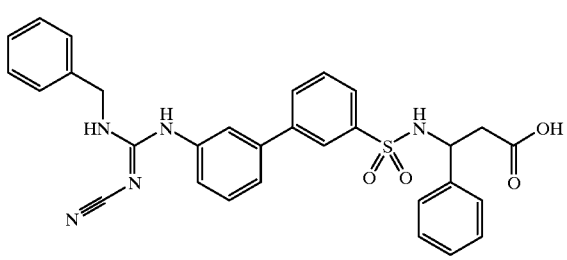

0.21 g (0.36 mmol) of Ethyl 3-[(3'-{[(benzylamino)(cyanoimino)methyl]amino}[1,1'-biphenyl]-3-yl)sulfonylamino]-3-propanoate 10.1.4 were dissolved in 4 ml 1,2-dimethoxyethane and 2 ml water. 0.21 g Lithium hydroxyde were added and the reaction mixture was stirred for 2 h at rt. The reaction being complete (tlc control), it was extracted with ether (2×20 ml) and the water phase was acidified (acetic acid) and extracted with 3×50 ml acetic acid ethyl ester. The resulting crude material was solidified with ether.

Mass spectrometry (ESI): 553

Retention time (TLC): 0.4 (dichloromethane/methanol 4+1)

m.p.: 90° C.

Example 10.2.4

Ethyl 3-[(3'-{[(o-pyridylmethylamino)(cyanoimino)methyl]-amino}[1,1'-biphenyl]-3-yl)sulfonylamino]-3-phenyl-propanoate

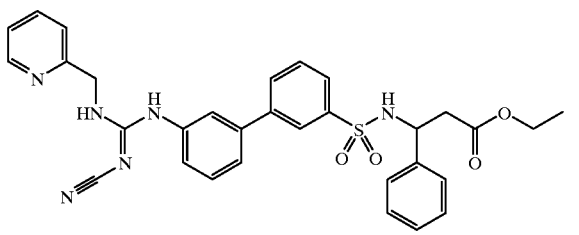

Ethyl 3-[(3'-{[(o-pyridylmethylamino)(cyanoimino)methyl]amino}[1,1'-biphenyl]-3-yl)sulfonylamino]-3-phenyl-propanoate is prepared according to the procedure of example 10.1.4 with the exception that, 2-aminomethylpyridine is used as an amine reagent instead of benzylamine.

Mass spectrometry (ESI): 583 m.p.: 82° C.

Example 10.2.5

3-[(3'-{[(o-Pyridylmethylamino)(cyanoimino)methyl]amino}-[1,1'-biphenyl]-3-yl)sulfonylamino]-3-phenyl-propanoic acid

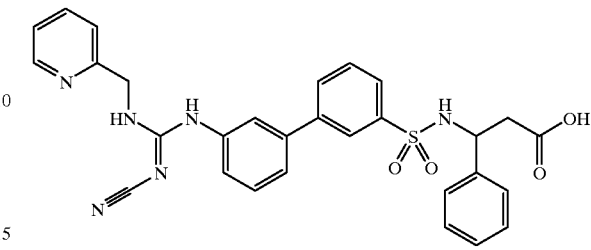

3-[(3'-{[(o-Pyridylmethlamino)(cyanoimino)methyl]amino)}[1,1'-biphenyl]-3-yl)sulfonylamino]-3-phenyl-propanoic acid is prepared from example 10.2.4 according to the procedure of example 10.1.5.

Mass spectrometry (ESI): 555 m.p.: 90° C.

Example 10.3.4

Ethyl 3-[(3'-{[(cyclopropylamino)(cyanoimino)methyl]amino}-[1,1'-biphenyl]-3-yl)sulfonylamino]-3-phenyl-propanoate

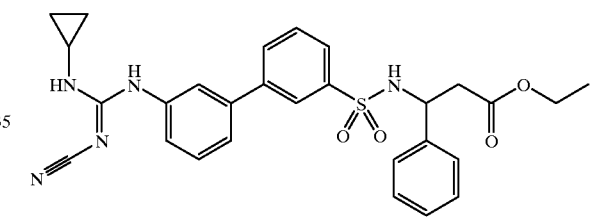

Ethyl 3-[(3'-{[(cyclopropylamino)(cyanoimino)methyl]amino}[1,1'-biphenyl]-3-yl)sulfonylamino]-3-phenyl-propanoate is prepared according to the procedure of example 10.1.4 with the exception that cyclopropylamine is used as an amine reagent instead of benzylamine.

Mass spectrometry (ESI): 532 m.p.: 82° C.

Example 10.3.5

3-[(3'-{[(cyclopropylamino)(cyanoimino)methyl]amino}[1,1'-biphenyl]-3-yl)sulfonylamino]-3-phenyl-propanoic acid

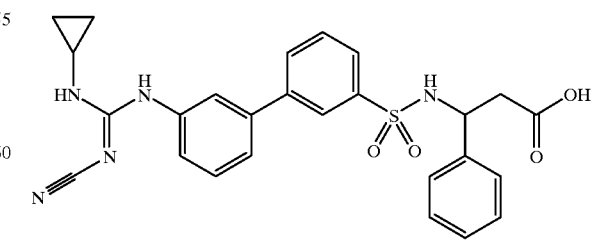

3-[(3'-{[(cyclopropylamino)(cyanoimino)methyl]amino}[1,1'-biphenyl]-3-yl)sulfonylamino]-3-phenyl-propanoic acid is prepared from example 10.3.4 according to the procedure of example 10.1.5.

Mass spectrometry (ESI): 504
m.p.: 120° C.

Example 11

General synthesis scheme:

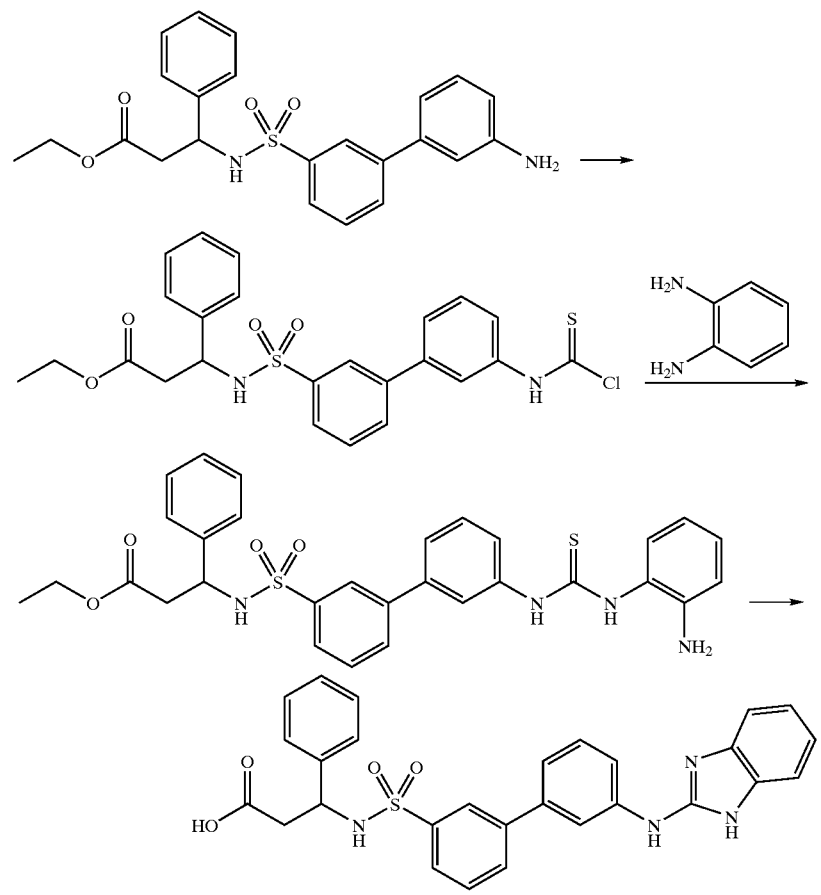

Example 11.1.1

Ethyl 3-{[(3'-{[(2-aminoanilino)carbothioyl]amino}[1,1'-biphenyl]-3-yl)sulfonyl]amino}-3-phenyl-propanoate

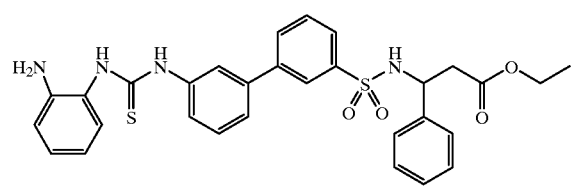

31.84 g (75 mmol) ethyl 3-{[(3'-amino[1,1'-biphenyl]-3-yl)sulfonyl]amino}-3-phenyl-propanoate 10.1.2 were dissolved in 600 ml toluene and 8.62 g thiophosgene were added. The mixture was refluxed for 2 h, evaporated and the residue dissolved in 200 ml toluene. This solution was added dropwise to a solution of o-phenylendiamine (12.2 g 113 mmol) in 500 ml tetrahydrofurane/toluene (1/1) at 40° C. The mixture was stirred for 12 h at room temperature, concentrated and purified (flash chromatography: dichloromethane/acetic acid ethyl ester10+1) to yield 43 g (100%).

Mass spectrometry (ESI): 574.

Retention time (HPLC): Rt=7.08 min (Kromasil C18, aqHClO$_4$ (1 proz.) in acetonitrile Gradient, flux: 0.5 ml/min, 210 nm).

Example 11.1.2

Ethyl 3-{[3'-(1H-benzimidazol-2-ylamino)[1,1'-biphenyl]-3-yl]-sulfonylamino}-3-phenyl-propanoate

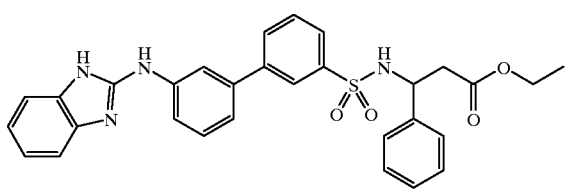

43 g (75mmol) of Ethyl 3-{[(3'-{[(2-aminoanilino)carbothioyl]amino}[1,1'-biphenyl]-3-yl)sulfonyl]amino}-3-phenyl propanoate 11.1.1 and 16.24 g (75 mmol) of yellow mercury oxide were mixed with 1.5l CHCl$_3$ and refluxed for

Example 11.1.3

Ethyl 3-{[3'-(1H-benzimidazol-2-ylamino)[1,1'-biphenyl]-3-yl]sulfonylamino}-3-phenyl-propanoate

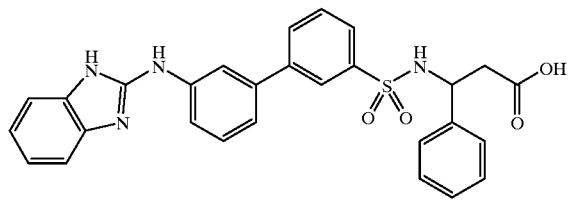

200 mg (0.37 mmol) Ethyl 3-{[3'-(1H-benzimidazol-2-ylamino)[1,1'-biphenyl]-3-yl]sulfonylamino}-3-phenyl-propanoate 11.1.2 were dissoyled in 20 ml 1,2,dimethoxyethane and 18 ml water. 0.2 g LiOH were added and after 2 h at room temperature, the solution was extracted with ether and the aqueous phase was acidified with acetic acid. The precipitate was collected and washed with water and ether. 0.163 mg (86%).

Mass spectrometry (ESI): 512.
m.p.: 180°

Example 12

Example 12.1.1

Methyl (2S)-3-(4-bromophenyl)-2-mesitylsulfonylaminopropanoate

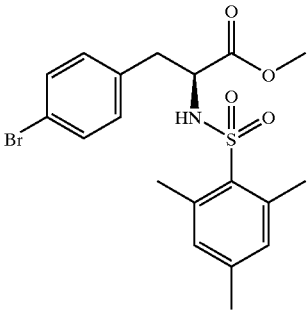

At 0° C., 9.35 g (42.77 mmol, 1.05 equiv.) mesitylenesulfonyl chloride (sulfonylating reagent) is added to a solution of 12.0 g (40.47 mmol, 1.0 equiv.) methyl (2S)-3-(4-bromophenyl)-2-aminopropanoate hydrochloride in 100 ml dry pyridine. The cooling bath is removed and the mixture is stirred at room temperature over night. Then, the pyridine is evaporated under reduced pressure and the semi-solid crude product is partitioned between 2-molar aqueous hydrochloric acid and ethyl acetate. The organic layer is successively washed with 2-molar aqueous hydrochloric acid, water and brine. Dried over unhydrous sodium sulfate. The product is filtered over a pad of silica, using cyclohexane/ethyl acetate 2:1 as the solvent. 15.5 g (35.20 mmol, 86% yield) are obtained as a white, crystalline solid.

Mass spectrometry (ESI): 462/464 (M+Na$^+$), 440/442 (M+H$^+$).

General synthesis scheme:

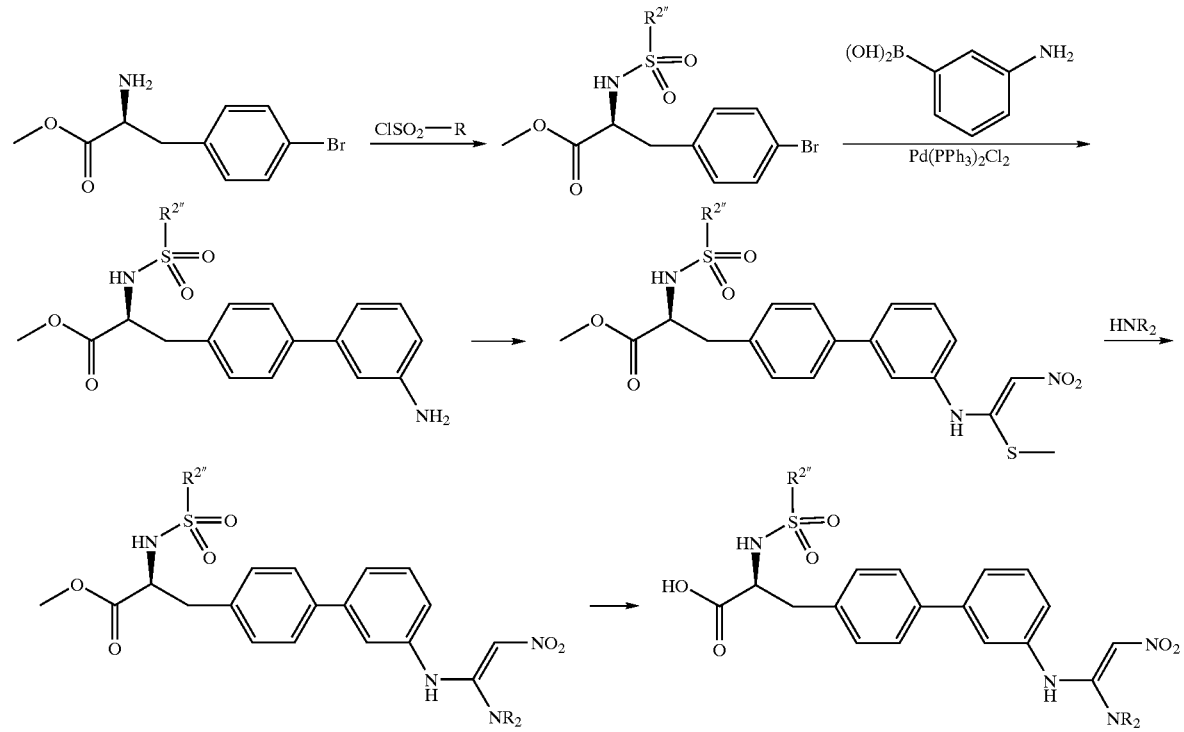

Retention time (TLC): $R_f$=0.70 (cyclohexane-ethyl acetate, 1:2).

$^1$H-NMR (400 MHz, dimethylsulfoxide-$d_6$): δ=8.31 (1H, d), 7.28 (2H, d), 7.00 (2H, d), 6.87 (2H, s), 3.82 (1H, m), 3.42 (3H, s), 2.90 (1H, dd), 2.72 (1H, dd), 2.39 (6H, s), 2.27 (3H, s).

Example 12.1.2

Methyl (2S)-3-(3'-amino[1,1'-biphenyl]-4-yl)-2-mesitylsulfonylamino-propanoate

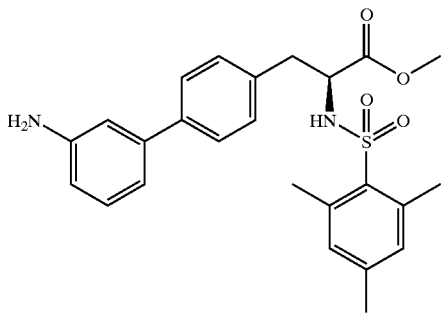

Under an atmosphere of argon, a vigorously stirred suspension of 25.0 g (56.77 mmol, 1.0 equiv.) methyl (2S)-3-(4-bromophenyl)-2-mesitylsulfonylaminopropanoate 12.1.1, 12.67 g (34.06 mmol, 1,2 equiv.) 3-aminophenylboronic acid hemisulfate and 1.2 g (1.70 mmol, 0.03 equiv.) dichlorobis(triphenylphosphino)-palladium in 350 ml dimethoxy ethane is treated with 62.5 ml (125 mmol) of a 2-molar solution of sodium carbonate in water. The mixture is heated to reflux. After three hours, the reaction is completed and the reaction mixture is cooled to room temperature. After dilution with ethyl acetate, the mixture is successiveley washed with 5% aqueous sodium dihydrogenphosphate, water and brine. Dried over anhydrous sodium sulfate. After removal of the solvent, the crude product is purified by suction filtration over silica using cyclohexane/ethyl acetate 2:1 as the solvent. 20.65 g (45.63 mmol, 80% yield) of a white amorphous solid are obtained.

Mass spaectrometry (ESI): 905 (2M+H$^+$), 453 (M+H$^+$)

Retention time (TLC): $R_f$=0.45 (cyclohexane/ethyl acetate, 1:2)

$^1$H-NMR (300 MHz, dimethylsulfoxide-$d_6$): δ=8.29 (1H, d), 7.30 (2H, d), 7.08 (1H, t), 7.07 (2H, d), 6.84 (2H, s), 6.80 (1H, s), 6.72 (1H, d), 6.55 (1H, d), 5.10 (2H, s), 3.87 (1H, m), 3.40 (3H, s), 2.95 (1H, dd), 2.80 (1H, dd), 2.42 (6H, s), 2.10 (3H, s).

Example 12.1.3

Methyl (2S)-2-[(mesitylsulfonyl)amino]-3-(3'-{[(Z)-1-(methylsulfanyl)-2-nitroethenyl]amino}[1,1'-phenyl]-4-yl)-propanoate

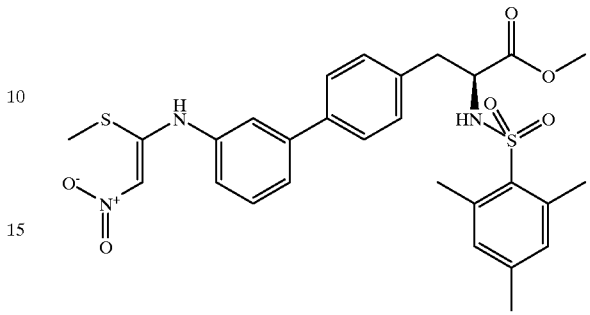

9.13 g (55.24 mmol) of 2-nitro-1,1-di(thiomethyl) ethylene and 2.50 g (5.52 mmol) of methyl (2S)-3-(3'-amino[1,1'-biphenyl]-4-yl)-2-mesitylsulfonylamino-propanoate 12.1.2 were refluxed in 450 ml n-propanol for 4 h. The reaction mixture was concentrated and purified via flash chromatography (dichloromethane/acetic acid ethyl ester 5+1). The product crystallized from dichloromethane/Ether to furnish 2.85 g (91%).

Mass spectrometry (ESI): 569.

Retention time (HPLC): Rt=9.77 min (Kromasil C18, H$_3$PO$_4$ in acetonitrile

Gradient, flux: 0.5 ml/min, 210 nm).

Retention time (TLC): Rf=0.60 (dichloromethane/acetic acid ethyl ester=10+1).

Example 12.1.4

Methyl (2S)-3-(3'-{[(E)-1-(cyclopropylamino)-2-nitroethenyl]-amino}[1,1'-biphenyl]-4-yl)-2-[(mesitylsulfonyl)amino]-propanoate

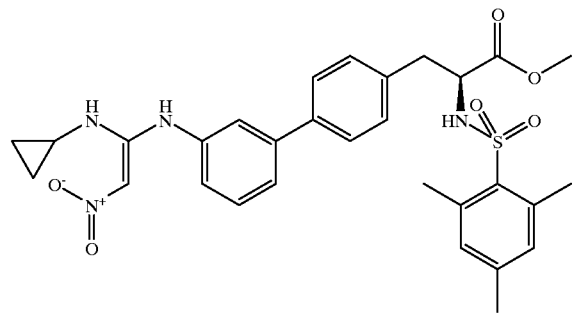

2.5 g (4.3 mmol) Methyl (2S-2-mesitylsulfonylamino-3-(3'-{[(Z)-1-(methylsulfanyl)-2-nitroethenyl]amino}[1,1'-biphenyl]-4yl)-propanoate 12.1.3 were dissolved in 60 ml propanol and 0.75 g cyclopropylamine (amine reagent) were added. The mixture was refluxed for 1 h concentrated and purified via flash chromatography (dichloromethane/methanol 10+1) to give 2.2 g (86%).

Mass spectrometry (ESI): 578.

Retetion time (HPLC): Rt=8.67 min (Kromasil C18, H3PO4 in acetonitrile

Gradient, flux: 0.5 m/min, 210 nm).

Example 12.1.5

(2S)-3-(3'-{[(E)-1-(cyclopropylamino)-2-nitroethenyl]amino}[1,1'-biphenyl]-4-yl)-2-[(mesitylsulfonyl)amino]-propanoic acid

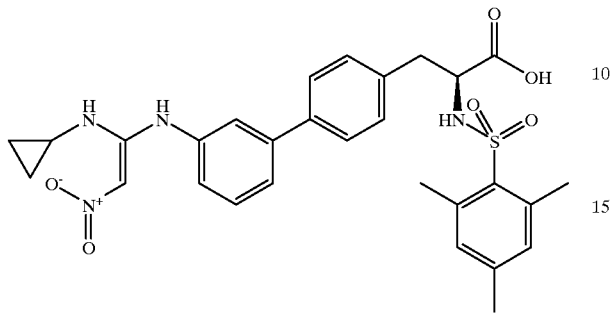

2 g (3.456 mmol) Methyl (2S)-3-(3'-{[(E)-1-(cyclopropylamino)-2-nitroethenyl]-amino}[1,1'-biphenyl]-4-yl)-2-mesitylsulfonylamino-propanoate 12.1.4 were dissolved in 90 ml 1,2 dimethoxymethane and 80 ml water. Then 2 g LiOH were added and the solution was stirred over night at rt. The mixture was extracted twice with ether and the residing aqueous phase was acidified (acetic acid). The precipitate was recristallized from dichloromethane/methanol to yield 1.3 g (66.6%)

Mass spectrometry (ESI): 564.

Retention time (HPLC): Rt=7.82 min (Kromasil C18, $H_3PO_4$ in acetonitrile

Gradient, flux: 0.5 ml/min, 210 nm).

m.p.: 149° C.

Example 12.2.3

Methyl (2S)-2-[((S)-campher-10-yl-sulfonyl)amino]-3-(3'-{[(Z)-1-(methylsulfanyl)-2-nitroethenyl]amino}[1,1'-biphenyl]-4-yl)-propanoate

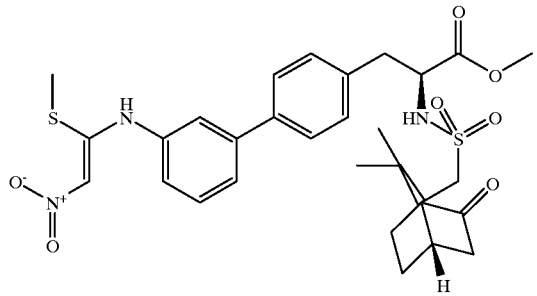

Methyl (2S)-2-[((S)-campher-10-yl-sulfonyl)amino]-3-(3'-{[(Z)-1-(methylsulfanyl)-2-nitroethenyl]amino}[1,1'-biphenyl]-4-yl)-propanoate is prepared according to the procedure of example 12.1.1–12.1.3, with the exception that (S)-(+)-campher-10-sulfonyl chloride is used as a sulfonylating reagent instead of mesitylenesulfonyl chloride.

Example 12.2.4

Methyl (2S)-3-(3'-{[(E)-1-(cyclopropylamino)-2-nitroethenyl]-amino}[1,1'-biphenyl]-4-yl)-2-[((S)-camper-10-yl-sulfonyl)amino]-propanoate

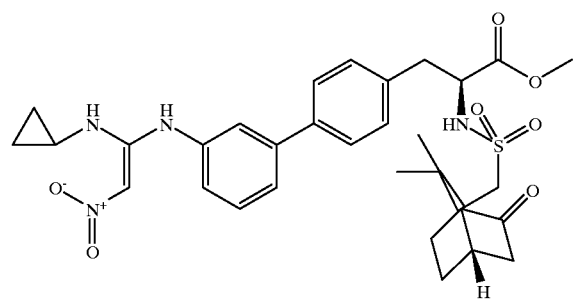

Methyl (2S)-3-(3'-{[(E)-1-(cyclopropylamino)-2-nitroethenyl]-amino}[1,1'-biphenyl]-4-yl)-2-[((S)-camper-10-yl-sulfonyl)amino]-propanoate is prepared from example 12.2.3 according to the procedure of example 12.1.4.

Example 12.2.5

(2S)-3-(3'-{[(E)-1-(cyclopropylamino)-2-nitroethenyl]amino}-[1,1'-biphenyl]-4-yl)-2-[((S)-camper-10-yl-sulfonyl)amino]-propanoate acid

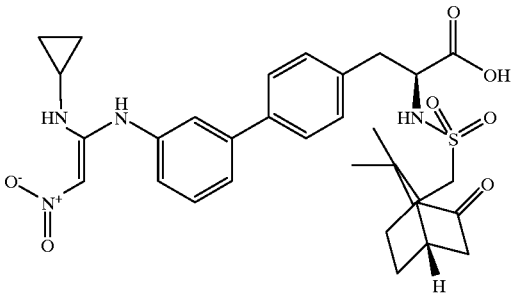

0.25 g Methyl (2S)-3-(3'-{[(E)-1-(cyclopropylamino)-2-nitroethenyl]amino}[1,1'-biphenyl]-4-yl)-2-[((S)-camper-10-yl-sulfonyl)amino]-propanoate 12.2.4 were saponified with LiOH as described above to yield 0.175 g (71%).

Mass spectrometry (ESI): 597.

Retention time (HPLC): Rt=7.42 min (Kromasil C18, $H_3PO_4$ in acetonitrile

Gradient, flux: 0.5 ml/min, 210 nM).

Retention time (TLC): Rf=0.4 (dichloromethane/methanol 4+1).

Example 13

General synthesis scheme:

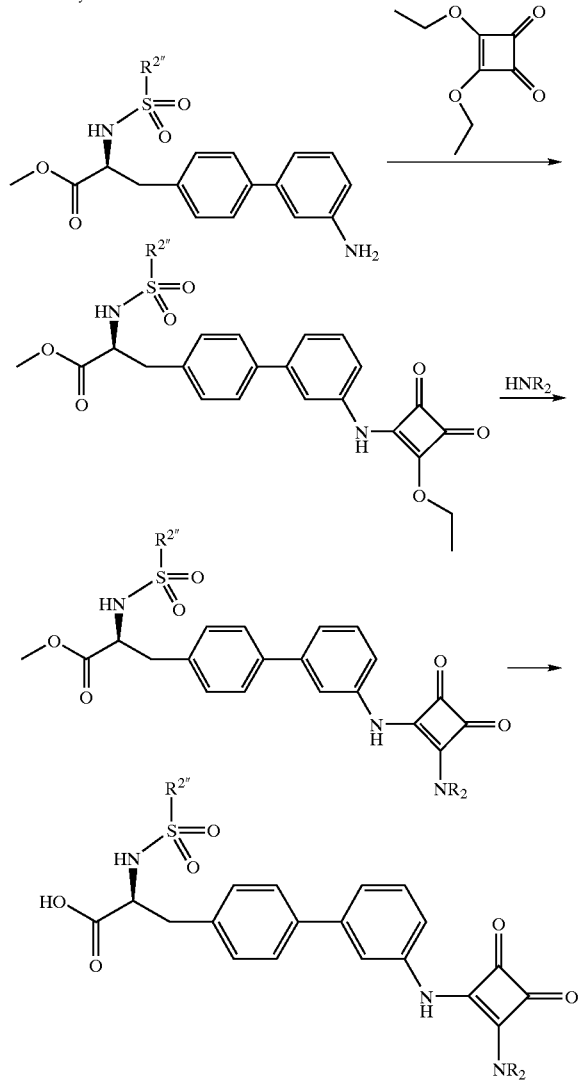

Example 13.1.1

Methyl (2S)-3-{3'-[(2-ethoxy-3,4-dioxo-1-cyclobuten-1-yl)-amino[1,1'-biphenyl]-4-yl}-2-mesitylsulfonylamino-propanoate

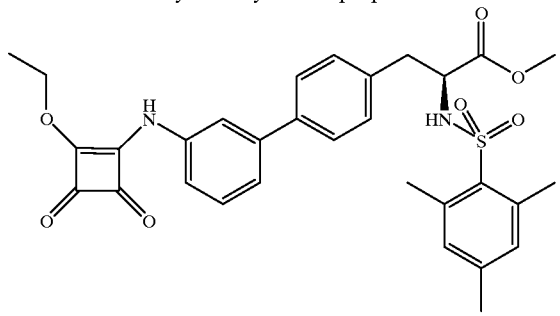

2 g of Methyl (2S)-3-(3'-amino[1,1'-biphenyl]-4-yl)-2-mesitylsulfonylamino-propanoate 12.1.2 were mixed with 0.75 g 3,4-diethoxy-3-cyclobuten-1,2-dion in 40 ml 1 propanol and refluxed for 20 h. Purification by flash chromatography (dichloromethane/acetic acid ethyl ester 10+1) yielded 1,5 g of the title compound.

Example 13.1.2

Methyl (2S)-3-(3'-{[2-(cyclopropylamino)-3,4-dioxo-1-cyclobuten-1-yl]amino}[1,1'-biphenyl]-4-yl)-2-[(mesitylsulfonyl)amino]-propanoate

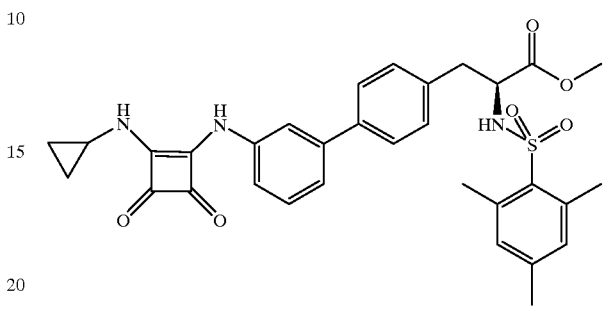

0.2 g methyl Methyl (2S)-3-{3'-[(2-ethoxy-3,4-dioxo-1-cyclobuten-1-yl)amino][1,1'-biphenyl]-4-yl}-2-mesitylsulfonylamino-propanoate 13.1.1 were dissolved in 10 ml iso-propanol and 0.24 ml cyclopropylamine were added. The mixture was refluxed for 2 h concentrated an purified via flash chromatography (dichloromethane/methanol 10+1) to obtain 0.2 g of the title material.

Example 13.1.3

(2S)-3-(3'-{[2-(cyclopropylamino)-3,4-dioxo-1-cyclobuten-1-yl]-amino}[1,1'-biphenyl]-4-yl)-2-[(mesitylsulfonyl)amino]-propanoic acid

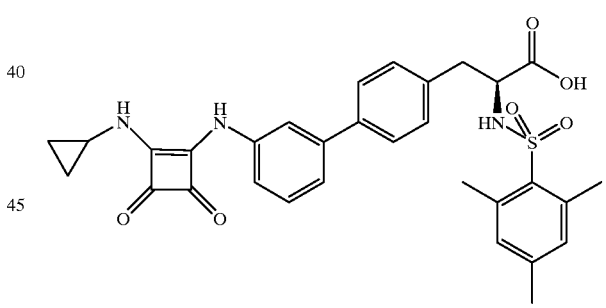

70 mg Methyl (2S)-3-(3'-{[2-(cyclopropylamino)-3,4-dioxo-1-cyclobuten-1-yl]-amino}[1,1'-biphenyl]-4-yl)-2-[(mesitylsulfonyl)amino]-propanoate 13.1.2 were dissolved in 1.6 ml dimethoxyethane and 0.8 ml water and 70 mg LiOH were added. The precipitate obtained after acidification was collected and purified by flash chromatography (dichloromethane/methanol 25+1) to yield 50 mg.

Mass spectrometry (ESI): 573.

Retention time (TLC): Rf=0.3 (dichloromethane/methanol 4+1).

Retention time (HPLC): Rt=7.27 min ((Kromasil C18, $HClO_4$ in acetonitrile

Gradient, flux: 0.5 ml/min, 210 nm).

m.p.: 164° C.

Example 14
General synthesis scheme:
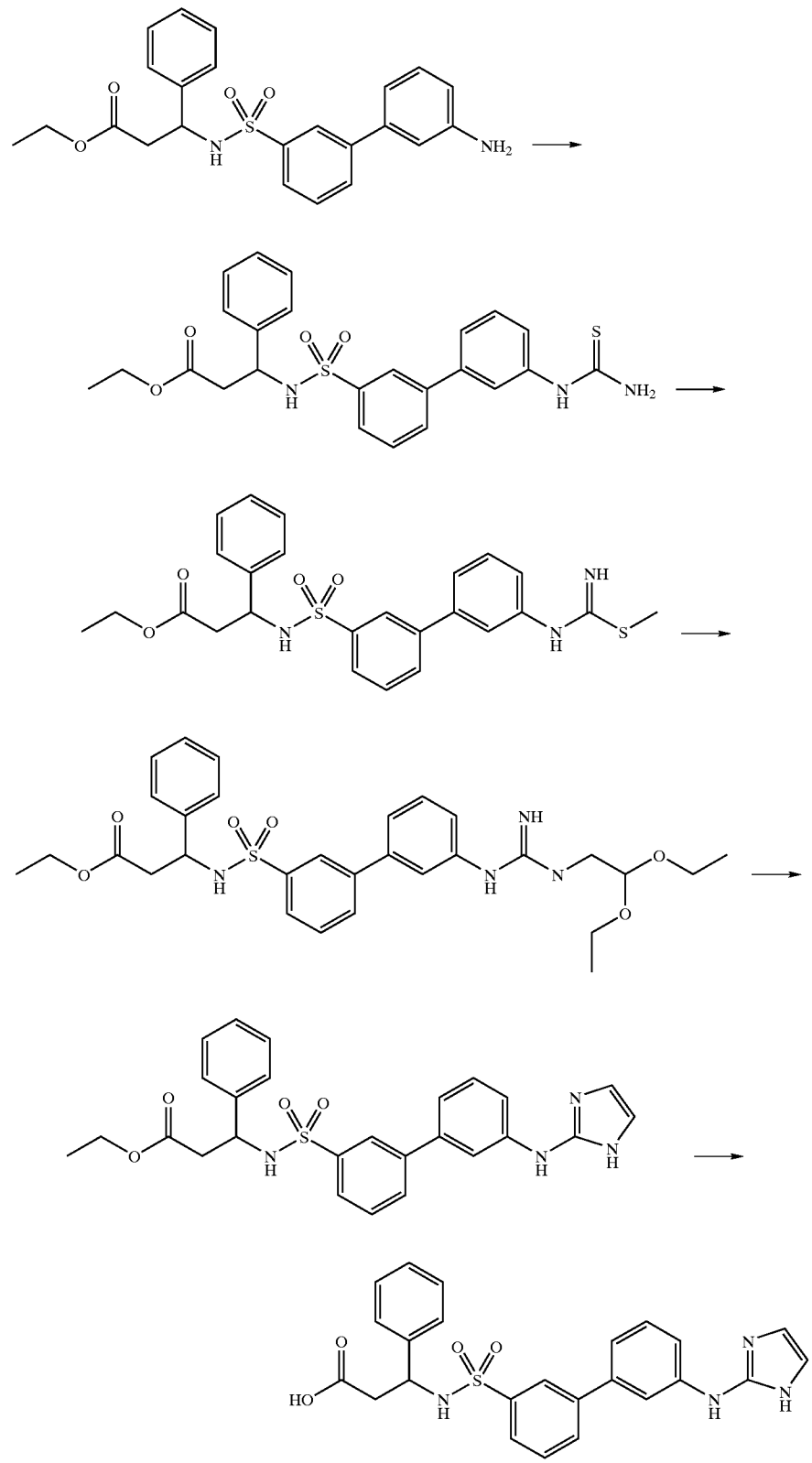

Example 14.1.1

Ethyl 3-[({3'-[(aminocarbothioyl)amino][1,1'-biphenyl]-3-yl}-sulfonyl)amino]-3-phenyl-propanoate

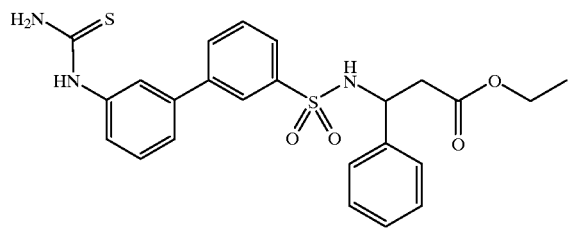

4.25 g of Ethyl 3-{[(3'-amino[1,1'-biphenyl]-3-yl)sulfonyl]amino}-3-phenyl-propanoate 10.1.2 and 1.26 g thiophosgene were disolved in 50 ml toluene refluxed for 1.5 h. The reaction mixture was concentrated and 50 ml tetrahydrofurane were added. NH₃ was bubbled into the solution for 30 min. Purification via flash chromatography (petrolium ether/acetic acid ethyl ester 1+1) and crystalisation (dichloromethane) gave 3.9 g of the title material.

Example 14.1.2

Ethyl 3-{[(3'-{[imino(methylsulfanyl)methyl]amino}[1,1'-biphenyl]-3-yl)sulfonyl]amino}-3-phenyl-propanoate

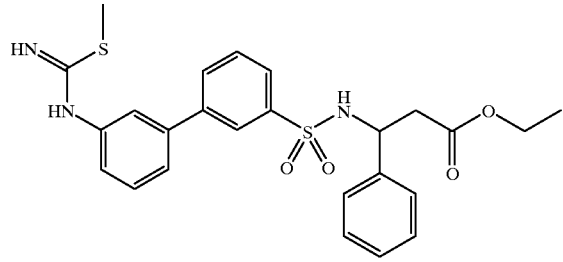

2.42 g of Ethyl 3-[({3'-[(aminocarbothioyl)amino][1,1'-biphenyl]-3-yl}sulfonyl)-amino]-3-phenylpropanoate 14.1.1 were dissolved in 80 ml methanol and 0.89 g Iodomethan were added. After reflux for 2 h, the reaction mixture was concentrated and crystalized from ether to obtain 3.1 g.

Example 14.1.3

Ethyl 3-[(3'-{[[(2,2-diethoxyethyl)amino](imino)methyl]amino}-1,1'-biphenyl]-3-yl)sulfonylamino]-3-phenyl-propanoate

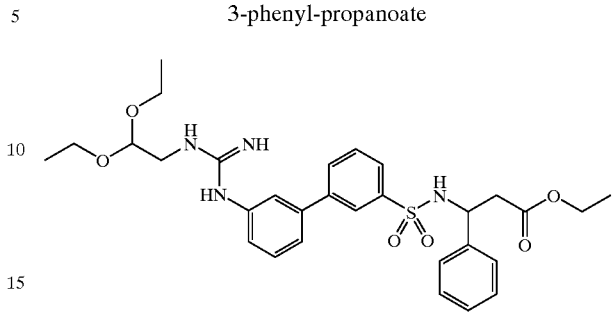

1.25 g Ethyl 3-{[(3'-{[imino(methylsulfanyl)methyl]amino}[1,1'-biphenyl]-3-yl)-sulfonylamino}-3-phenyl-propanoate 14.1.2 were dissolved in 20 ml n-propanol and 0.32 g aminoacetaldehyde-diethylacetal were added dropwise to the boiling solution within 6 h. flash chromatography (dichloromethane/acetic acid ethyl ester 4+1) yielded 1.1 g.

Example 14.1.4

3-{[3'-(1H-imidazol-2-ylamino)-1,1'-biphenyl]-3-yl]sulfonyl}-3-phenyl-propanoic acid

Example 14.1.5

3-{[3'-(2-amino-1H-imidazol-1-yl)[1,1'-biphenyl]-3-yl]sulfonyl}-3-phenyl-propanoic acid

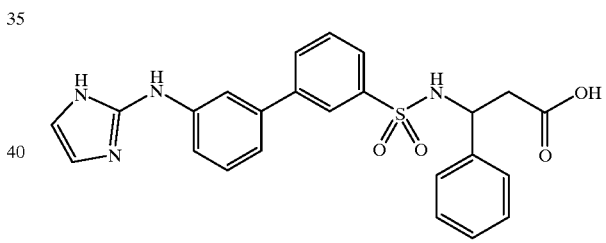

and

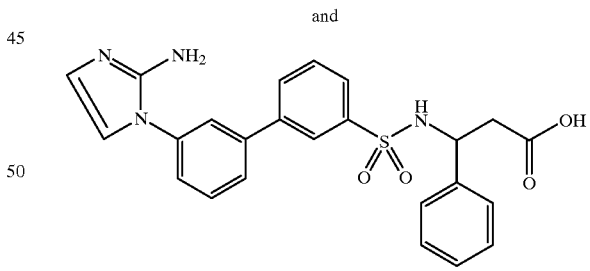

1 g Ethyl 3-[(3'-{[[(2,2-diethoxyethyl)amino](imino)methyl]amino}[1,1'-biphenyl]-3-yl)sulfonylamino]-3-phenyl-propanoate 14.1.3 was stirred in 100 ml 6N aq HCl at reflux for 1 h. Afterwards, the solution was made basic NaOH), extracted with dichloromethane and acidified (acetic acid). The separated crystalline material (230 mg) was separated via HPLC to yield 94 mg 3-{[3'-(1H-imidazol-2-ylamino)[1,1'-biphenyl]-3-yl]sulfonyl}-3-phenyl-propanoic acid 14.1.4:

Retention time (HPLC): Rt=7.09 min; Kromasil C18, H₃PO₄ in acetonitrile

Gradient, flux: 0.5 ml/min, 210 nm) and 38 mg 3-{[3'-(2-amino-1H-imidazol-1-yl)[1,1'-biphenyl]-3-yl]sulfonyl}-3-phenyl-propanoic acid 14.15:

Retention time (HPLC): Rt=8.77 min; Kromasil C18, H₃PO₄ in acetonitrile

Gradient, flux: 0.5 ml/min, 210 nm).

Example 15

General synthesis scheme:

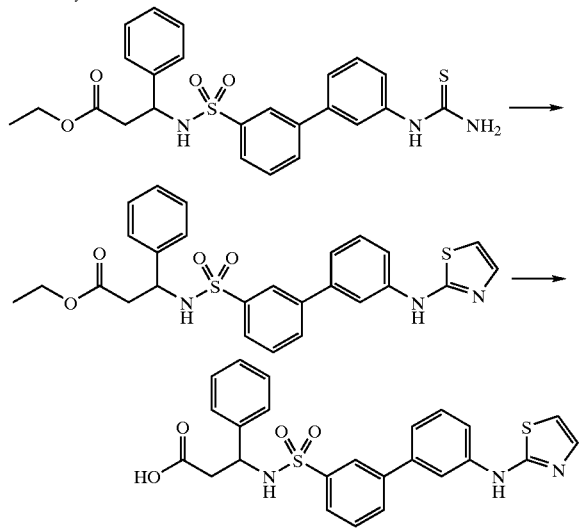

Example 15.1.1

Ethyl 3-phenyl-3-{[3'-(1,3-thiazol-2-ylamino)[1,1'-biphenyl]-3-yl]sulfonylamino}-propanoate

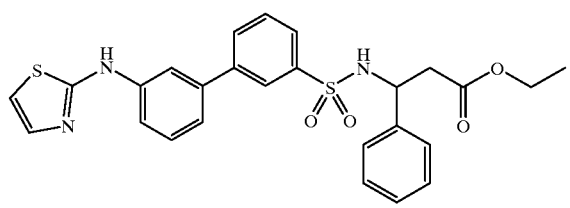

0.97 g of Ethyl 3-[({3'-[(aminocarbothioyl)amino][1,1'-biphenyl]-3-yl}sulfonyl)-amino]-3-phenyl-propanoate 14.1.1 and 0.48 g of 1,2-dichloroethylether were heated in water and i-propanol was added such that a clear solution resulted. After 1 h an additional 100 mg of 1,2 dichloroethylether were added and reflux was continued for 1 h.

After aqueous work-up and flash chromatography, 0.62 g of the title compound resulted.

Example 15.1.2

3-phenyl-3-{[3'-(1,3-thiazol-2-ylamino)[1,1'-biphenyl]-3-yl]sulfonylamino}-propanoic acid

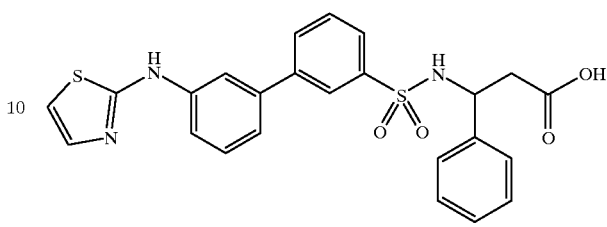

0.2 g of Ethyl 3-phenyl-3-{[3'-(1,3-thiazol-2-ylamino)[1,1'-biphenyl]-3-yl]sulfonylamino}-propanoate 15.1.1 were saponified in 15 ml dimethoxyethane 12 ml water and 0.2 g LiOH. After aqueos work-up and flash chromatography (dichloromethane/methanol 10+1) 65 mg were obtained.

Mass spectrometry (ESI): 480.

m.p: 130° C. (decomposition).

Example 16

General synthesis scheme:

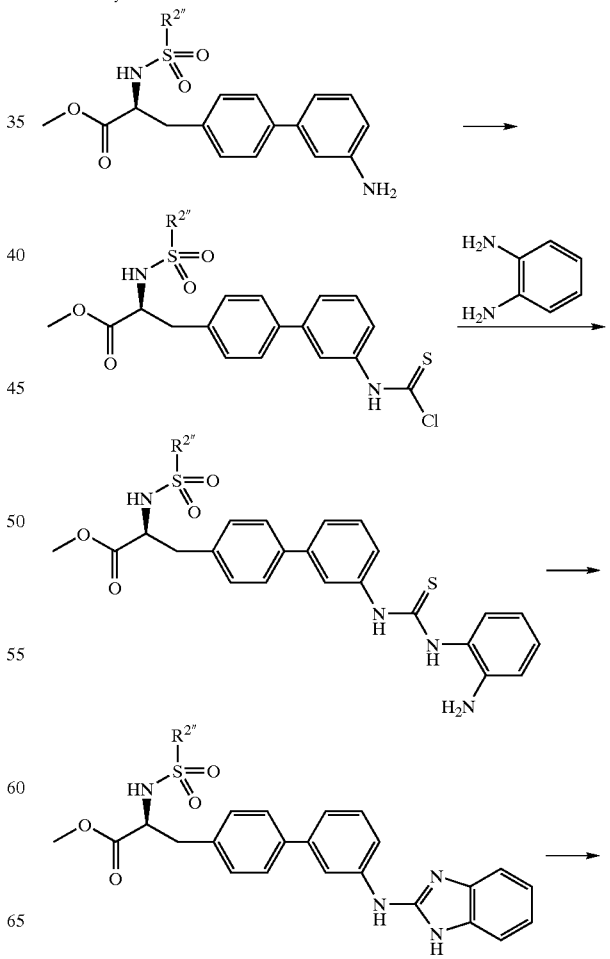

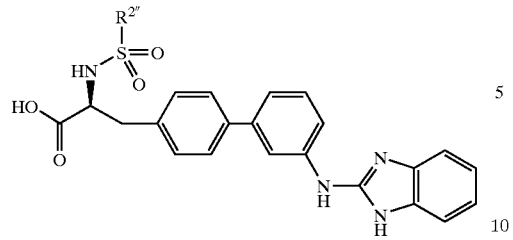

Example 16.1.1

Methyl (2S)-3-(3'-{[(2-aminoanilino)carbothioyl]amino}[1,1'-biphenyl]-4-yl)-2-[(mesitylsulfonyl)amino]-propanoate

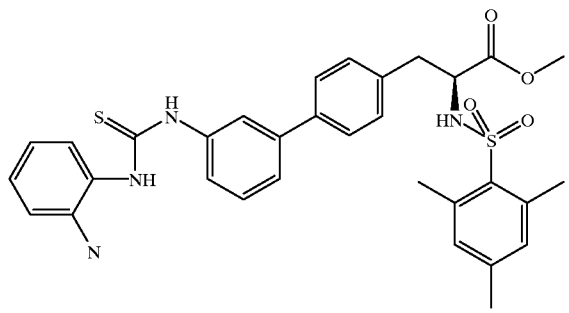

0.91 g of Methyl (2S)-3-(3'-amino[1,1'-biphenyl]-4-yl)-2-[(mesitylsulfonyl)amino]-propanoate 12.1.2 were dissolved in 20 ml toluene and 0.23 g thiophsogene were added. The reaction mixture was refluxed for 2 h, concentrated, redissolved in 20 ml toluene and added dropwise to a solution of o-phenylendiamine in toluene at 40° C. Stirring for 2 h resulted in a precipitate that was collected to yield 0.73 g of the title compound.

Example 16.1.2

Methyl (2S)-3-(3'-{[(2-aminoanilino)carbothioyl]amino}[1,1'-biphenyl]-4-yl)-2-[(mesitylsulfonyl)amino]-propanoate

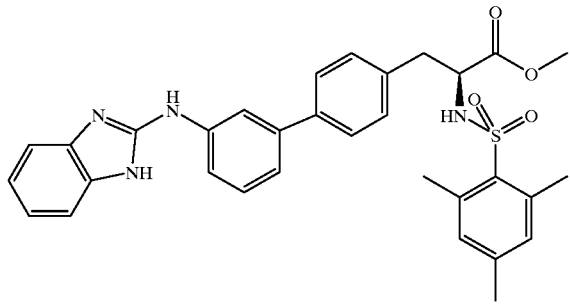

0.4 g of Methyl (2S)-3-(3'-{[(2-aminoanilino)carbothioyl]amino}[1,1'-biphenyl]-4-yl)-2-[(mesitylsulfonyl)amino]-propanoate 16.1.1 were dissolved in CHCl₃ (30 ml) and yellow HgO (0.14 g) were added. After 8 h of reflux, purification by flash chromatography (dichloromethane/acetic acid ethyl ester 10+1) yielded 336 mg of the title compound.

Example 16.1.3

(2S)-3-[3'-(1H-benzimidazol-2-ylamino)[1,1'-biphenyl]-4-yl]-2-[(mesitylsulfonyl)amino]propanoic acid

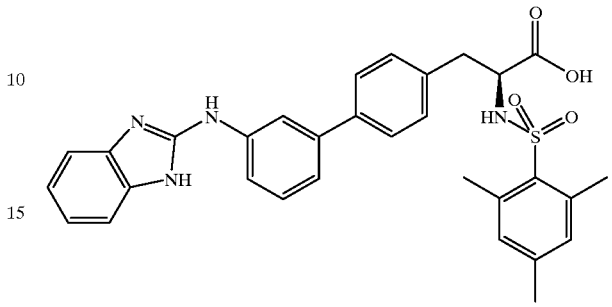

0.19 g Methyl (2S)-3-(3'-{[(2-aminoanilino)carbothioyl]amino}[1,1'-biphenyl]-4-yl)-2-[(mesitylsulfonyl)amino]-propanoate 16.1.2 were saponified in 15 ml dimethoxyethane 12 ml water and 0.19 g LiOH. Aqueous workup and recrystallization (methanol) yielded 0.13 g.

Mass spectrometry (ESI): 554

Retention time (HPLC): Rt=7.1 min (Kromasil C18, $H_3PO_4$ in acetonitrile

Gradient flux: 0.5 ml/min, 210 nm).

m.p.: 190° C. (decomp).

Example 17

General synthesis scheme:

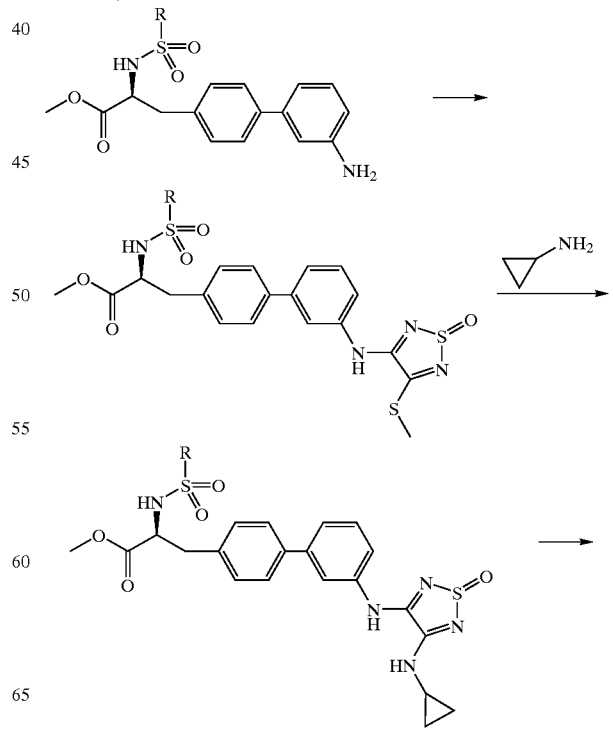

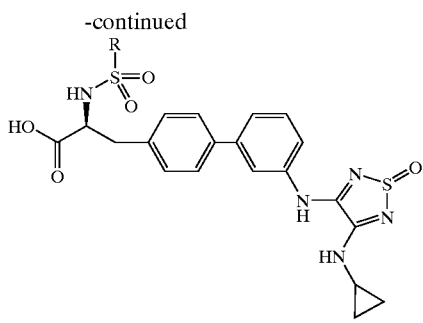

Example 17.1.1

Methyl (2S)-2-[(mesitylsulfonyl)amino]-3-(3'-{[4-(methylsulfanyl)-1-oxo-1H-1[lambda]4,2,5-thiadiazol-3-yl]amino}[1,1'-biphenyl]-4-yl)-propanoate

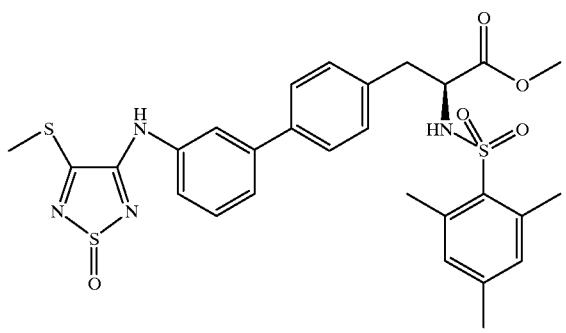

0.50 g of Methyl (2S)-3-(3'-amino[1,1'-biphenyl]-4-yl)-2-[(mesitylsulfonyl)amino]-propanoate 12.1.2 and 0.64 g of 3,4-bis(methylthio)-1,2,5-thiadiazole-1-oxide (J.Am.Chem.Soc. 1982, 1375–80) were dissolved in 10 ml n-propanol and refluxed over night. Purification by flash chromatography (dichloromethane/acetic acid ethyl ester= 10+1) yielded 0.258 g of the title compound.

Example 17.1.2

Methyl (2S)-2-[(mesitylsulfonyl)amino]-3-(3'-{[4-(cyclopropylamino)-1-oxo-1H -1[lambda]4,2,5-thiadiazol-3-yl]amino}[1,1'-biphenyl]-4-yl)-propanoate

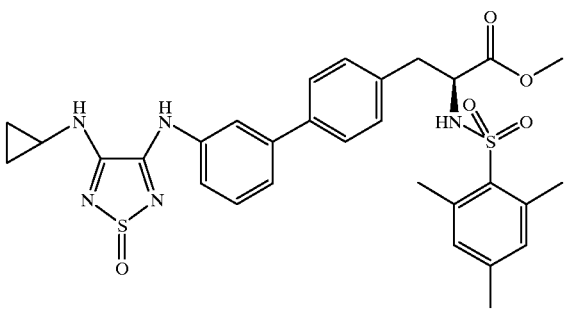

0.24 g of Methyl (2S)-2-[(mesitylsulfonyl)amino]-3-(3'-{[4-(methylsulfanyl)-1-oxo-1H-1[lambda]4,2,5-thiadiazol-3-yl]amino}[1,1'-biphenyl]-4-yl)-propanoate 17.1.1 were dissolved in n-propanol and heated to 50° together with 0.23 g cyclopropylamine for 2 h. flash chromatography (dichloromethane/acetic acid ethyl ester) yielded 214 mg of the title compound.

Example 17.1.3

(2S)-2-[(Mesitylsulfonyl)amino]-3-(3'-{[4-(cyclopropylamino)-1-oxo-1H-1[lambda]4,2,5-thiadiazol-3-yl]amino}[1,1'-biphenyl]-4-yl)-propanoate acid

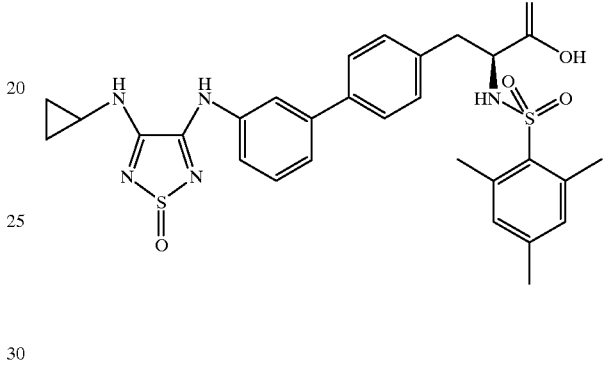

190 mg of Methyl (2S)-2-[(mesitylsulfonyl)amino]-3-(3-{[4-(cyclopropylamino)-1-oxo-1H-1[lambda]4,2,5-thiadiazol-3-yl]amino}[1,1'-biphenyl]-4-yl)-propanoate 17.1.2 were saponified in 20 ml dimethoxyethane and 20 ml water. By addition of 0.19 mg LiOH Acidification (acetic acid) and crystallisation (acetic acid ethyl ester) yielded 97 mg of yellow crystals.

Mass spectrometry: 594.

m.p. 180° C. (decomposition).

Example 18

General synthesis scheme:

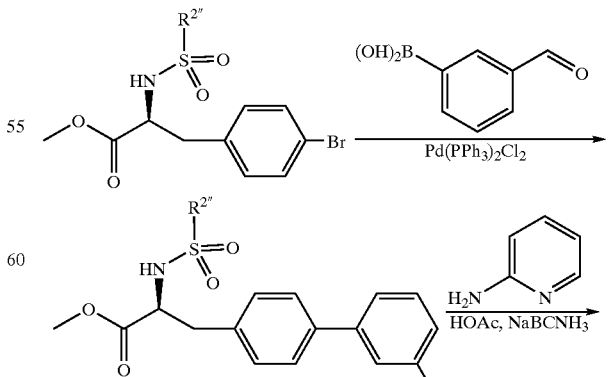

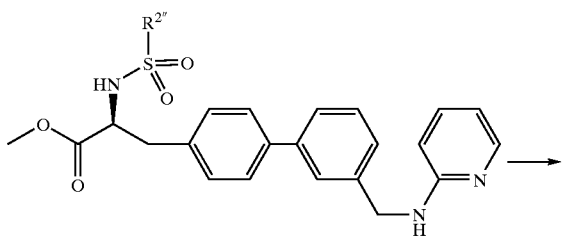

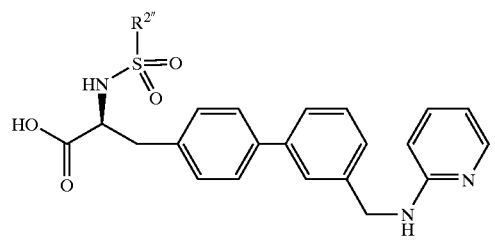

Example 18.1.1

Methyl (2S)-3-(3'-formyl[1,1'-biphenyl]-4-yl)-2-mesitysulfonylamino-propanoate

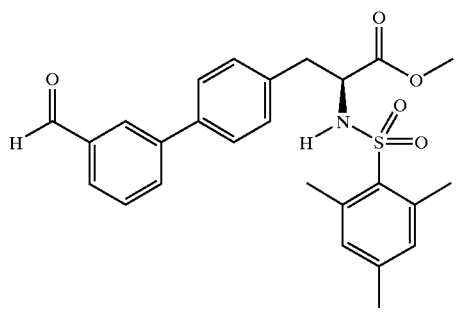

Under an atmosphere of argon, a vigorously stirred suspension of 10.0 g (22.71 mmol, 1.0 equiv.) methyl (2S)-3-(4-bromophenyl)-2-mesitylsulfonylamino-propanoate 12.1.1, 3.75 g (24.98 mmol, 1,1 equiv.) 3-formyl phenyl boronic acid and 0.48 g (0.68 mmol, 0.03 equiv.) dichlorobis (triphenylphosphino)-palladium in 120 ml dimethoxy ethane is treated with 13.67 ml (27.34 mmol, 1.2 equiv.) of a 2-molar solution of sodium carbonate in water. The mixture is heated to reflux. After five hours, the reaction is completed and the reaction mixture is cooled to room temperature. After dilution with ethyl acetate, the mixture is successiveley washed with 5% aqueous sodium dihydrogenphosphate, water and brine. Dried over anhydrous sodium sulfate. After removal of the solvent, the crude product is purified by suction filtration over silica using cyclohexane/ethyl acetate 4:1 as the solvent. 9.6 g (20.62 mmol, 91% yield) of a colorless glass-like solid.

Mass spectrometry (ESI): 488 (M+Na$^+$), 466 (M+H$^+$).

Retention time (TLC): R$_f$=0.20 (cyclohexane/ethyl acetate, 4:1)

$^1$H-NMR (300 MHz, dimethylsulfoxide-d$_6$): δ=10.11 (1H, s), 8.32 (1H, d), 8.15 (1H, pseudo-t), 7.98 (1H, pseudo-td), 7.89 (1H, pseudo-td), 7.69 (1H, pseudo-t), 7.50 (2H, d), 7.18 (2H, d), 6.81 (2H, s), 3.91 (1H, m), 3.42 (3H, s), 3.00 (1H, dd), 2.82 (1H, dd), 2.41 (6H, s), 2.03 (3H, s).

Example 18.1.2

Methyl (2S)-2-mesitylsulfonylamino-3-{3'-[(2-pyridinylamino)methyl][1,1'-biphenyl]-4-yl}-propanoate

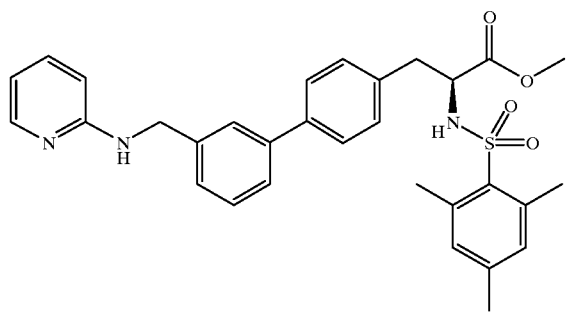

A solution of 9.20 g (19.76 mmol, 1.0 equiv.) methyl (2S)-3-(3-formyl[1,1'-biphenyl]-4-yl)-2-mesitylsulfonylamino-propanoate 18.1.1 and 3.72 g (39.52 mmol, 2.0 equiv.) 2-aminopyridine in a mixture of 18 ml acetic acid and 250 ml methanol is stirred at room temperature. After five hours, 4.97 g (79.04 mmol, 4.0 equiv.) sodium cyanoborohydride are added and the mixture is kept stirring for over night. With caution (HCN !), 100 ml aqueous 2-molar hydrochloric acid are added. Most of the solvent is removed on a rotary evaporator at 80° C. The residue is neutralized with 2-molar aqueous sodium hydroxide. The product is beeing extracted with ethyl acetate. The organic layer is washed with brine and dried over unhydrous sodium sulfate. After evaporation of the solvent, the crude product is purified by suction filtration over silica with dichloromethane/ethyl acetate 4:1 as the solvent. The product thus obtained is further purified by recrystallization from diethyl ether with a minimum amount of ethyl acetate. 5.4 g (9.93 mmol, 50% yield) of an off-white solid are obtained.

Mass spectrometry (DCI/NH$_3$): 544 (M+H$^+$)

Retention time (TLC): R$_f$=0.11 (dichloromethane/ethyl acetate, 5:1)

$^1$H-NMR (300 MHz, dimethylsulfoxide-d$_6$): δ=8.30 (1H, d), 7.96 (1H, dd), 7.58 (1H, s), 7.44 (1H, d), 7.41–7.29 (5H, m), 7.11 (2H, d), 7.04 (1H, t), 6.78 (2H, s), 6.53 (1H, d), 6.47 (1H, dd), 4.54 (2H, d), 3.88 (1H, m), 3.42 (3H, s), 2.97 (1H, dd), 2.79 (1H, dd), 2.38 (6H, s), 2.01 (3H, s).

Example 18.1.3

(2S)-2-Mesitylsulfonylamino-3-{3'-[(2-pyridinylamino)-methyl][1,1'-biphenyl]-4-yl}-propanoic acid

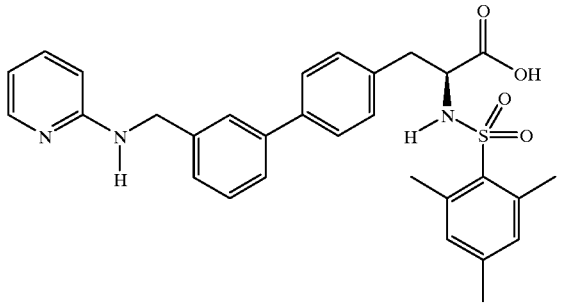

A solution of 100 mg (0.184 mmol) methyl (2S)-2-mesitylsulfonylamino-3-{3'-[(2-pyridinylamino)methyl][1,1'-biphenyl]-4-yl}-propanoate 18.1.2 in a mixture of 5 ml tetrahydrofurane and 2-molar aqueous sodium hydroxide is stirred at room temperature. After 20 hours, diluted hydrochloric acid is added until the pH reaches 3–4. The product precipitates and is collected by filtration and washed with water tetrahydrofurane. 86 mg (0.162 mmol, 88% yield) of a white solid are obtained.

Mass spectrometry (ESI): 530 (M+H$^+$)

Retention time (TLC): R$_f$=0.20 (ethyl acetate/methanol, 4:1)

$^1$H-NMR (300 MHz, dimethylsulfoxide-d$_6$): δ=7.97 (1H, dd), 7.57 (1H, s), 7.43 (1H, d), 7.40–7.27 (6H, m), 7.12 (2H, d), 7.02 (1H, t), 6.81 (2H, s), 6.53 (1H, d), 6.47 (1H, dd), 4.53 (2H, d), 3.52 (1H, m), 2.97–2.82 (2H, m), 2.43 (6H, s), 2.06 (3H, s).

Example 18.2.2

Methyl (2S)-2-mesitylsulfonylamino-3-{3'-[(1,3-thiazol-2-ylamino)methyl][1,1'-biphenyl]-4-yl}-propanoate

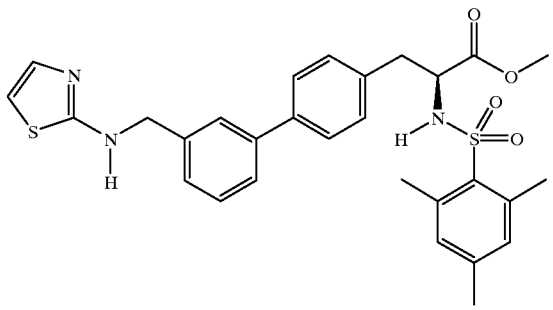

A solution of 500 mg (1.074 mmol, 1.0 equiv.) methyl (2S)-3-(3-formyl[1,1'-biphenyl]-4-yl)-2-[(mesitylsulfonyl) amino]-propanoate 18.1.1 118.3 mg (1.181 mmol, 1.1 equiv.) 2-aminothiazole and 100 mg piperidine in 5 ml tetrahydrofurane is warmed to 90° C. in an oil bath. Upon reaching this temperature, the solvent is carefully removed under vacuo (14 Torr) and the reaction mixture is kept for four hours at 90° C. and 14 Torr. After cooling to room temperature, the material is dissolved in 50 ml methanol and 675 mg (10.74 mmol, 10.0 equiv.) sodium cyanoborohydride are added. The mixture is stirred at room temperature over night. Then, the solvent is removed on a rotatory evaporator and the residue is taken up with ethyl acetate and successively washed with 5% aqueous sodium dihydrogenphosphate and brine. Dried over unhydrous sodium sulfate. The crude product is purified by flash chromatography (silica, cyclohexane/ethyl acetate 4:1). 240 mg (0.437 mmol, 41% yield) of a white solid are obtained.

Mass spectrometry (ESI): 550 (M+H$^+$)

Retention time (TLC): R$_f$=0.20 (dichloromethane/ethyl acetate, 7:3)

$^1$H-NMR (300 MHz, dimethylsulfoxide-d$_6$): δ=8.29 (1H, d), 8.07 (1H, t), 7.60 (1H, s), 7.48 (1H, d), 7.41 (1H, t), 7.38 (2H, d), 7.32 (1H, d), 7.11 (2H, d), 7.01 (1H, d), 6.79 (2H, s), 6.61 (1H, d), 4.52 (2H, d), 3.88 (1H, m), 3.42 (3H, s), 2.97 (1H, dd), 2.79 (1H, dd), 2.40 (6H, s), 2.02 (3H, s).

Example 18.2.3

(2S)-2-Mesitylsulfonylamino-3-{3'-[(1,3-thiazol-2-ylamino)methyl][1,1'-biphenyl]-4-yl}-propanoic acid

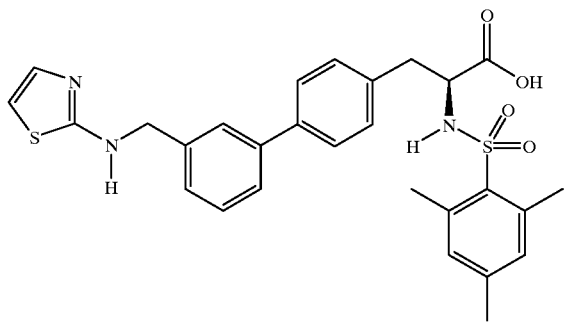

To a solution of 125 mg (0.227 mmol) methyl (2S)-2-mesitylsulfonylamino-3-{3'-[(1,3-thiazol-2-ylamino) methyl][1,1'-biphenyl]-4-yl}-propanoate 18.2.2 in 8 ml tetrahydrofurane is added 8 ml aqueous 2-molar sodium hydroxide. The mixture is vigorously stirred over night at room temperature. Then, the pH is adjusted to 3 by addition of 6-molar aqueous hydrochloric acid. The precipitated product is isolated by filtration and washed with water and a small amount of tetrahydrofurane. 110 mg (0.205 mmol, 90% yield) of a white solid are obtained.

Mass spectrometry (ESI): 536 (M+H$^+$), 558 (M+Na$^+$)

Retention time (TLC): R$_f$=0.16 (ethyl acetate/methanol, 3:1)

$^1$H-NMR (300 MHz, dimethylsulfoxide-d$_6$): δ=8.04 (1H, t), 7.59 (1H, s), 7.48(1H, d), 7.39 (1H, t), 7.37 (2H, d), 7.30 (1H, d), 7.17 (2H, d), 7.01 (1H, d), 6.92 (2H, s), 6.89 (1H, broad), 6.60 (1H, d), 4.51 (2H, d), 3.30 (1H, m, obscured by the water signal), 3.02 (1H, dd), 2.92 (1H, dd), 2.51 (6H, s, obscured by the dimethylsulfoxide signal), 2.16 (3H, s)

Example 19

General synthesis scheme:

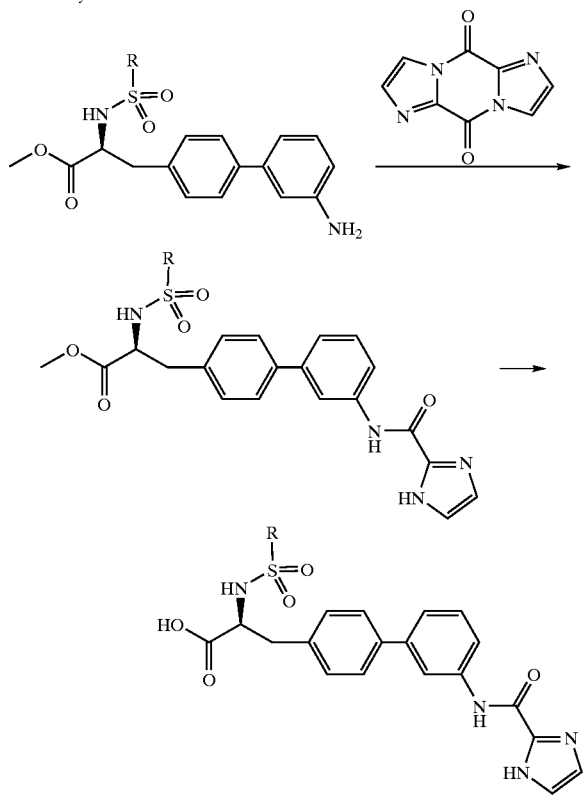

Example 19.1.1

Methyl (2S)-3-{3'-[(1H-imidazol-2-ylcarbonyl)amino][1,1'-biphenyl]-4-yl}-2-[(mesitylsulfonyl)amino]-propanoate

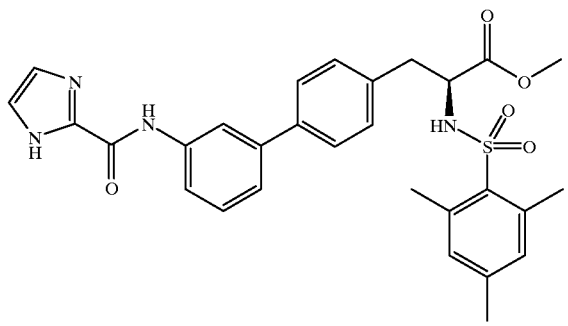

To a solution of 200 mg (0.44 mmol, 1.0 equiv.) methyl (2S)-3-(3-amino[1,1'-biphenyl]-4yl)-2-mesitylsulfonylamino-propanoate 12.1.2 in 10 ml dry tetrahydrofurane are added 140 µl (1.77 mmol, 4.0 equiv.) pyridine and a suspension of 46 mg (0.24 mmol, 1.1 equiv.) 5H,10H-diimidazo[1,2-a:1,2-d]pyrazine-5,10-dione in a mixture of 5 ml tetrahydrofurane and 1ml N,N-dimethyl formamide. The resulting suspension is stirred at room temperature for 72 hours. The reaction mixture is concentrated in vacuo and then taken up in ethyl acetate. The organic layer is successively washed with 5% aqueous sodium dihydrogenphosphate, water and brine. Dried over unhydrous sodium sulfate. The crude product is purified by flash chromatography (silica, cyclohexane/erthyl acetate, 1:1). 181 mg (0.33 mmol, 74% yield) of an off-white solid are obtained.

Mass spectrometry (ESI): 1093 (2M+H$^+$), 547 (M+H$^+$)

Retention time (TLC): $R_f$=0.53 (cyclohexane/ethyl acetate, 1:2)

$^1$H-NMR (300 MHz, dimethylsulfoxide-d$_6$): δ=13.21 (1H, s broad), 10.40 (1H, s), 8.32 (1H, d), 8.13 (1H, s), 7.88(1H, d), 7.45–7.32(5H, m), 7.16(2H, d), 7.11 (1H, s), 6.82 (2H, s), 3.89 (1H, m), 3.44 (3H, s), 2.98 (1H, dd), 2.81 (1H, dd), 2.42 (6H, s), 2.03 (3H, s).

Example 19.1.2

(2S)-3-{3'-[(1H-imidazol-2-ylcarbonyl)amino[]1,1'-biphenyl]-4-yl}-2-[(mesitylsulfonyl)amino-propanoic acid

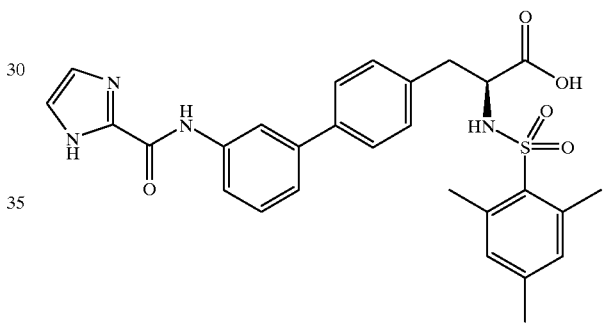

8 ml 2-molar aqueous sodium hydroxide are added to a solution of 130 mg (0.24 mmol) methyl (2S)-3-{3'-[(1H-imidazol-2-ylcarbonyl)amino][1,1'-biphenyl]-4-yl}-2-mesitylsulfonylamino-propanoate 19.1.1 in 8 ml tetrahydrofurane. After stirring at room temperature for 20 hours, the mixture is concentrated under reduced pressure. The pH is adjusted to 5 by the addition of 2-molar aqueous hydrochloric acid. The product precipitates upon acidification and is filtered off. It is washed with water and a small amount of tetrahydrofurane. 101 mg (0.19 mmol, 80% yield) of an off-white solid are obtained.

Mass spectrometry (ESI): 533 (M+H$^+$).

Retention time (TLC): $R_f$=0.10 (dichloromethane/methanol, 10:1)

$^1$H-NMR (300 MHz, dimethylsulfoxide-d$_6$): δ=13.27 (1H, s broad), 12.70 (1H, very broad), 10.47 (1H, s), 8.15 (1H, s), 8.13 (1H, d), 7.88 (1H, d), 7.45–7.32 (5H, m), 7.17 (1H, s), 7.11 (2H, d), 6.78 (2H, s), 3.79 (1H, m), 2.98 (1H, dd), 2.73 (1H, dd), 2.40 (6H, s), 1.98 (3H, s).

Example 20

General synthesis scheme:

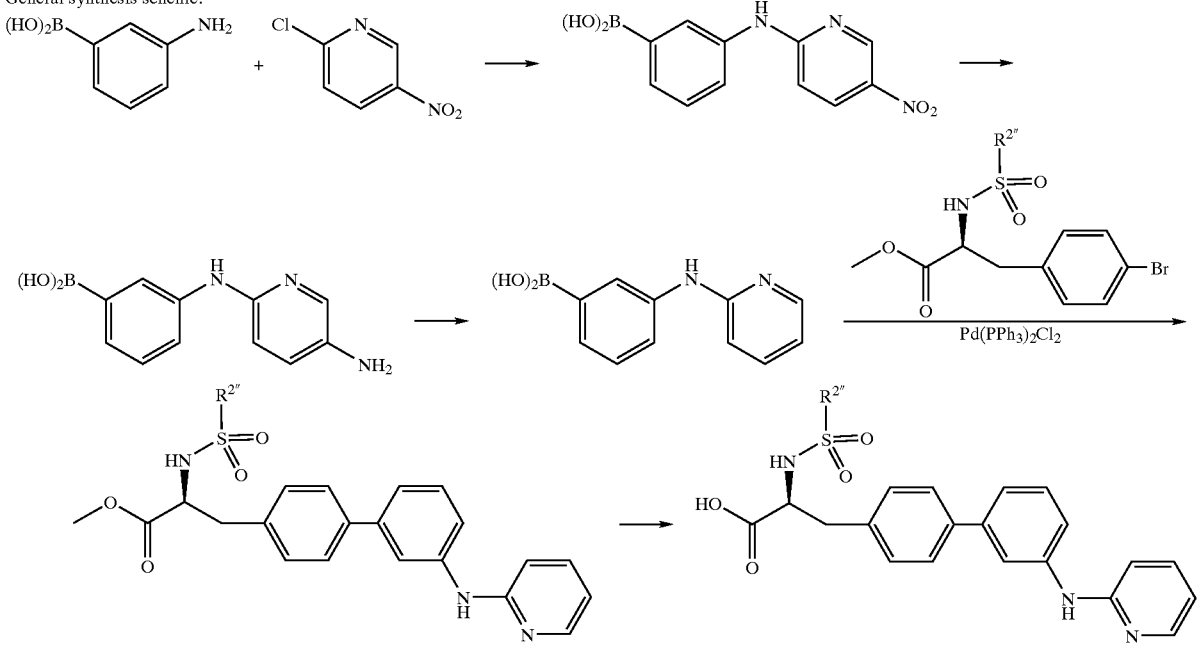

Example 20.1.1

3-[(5-Nitro-2-pyridinyl)amino]-phenylboronic acid

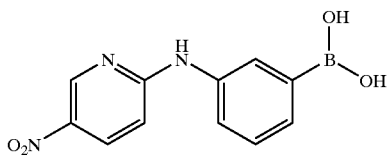

A mixture of 2.0 g (5.377 mmol, 1.0 equiv.) 3-aminophenylboronic acid hemisulfate, 1.7 g (10.75 mmol, 1.0 equiv.) 2-chloro-5-nitropyridine and 2.28 g (21.51 mmol) sodium carbonate in 20 ml dry N-methyl pyrrolidinone is heated to 100° C. under an atmosphere of argon. After 5 hours, the mixture is allowed to cool to room temperature. 5% aqueous sodium dihydrogenphosphate and ether are added and the heterogeneous mixture is stirred for a while. The product precipitates and is collected by filtration. It is washed with water and ether. 2.0 g (7.721 mmol, 72% yield) of a yellow solid is obtained which is about 90% pure and used for the next step without further purification.

Retention time (TLC): $R_f$=0.24 (dichloromethane/methanol, 100:5)

$^1$H-NMR (300 MHz, dimethylsulfoxide-$d_6$): δ10.05 (1H, s), 9.02 (1H, d), 8.27 (1H, dd), 8.02 (2H, s broad), 7.87 (1H, s), 7.83 (1H, d), 7.53 (1H, d), 7.34 (1H, t), 6.89 (1H, d).

Example 20.1.2

3-1(5-Amino-2-pyridinyl)amino]-phenylboronic acid

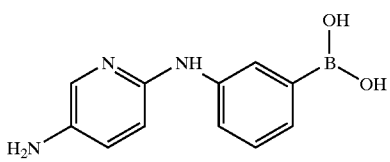

A solution of 1.50 g (5.791 mnmol) 3-[(5-nitro-2-pyridinyl)amino]-phenylboronic acid 20.1.1 in 50 ml ethanol is hydrogenated at room temperature and ambient pressure in the presence of 70 mg palladium on charcoal (10%). After 20 hours, the mixture is filtered over a pad of cellite and the solution is concentrated to dryness. The product is purified by flash chromatography (silica, ethyl acetate/methanol, 9:1) to afford 0.85 g (3.711 mmol, 64% yield) of an off-white solid.

Retention time (TLC): $R_f$=0.30 (ethyl acetate/methanol, 9:1)

$^1$H-NMR (300 MHz, dimethylsulfoxide-$d_6$): δ=8.21 (1H, s), 7.80 (2H, s), 7.66 (1H, dd), 7.63 (1H, s), 7.60 (1H, d), 7.19 (1H, d), 7.12 (1H, t), 6.93 (1H, dd), 6.67 (1H, d), 4.61 (2H, s broad).

Example 20.1.3

3-(2-Pyridinylamino)-phenylboronic acid

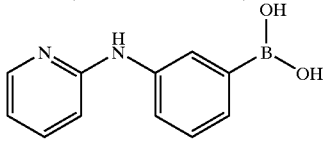

A solution of 219 mg (3.165 mmol, 1.45 equiv.) sodium nitrite in 5 ml water is added dropwise to a solution of 500 mg 3-[(5-amino-2-pyridinyl)amino]-phenylboronic acid 20.1.2 in 10 ml 18% aqueous hydrochloric acid at 0° C. After 15 minutes at 0° C., 10 ml phosphinic acid are added and stirring is continued at 0° C. for another 30 minutes. Then, the pH of the mixture is adjusted to 5–6 by the addition of 45% aqueous sodium hydroxide. The product is extracted with ethyl acetate. The organic layer is washed with brine and dried over unhydrous sodium sulfate. After removal of the solvent, the product is purified by crystallization from ether with a minimum amount of ethyl acetate. 165 mg (0.771 mmol, 35% yield) of a white solid are obtained.

Retention time (TLC): $R_f$=0.57 (ethyl acetate/methanol, 4:1)

$^1$H-NMR (300 MHz, dimethylsulfoxide-$d_6$): δ=8.85 (1H, s), 8.11 (1H, dd), 7.88 (2H, s), 7.83 (1H, d), 7.80 (1H, s), 7.52 (1H, dt), 7.33 (1H, d), 7.22 (1H, t), 6.82 (1H, d), 6.69 (1H, dd).

Example 20.1.4

Methyl (2S)-2-[(mesitylsulfonyl)amino]-3-[3'-(2-pyridinylamino)-[1,1-biphenyl]-4-yl]propanoate

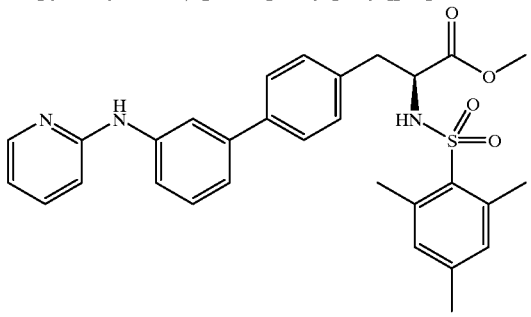

Under an atmosphere of argon, a vigorously stirred suspension of 417 mg (0.946 mmol, 1.0 equiv.) methyl (2S)-3-(4-bromophenyl)-2-[(mesitylsulfonyl)amino]-propanoate 20.1.3, 243 mg (1.135 mmol, 1,2 equiv.) 3-(2-pyridinylamino)phenylboronic acid and 33 mg (0.047 mmol, 0.05 equiv.) dichlorobis(triphenylphosphino)-palladium in 15 ml dimethoxy ethane is treated with 0.62 ml (1.25 mmol) of a 2-molar solution of sodium carbonate in water. The mixture is heated to reflux. After six hours, the reaction is completed and the reaction mixture is cooled to room temperature. After dilution with ethyl acetate, the mixture is successively washed with 5% aqueous sodium dihydrogenphosphate, water and brine. Dried over anhydrous sodium sulfate. After removal of the solvent, the crude product is purified by flash chromatography (silica, cyclohexane/ethyl acetate, 3:1). 84 mg (0.159 mmol, 14% yield) of a yellowish solid are obtained.

Mass spectrometry (ESI): 530 (M+H$^+$)

Retention time (TLC): $R_f$=0.54 (ethyl acetate/methanol, 4:1)

$^1$H-NMR (300 MHz, dimethylsulfoxide-$d_6$): 9.06 (1H, s), 8.30 (1H, d), 8.17 (1H, dd), 7.94 (1H, s), 7.67 (1H, d), 7.58 (1H, dt), 7.37 (2H, d), 7.33 (1H, t), 7.12 (2H, d), 7.11 (1H, d), 6.87 (1H, d), 6.83 (2H, s), 6.74 (1H, dd), 3.89 (1H, m), 3.42 (3H, s), 2.98 (1H, dd), 2.81 (1H, dd), 2.42 (6H, s), 2.04 (3H, s)

Example 20.1.5

(2S)-2-[(Mesitylsulfonyl)amino]-3-[3'-(2-pyridinylamino)[1,1'-biphenyl]-4-yl]-propanoic acid

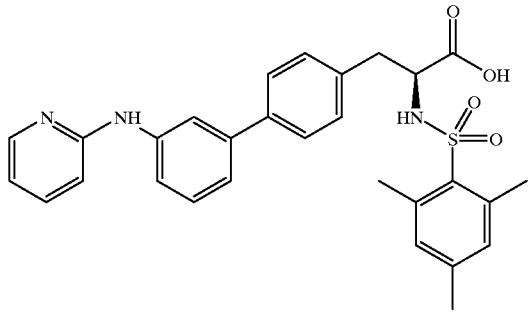

A solution of 84 mg (0.159 mmol) methyl (2S)-2-[(mesitylsulfonyl)amino]-3-[3'-(2-pyridinylamino)[1,1'-biphenyl]-4-yl]-propanoate 20.1.4 in a mixture of 3.5 ml tetrahydrofurane and 3.5 ml 2-molar aqueous sodium hydroxide is stirred at room temperature. After 20 hours, the mixture is acidified with hydrochloric acid to pH 4–5. The product precipitates and is isolated by filtration. It is washed with water and tetrahydrofuran. A pale yellowish solid is obtained: 53 mg (0.103 mmol, 65% yield).

Mass spectrometry (ESI): 516 (M+H$^+$)

Retention time (TLC): $R_f$=0.20 (ethyl acetate/methanol, 4:1)

$^1$H-NMR (300 MHz, dimethylsulfoxide-$d_6$): δ12.70 (1H, s broad), 9.07 (1H, s), 8.18 (1H, d), 8.07 (1H, d), 7.93 (1H, s), 7.67 (1H, d), 7.58 (1H, dt), 7.32 (1H, t), 7.31 (2H, d), 7.10 (2H, d), 6.87 (1H, d), 6.80 (2H, s), 6.75 (1H, dd), 3.80 (1H, m), 2.98 (1H, dd), 2.76 (1H, dd), 2.41 (6H, s), 2.00 (3H, s).

Example 20.2.1

Methyl 3-{[(5-bromo-2-methoxyphenyl)sulfonyl]amino}-3-phenylpropanoate

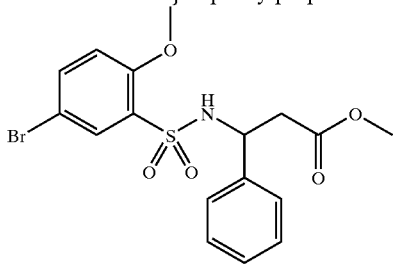

At 0° C., a solution of 10.73 g (37.59 mmol, 1.0 equiv.) (5-bromo-2-methoxyphenyl)sulfonyl chloride in 20 ml dry tetrahydrofurane is added to a solution of 8.51 g (39.47 mmol, 1.05 equiv.) methyl 3-amino-3-phenylpropionate hydrochloride and 30.4 ml (375.9 mmol, 10 equiv.) pyridine in 40 ml dry tetrahydrofurane. After the addition is completed, the cooling bath is removed and stirring continued over night. A white precipitate is formed. Most of the solvent and the pyridine is removed on a rotatory evaporator.

The residue is acidified with dilute hydrochloric acid and the product is extracted with dichloromethane. The organic layer is successively washed with water and brine. Dried over unhydrous sodium sulfate. The crude product is purified by crystallization from ethyl acetate to afford 13.33 g (31.12 mmol, 78% yield) as a white solid.

Mass spectrometry (DCI/NH$_3$): 445/447 (M+NH$_4^+$)

Retention time (TLC): R$_f$=0.48 (dichloromethane/methanol, 100:2)

$^1$H-NMR (400 MHz, dimethylsulfoxide-d$_6$): δ=8.15 (1H, d), 7.57 (1H, d), 7.53 (1H, dd), 7.09 (5H, m), 6.81 (1H, d), 4.62 (1H, quart), 3.71 (3H, s), 3.48 (3H, s), 2.87 (1H, dd), 2.68 (1H, dd).

Example 20.2.2

3-[(3-Nitro-2-pyridinyl)amino]-phenylboronic acid

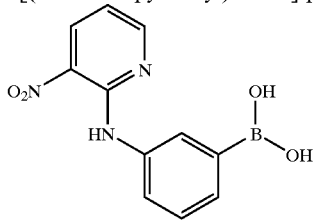

A mixture of 2.0 g (11.53 mmol, 1.0 equiv.) 3-aminophenylboronic acid hydrochloride, 1.83 g (11.53 mmol, 1.0 equiv.) 2-chloro-3-nitropyridine and 2.44 g (23.07 mmol, 2.0 equiv.) sodium carbonate in 20 ml of dry N-methylpyrrolidinone is heated to 100° C. under an atmosphere of argon. After five hours, the reaction is completed and the mixture is allowed to cool to room temperature. It is poured in a mixture of diethyl ether and 5% aqueous sodium dihydrogenphosphate. The product precipitates and is collected by filtration. It is washed with small amounts of water and ether. 2.25 g (8.686 mmol, 75% yield) of a yellow solid is obtained which is of about 90% purity and is used for the next step as such.

Retention time (TLC): R$_f$=0.39 (dichloromethane/methanol, 100:5)

$^1$H-NMR (300 MHz, dimethylsulfoxide-d$_6$): δ=9.96 (1H, s), 8.55–8.50 (2H, m), 8.03 (2H, s), 7.87 (1H, s), 7.79 (1H,d), 7.58 (1H, d), 7.35 (1H, t), 6.98 (1H, dd).

Example 20.2.3

Methyl 3-[({4-methoxy-3'-[(3-nitro-2-pyridinyl)amino][1,1'-biphenyl]-3-yl}sulfonylamino]-3-phenylpropanoate

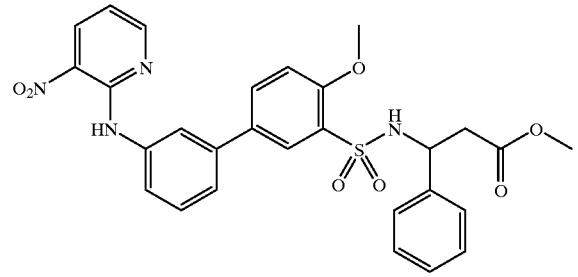

Under an atmosphere of argon, a vigorously stirred suspension of 100 mg (0.386 mmol, 1.0 equiv.) 3-[(3-nitro-2-pyridinyl)amino]-phenylboronic acid 20.2.2, 165 mg (0.386 mmol, 1.0 equiv.) methyl 3-{[(5-bromo-2-methoxyphenyl)sulfonyl]amino}-3-phenylpropanoate 20.2.1 and 14 mg (0.019 mmol, 0.05 equiv.) dichlorobis(triphenylphosphino)-palladium in 5 ml dimethoxy ethane is treated with 0.24 ml (0.48 mmol) of a 2-molar solution of sodium carbonate in water. The mixture is heated to reflux. After four hours, the reaction is completed and the reaction mixture is cooled to room temperature. After dilution with ethyl acetate, the mixture is successively washed with 5% aqueous sodium dihydrogenphosphate, water and brine. Dried over anhydrous sodium sulfate. After removal of the solvent, the crude product is used for the next step without further purification. 85 mg (0.151 mmol, 39% yield) yellow solid.

Mass spectrometry (ESI): 585 (M+Na$^+$), 563 (M+H$^+$)

Retention time (TLC): R$_f$=0.47 (cyclohexane/ethyl acetate, 1:2)

$^1$H-NMR (300 MHz, dimethylsulfoxide-d$_6$): δ10.04 (1H, s), 8.57–8.51 (2H, m), 7.98 (1H, d), 7.81 (1H, s), 7.80 (1H, d), 7.71–7.66 (2H, m), 7.45 (1H, t), 7.31 (1H, d), 7.12–7.00 (6H, m), 6.92 (1H, d), 4.68 (1H, quart), 3.77 (3H, s), 3.47 (3H, s), 2.89 (1H, dd), 2.70 (1H, dd).

Example 20.2.4

3-({4-Methoxy-3'-[(3-nitro-2-pyridinyl)amino][1,1'-biphenyl]-3-yl}sulfonylamino)-3-phenyl-propanoic acid

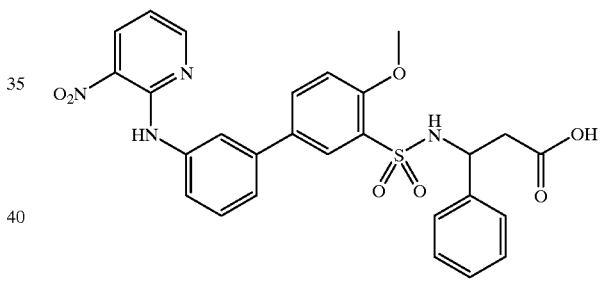

A solution of 75 mg (0.133 mmol) methyl 3-[({4-methoxy-3-[(3-nitro-2-pyridinyl)amino][1,1'-biphenyl]-3-yl}sulfonyl)amino]-3-phenylpropanoate 20.2.3 in a mixture of 5 ml tetrahydrofurane and 5 ml 2-molar aqueous sodium hydroxide is stirred at room temperature for 20 hours. Diluted hydrochloric acid is added until pH 3–4 is reached. The product precipitates and is isolated by filtration. Washed with water and a small amount of tetrahydrofurane. 40 mg (0.073 mmol, 52% yield) of a pale yellowish solid are obtained.

Mass spectrometry (DCI/NH$_3$): 549 (M+H$^+$)

$^1$H-NMR (300 MHz, dimethylsulfoxide-d$_6$): δ=12.15 (1H, s broad), 10.02 (1H, s), 8.56–8.50 (2H, m), 7.92 (1H, d), 7.81 (1H, s), 7.79 (1H, d), 7.70–7.61 (2H, m), 7.49 (1H, t), 7.31 (1H, d), 7.11–7.00 (6H, m), 6.91 (1H, d), 4.63 (1H, quart), 3.77 (3H, s), 2.79 (1H, dd), 2.61 (1H, dd).

According to the various methods described above the following further examples can be prepared:

| structure | MW | example | MS | Rf (TLC) [min.] | Rt (HPLC) [min.] (%) | m.p. [° C.] | method |
|---|---|---|---|---|---|---|---|
| 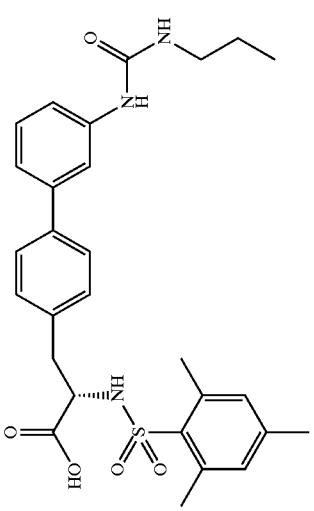 | 523.66 | 1.76 | 524 | | 10.4 | | 1 |
| 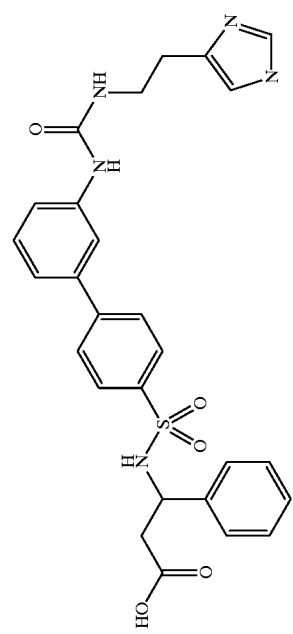 | 533.61 | 4.10 | 534 | | 6.4 | | 4 |
| 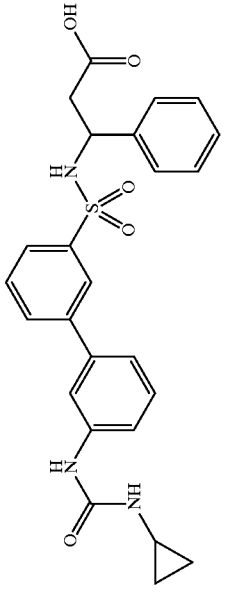 | 479.56 | 4.11 | 480 | | 8.4 | | 4 |

| structure | MW | example | MS | Rf (TLC) [min.] | Rt (HPLC) [min.] (%) | m.p. [° C.] | method |
|---|---|---|---|---|---|---|---|
| | 529.62 | 4.12 | 530 | | 9.8 | | 4 |
| 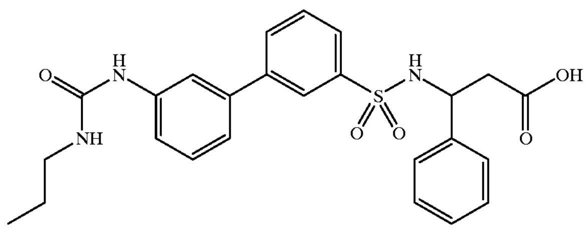 | 481.58 | 4.13 | 482 | | 8.9 | | 4 |
| | 529.62 | 4.14 | 530 | | 9.6 | | 4 |

-continued

| structure | MW | example | MS | Rf (TLC) [min.] | Rt (HPLC) [min.] (%) | m.p. [° C.] | method |
|---|---|---|---|---|---|---|---|
| 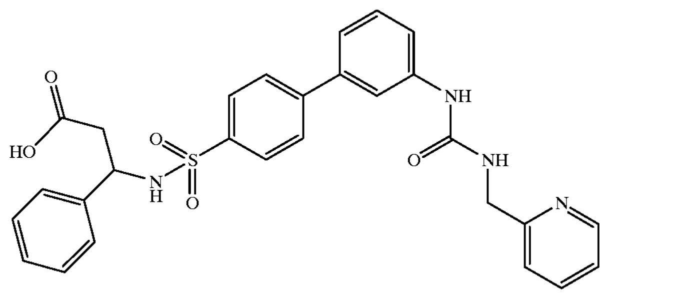 | 530.61 | 4.15 | 531 | | 6.6 | | 4 |
| 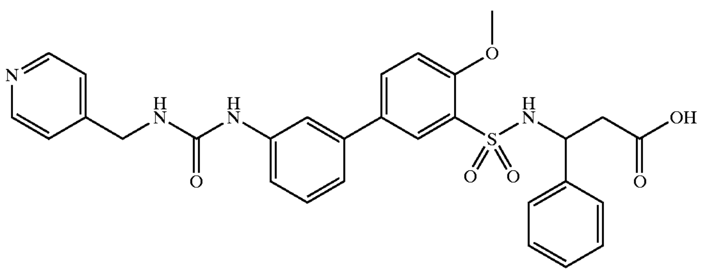 | 560.63 | 4.16 | 561 | | 6.5 | | 4 |
| 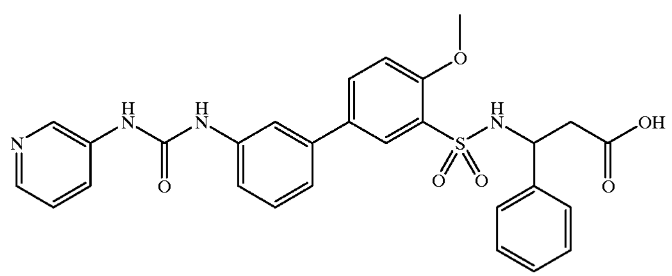 | 546.61 | 4.17 | 547 | | 6.9 | | 4 |

-continued

| structure | MW | example | MS | Rf (TLC) [min.] | Rt (HPLC) [min.] (%) | m.p. [° C.] | method |
|---|---|---|---|---|---|---|---|
| 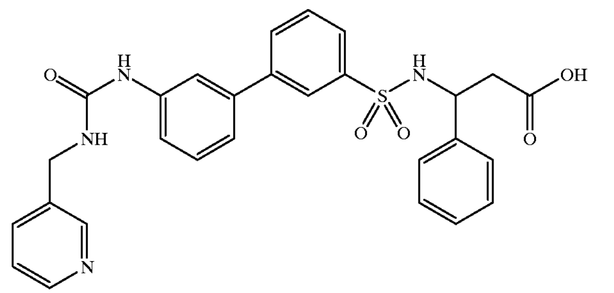 | 530.61 | 4.18 | 531 | | 6.6 | | 4 |
| 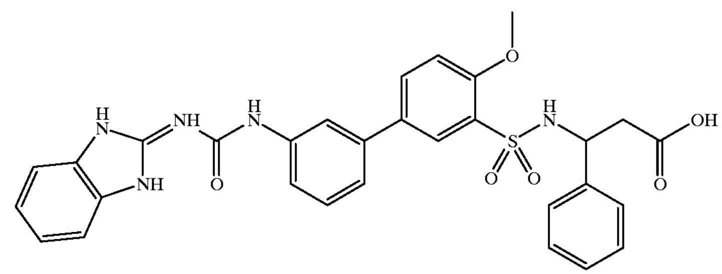 | 585.64 | 4.19 | 586 | | 8.4 | | 4 |
| 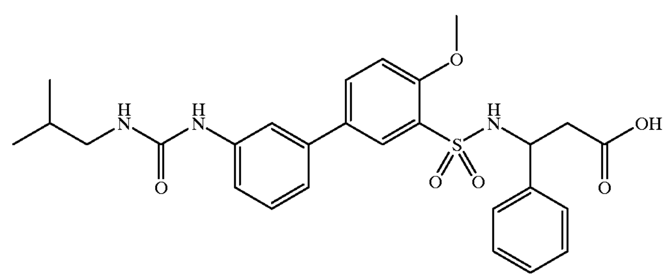 | 525.63 | 4.20 | 526 | | 9.3 | | 4 |

| structure | MW | example | MS | Rf (TLC) [min.] | Rt (HPLC) [min.] (%) | m.p. [° C.] | method |
|---|---|---|---|---|---|---|---|
| 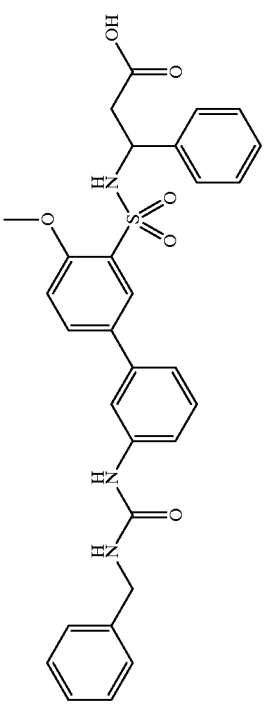 | 559.65 | 4.21 | 560 | | 9.6 | | 4 |
| 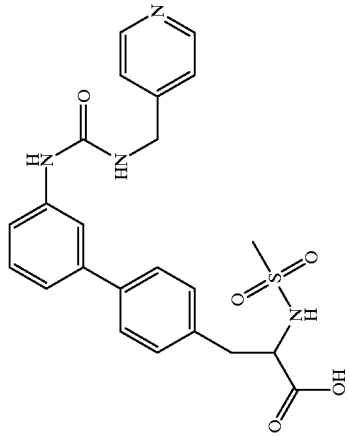 | 468.54 | 1.77 | 469 | | 5.2 | | 1 |
| 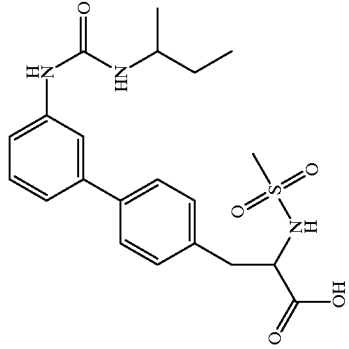 | 433.53 | 1.78 | 434 | | 8.1 | | 1 |

-continued
| structure | MW | example | MS | Rf (TLC) [min.] | Rt (HPLC) [min.] (%) | m.p. [° C.] | method |
|---|---|---|---|---|---|---|---|
| 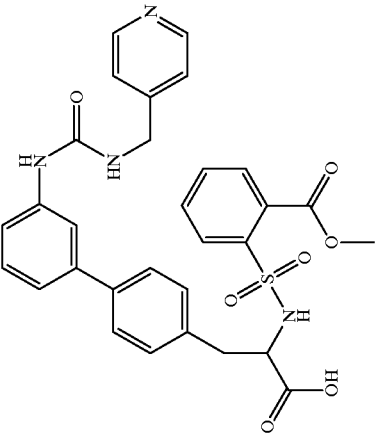 | 588.64 | 1.79 | 589 | | 7.0 | | 1 |
| 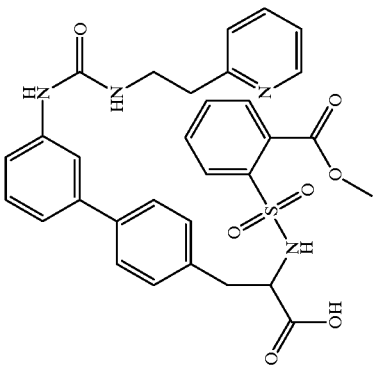 | 602.67 | 1.80 | 603 | | 8.0 | | 1 |

-continued

| structure | MW | example | MS | Rf (TLC) [min.] | Rt (HPLC) [min.] (%) | m.p. [° C.] | method |
|---|---|---|---|---|---|---|---|
| 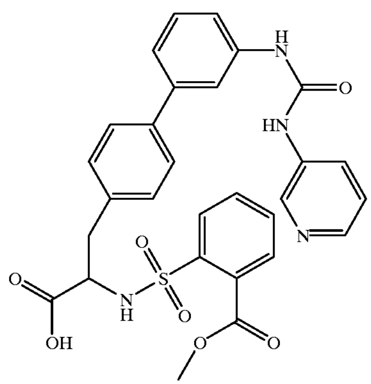 | 574.62 | 1.81 | 575 | | 7.5 | | 1 |
| 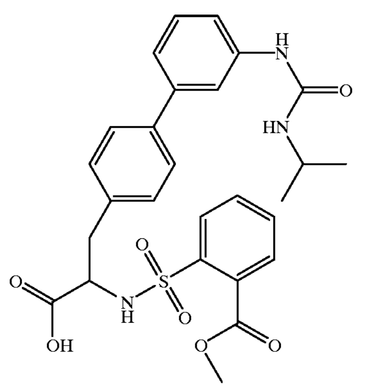 | 539.61 | 1.82 | 540 | | 9.4 | | 1 |

| structure | MW | example | MS | Rf (TLC) [min.] | Rt (HPLC) [min.] (%) | m.p. [° C.] | method |
|---|---|---|---|---|---|---|---|
| 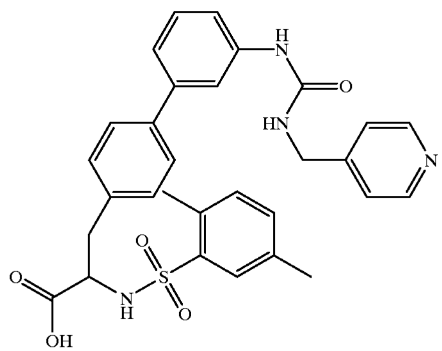 | 558.66 | 1.83 | 559 | | 7.5 | | 1 |
| 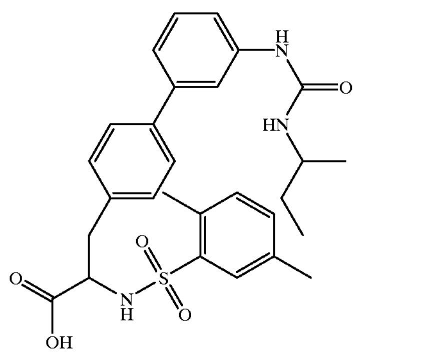 | 523.66 | 1.84 | 524 | | 10.4 | | 1 |

-continued

| structure | MW | example | MS | Rf (TLC) [min.] | Rt (HPLC) [min.] (%) | m.p. [° C.] | method |
|---|---|---|---|---|---|---|---|
| 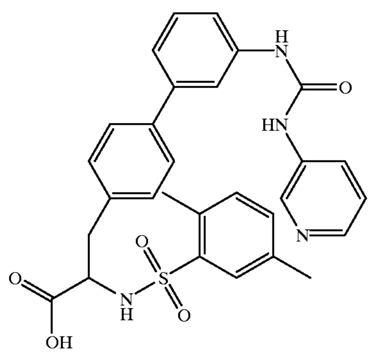 | 544.63 | 1.85 | 545 | | 7.9 | | 1 |
| 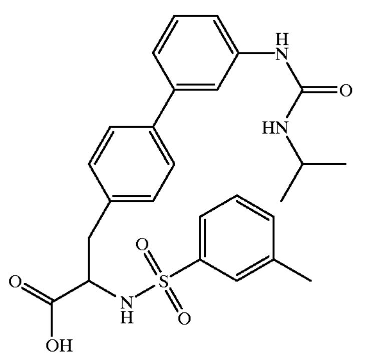 | 495.60 | 1.86 | 496 | | 9.4 | | 1 |

-continued

| structure | MW | example | MS | Rf (TLC) [min.] | Rt (HPLC) [min.] (%) | m.p. [° C.] | method |
|---|---|---|---|---|---|---|---|
| 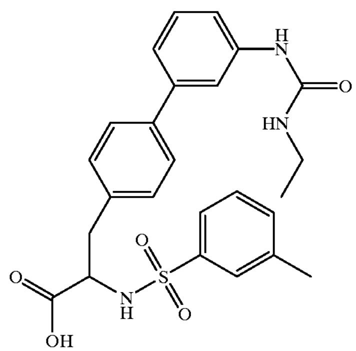 | 481.58 | 1.87 | 482 | | 8.9 | | 1 |
| 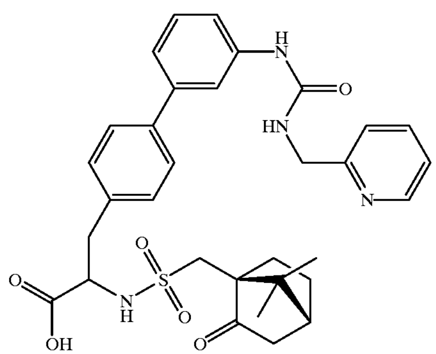 | 604.73 | 1.88 | 605 | | 7.3 | | 1 |

-continued

| structure | MW | example | MS | Rf (TLC) [min.] | Rt (HPLC) [min.] (%) | m.p. [° C.] | method |
|---|---|---|---|---|---|---|---|
| (structure 1) | 604.73 | 1.89 | 605 | | 7.2 | | 1 |
| (structure 2) | 588.64 | 1.90 | 589 | | 7.4 | | 1 |

-continued

| structure | MW | example | MS | Rf (TLC) [min.] | Rt (HPLC) [min.] (%) | m.p. [° C.] | method |
|---|---|---|---|---|---|---|---|
| 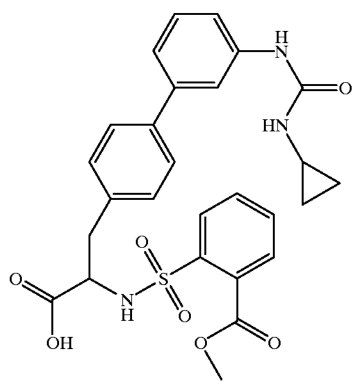 | 537.60 | 1.91 | 538 | | 8.9 | | 1 |
| 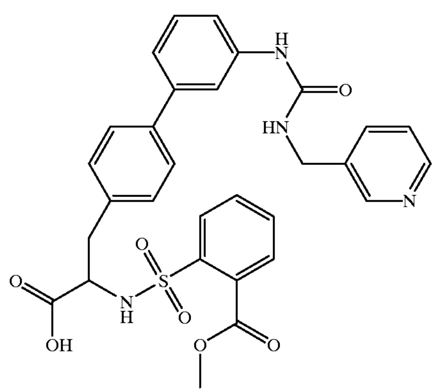 | 588.64 | 1.92 | 589 | | 7.1 | | 1 |

-continued

| structure | MW | example | MS | Rf (TLC) [min.] | Rt (HPLC) [min.] (%) | m.p. [° C.] | method |
|---|---|---|---|---|---|---|---|
| 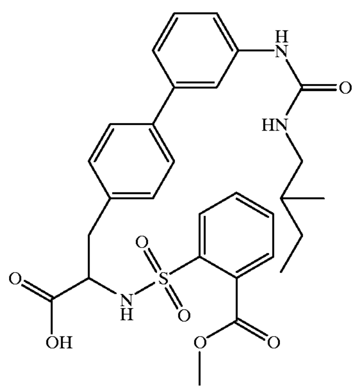 | 567.67 | 1.93 | 568 | | 10.5 | | 1 |
| 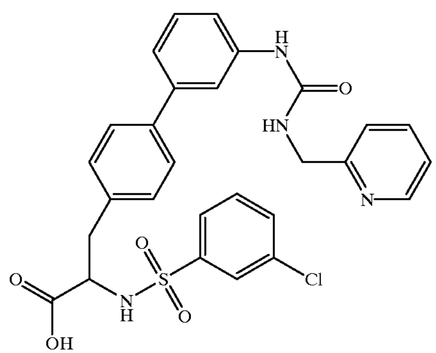 | 565.05 | 1.94 | 566 | | 7.5 | | 1 |

-continued

| structure | MW | example | MS | Rf (TLC) [min.] | Rt (HPLC) [min.] (%) | m.p. [° C.] | method |
|---|---|---|---|---|---|---|---|
| 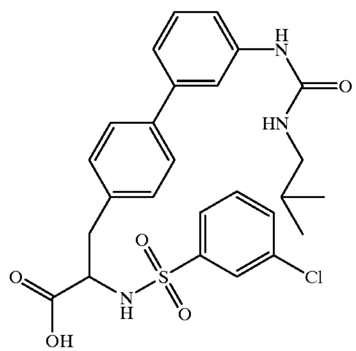 | 530.05 | 1.95 | 531 | | 10.4 | | 1 |
| 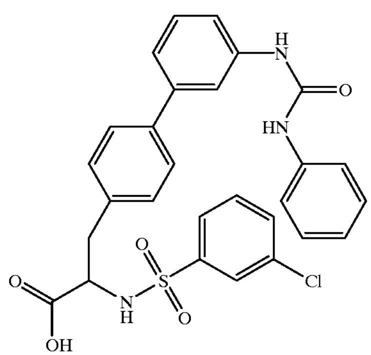 | 550.04 | 1.96 | 551 | | 10.6 | | 1 |

-continued

| structure | MW | example | MS | Rf (TLC) [min.] | Rt (HPLC) [min.] (%) | m.p. [°C] | method |
|---|---|---|---|---|---|---|---|
| 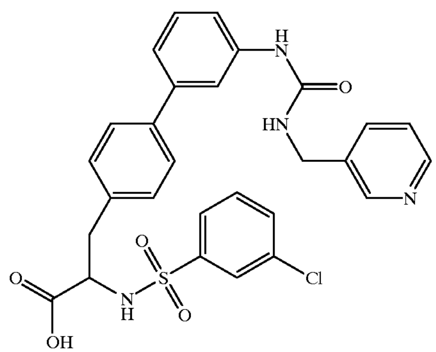 | 565.05 | 1.97 | 566 | | 7.3 | | 1 |
| 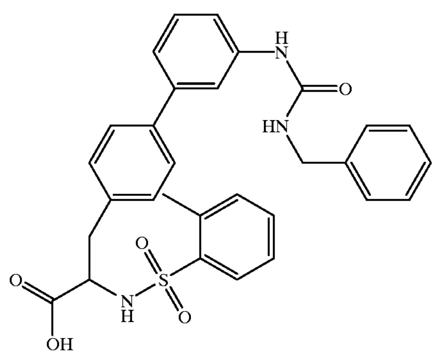 | 543.65 | 1.98 | 544 | | 10.2 | | 1 |

| structure | MW | example | MS | Rf (TLC) [min.] | Rt (HPLC) [min.] (%) | m.p. [° C.] | method |
|---|---|---|---|---|---|---|---|
| 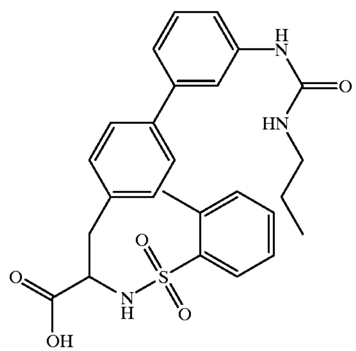 | 495.60 | 1.99 | 496 | | 9.4 | | 1 |
| 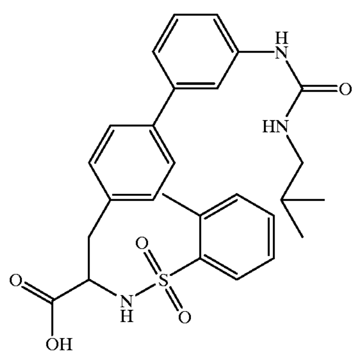 | 509.63 | 1.100 | 510 | | 10.1 | | 1 |

-continued

| structure | MW | example | MS | Rf (TLC) [min.] | Rt (HPLC) [min.] (%) | m.p. [° C.] | method |
|---|---|---|---|---|---|---|---|
| 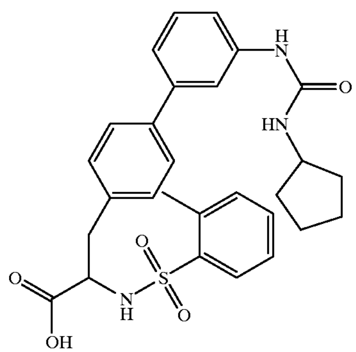 | 521.64 | 1.101 | 522 | | 10.1 | | 1 |
| 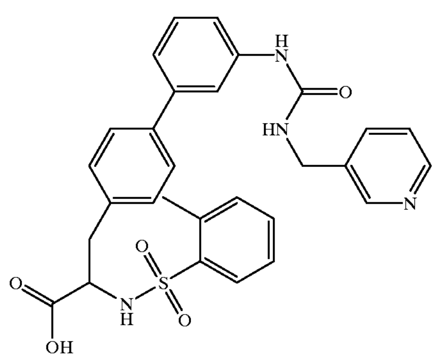 | 544.63 | 1.102 | 545 | | 7.1 | | 1 |

-continued

| structure | MW | example | MS | Rf (TLC) [min.] | Rt (HPLC) [min.] (%) | m.p. [° C.] | method |
|---|---|---|---|---|---|---|---|
| 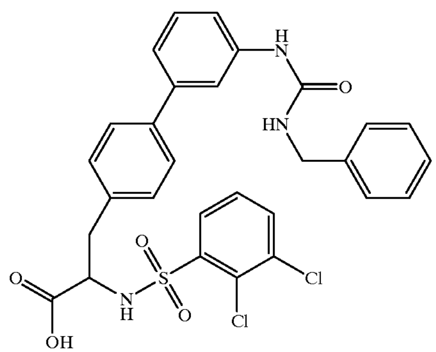 | 598.51 | 1.103 | 599 | | 10.5 | | 1 |
| 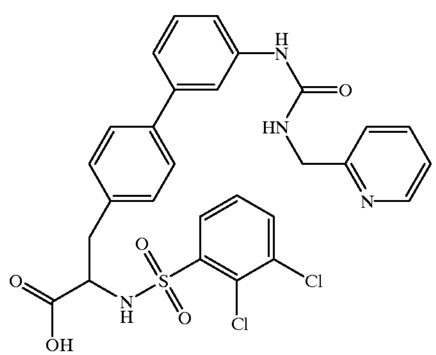 | 599.50 | 1.104 | 600 | | 7.6 | | 1 |

-continued
| structure | MW | example | MS | Rf (TLC) [min.] | Rt (HPLC) [min.] (%) | m.p. [° C.] | method |
|---|---|---|---|---|---|---|---|
| 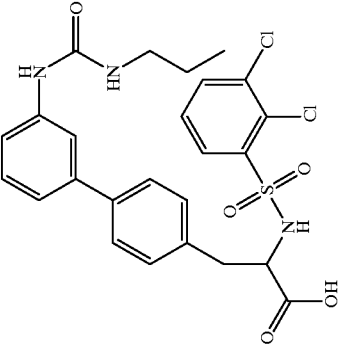 | 550.47 | 1.105 | 551 | | 9.8 | | 1 |
| 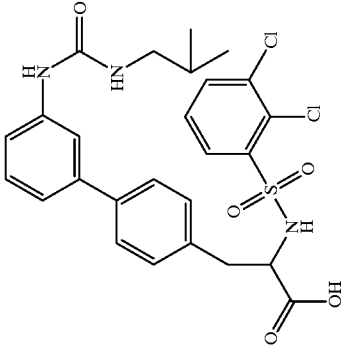 | 564.49 | 1.106 | 565 | | 10.4 | | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 522.41 | 1.107 | 523 | | 8.8 | | 1 |
| (structure) | 576.50 | 1.108 | 577 | | 10.5 | | 1 |

-continued

| structure | MW | example | MS | Rf (TLC) [min.] | Rt (HPLC) [min.] (%) | m.p. [° C.] | method |
|---|---|---|---|---|---|---|---|
| 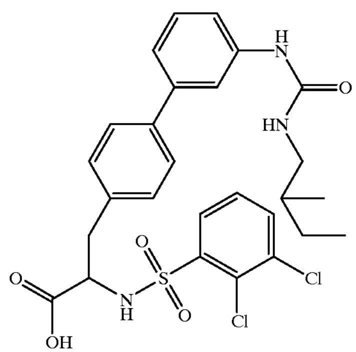 | 578.52 | 1.109 | 579 | | 10.9 | | 1 |
| 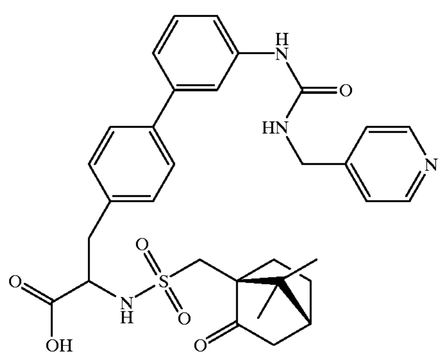 | 604.73 | 1.110 | 605 | | 7.0 | | 1 |

-continued

| structure | MW | example | MS | Rf (TLC) [min.] | Rt (HPLC) [min.] (%) | m.p. [° C.] | method |
|---|---|---|---|---|---|---|---|
| 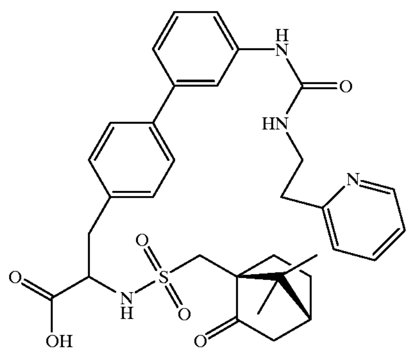 | 618.76 | 1.111 | 619 | | 7.3 | | 1 |
| 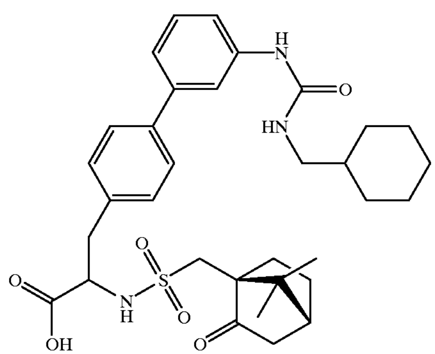 | 609.79 | 1.112 | 610 | | 11.3 | | 1 |

-continued
| structure | MW | example | MS | Rf (TLC) [min.] | Rt (HPLC) [min.] (%) | m.p. [°C] | method |
|---|---|---|---|---|---|---|---|
| 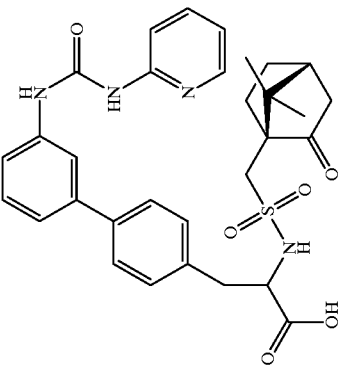 | 590.70 | 1.113 | 591 | | 8.4 | | 1 |
| 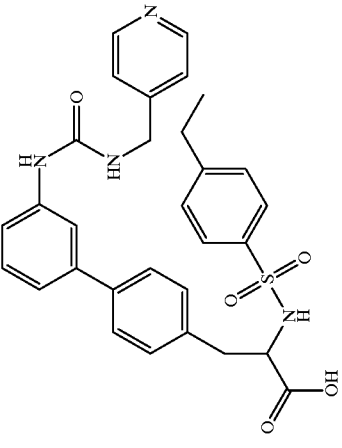 | 558.66 | 1.114 | 559 | | 7.5 | | 1 |

-continued

| structure | MW | example | MS | Rf (TLC) [min.] | Rt (HPLC) [min.] (%) | m.p. [° C.] | method |
|---|---|---|---|---|---|---|---|
| 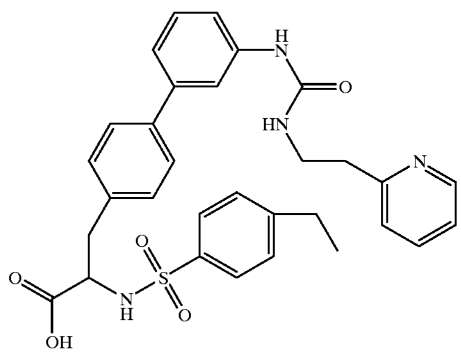 | 572.69 | 1.115 | 573 | | 7.8 | | 1 |
| 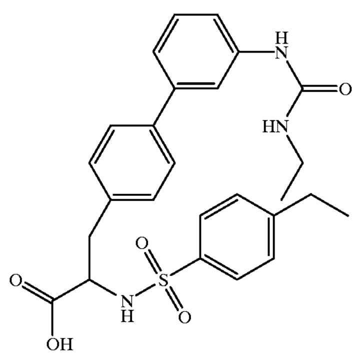 | 495.60 | 1.116 | 496 | | 9.4 | | 1 |

-continued

| structure | MW | example | MS | Rf (TLC) [min.] | Rt (HPLC) [min.] (%) | m.p. [° C.] | method |
|---|---|---|---|---|---|---|---|
| 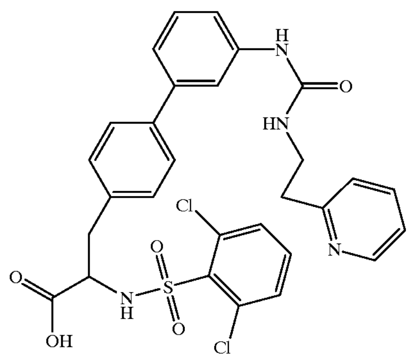 | 513.52 | 1.117 | 514 | | 7.5 | | 1 |
| 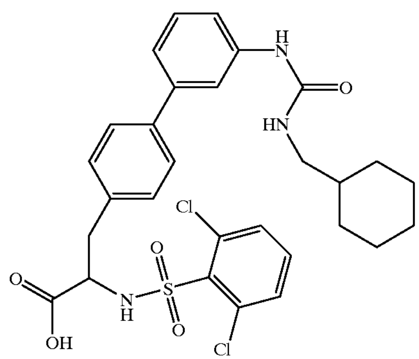 | 604.56 | 1.118 | 605 | | 11.6 | | 1 |

-continued
| structure | MW | example | MS | Rf (TLC) [min.] | Rt (HPLC) [min.] (%) | m.p. [° C.] | method |
|---|---|---|---|---|---|---|---|
| 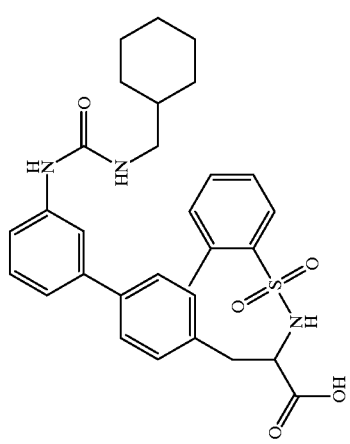 | 649.69 | 1.119 | 650 | | 11.2 | | 1 |
| 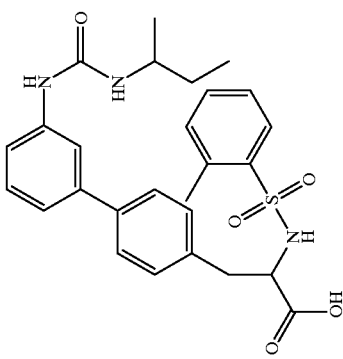 | 509.63 | 1.120 | 510 | | 9.9 | | 1 |

-continued

| structure | MW | example | MS | Rf (TLC) [min.] | Rt (HPLC) [min.] (%) | m.p. [° C.] | method |
|---|---|---|---|---|---|---|---|
| 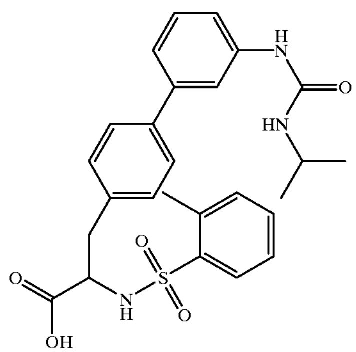 | 495.60 | 1.121 | 496 | | 9.4 | | 1 |
| 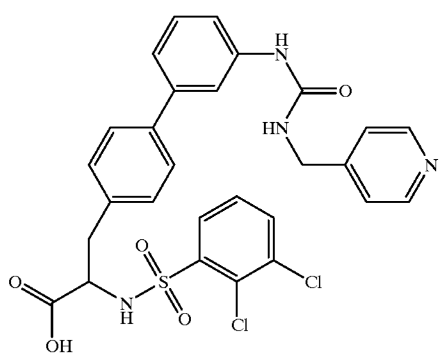 | 599.50 | 1.122 | 600 | | 7.4 | | 1 |

-continued

| structure | MW | example | MS | Rf (TLC) [min.] | Rt (HPLC) [min.] (%) | m.p. [° C.] | method |
|---|---|---|---|---|---|---|---|
| 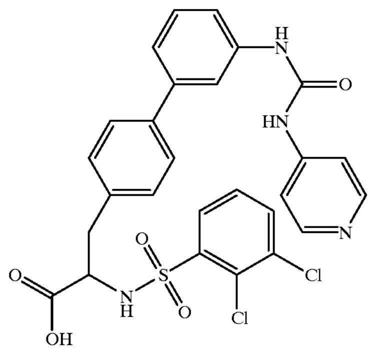 | 585.47 | 1.123 | 586 | | 8.0 | | 1 |
| 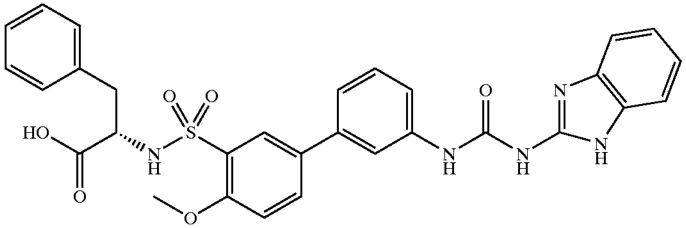 | 585.64 | 4.22 | 586 | | 8.7 | | 4 |
| 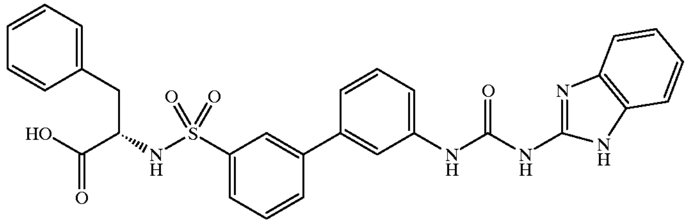 | 555.62 | 4.23 | 556 | | 8.8 | | 4 |

-continued

| structure | MW | example | MS | Rf (TLC) [min.] | Rt (HPLC) [min.] (%) | m.p. [° C.] | method |
|---|---|---|---|---|---|---|---|
| 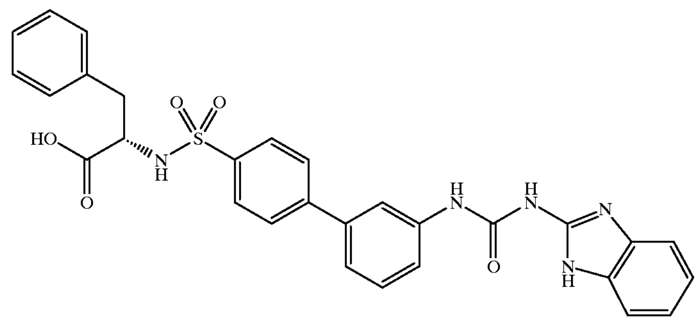 | 555.62 | 4.24 | 556 | | 8.7 | | 4 |
| 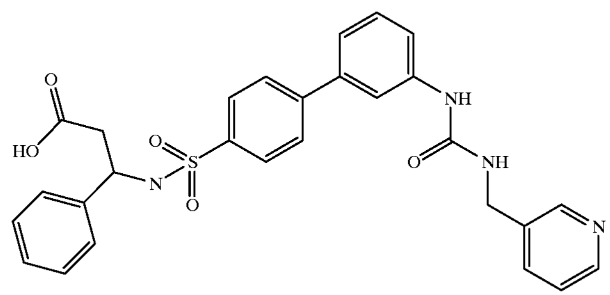 | 530.61 | 4.25 | 531 | | 6.5 | | 4 |
| 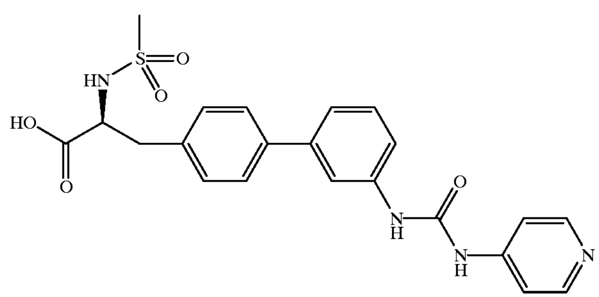 | 454.51 | 1.124 | 455 | | 5.3 | | 1 |

| structure | MW | example | MS | Rf (TLC) [min.] | Rt (HPLC) [min.] (%) | m.p. [° C.] | method |
|---|---|---|---|---|---|---|---|
| 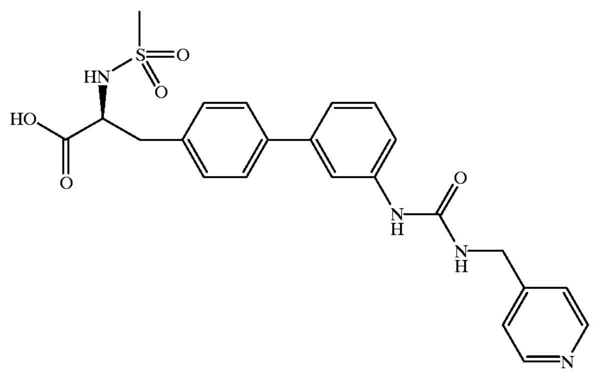 | 468.54 | 1.125 | 469 | | 4.5 | | 1 |
| 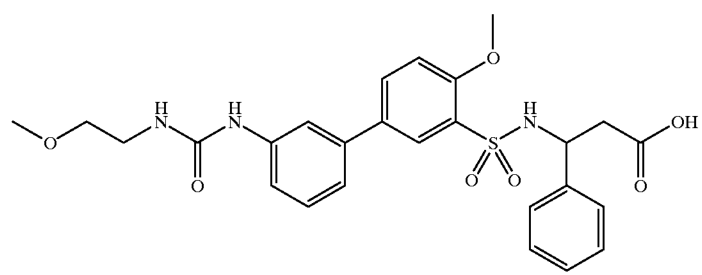 | 527.60 | 4.26 | 528 | | 7.9 | | 4 |
| 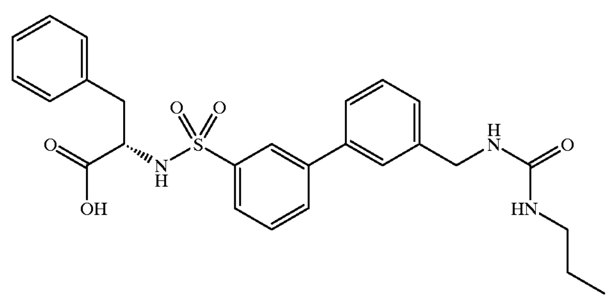 | 495.60 | 4.27 | 496 | | 9.3 | | 4 |

-continued

| structure | MW | example | MS | Rf (TLC) [min.] | Rt (HPLC) [min.] (%) | m.p. [° C.] | method |
|---|---|---|---|---|---|---|---|
| 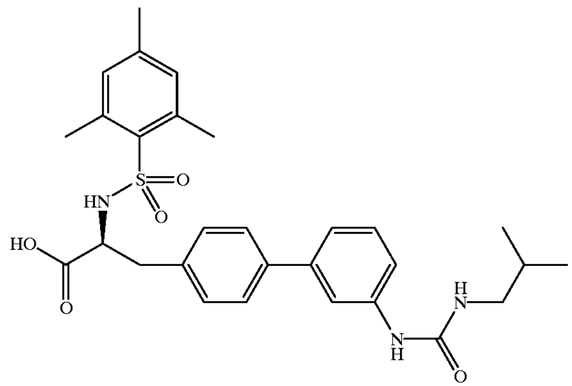 | 537.68 | 1.126 | 538 | | 11.1 | | 1 |
| 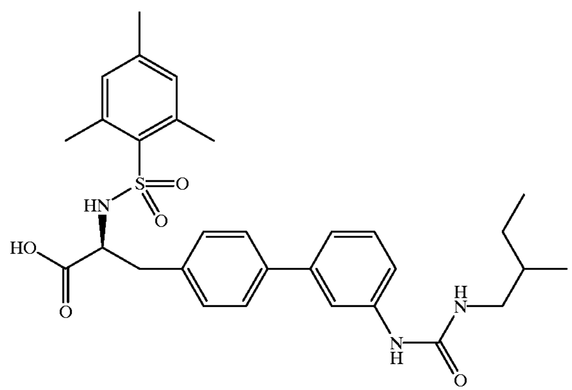 | 551.71 | 1.127 | 552 | | 11.6 | | 1 |

-continued

| structure | MW | example | MS | Rf (TLC) [min.] | Rt (HPLC) [min.] (%) | m.p. [° C.] | method |
|---|---|---|---|---|---|---|---|
| 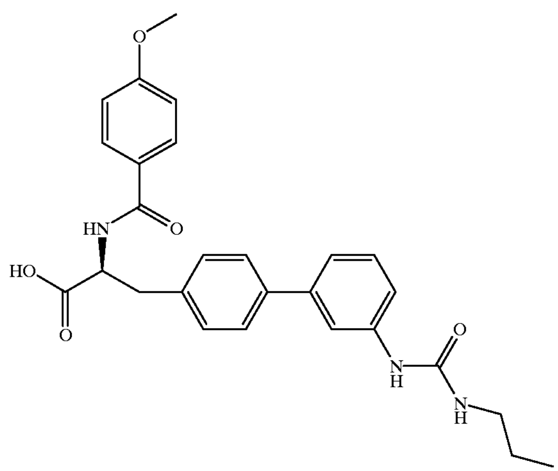 | 475.55 | 1.128 | 476 | | 9.0 | | 1 |
| 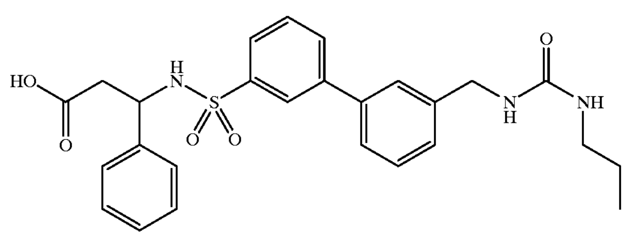 | 495.60 | 4.28 | 496 | | 8.7 | | 4 |

| MW | example | MS | Rf (TLC) [min.] | Rt (HPLC) [min.] (%) | m.p. [° C.] | method |
|---|---|---|---|---|---|---|
| 473.57 | 1.129 | 474 | | 8.3 | | 1 |
| 474.56 | 1.130 | 475 | | 8.9 | | 1 |

| structure | MW | example | MS | Rf (TLC) [min.] | Rt (HPLC) [min.] (%) | m.p. [° C.] | method |
|---|---|---|---|---|---|---|---|
| 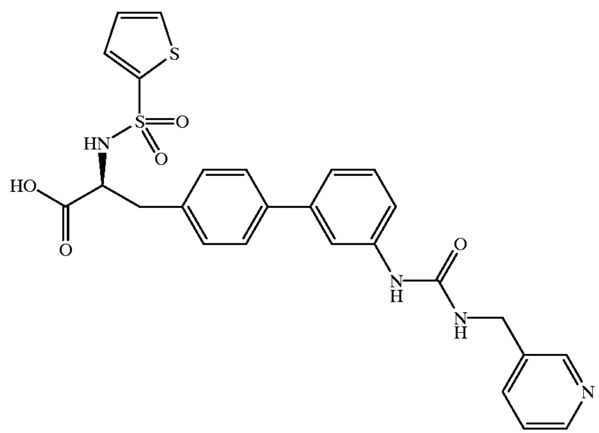 | 536.63 | 1.131 | 537 | | 6.7 | | 1 |
| 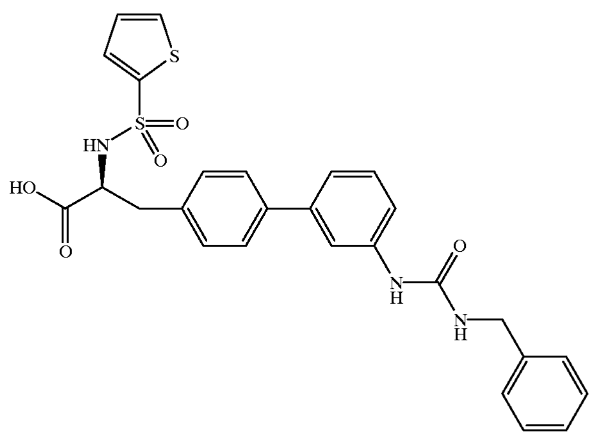 | 535.65 | 1.132 | 536 | | 9.8 | | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 495.60 | 1.133 | 496 | | 9.4 | | 1 |
| (structure) | 598.51 | 1.134 | 599 | | 11.0 | | 1 |

| structure | MW | example | MS | Rf (TLC) [min.] | Rt (HPLC) [min.] (%) | m.p. [° C.] | method |
|---|---|---|---|---|---|---|---|
| 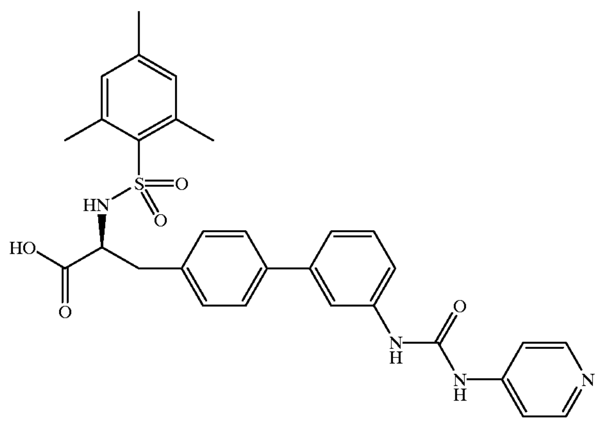 | 558.66 | 1.135 | 559 | | 8.5 | | 1 |
| 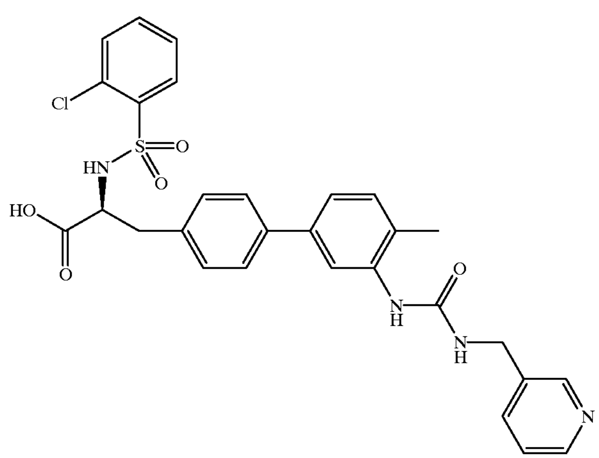 | 579.08 | 1.136 | 580 | | 7.2 | | 1 |

| structure | MW | example | MS | Rf (TLC) [min.] | Rt (HPLC) [min.] (%) | m.p. [° C.] | method |
|---|---|---|---|---|---|---|---|
| 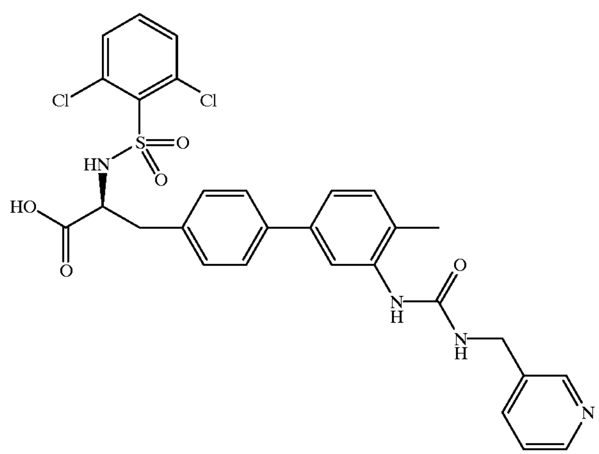 | 613.52 | 1.137 | 614 | | 7.7 | | 1 |
| 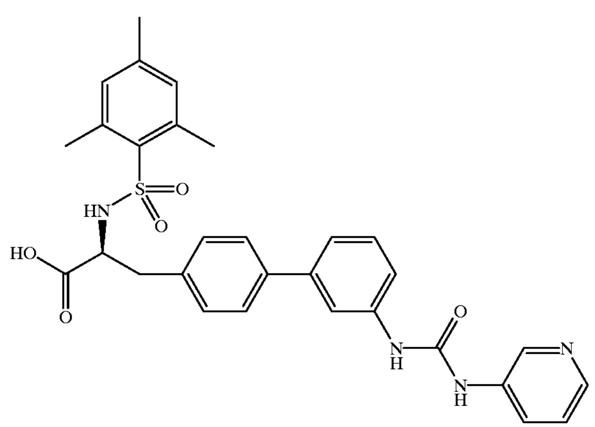 | 558.66 | 1.138 | 559 | | 8.3 | | 1 |

-continued
| structure | MW | example | MS | Rf (TLC) [min.] | Rt (HPLC) [min.] (%) | m.p. [° C.] | method |
|---|---|---|---|---|---|---|---|
| 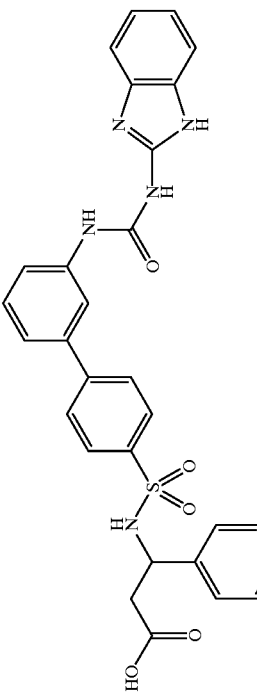 | 570.63 | 4.29 | 571 | | 6.3 | | 4 |
| 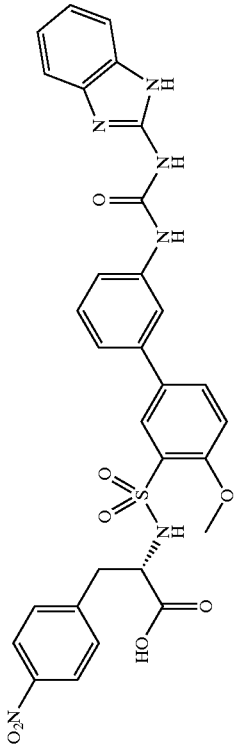 | 630.64 | 4.30 | 631 | | 8.7 | | 4 |
| 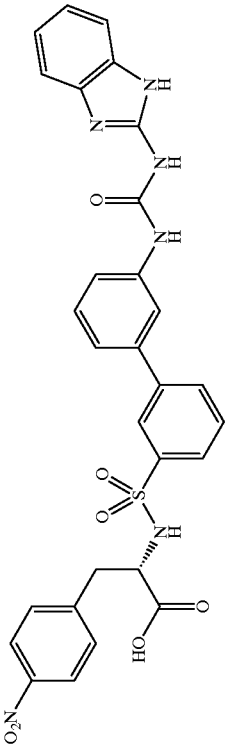 | 600.61 | 4.31 | 601 | | 8.8 | | 4 |

-continued

| structure | MW | example | MS | Rf (TLC) [min.] | Rt (HPLC) [min.] (%) | m.p. [° C.] | method |
|---|---|---|---|---|---|---|---|
| 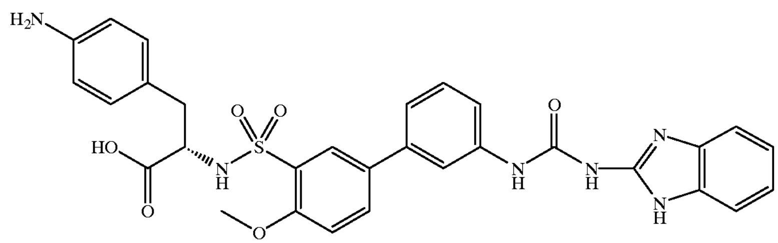 | 600.66 | 4.32 | 601 | | 6.3 | | 4 |
| 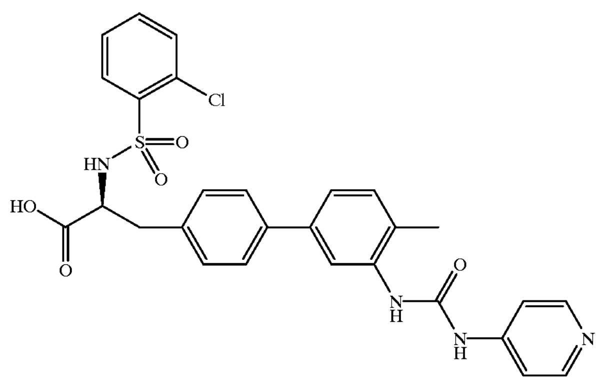 | 565.05 | 1.139 | 566 | | 7.8 | | 1 |
| 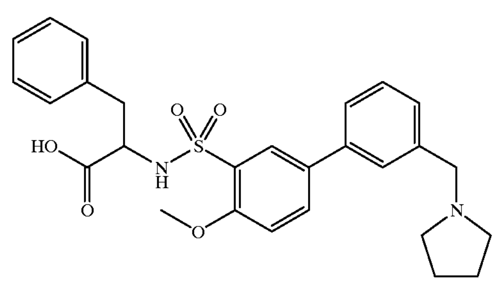 | 494.61 | 8.8 | 495 | | 7.3 | | 8 |

-continued

| structure | MW | example | MS | Rf (TLC) [min.] | Rt (HPLC) [min.] (%) | m.p. [° C.] | method |
|---|---|---|---|---|---|---|---|
| | 600.61 | 4.33 | 601 | | 8.4 | | 4 |
| | 600.61 | 4.34 | 601 | | 8.3 | | 4 |
| 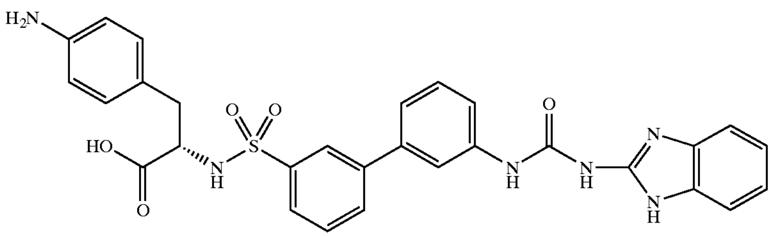 | 570.63 | 4.35 | 571 | | 6.3 | | 4 |

| structure | MW | example | MS | Rf (TLC) [min.] | Rt (HPLC) [min.] (%) | m.p. [°C.] | method |
|---|---|---|---|---|---|---|---|
| 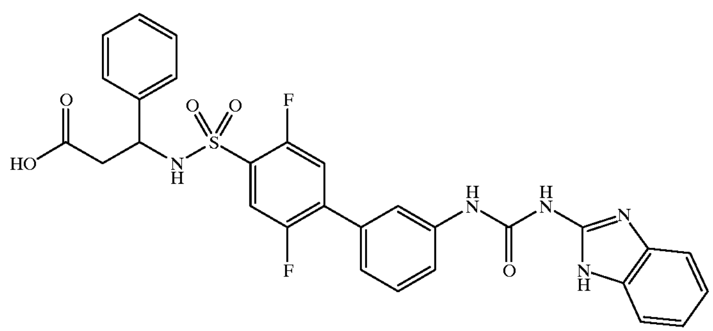 | 591.60 | 4.36 | 592 | | 8.7 | | 4 |
| 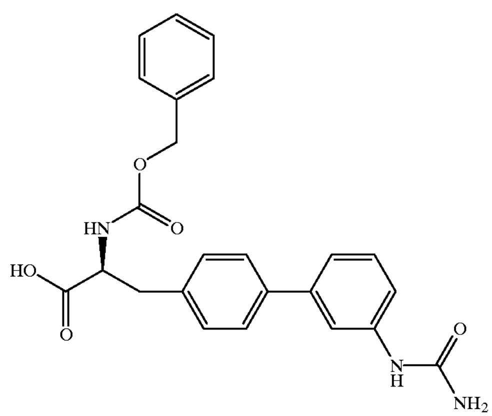 | 433.47 | 1.140 | 434 | | 8.2 | | 1 |

-continued

| structure | MW | example | MS | Rf (TLC) [min.] | Rt (HPLC) [min.] (%) | m.p. [° C.] | method |
|---|---|---|---|---|---|---|---|
| 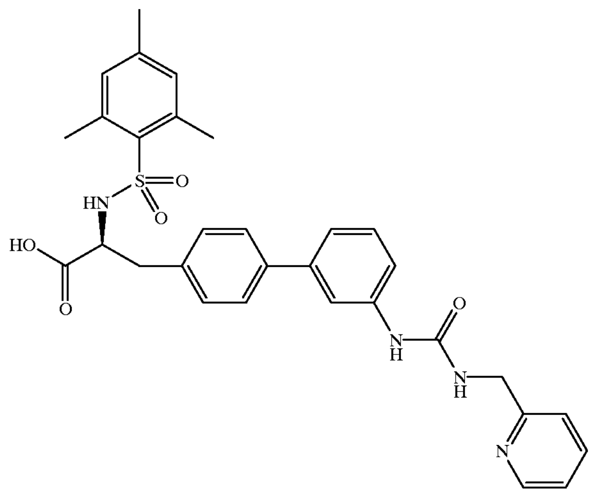 | 572.69 | 1.141 | 573 | | 8.1 | | 1 |
| 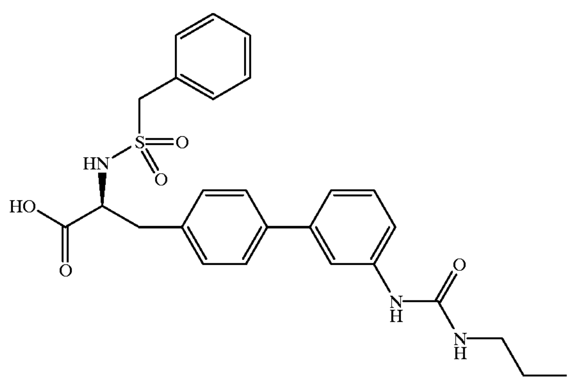 | 495.60 | 1.142 | 496 | | 9.4 | | 1 |

| structure | MW | example | MS | Rf (TLC) [min.] | Rt (HPLC) [min.] (%) | m.p. [° C.] | method |
|---|---|---|---|---|---|---|---|
| 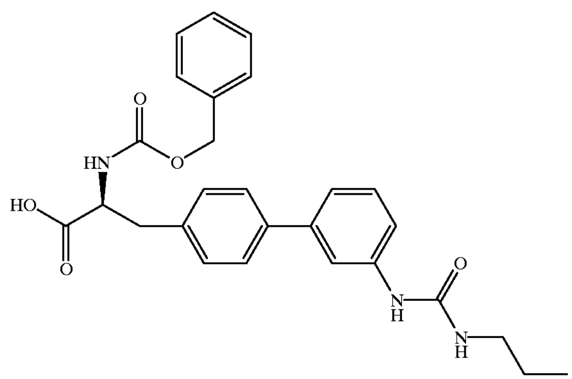 | 475.55 | 1.143 | 476 | | 9.7 | | 1 |
| 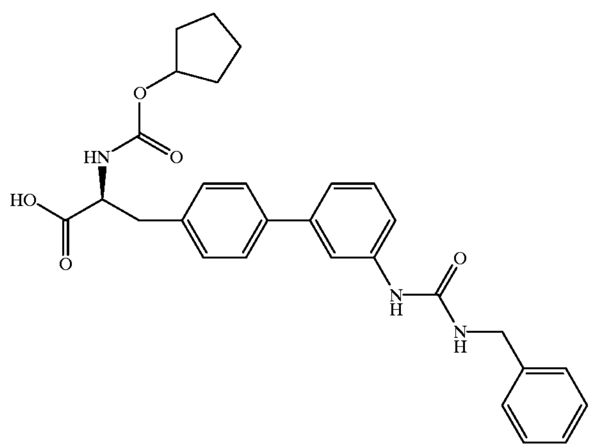 | 501.59 | 1.144 | 502 | | 10.3 | | 1 |

-continued

| MW | example | MS | Rf (TLC) [min.] | Rt (HPLC) [min.] (%) | m.p. [° C.] | method |
|---|---|---|---|---|---|---|
| 453.54 | 1.145 | 454 | | 9.8 | | 1 |
| 541.63 | 1.146 | 542 | | 9.2 | | 1 |

-continued

| structure | MW | example | MS | Rf (TLC) [min.] | Rt (HPLC) [min.] (%) | m.p. [° C.] | method |
|---|---|---|---|---|---|---|---|
| 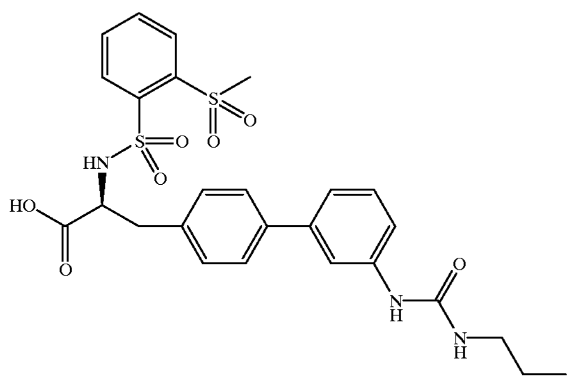 | 559.66 | 1.147 | 560 | | 9.2 | | 1 |
| 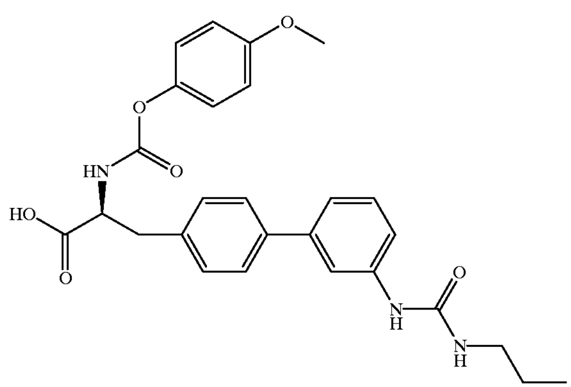 | 491.55 | 1.148 | 492 | | 9.4 | | 1 |

-continued

| structure | MW | example | MS | Rf (TLC) [min.] | Rt (HPLC) [min.] (%) | m.p. [° C.] | method |
|---|---|---|---|---|---|---|---|
| 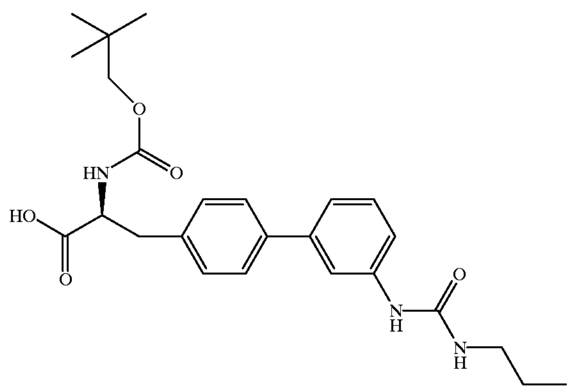 | 455.56 | 1.149 | 456 | | 10.0 | | 1 |
| 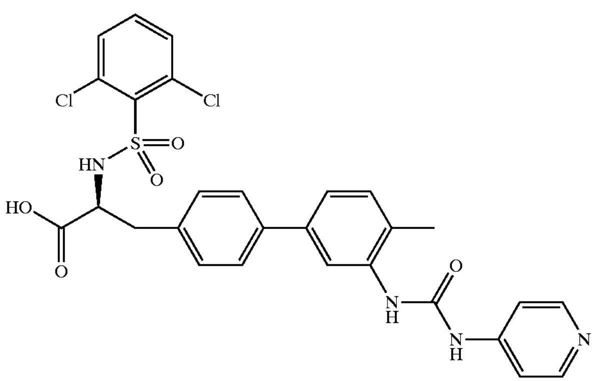 | 599.50 | 1.150 | 600 | | 8.4 | | 1 |

-continued

| structure | MW | example | MS | Rf (TLC) [min.] | Rt (HPLC) [min.] (%) | m.p. [° C.] | method |
|---|---|---|---|---|---|---|---|
| 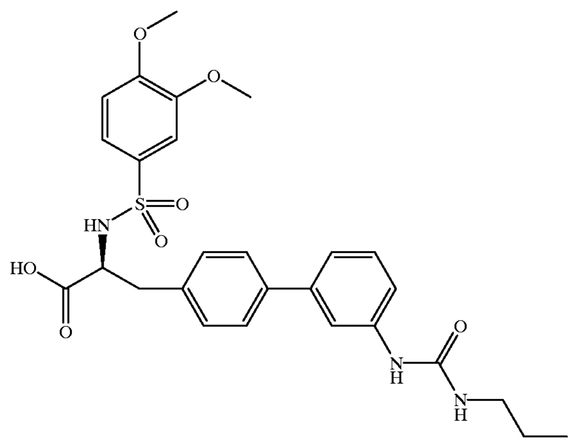 | 541.63 | 1.151 | 542 | | 8.7 | | 1 |
| 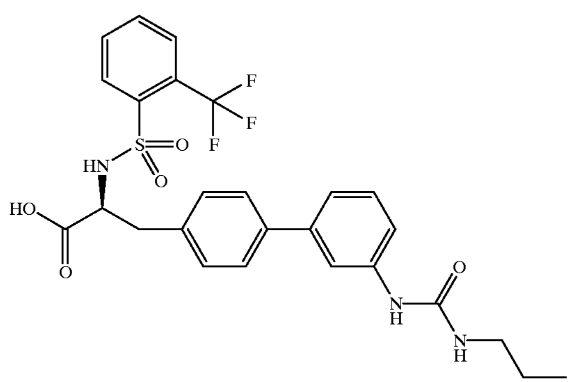 | 549.57 | 1.152 | 550 | | 9.8 | | 1 |

-continued

| MW | example | MS | Rf (TLC) [min.] | Rt (HPLC) [min.] (%) | m.p. [° C.] | method |
|---|---|---|---|---|---|---|
| 441.53 | 1.153 | 442 | | 9.6 | | 1 |
| 624.16 | 1.154 | 625 | | 11.2 | | 1 |

| structure | MW | example | MS | Rf (TLC) [min.] | Rt (HPLC) [min.] (%) | m.p. [° C.] | method |
|---|---|---|---|---|---|---|---|
| 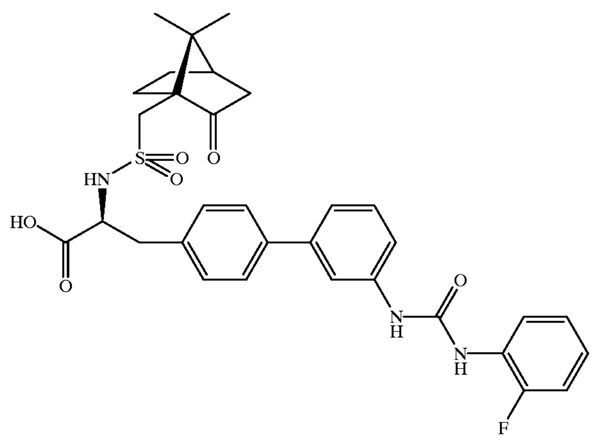 | 607.71 | 1.155 | 608 | | 10.8 | | 1 |
| 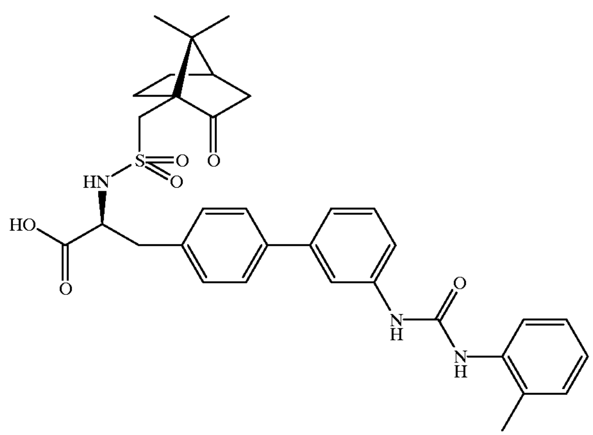 | 603.74 | 1.156 | 604 | | 10.6 | | 1 |

-continued
| structure | MW | example | MS | Rf (TLC) [min.] | Rt (HPLC) [min.] (%) | m.p. [° C.] | method |
|---|---|---|---|---|---|---|---|
| 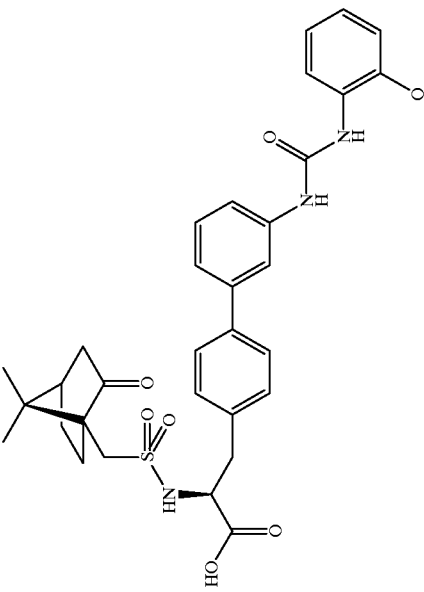 | 605.72 | 1.157 | 606 | | 10.0 | | 1 |
| 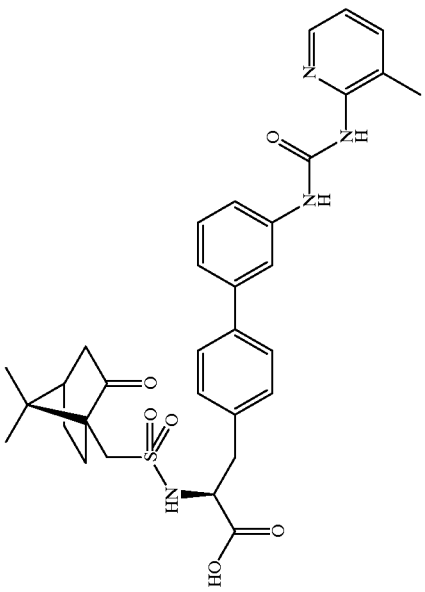 | 604.73 | 1.158 | 605 | | 8.5 | | 1 |

-continued

| structure | MW | example | MS | Rf (TLC) [min.] | Rt (HPLC) [min.] (%) | m.p. [° C.] | method |
|---|---|---|---|---|---|---|---|
| 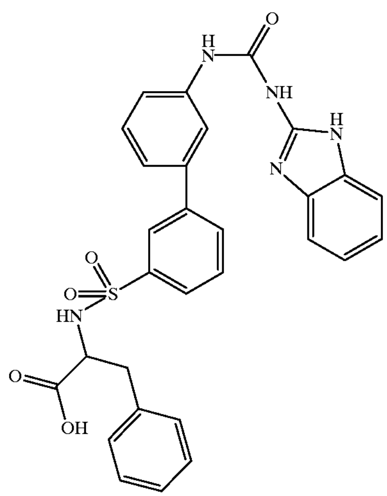 | 555.62 | 4.37 | 556 | | 8.9 | | 4 |
| 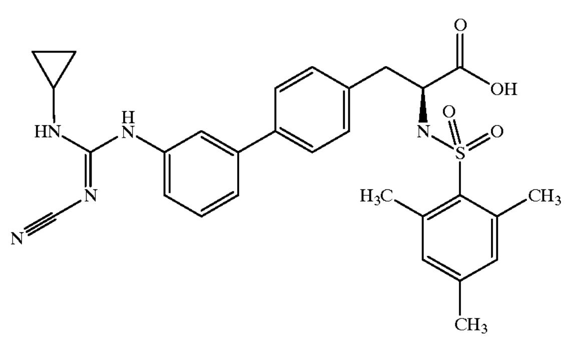 | 545.67 | 10.4 | 546 | 0.46 G | 8.1 | 10 | |

-continued

| MW | example | MS | Rf (TLC) [min.] | Rt (HPLC) [min.] (%) | m.p. [° C.] | method |
|---|---|---|---|---|---|---|
| 439.49 | 1.159 | 440 | | 6.8 | | 1 |
| 627.04 | 12.3 | 628 | 0.34 H | 7.9 | | 12 |
| 646.77 | 12.4 | 647 | 0.45 H | | | 12 |

-continued

| structure | MW | example | MS | Rf (TLC) [min.] | Rt (HPLC) [min.] (%) | m.p. [° C.] | method |
|---|---|---|---|---|---|---|---|
| 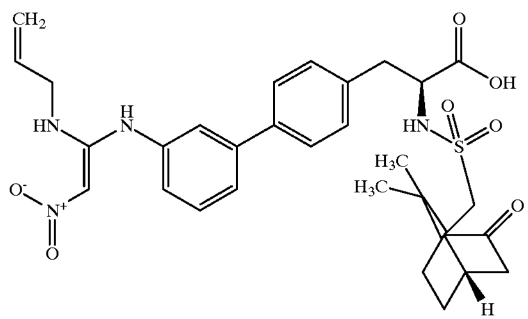 | 596.71 | 12.5 | 597 | | | 150 (dec.) | 12 |
| 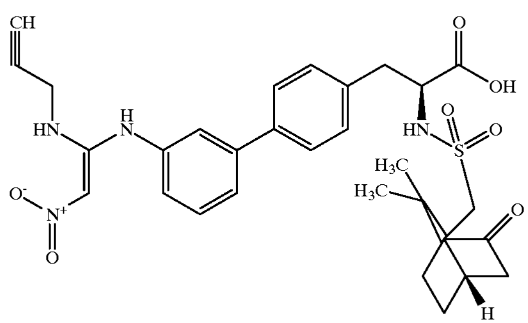 | 594.69 | 12.6 | 595 | | | 185 (dec.) | 12 |
| 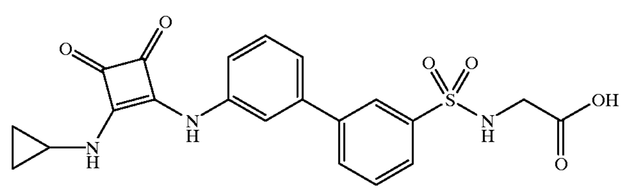 | 441.47 | 13.2 | 442 | | | 204 (dec.) | 13 |

-continued
| structure | MW | example | MS | Rf (TLC) [min.] | Rt (HPLC) [min.] (%) | m.p. [° C.] | method |
|---|---|---|---|---|---|---|---|
| 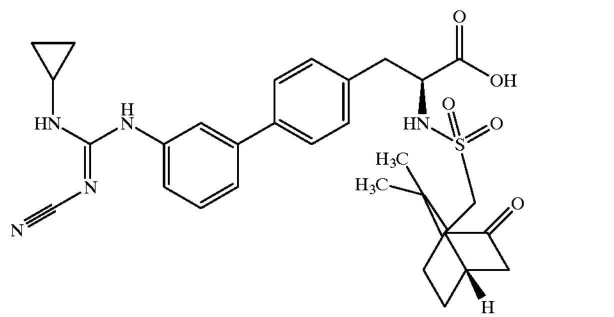 | 577.71 | 10.5 | 578 | | | 178 | 10 |
| 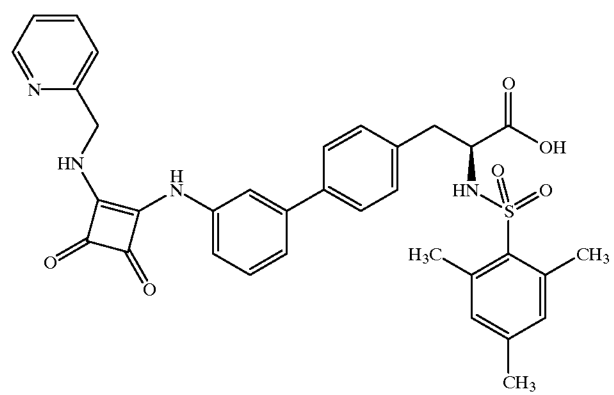 | 624.72 | 13.3 | 625 | | | 214 (dec.) | 13 |

-continued

| structure | MW | example | MS | Rf (TLC) [min.] | Rt (HPLC) [min.] (%) | m.p. [°C.] | method |
|---|---|---|---|---|---|---|---|
| (structure 1) | 547.68 | 10.6 | 548 | | | 184 | 10 |
| (structure 2) | 559.69 | 10.7 | 560 | 0.4 H | | | 10 |

-continued

| structure | MW | example | MS | Rf (TLC) [min.] | Rt (HPLC) [min.] (%) | m.p. [° C.] | method |
|---|---|---|---|---|---|---|---|
| 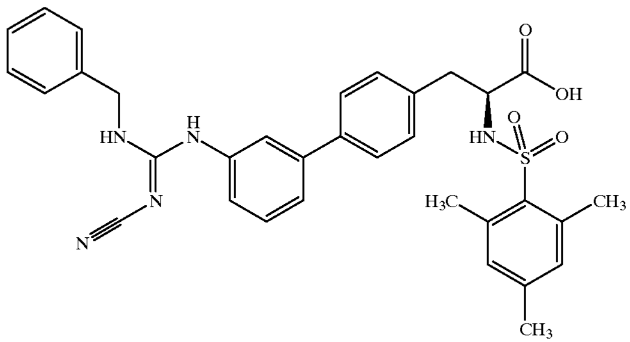 | 595.73 | 10.8 | 596 | | | 169 | 10 |
| 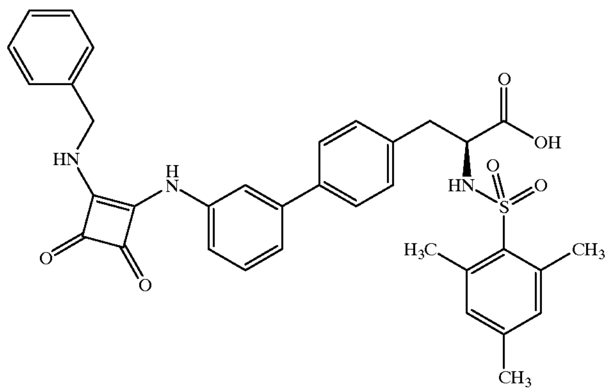 | 623.73 | 13.4 | 624 | | | 226 (dec.) | 13 |
| 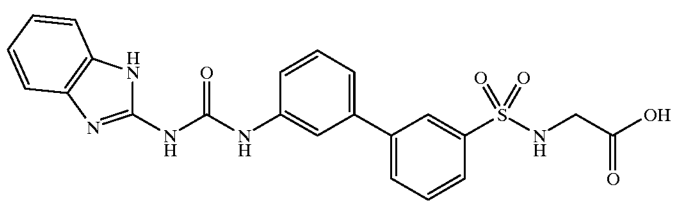 | 465.49 | 4.38 | 466 | | | 172 | 4 |

| structure | MW | example | MS | Rf (TLC) [min.] | Rt (HPLC) [min.] (%) | m.p. [° C.] (dec.) | method |
|---|---|---|---|---|---|---|---|
| 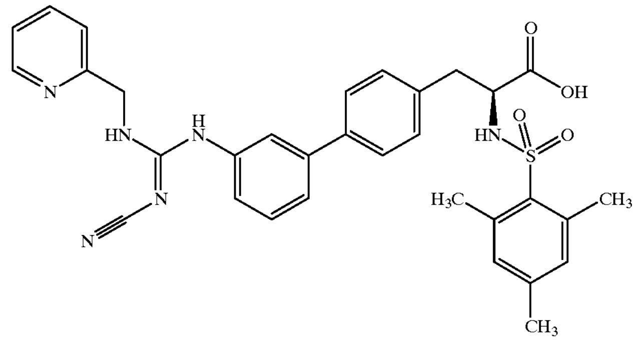 | 596.71 | 10.9 | 597 | | | 174 | 10 |
| 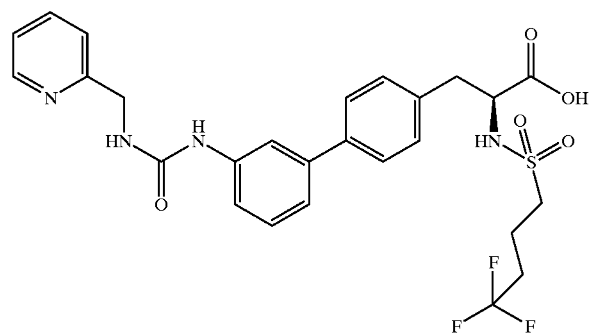 | 564.59 | 1.160 | 565 | 0.20 H | 6.3 | | 1 |
| 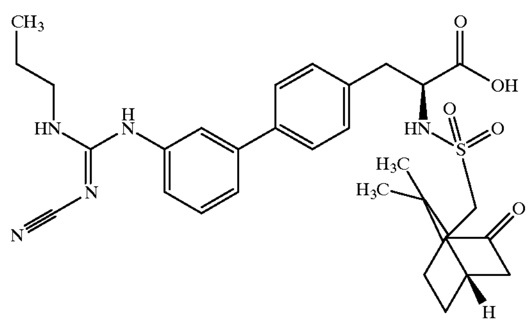 | 579.72 | 10.10 | 580 | | 8.14 | | 10 |

-continued

| structure | MW | example | MS | Rf (TLC) [min.] | Rt (HPLC) [min.] (%) | m.p. [° C.] | method |
|---|---|---|---|---|---|---|---|
| 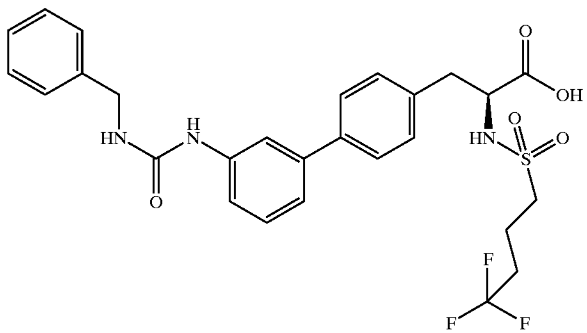 | 563.60 | 1.161 | 564 | | | 163 | 1 |
| 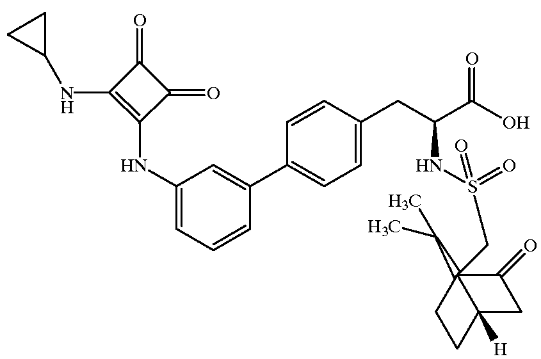 | 605.72 | 13.5 | 606 | | | 152 | 13 |

-continued
| structure | MW | example | MS | Rf (TLC) [min.] | Rt (HPLC) [min.] (%) | m.p. [° C.] | method |
|---|---|---|---|---|---|---|---|
| 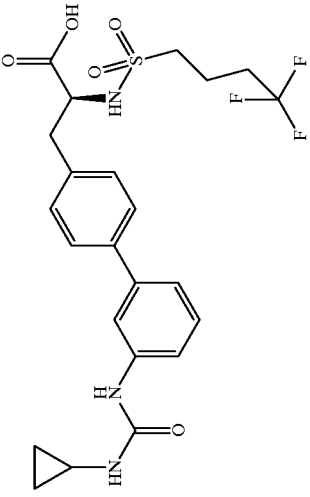 | 513.54 | 1.162 | 514 | | | 202 | 1 |
| 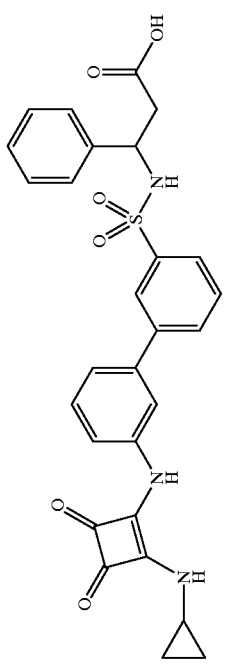 | 607.65 | 13.6 | 508 | | | 191 (dec.) | 13 |
| 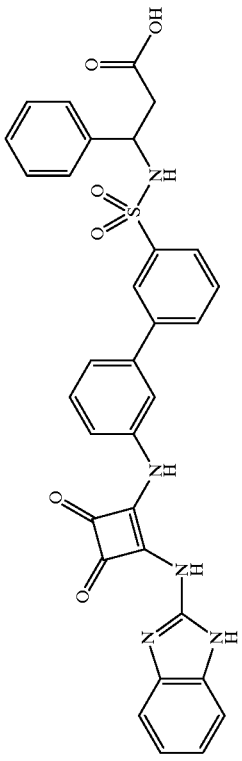 | 531.59 | 13.7 | 532 | | | 214 (dec.) | 13 |

-continued

| structure | MW | example | MS | Rf (TLC) [min.] | Rt (HPLC) [min.] (%) | m.p. [° C.] | method |
|---|---|---|---|---|---|---|---|
| 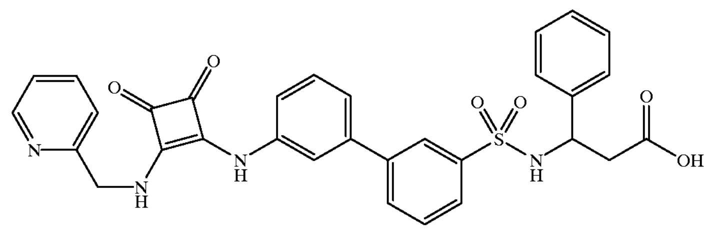 | 582.64 | 13.8 | 583 | | | 149 (dec.) | 13 |
| 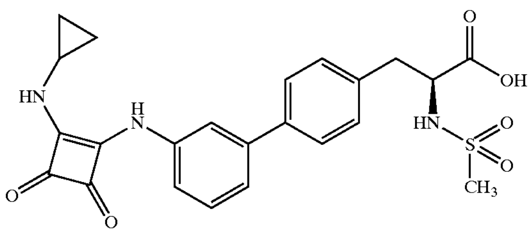 | 469.52 | 13.9 | 470 | | | 210 (dec.) | 13 |
| 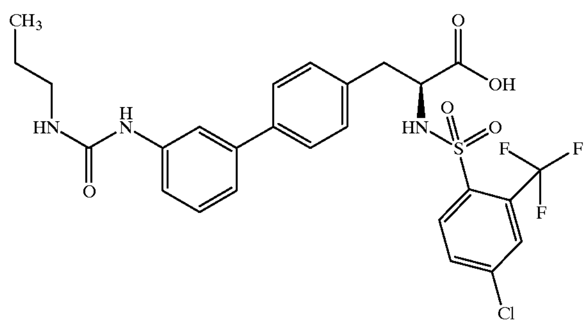 | 584.02 | 1.163 | 585 | 0.35 G | 8.6 | | 1 |

-continued

| structure | MW | example | MS | Rf (TLC) [min.] | Rt (HPLC) [min.] (%) | m.p. [° C.] | method |
|---|---|---|---|---|---|---|---|
| 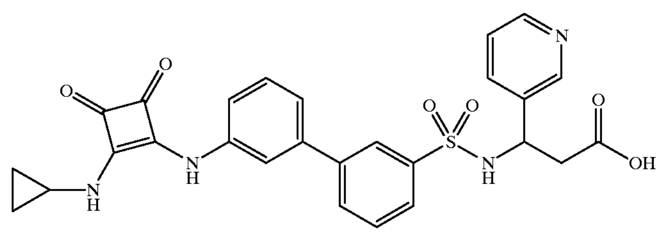 | 532.58 | 13.10 | 533 | 0.15 H | 5.9 | | 13 |
| 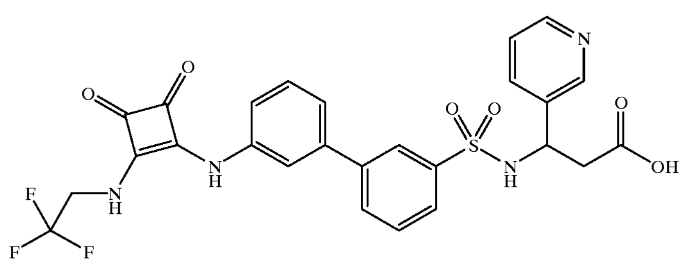 | 574.54 | 13.11 | 575 | | | 219 (dec.) | 13 |
| 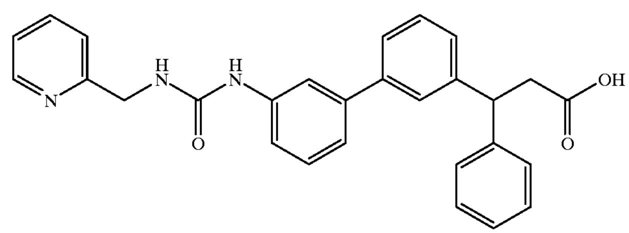 | 451.53 | 1.164 | 452 | 0.34 G | 7.5 | | 1 |

-continued

| structure | MW | example | MS | Rf (TLC) [min.] | Rt (HPLC) [min.] (%) | m.p. [° C.] | method |
|---|---|---|---|---|---|---|---|
| | 647.76 | 12.7 | 648 | | | 126 (dec.) | 12 |
| | 647.76 | 12.8 | 648 | | | 170 | 12 |
| 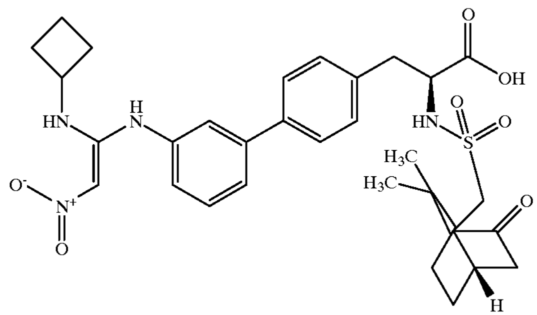 | 610.74 | 12.9 | 611 | | | 151 (dec.) | 12 |

-continued
| structure | MW | example | MS | Rf (TLC) [min.] | Rt (HPLC) [min.] (%) | m.p. [° C.] | method |
|---|---|---|---|---|---|---|---|
| 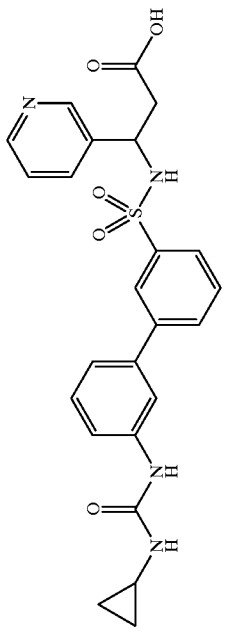 | 480.55 | 4.39 | 481 | | | 144 | 4 |
| 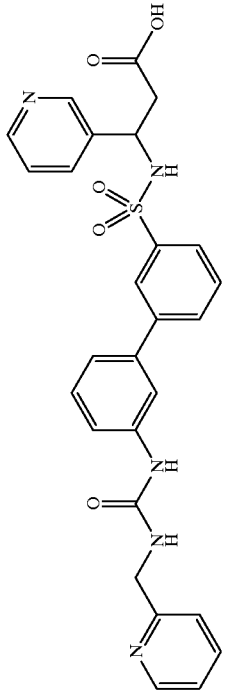 | 531.59 | 4.40 | 532 | | | 176 | 4 |
| 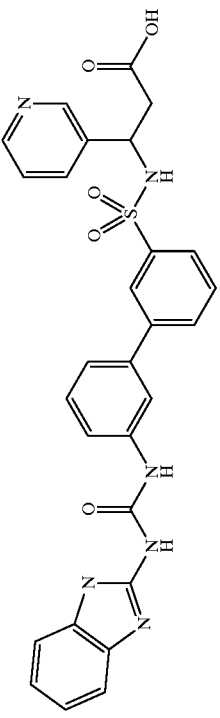 | 556.60 | 4.41 | 557 | | | 170 | 4 |
| 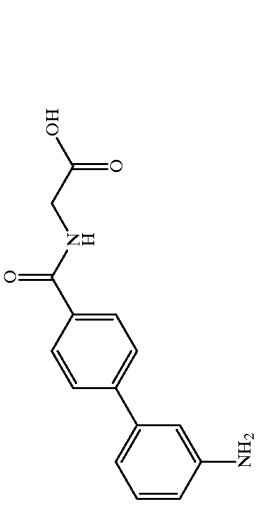 | 270.29 | 4.42 | 271 | | 3.7 | | 4 |

| structure | MW | example | MS | Rf (TLC) [min.] | Rt (HPLC) [min.] (%) | m.p. [° C.] | method |
|---|---|---|---|---|---|---|---|
| (structure 1) | 353.38 | 4.43 | 354 | | 3.7 | | 4 |
| (structure 2) | 355.40 | 4.44 | 356 | | 3.4 | | 4 |

-continued
| structure | MW | example | MS | Rf (TLC) [min.] | Rt (HPLC) [min.] (%) | m.p. [°C.] | method |
|---|---|---|---|---|---|---|---|
| 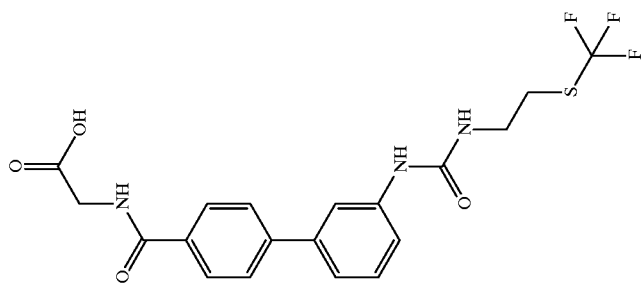 | 441.43 | 4.45 | 442 | | 3.9 | | 4 |

-continued
| structure | MW | example | MS | Rf (TLC) [min.] | Rt (HPLC) [min.] (%) | m.p. [° C.] | method |
|---|---|---|---|---|---|---|---|
| 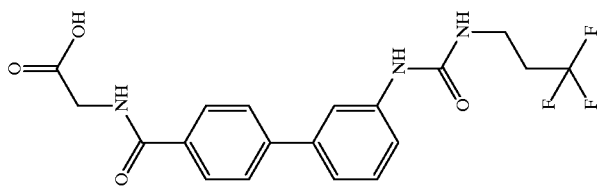 | 409.37 | 4.46 | 410 | | 3.7 | | 4 |

| structure | MW | example | MS | Rf (TLC) [min.] | Rt (HPLC) [min.] (%) | m.p. [° C.] | method |
|---|---|---|---|---|---|---|---|
| 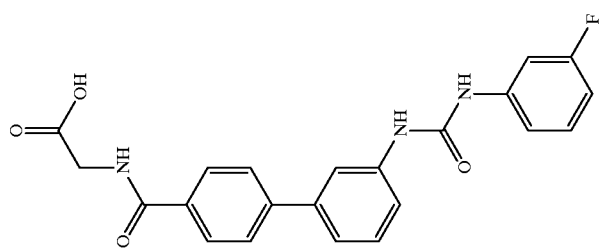 | 407.40 | 4.47 | 408 | | 4.0 | | 4 |

-continued
| structure | MW | example | MS | Rf (TLC) [min.] | Rt (HPLC) [min.] (%) | m.p. [° C.] | method |
|---|---|---|---|---|---|---|---|
| 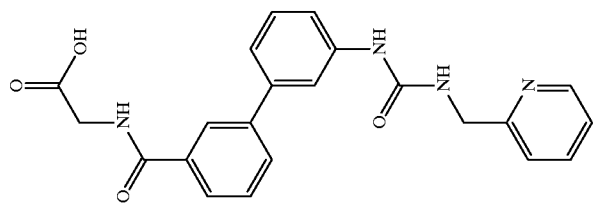 | 404.43 | 4.48 | 405 | | 2.6 | | 4 |

-continued

| structure | MW | example | MS | Rf (TLC) [min.] | Rt (HPLC) [min.] (%) | m.p. [° C.] | method |
|---|---|---|---|---|---|---|---|
| [structure: biphenyl with glycine amide and cyclopropyl urea] | 353.38 | 4.49 | 354 | | 3.4 | | 4 |
| [structure: biphenyl with glycine amide and isopropyl urea] | 355.40 | 4.50 | 356 | | 3.5 | | 4 |

-continued
| structure | MW | example | MS | Rf (TLC) [min.] | Rt (HPLC) [min.] (%) | m.p. [° C.] | method |
|---|---|---|---|---|---|---|---|
| 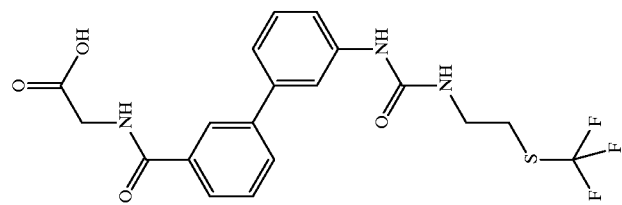 | 441.43 | 4.51 | 442 | | 4.0 | | 4 |

| structure | MW | example | MS | Rf (TLC) [min.] | Rt (HPLC) [min.] (%) | m.p. [° C.] | method |
|---|---|---|---|---|---|---|---|
| (structure with CF3 propyl urea biphenyl glycine) | 409.37 | 4.52 | 410 | | 3.7 | | 4 |
| (structure with 3-fluorophenyl urea biphenyl glycine) | 407.40 | 4.53 | 408 | | 4.1 | | 4 |

-continued

| structure | MW | example | MS | Rf (TLC) [min.] | Rt (HPLC) [min.] (%) | m.p. [° C.] | method |
|---|---|---|---|---|---|---|---|
| 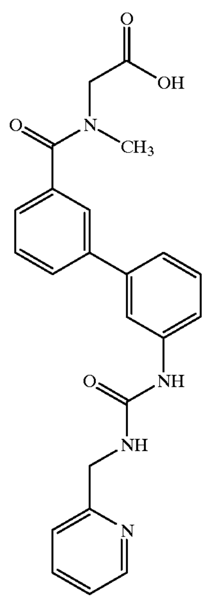 | 418.46 | 6.2 | 419 | | 2.7 | | 6 |

-continued

| structure | MW | example | MS | Rf (TLC) [min.] | Rt (HPLC) [min.] (%) | m.p. [°C] | method |
|---|---|---|---|---|---|---|---|
| [structure] | 367.41 | 6.3 | 368 | | 3.4 | | 6 |
| [structure] | 369.42 | 6.4 | 370 | | 3.5 | | 6 |

-continued
| structure | MW | example | MS | Rf (TLC) [min.] | Rt (HPLC) [min.] (%) | m.p. [° C.] | method |
|---|---|---|---|---|---|---|---|
| 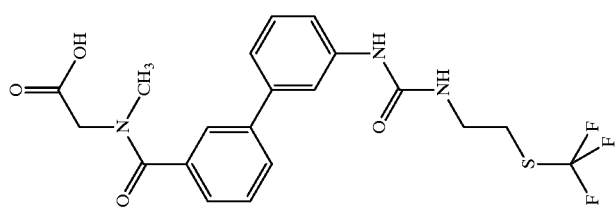 | 455.46 | 6.5 | 456 | | 4.0 | | 6 |

-continued

| structure | MW | example | MS | Rf (TLC) [min.] | Rt (HPLC) [min.] (%) | m.p. [° C.] | method |
|---|---|---|---|---|---|---|---|
| [structure] | 423.40 | 6.6 | 424 | | 3.8 | | 6 |
| [structure] | 421.43 | 6.7 | 422 | | 3.6 | | 6 |

-continued

| structure | MW | example | MS | Rf (TLC) [min.] | Rt (HPLC) [min.] (%) | m.p. [° C.] | method |
|---|---|---|---|---|---|---|---|
| [structure] | 418.46 | 6.8 | 419 | | 2.6 | | 6 |

-continued
| structure | MW | example | MS | Rf (TLC) [min.] | Rt (HPLC) [min.] (%) | m.p. [° C.] | method |
|---|---|---|---|---|---|---|---|
| 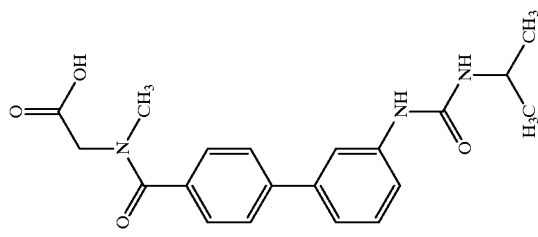 | 369.42 | 6.9 | 370 | | 3.5 | | 6 |

-continued

| structure | MW | example | MS | Rf (TLC) [min.] | Rt (HPLC) [min.] (%) | m.p. [° C.] | method |
|---|---|---|---|---|---|---|---|
| (structure 1) | 455.46 | 6.10 | 456 | | 4.0 | | 6 |
| (structure 2) | 482.56 | 1.165 | 483 | | 2.6 (94) | | 1 |

-continued

| structure | MW | example | MS | Rf (TLC) [min.] | Rt (HPLC) [min.] (%) | m.p. [° C.] | method |
|---|---|---|---|---|---|---|---|
| 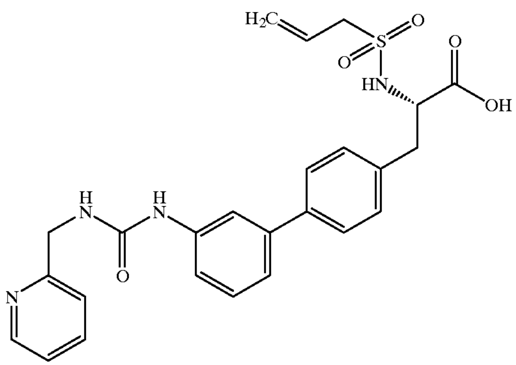 | 494.57 | 1.166 | 495 | | 2.7 (96) | | 1 |
| 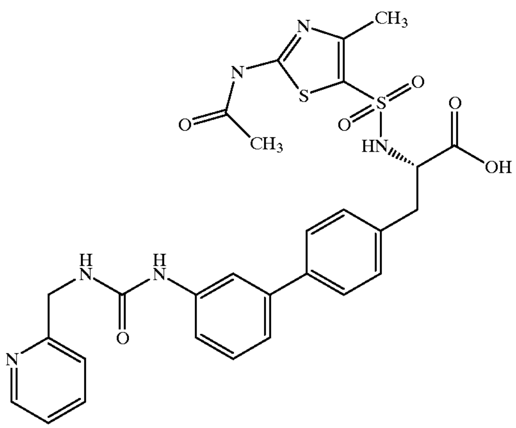 | 608.70 | 1.167 | 609 | | 2.7 | | 1 |

-continued

| structure | MW | example | MS | Rf (TLC) [min.] | Rt (HPLC) [min.] (%) | m.p. [°C] | method |
|---|---|---|---|---|---|---|---|
| 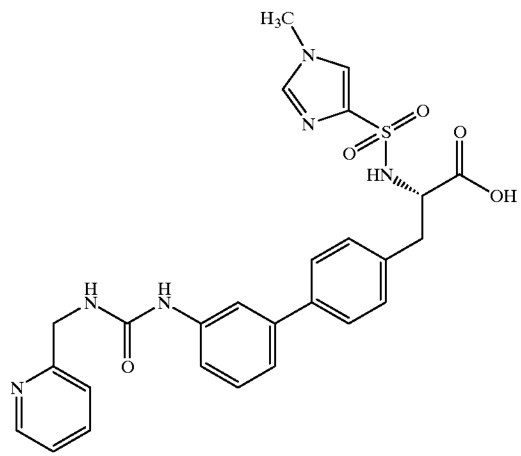 | 534.60 | 1.168 | 535 | | 2.5 | | 1 |
| 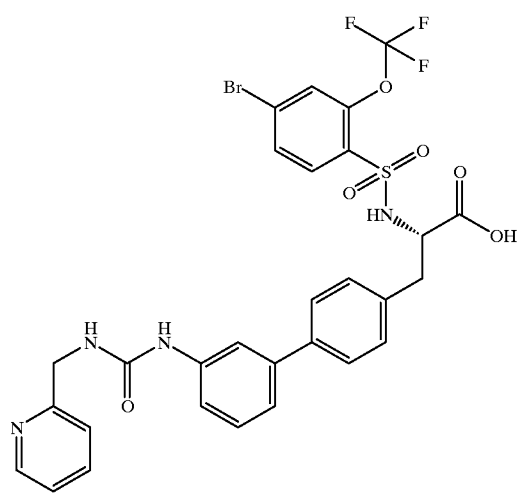 | 693.50 | 1.169 | 694 | | 3.4 | | 1 |

-continued

| structure | MW | example | MS | Rf (TLC) [min.] | Rt (HPLC) [min.] (%) | m.p. [° C.] | method |
|---|---|---|---|---|---|---|---|
| 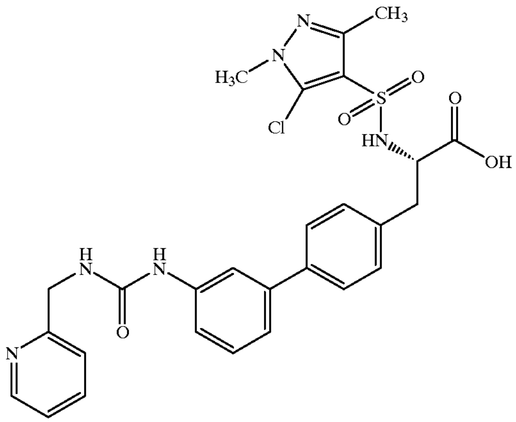 | 583.70 | 1.170 | 584 | | 2.8 | | 1 |
| 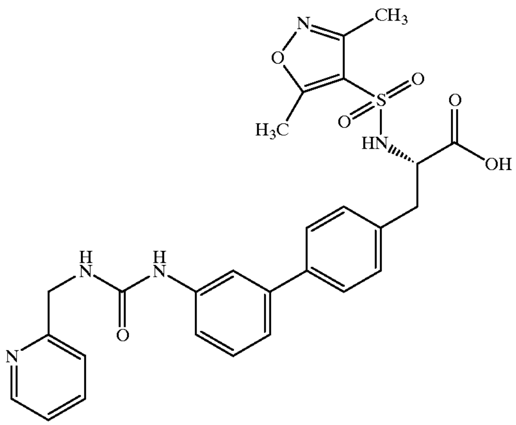 | 549.61 | 1.171 | 550 | | 2.8 | | 1 |

-continued

| structure | MW | example | MS | Rf (TLC) [min.] | Rt (HPLC) [min.] (%) | m.p. [° C.] | method |
|---|---|---|---|---|---|---|---|
| 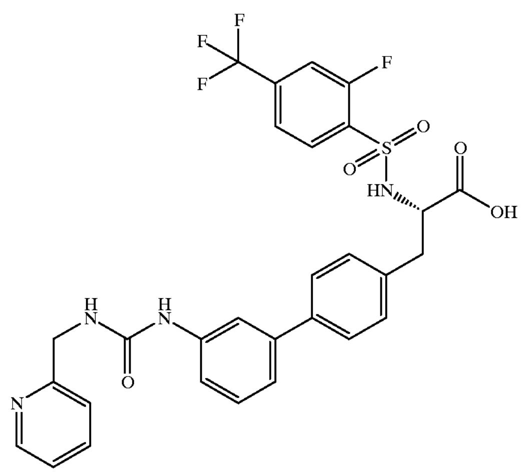 | 616.60 | 1.172 | 617 | | 3.2 (67) | | 1 |
| 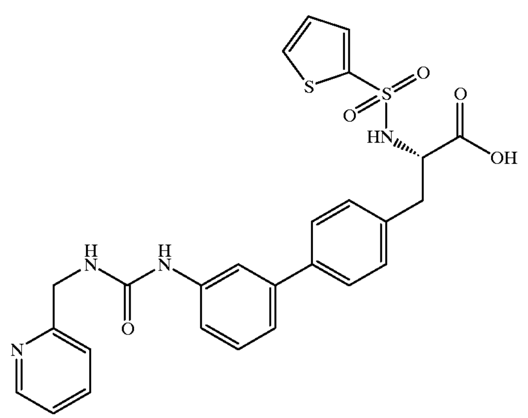 | 536.63 | 1.173 | 537 | | 2.9 (92) | | 1 |

| structure | MW | example | MS | Rf (TLC) [min.] | Rt (HPLC) [min.] (%) | m.p. [° C.] | method |
|---|---|---|---|---|---|---|---|
| (benzothiadiazole-sulfonyl biphenyl benzylurea structure) | 588.67 | 1.174 | 589 | | 2.8 (96) | | 1 |
| (acetamido-phenylsulfonyl biphenyl benzylurea structure) | 587.66 | 1.175 | 588 | | 2.6 (100) | | 1 |

| structure | MW | example | MS | Rf (TLC) [min.] | Rt (HPLC) [min.] (%) | m.p. [° C.] | method |
|---|---|---|---|---|---|---|---|
| (structure 1) | 616.70 | 1.176 | 617 | | 2.7 (100) | | 1 |
| (structure 2) | 524.60 | 1.177 | 525 | | 3.8 (77) | | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 431.51 | 1.178 | 432 | | 3.4 (69) | | 1 |
| (structure) | 443.53 | 1.179 | 444 | | 3.5 | | 1 |
| (structure) | 557.65 | 1.180 | 558 | | 3.4 | | 1 |

-continued

| structure | MW | example | MS | Rf (TLC) [min.] | Rt (HPLC) [min.] (%) | m.p. [° C.] | method |
|---|---|---|---|---|---|---|---|
| 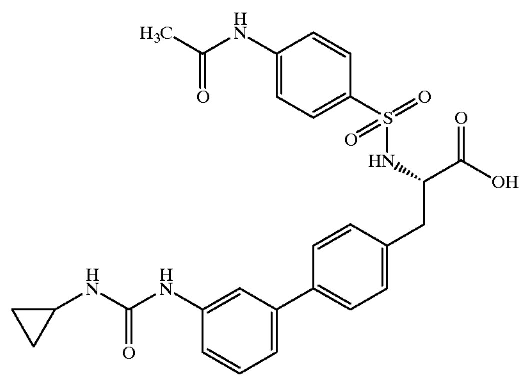 | 536.61 | 1.181 | 537 | | 3.4 | | 1 |
| 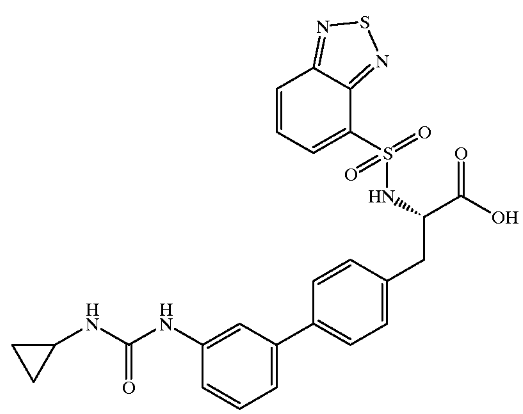 | 537.62 | 1.182 | 538 | | 3.5 | | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 485.58 | 1.183 | 486 | | 3.6 | | 1 |
| (structure) | 498.56 | 1.184 | 499 | | 3.6 | | 1 |

-continued

| structure | MW | example | MS | Rf (TLC) [min.] | Rt (HPLC) [min.] (%) | m.p. [° C.] | method |
|---|---|---|---|---|---|---|---|
| 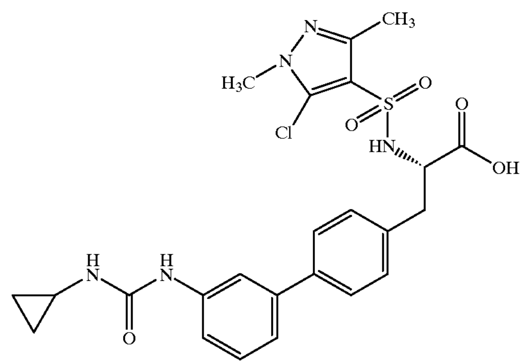 | 532.02 | 1.185 | 532 | | 3.5 | | 1 |
| 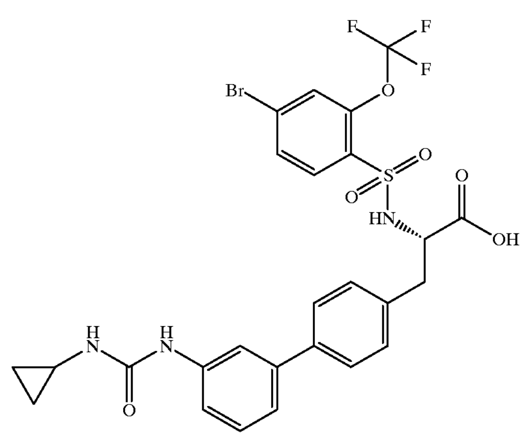 | 642.45 | 1.186 | 642 | | 4.2 | | 1 |

-continued
| structure | MW | example | MS | Rf (TLC) [min.] | Rt (HPLC) [min.] (%) | m.p. [° C.] | method |
|---|---|---|---|---|---|---|---|
| 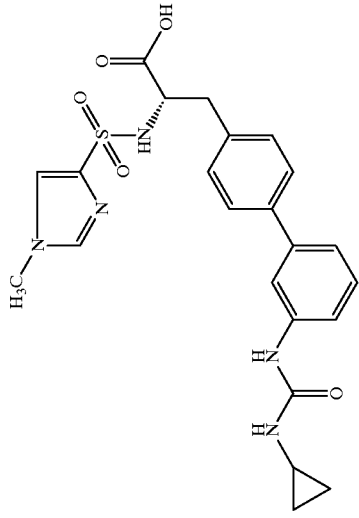 | 483.55 | 1.187 | 484 | | 3.1 | | 1 |
| 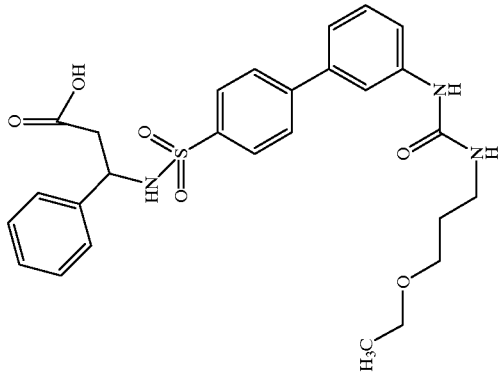 | 525.63 | 4.54 | 526 | | 3.7 (69) | | 4 |

-continued
| structure | MW | example | MS | Rf (TLC) [min.] | Rt (HPLC) [min.] (%) | m.p. [° C.] | method |
|---|---|---|---|---|---|---|---|
| 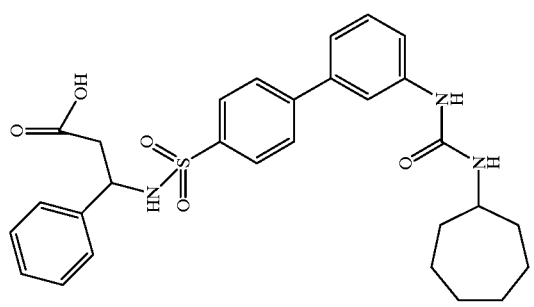 | 535.67 | 4.55 | 536 | | 4.3 (93) | | 4 |

-continued

| structure | MW | example | MS | Rf (TLC) [min.] | Rt (HPLC) [min.] (%) | m.p. [° C.] | method |
|---|---|---|---|---|---|---|---|
| 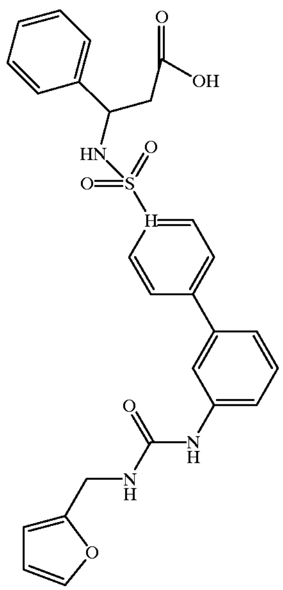 | 519.58 | 4.56 | 520 | | 3.9 (100) | | 4 |

-continued

| structure | MW | example | MS | Rf (TLC) [min.] | Rt (HPLC) [min.] (%) | m.p. [° C.] | method |
|---|---|---|---|---|---|---|---|
| 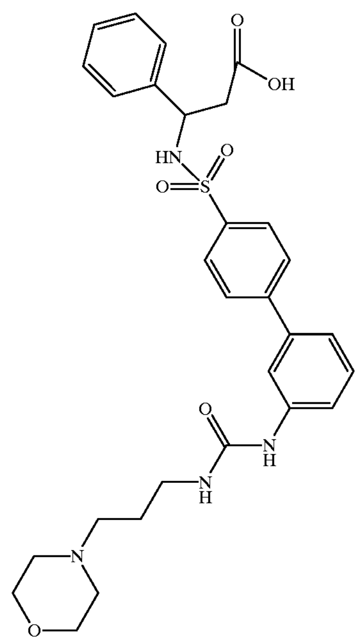 | 566.68 | 4.57 | 567 | | 3.9 (91) | | 4 |

| structure | MW | example | MS | Rf (TLC) [min.] | Rt (HPLC) [min.] (%) | m.p. [°C] | method |
|---|---|---|---|---|---|---|---|
| (structure) | 507.61 | 4.58 | 508 | | 4.0 (100) | | 4 |
| (structure) | 557.65 | 4.59 | 558 | | 3.5 (100) | | 4 |

-continued
| structure | MW | example | MS | Rf (TLC) [min.] | Rt (HPLC) [min.] (%) | m.p. [°C.] | method |
|---|---|---|---|---|---|---|---|
| 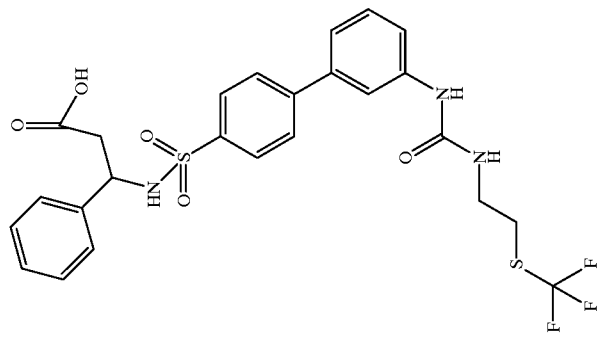 | 567.61 | 4.60 | 568 | | 4.1 (100) | | 4 |

-continued
| structure | MW | example | MS | Rf (TLC) [min.] | Rt (HPLC) [min.] (%) | m.p. [° C.] | method |
|---|---|---|---|---|---|---|---|
| 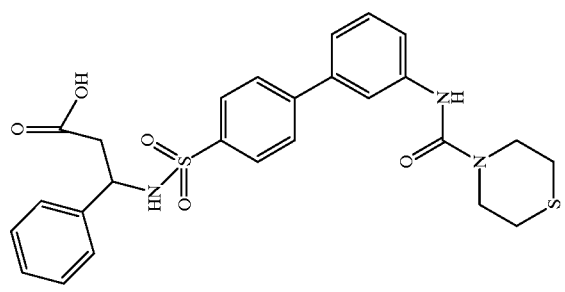 | 525.65 | 4.61 | 526 | | 3.9 (100) | | 4 |
In the structural formulas of the examples below hydrogens are not shown for the sake of simplicity. All free valences shall be considered as saturated with hydrogen. This applies to carbon atoms as well as hetero atoms.

-continued
| structure | MW | example | MS | Rf (TLC) [min.] | Rt (HPLC) [min.] (%) | m.p. [° C.] | method |
|---|---|---|---|---|---|---|---|
| 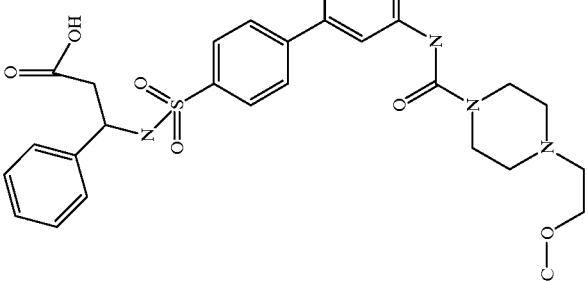 | 566.68 | 4.62 | 567 | | 3.0 (95) | | 4 |
| 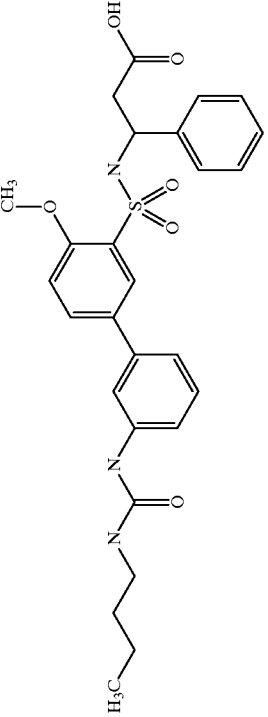 | 525.63 | 4.63 | 526 | 0.18 C | | 190 | 4 |

-continued

| structure | MW | example | MS | Rf (TLC) [min.] | Rt (HPLC) [min.] (%) | m.p. [° C.] | method |
|---|---|---|---|---|---|---|---|
| 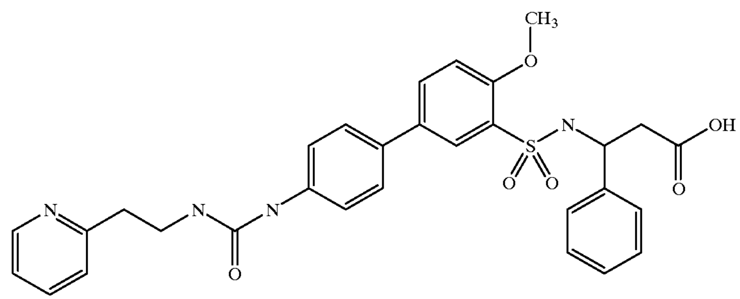 | 574.66 | 4.64 | 575 | 0.41 A | | 137 | 4 |
| 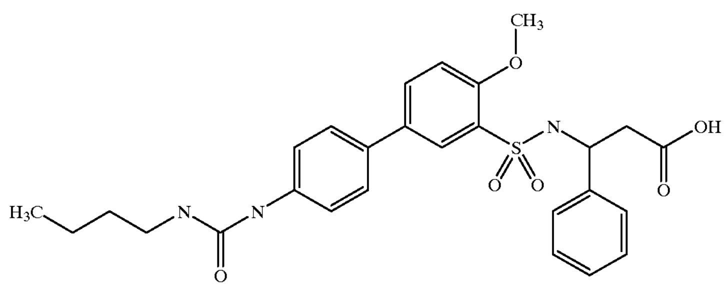 | 525.63 | 4.65 | 526 | 0.44 A | | 125 | 4 |
| 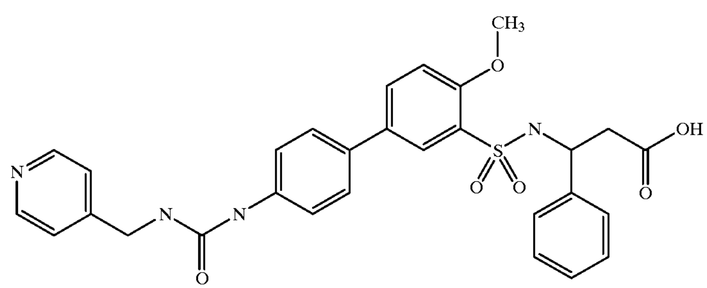 | 560.63 | 4.66 | 561 | 0.17 A | | 145 | 4 |

-continued
| structure | MW | example | MS | Rf (TLC) [min.] | Rt (HPLC) [min.] (%) | m.p. [° C.] | method |
|---|---|---|---|---|---|---|---|
|  | 560.63 | 4.67 | 561 | 0.19 A | | 161 | 4 |
| 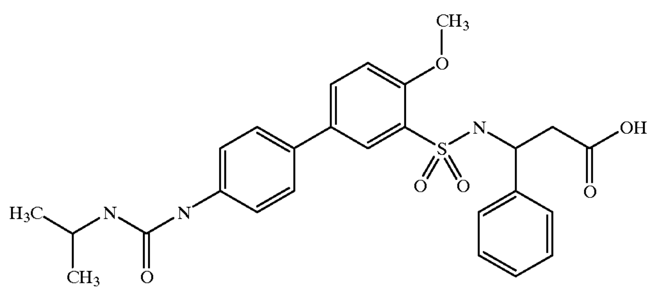 | 511.60 | 4.68 | 512 | 0.46 A | | 115 | 4 |
| 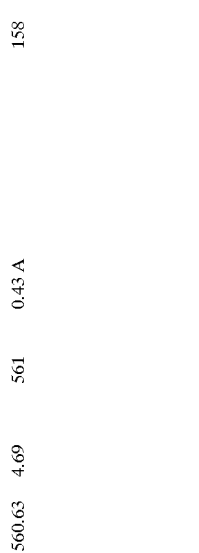 | 560.63 | 4.69 | 561 | 0.43 A | | 158 | 4 |

-continued

| structure | MW | example | MS | Rf (TLC) [min.] | Rt (HPLC) [min.] (%) | m.p. [° C.] | method |
|---|---|---|---|---|---|---|---|
| 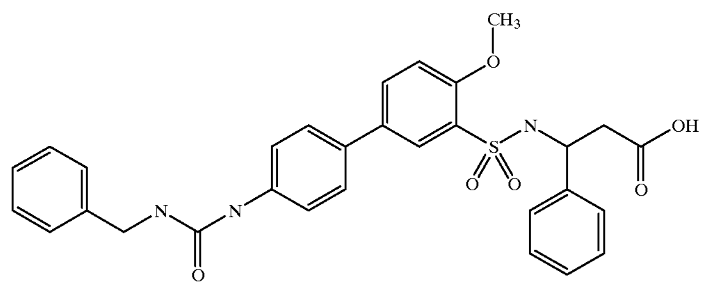 | 559.65 | 4.70 | 560 | 0.54 A | | 150 | 4 |
| 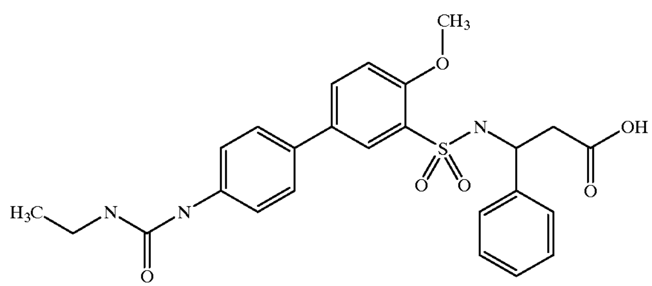 | 497.57 | 4.71 | 498 | | | 134 | 4 |
| 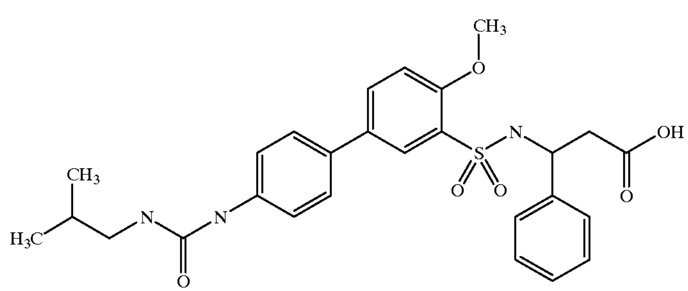 | 525.63 | 4.72 | 526 | | | 126 | 4 |

-continued

| structure | MW | example | MS | Rf (TLC) [min.] | Rt (HPLC) [min.] (%) | m.p. [° C.] | method |
|---|---|---|---|---|---|---|---|
| 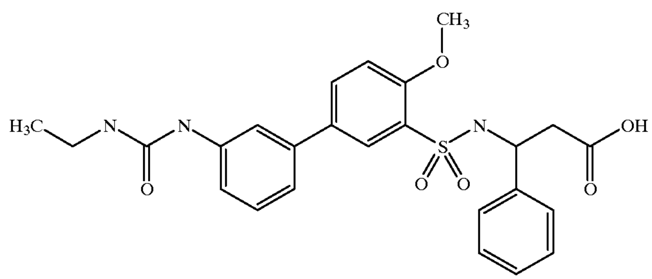 | 497.57 | 4.73 | 498 | | | >250 | 4 |
| 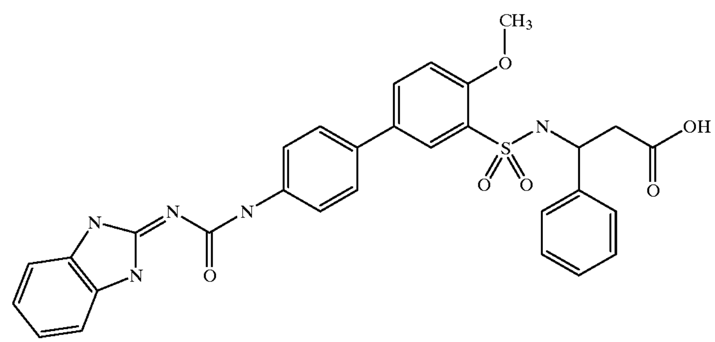 | 585.64 | 4.74 | 586 | | | 209 | 4 |
| 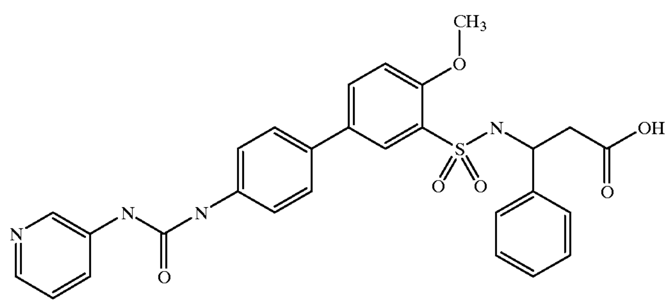 | 546.61 | 4.75 | 547 | | | 188 | 4 |

-continued

| structure | MW | example | MS | Rf (TLC) [min.] | Rt (HPLC) [min.] (%) | m.p. [° C.] | method |
|---|---|---|---|---|---|---|---|
| 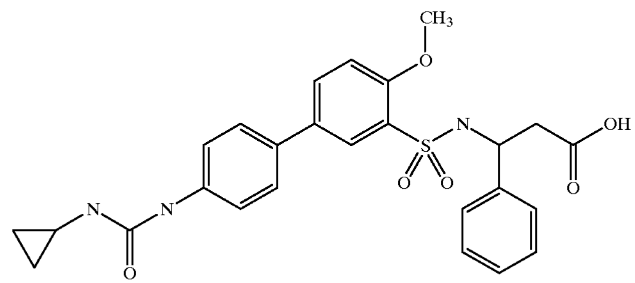 | 509.59 | 4.76 | 510 | | | 234 | 4 |
| 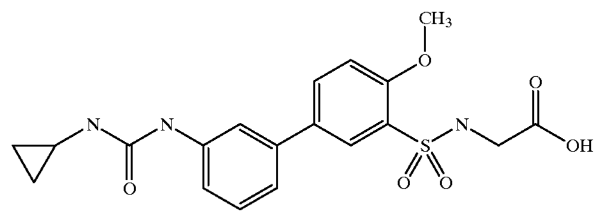 | 419.46 | 4.77 | 420 | | | 128 | 4 |
| 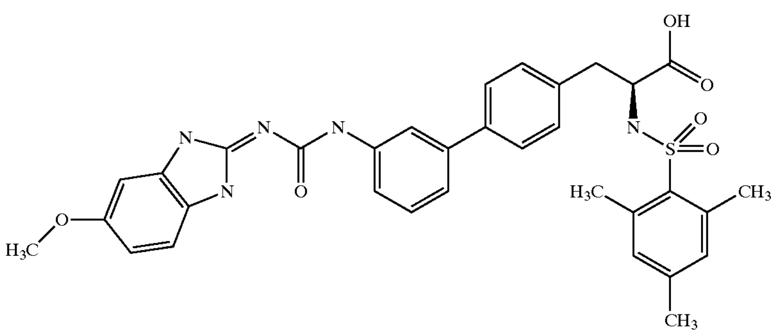 | 627.72 | 1.188 | 628 | | | 215 | 1 |

-continued

| structure | MW | example | MS | Rf (TLC) [min.] | Rt (HPLC) [min.] (%) | m.p. [° C.] (dec.) | method |
|---|---|---|---|---|---|---|---|
| 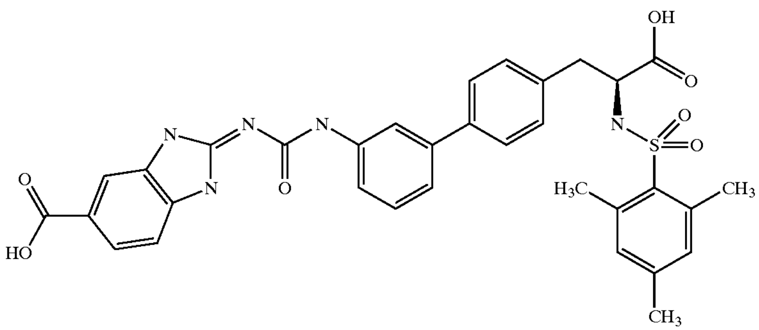 | 641.71 | 1.189 | 642 | 0.10 D | | 256 | 1 |
| 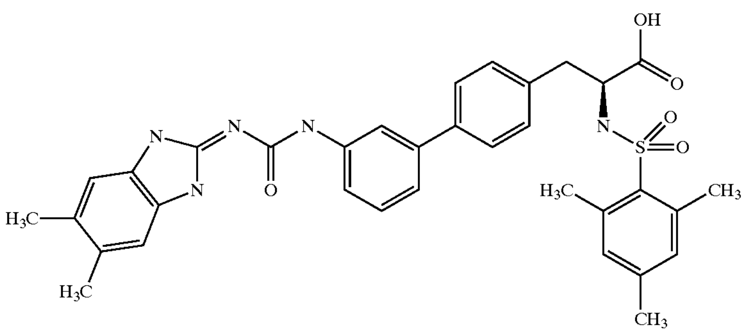 | 625.75 | 1.190 | 626 | 0.10 D | | 202 | 1 |
| 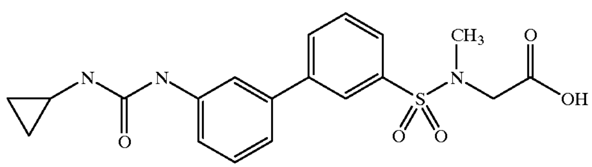 | 403.46 | 6.11 | 404 | 0.02 B | | 117 | 6 |
| 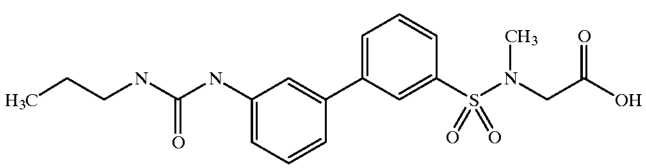 | 405.48 | 6.12 | 406 | 0.02 B | | 90 | 6 |

-continued

| structure | MW | example | MS | Rf (TLC) [min.] | Rt (HPLC) [min.] (%) | m.p. [° C.] | method |
|---|---|---|---|---|---|---|---|
| 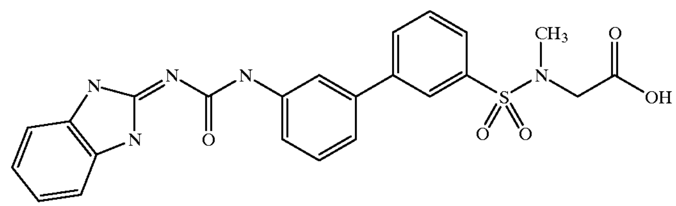 | 479.52 | 6.13 | 480 | 0.02 B | | 184 | 6 |
| 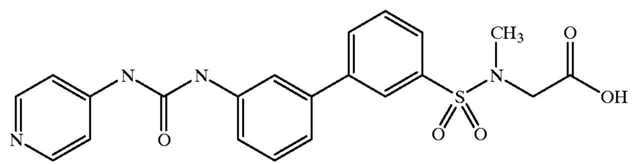 | 440.48 | 6.14 | 441 | 0.02 B | | 142 | 6 |
| 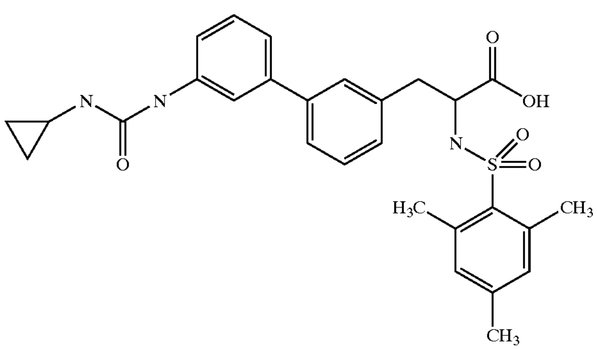 | 521.64 | 1.191 | 522 | 0.02 B | | 214 | 1 |

-continued

| structure | MW | example | MS | Rf (TLC) [min.] | Rt (HPLC) [min.] (%) | m.p. [° C.] | method |
|---|---|---|---|---|---|---|---|
| (structure 1) | 523.66 | 1.192 | 524 | 0.01 B | | 136 | 1 |
| (structure 2) | 572.69 | 1.193 | 573 | 0.02 B | | 118 | 1 |

-continued

| structure | MW | example | MS | Rf (TLC) [min.] | Rt (HPLC) [min.] (%) | m.p. [°C] | method |
|---|---|---|---|---|---|---|---|
| 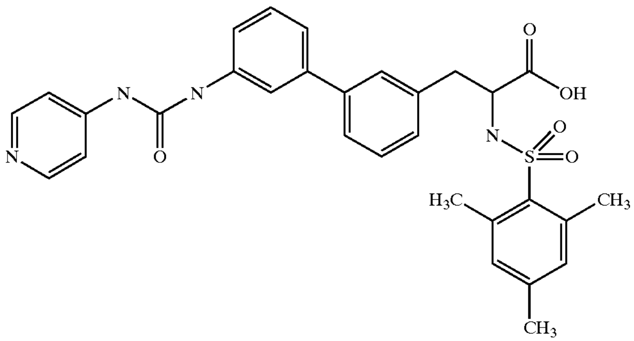 | 558.66 | 1.194 | 559 | 0.02 B | | 207 | 1 |
| 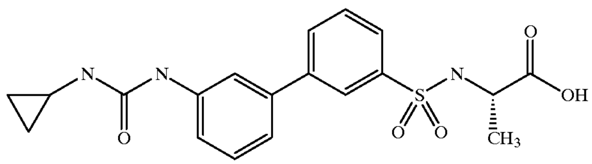 | 403.46 | 4.78 | 404 | 0.22 D | | | 4 |
| 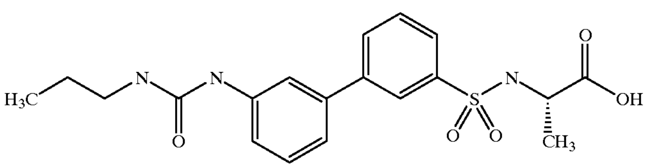 | 405.48 | 4.79 | 406 | 0.25 D | | | 4 |
| 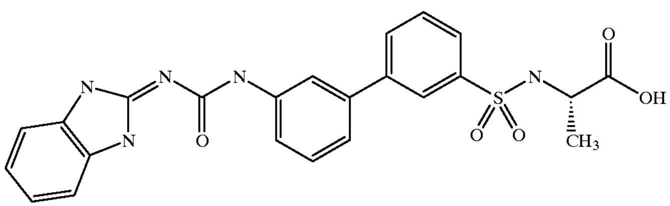 | 479.52 | 4.80 | 480 | 0.10 D | | 218 | 4 |

-continued

| structure | MW | example | MS | Rf (TLC) [min.] | Rt (HPLC) [min.] (%) | m.p. [° C.] | method |
|---|---|---|---|---|---|---|---|
| 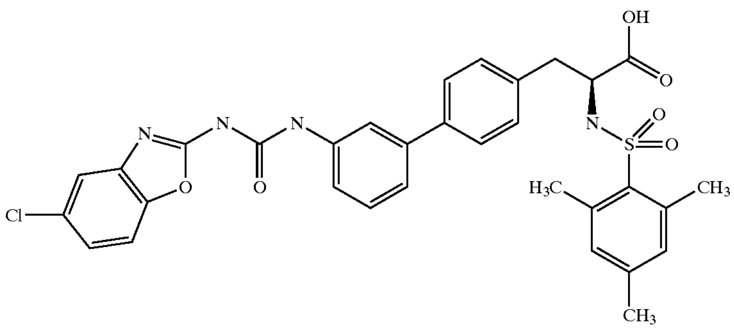 | 633.13 | 1.195 | 634 | 0.22 D | | 220 | 1 |
| 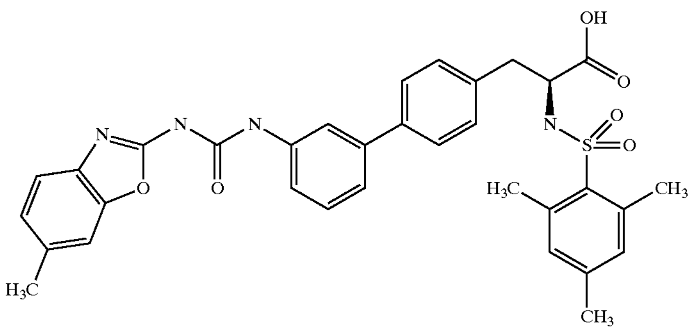 | 612.71 | 1.196 | 613 | 0.22 D | | 213 | 1 |
| 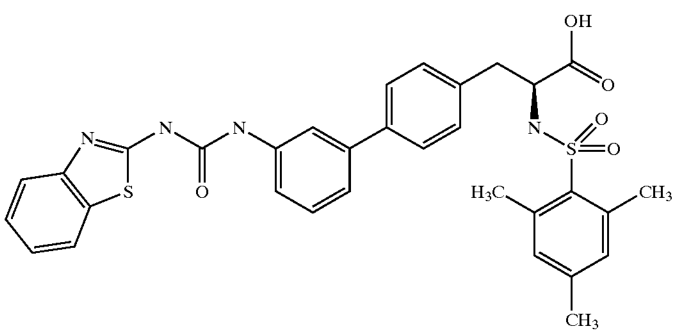 | 614.75 | 1.197 | 615 | 0.22 B | | 198 | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 564.69 | 1.198 | 565 | 0.22 D | | 212 | 1 |
| (structure) | 628.77 | 1.199 | 629 | 0.22 D | | 220 | 1 |
| (structure) | 644.77 | 1.200 | 645 | 0.22 D | | 225 | 1 |

-continued

| structure | MW | example | MS | Rf (TLC) [min.] | Rt (HPLC) [min.] (%) | m.p. [° C.] | method |
|---|---|---|---|---|---|---|---|
| 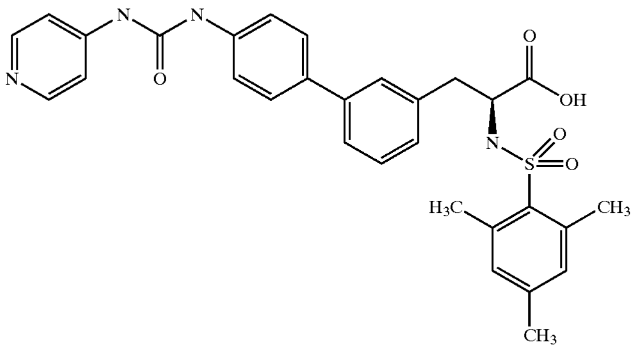 | 558.66 | 1.201 | 559 | 0.01 B | | 188 | 1 |
| 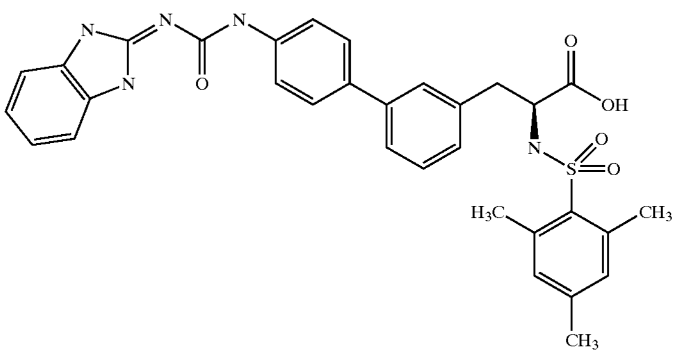 | 597.70 | 1.202 | 598 | 0.02 B | | 193 | 1 |

-continued

| structure | MW | example | MS | Rf (TLC) [min.] | Rt (HPLC) [min.] (%) | m.p. [° C.] | method |
|---|---|---|---|---|---|---|---|
| (structure 1.203) | 523.66 | 1.203 | 524 | 0.02 B | | 119 | 1 |
| (structure 1.204) | 565.67 | 1.204 | 566 | 0.22 D | | 202 | 1 |
| (structure 1.205) | 438.55 | 1.205 | 439 | | | 289 | 1 |

-continued

| structure | MW | example | MS | Rf (TLC) [min.] | Rt (HPLC) [min.] (%) | m.p. [° C.] | method |
|---|---|---|---|---|---|---|---|
| 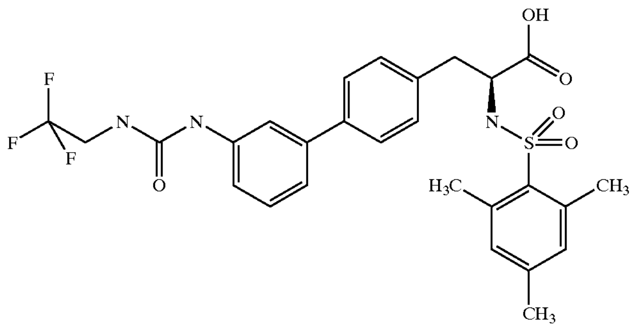 | 563.60 | 1.206 | 564 | 0.22 D | | 124 | 1 |
| 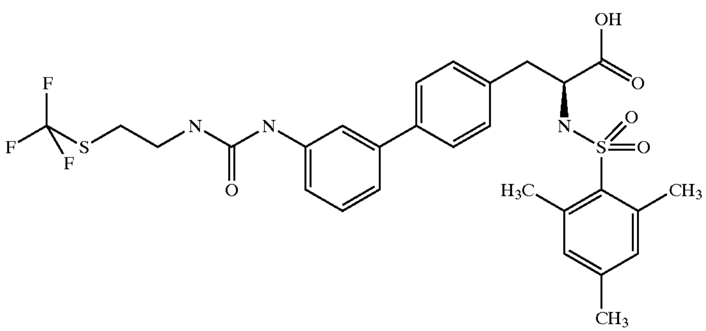 | 609.69 | 1.207 | 610 | 0.22 D | | 138 | 1 |
| 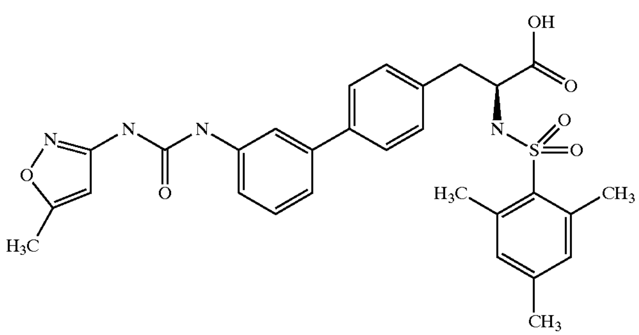 | 562.65 | 1.208 | 563 | 0.22 D | | 189 | 1 |

-continued

| structure | MW | example | MS | Rf (TLC) [min.] | Rt (HPLC) [min.] (%) | m.p. [° C.] | method |
|---|---|---|---|---|---|---|---|
| (structure) | 604.73 | 1.209 | 605 | 0.22 D | | 180 | 1 |
| (structure) | 597.70 | 1.210 | 598 | 0.22 D | | 207 | 1 |
| (structure) | 405.48 | 4.81 | 406 | 0.22 D | | 126 | 4 |

-continued

| structure | MW | example | MS | Rf (TLC) [min.] | Rt (HPLC) [min.] (%) | m.p. [° C.] | method |
|---|---|---|---|---|---|---|---|
| 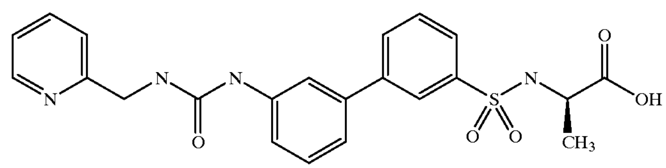 | 454.51 | 4.82 | 455 | 0.22 D | | 149 | 4 |
| 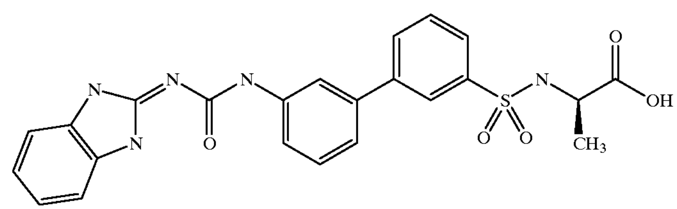 | 479.52 | 4.83 | 480 | 0.22 D | | 158 | 4 |
| 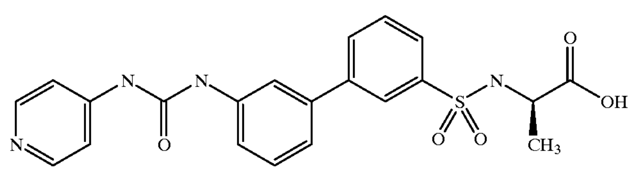 | 440.48 | 4.84 | 441 | 0.22 D | | 169 | 4 |
| 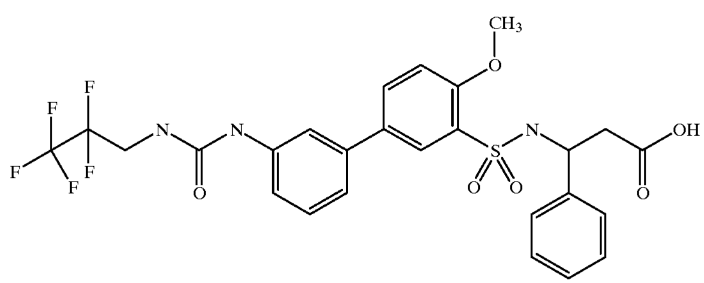 | 601.55 | 4.85 | 602 | 0.22 D | | 147 | 4 |

-continued

| structure | MW | example | MS | Rf (TLC) [min.] | Rt (HPLC) [min.] (%) | m.p. [° C.] | method |
|---|---|---|---|---|---|---|---|
| 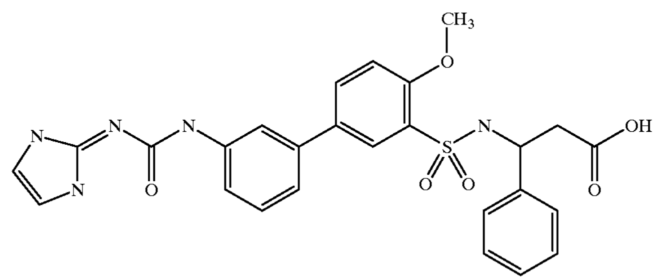 | 535.58 | 4.86 | 536 | 0.12 F | | 209 | 4 |
| 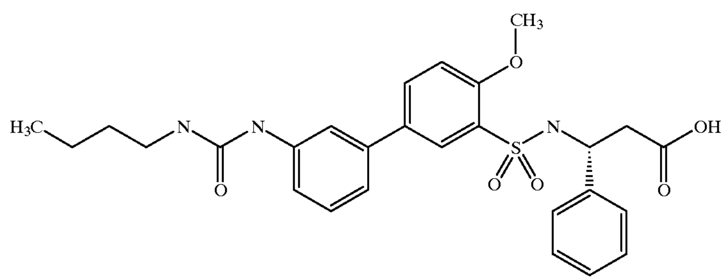 | 525.63 | 4.87 | 526 | 0.38 A | | 122 (dec.) | 4 |
| 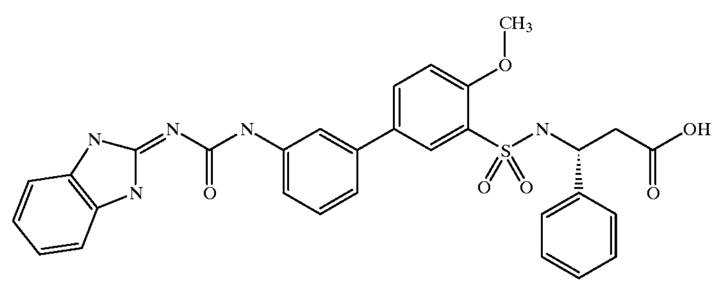 | 585.64 | 4.88 | 586 | 0.18 A | | 151 (dec.) | 4 |

| structure | MW | example | MS | Rf (TLC) [min.] | Rt (HPLC) [min.] (%) | m.p. [° C.] | method |
|---|---|---|---|---|---|---|---|
| 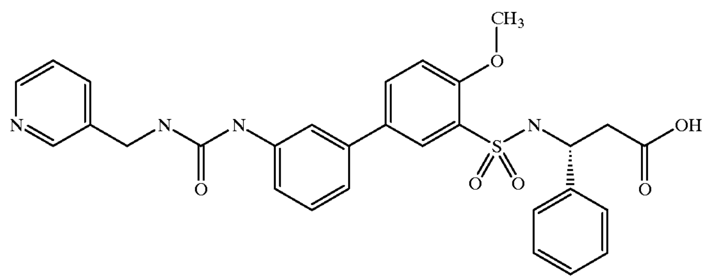 | 560.63 | 4.89 | 561 | 0.23 A | | 224 (dec.) | 4 |
| 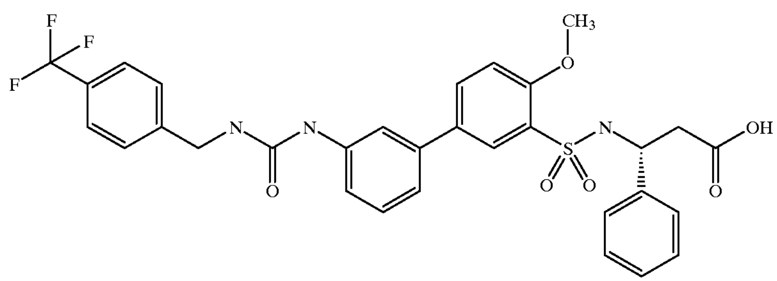 | 627.64 | 4.90 | 628 | 0.40 A | | 111 (dec.) | 4 |
| 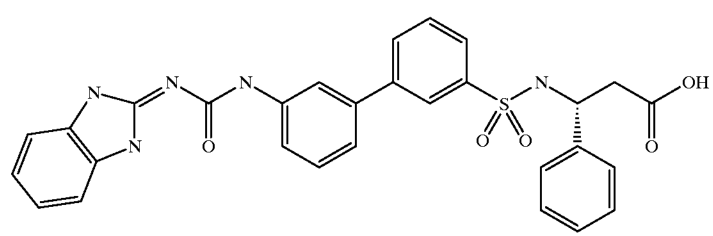 | 555.62 | 4.91 | 556 | 0.01 B | | 189 | 4 |

-continued

| structure | MW | example | MS | Rf (TLC) [min.] | Rt (HPLC) [min.] (%) | m.p. [°C.] | method |
|---|---|---|---|---|---|---|---|
| 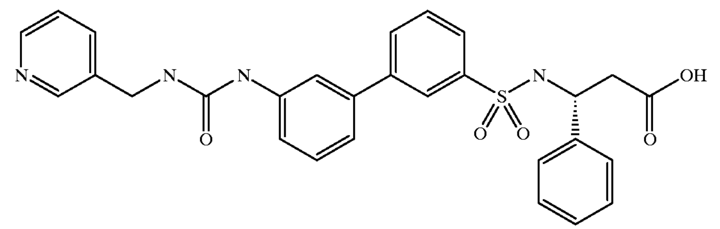 | 530.61 | 4.92 | 531 | 0.02 B | | 126 | 4 |
| 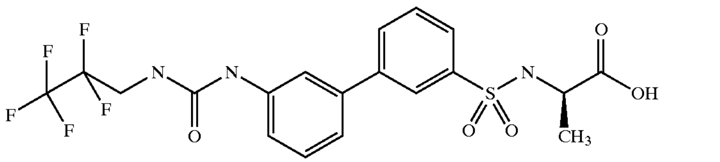 | 495.43 | 4.93 | 496 | 0.12 F | | 112 | 4 |
| 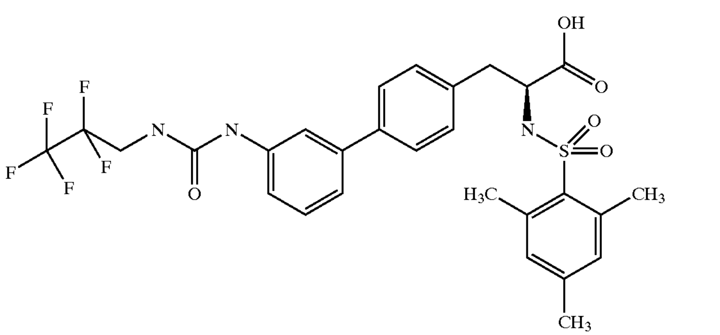 | 613.61 | 1.211 | 614 | 0.12 F | | 126 | 1 |
| 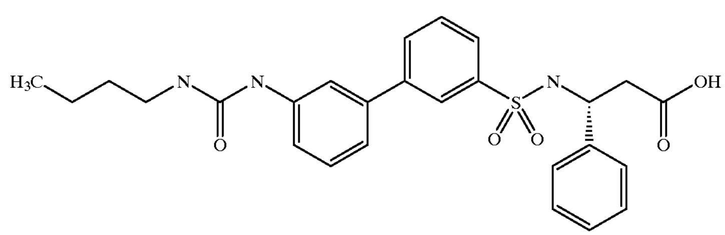 | 495.60 | 4.94 | 496 | 0.11 F | | 152 | 4 |

-continued

| structure | MW | example | MS | Rf (TLC) [min.] | Rt (HPLC) [min.] (%) | m.p. [° C.] | method |
|---|---|---|---|---|---|---|---|
| (structure) | 597.62 | 4.95 | 598 | 0.13 F | | 186 | 4 |
| (structure) | 639.70 | 1.212 | 640 | | | 154 | 1 |
| (structure) | 525.63 | 4.96 | 526 | 0.12 F | | 156 | 4 |

-continued

| structure | MW | example | MS | Rf (TLC) [min.] | Rt (HPLC) [min.] (%) | m.p. [° C.] | method |
|---|---|---|---|---|---|---|---|
| (structure) | 577.64 | 4.97 | 578 | 0.12 F | | 162 | 4 |
| (structure) | 592.68 | 20.3 | 593 | 0.32 F | | 207 | 20 |
| (structure) | 518.60 | 20.4 | 519 | 0.32 F | | >240 | 20 |

-continued

| structure | MW | example | MS | Rf (TLC) [min.] | Rt (HPLC) [min.] (%) | m.p. [°C.] | method |
|---|---|---|---|---|---|---|---|
| 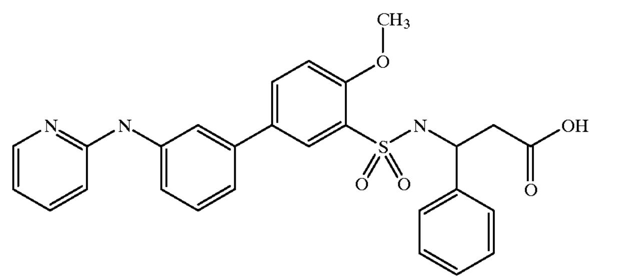 | 503.58 | 20.5 | 504 | 0.12 C | | >240 | 20 |
| 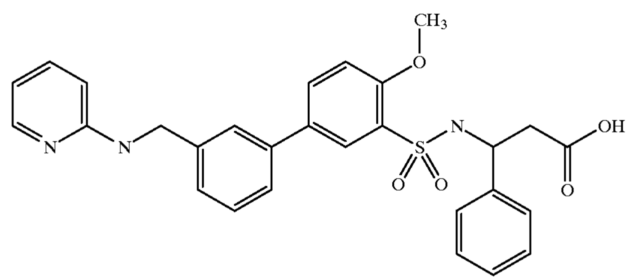 | 517.61 | 18.3 | 518 | 0.22 C | | 138 | 18 |
| 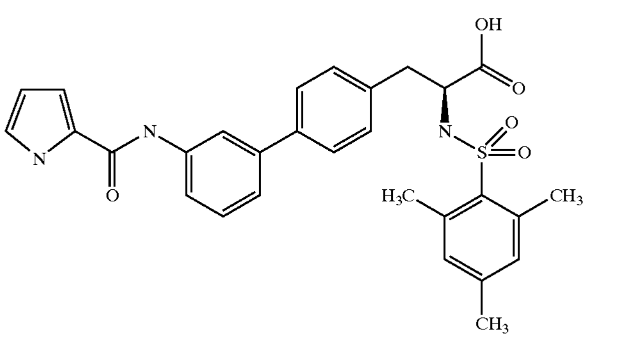 | 531.64 | 19.2 | 532 | 0.44 D | | 140 (dec.) | 19 |

| structure | MW | example | MS | Rf (TLC) [min.] | Rt (HPLC) [min.] (%) | m.p. [° C.] | method |
|---|---|---|---|---|---|---|---|
| 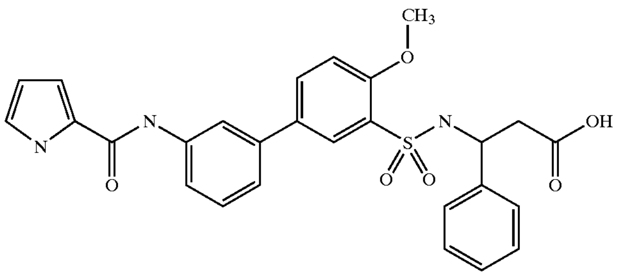 | 519.58 | 19.3 | 520 | 0.46 D | | 234 | 19 |
| 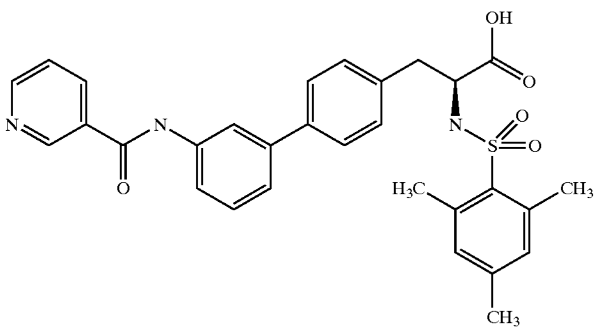 | 543.65 | 19.4 | 544 | 0.23 D | | >240 | 19 |
| 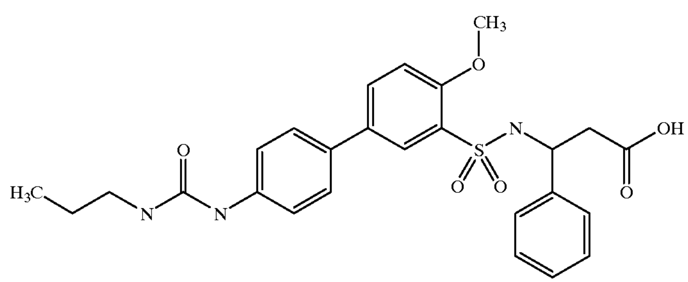 | 511.60 | 4.98 | 512 | 0.17 B | | 116 | 4 |

-continued

| structure | MW | example | MS | Rf (TLC) [min.] | Rt (HPLC) [min.] (%) | m.p. [° C.] | method |
|---|---|---|---|---|---|---|---|
| (structure) | 604.73 | 1.213 | 605 | 0.10 D | | 202 | 1 |
| (structure) | 590.70 | 1.214 | 591 | 0.10 D | | 207 | 1 |
| (structure) | 629.74 | 1.215 | 630 | 0.10 D | | 222 | 1 |

-continued

| structure | MW | example | MS | Rf (TLC) [min.] | Rt (HPLC) [min.] (%) | m.p. [° C.] | method |
|---|---|---|---|---|---|---|---|
| 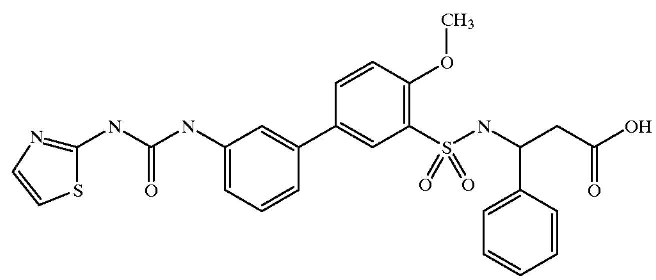 | 552.63 | 4.99 | 553 | 0.22 D | | >240 | 4 |
| 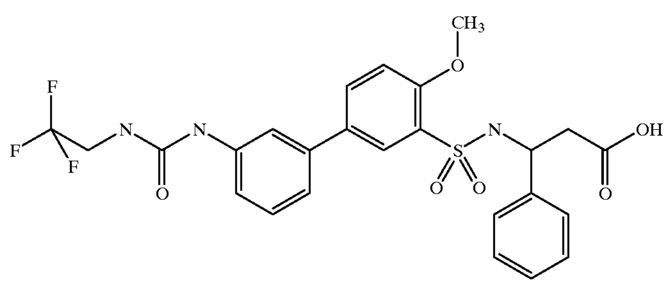 | 551.55 | 4.100 | 552 | 0.22 D | | >240 | 4 |
| 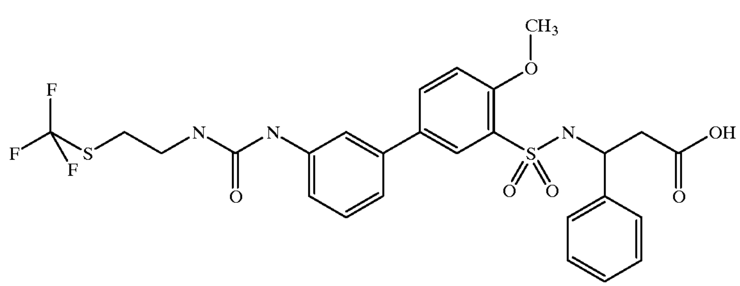 | 597.64 | 4.101 | 598 | 0.22 D | | >240 | 4 |

| MW | example | MS | Rf (TLC) [min.] | Rt (HPLC) [min.] (%) | m.p. [° C.] | method |
|---|---|---|---|---|---|---|
| 627.64 | 4.102 | 628 | 0.22 D | | >240 | 4 |
| 629.65 | 4.103 | 630 | 0.22 D | | >240 | 4 |
| 613.70 | 4.104 | 614 | 0.22 D | | >240 | 4 |

| MW | example | MS | Rf (TLC) [min.] | Rt (HPLC) [min.] (%) | m.p. [° C.] | method |
|---|---|---|---|---|---|---|
| 615.67 | 4.105 | 616 | 0.22 D | | >240 | 4 |
| 553.62 | 4.106 | 554 | 0.22 D | | >240 | 4 |
| 568.70 | 18.4 | 569 | 0.20 C | | >240 | 18 |

-continued
| structure | MW | example | MS | Rf (TLC) [min.] | Rt (HPLC) [min.] (%) | m.p. [° C.] | method |
|---|---|---|---|---|---|---|---|
| 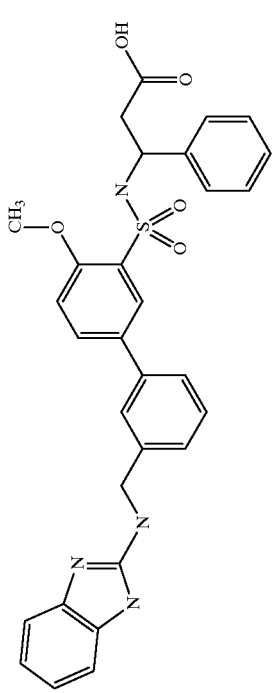 | 556.65 | 18.5 | 557 | 0.20 E | | >240 | 18 |
| 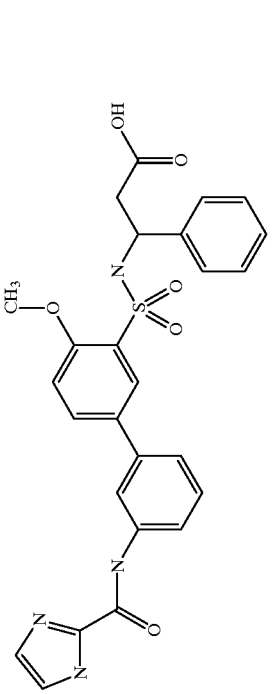 | 520.57 | 19.5 | 521 | 0.10 B | | >200 | 19 |
| 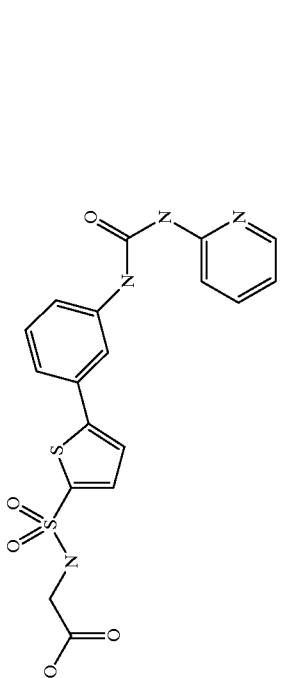 | 432.48 | 4.107 | 433 | | 6.2 | | 4 |

| structure | MW | example | MS | Rf (TLC) [min.] | Rt (HPLC) [min.] (%) | m.p. [° C.] | method |
|---|---|---|---|---|---|---|---|
| (structure) | 432.48 | 4.108 | 433 | | 5.4 | | 4 |
| (structure) | 446.51 | 4.109 | 447 | | 5.1 | | 4 |
| (structure) | 432.48 | 4.110 | 433 | | 5.6 | | 4 |

-continued

| structure | MW | example | MS | Rf (TLC) [min.] | Rt (HPLC) [min.] (%) | m.p. [° C.] | method |
|---|---|---|---|---|---|---|---|
| 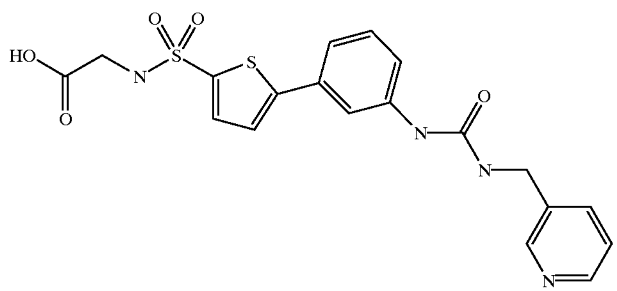 | 446.51 | 4.111 | 447 | | 5.1 | | 4 |
| 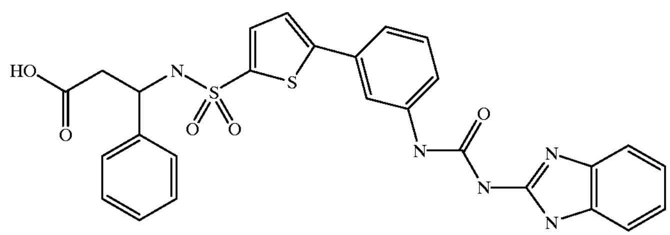 | 561.64 | 4.112 | 562 | | 8.3 | | 4 |
| 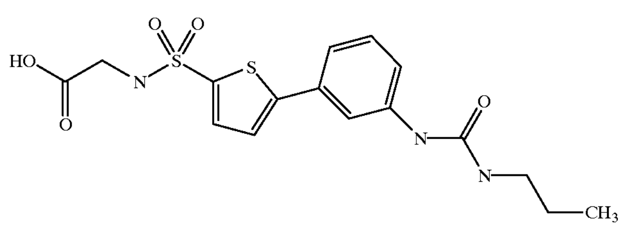 | 397.47 | 4.113 | 398 | | 7.4 | | 4 |

-continued

| structure | MW | example | MS | Rf (TLC) [min.] | Rt (HPLC) [min.] (%) | m.p. [° C.] | method |
|---|---|---|---|---|---|---|---|
| | 536.63 | 4.114 | 537 | | 6.5 | | 4 |
| | 536.63 | 4.115 | 537 | | 6.6 | | 4 |
| 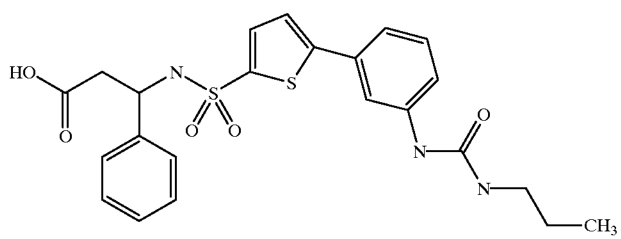 | 487.60 | 4.116 | 488 | | 9.0 | | 4 |

| structure | MW | example | MS | Rf (TLC) [min.] | Rt (HPLC) [min.] (%) | m.p. [° C.] | method |
|---|---|---|---|---|---|---|---|
| 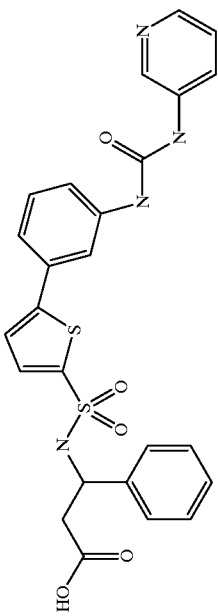 | 522.61 | 4.117 | 523 | | 6.9 | | 4 |
| 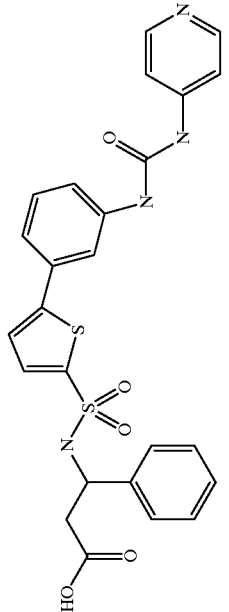 | 522.61 | 4.118 | 523 | | 7.0 | | 4 |
| 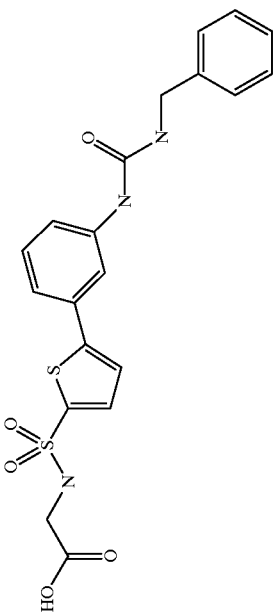 | 445.52 | 4.119 | 446 | | 8.5 | | 4 |
| 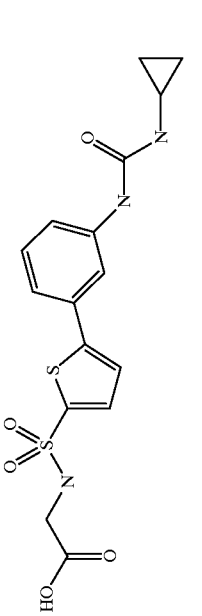 | 395.46 | 4.120 | 396 | | 7.8 | | 4 |

-continued

| structure | MW | example | MS | Rf (TLC) [min.] | Rt (HPLC) [min.] (%) | m.p. [° C.] | method |
|---|---|---|---|---|---|---|---|
| 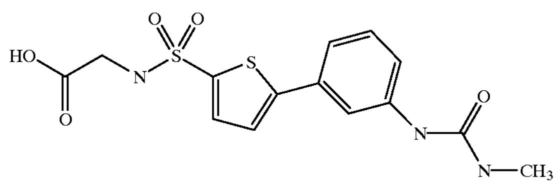 | 369.42 | 4.121 | 370 | | 6.1 | | 4 |
| 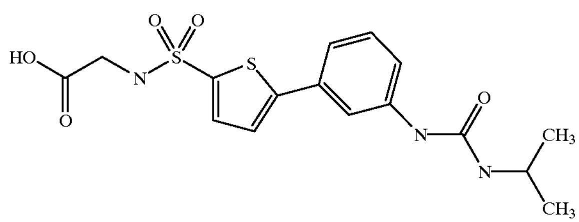 | 397.47 | 4.122 | 398 | | 7.5 | | 4 |
| 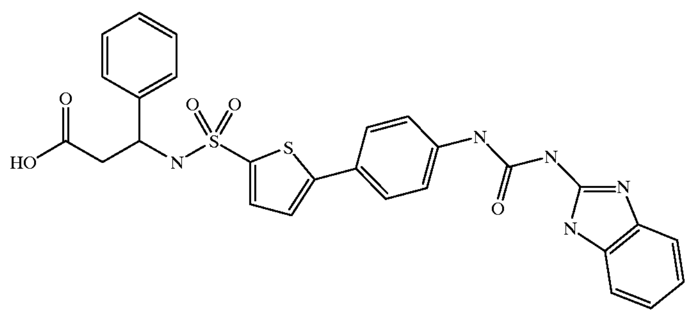 | 561.64 | 4.123 | 562 | | 8.3 | | 4 |

| MW | example | MS | Rf (TLC) [min.] | Rt (HPLC) [min.] (%) | m.p. [° C.] | method |
|---|---|---|---|---|---|---|
| 575.67 | 4.124 | 576 | | 8.4 | | 4 |
| 522.61 | 4.125 | 523 | | 7.7 | | 4 |
| 535.65 | 4.126 | 536 | | 9.5 | | 4 |

-continued

| structure | MW | example | MS | Rf (TLC) [min.] | Rt (HPLC) [min.] (%) | m.p. [° C.] | method |
|---|---|---|---|---|---|---|---|
| | 536.63 | 4.127 | 537 | | 6.2 | | 4 |
| 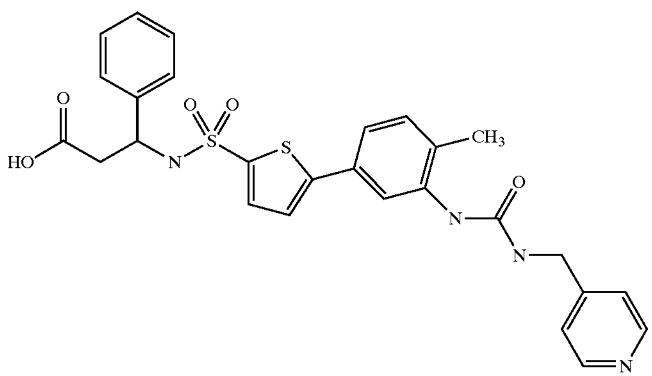 | 550.66 | 4.128 | 551 | | 6.7 | | 4 |
| | 536.63 | 4.129 | 537 | | 6.6 | | 4 |

-continued

| structure | MW | example | MS | Rf (TLC) [min.] | Rt (HPLC) [min.] (%) | m.p. [° C.] | method |
|---|---|---|---|---|---|---|---|
| | 487.60 | 4.130 | 488 | | 7.1 | | 4 |
| | 487.60 | 4.131 | 488 | | 8.7 | | 4 |
| 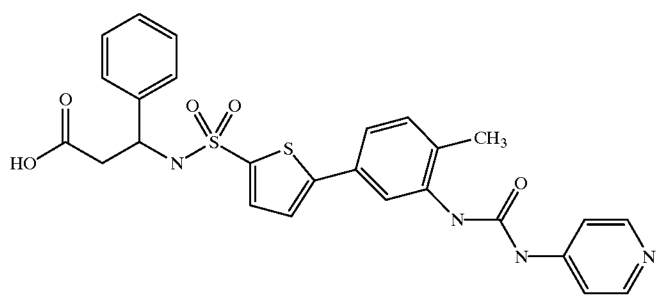 | 536.63 | 4.132 | 537 | | 6.6 | | 4 |

-continued

| structure | MW | example | MS | Rf (TLC) [min.] | Rt (HPLC) [min.] (%) | m.p. [° C.] | method |
|---|---|---|---|---|---|---|---|
| 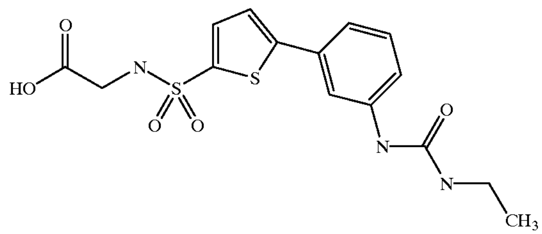 | 383.45 | 4.133 | 384 | | 6.8 | | 4 |
| 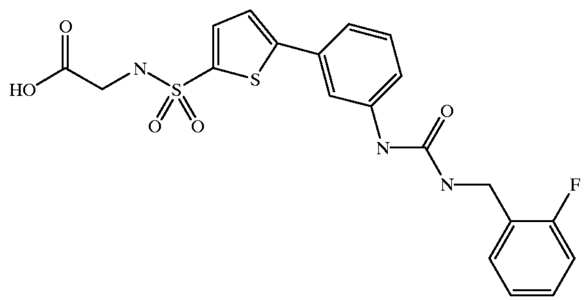 | 463.51 | 4.134 | 464 | | 8.7 | | 4 |
| 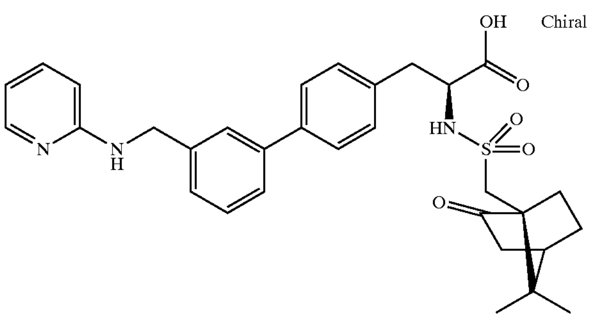 | 561.71 | 18.6 | 562 | 0.13 C | | | 18 |

-continued

| structure | MW | example | MS | Rf (TLC) [min.] | Rt (HPLC) [min.] (%) | m.p. [° C.] | method |
|---|---|---|---|---|---|---|---|
| (structure) | 439.537 | 18.7 | 440 | 0.04 C | | >240 | 18 |
| (structure) | 505.572 | 18.8 | 506 | 0.08 C | | >240 | 18 |
| (structure) | 493.608 | 18.9 | 494 | 0.05 C | | >240 | 18 |

-continued
| structure | MW | example | MS | Rf (TLC) [min.] | Rt (HPLC) [min.] (%) | m.p. [° C.] | method |
|---|---|---|---|---|---|---|---|
| 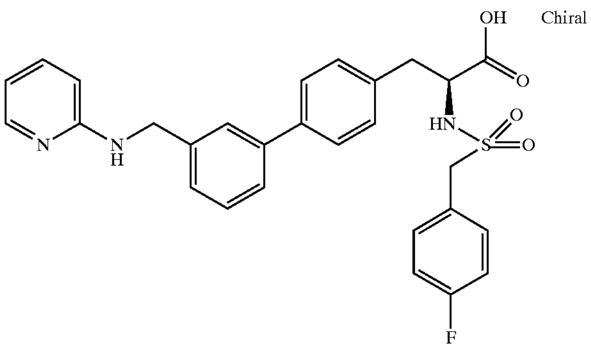 | 519.6 | 18.10 | 520 | 0.06 C | | >240 | 18 |
| 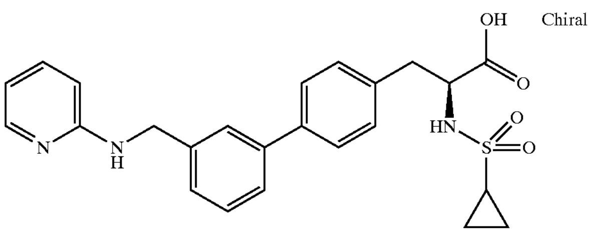 | 451.549 | 18.11 | 452 | 0.02 C | | >240 | 18 |
| 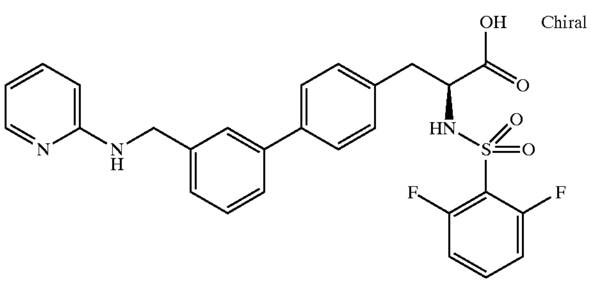 | 523.563 | 18.12 | 524 | 0.08 C | | >240 | 18 |

-continued
| structure | MW | example | MS | Rf (TLC) [min.] | Rt (HPLC) [min.] (%) | m.p. [° C.] | method |
|---|---|---|---|---|---|---|---|
| 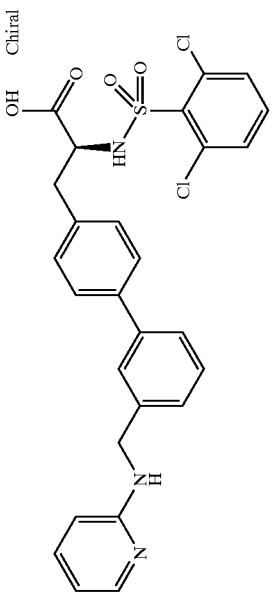 | 556.472 | 18.13 | 557 | 0.1 C | | >240 | 18 |
| 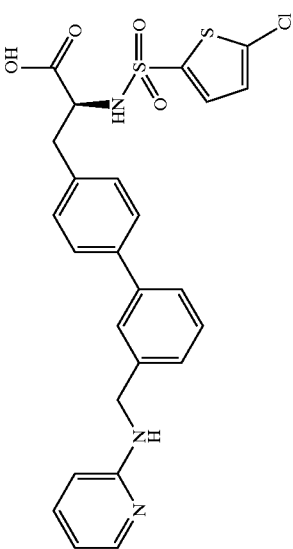 | 528.053 | 18.14 | 529 | 0.12 C | | >240 | 18 |
| 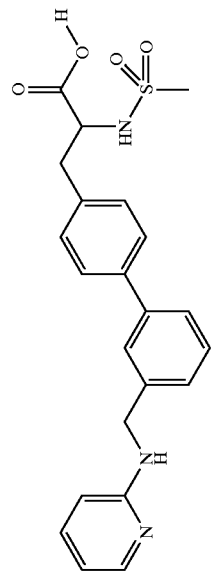 | | 18.15 | | | | | 18 |

-continued

| structure | MW | example | MS | Rf (TLC) [min.] | Rt (HPLC) [min.] (%) | m.p. [° C.] | method |
|---|---|---|---|---|---|---|---|
| | | 18.16 | | | | | 18 |
| | | 18.17 | | | | | 18 |
| | | 18.18 | | | | | 18 |

-continued

| structure | MW | example | MS | Rf (TLC) [min.] | Rt (HPLC) [min.] (%) | m.p. [° C.] | method |
|---|---|---|---|---|---|---|---|
| | | 18.19 | | | | | 18 |
| | | 18.20 | | | | | 18 |
| | | 18.21 | | | | | 18 |

-continued

| structure | MW | example | MS | Rf (TLC) [min.] | Rt (HPLC) [min.] (%) | m.p. [° C.] | method |
|---|---|---|---|---|---|---|---|
| | | 18.22 | | | | | 18 |
| | | 18.23 | | | | | 18 |
| | | 18.24 | | | | | 18 |

-continued

| structure | MW | example | MS | Rf (TLC) [min.] | Rt (HPLC) [min.] (%) | m.p. [° C.] | method |
|---|---|---|---|---|---|---|---|
| | | 18.25 | | | | | 18 |
| 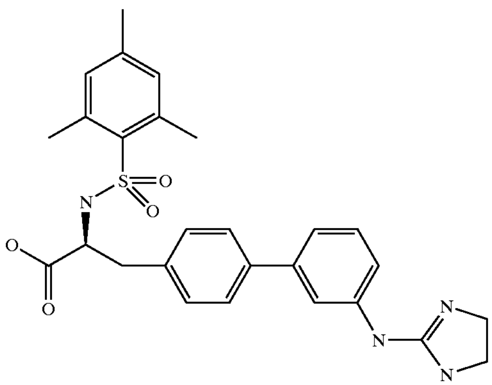 | 506.63 | 7.2 | 507 | | 8.0 | | 7 |

TLC methods:
A: dichloromethane/methanol 10:2
B: dichloromethane/methanol 10:1
C: acetic acid ethyl ester/methanol 4:1
D: acetic acid ethyl ester/methanol 3:1
E: acetic acid ethyl ester/methanol 2:1
F: acetic acid ethyl ester/methanol 1:1
G: dichloromethane/methanol 10 + 1
H: dichloromethane/methanol 4 + 1
dec. = decomposition Biological Investigations a) Binding to the $\alpha_v\beta_3$ Receptor $\alpha_v\beta_3$ from human A375 cells were purified according to a procedure described by Wong et al. (Molecular Pharmacology, 50, 529–537, 1996). 10 µl $\alpha_v\beta_3$ (5 ng) in TBS pH 7.6, 2 mM $CaCl_2$, 1 mM $MgCl_2$, 1% n/octylglucopyranoside; 10 µl of the substance to be tested in TBS pH 7.6, 0.1% dimethylsulfoxide (DMSO), and 45 µl TBS pH 7.6, 2 mM $CaCl_2$, 1 mM $MgCl_2$, 1 mM $MnCl_2$ were each incubated for 1 h at room temperature. Subsequently 25 µl WGA SPA beads (Amersham, 4 mg/ml) and 10 µl echistatin (0.1 µCi, Amersahm, marked with chloroamine-T per well were added. After 16 h at room temperature the probes were measured with the aid of a scintillation measurement device (Wallac 1450). The test results of a selection of compounds are shown in Table 1 below.

b) Smooth Muscle Cell (SMC) Migration Test

Smooth muscle cells from humans or rats were used. The migration of the cells was determined in a horizontal measuring arrangement (Falcon).

The horizontal migration was determined in 6-well plates coated with vitronectin (1 µg/cm²). The cells were suspended in a medium (DMEM:F12/0, 12% BSA-rat smooth muscle cells or MCDB 131 with 0.2% BSA-human smooth muscle cells), inoculated and allowed to grow to confluence. Half of the smooth muscle cell lawn was then scraped off, and the cells were treated with different concentrations of the test compounds. The mixtures were incubated for 24 hours at 37° C. in the presence of 5% $CO_2$ After the incubation, the smooth muscle cell migration was determined by measurement of the migration distance and the cell density of the migrated cells. The test results of a selection of compounds are shown in Table 1 below.

b) Rat Carotid Balloon Injury Model

The right common carotid and external carotid artery of anaesthetized male Wistar rats are surgically exposed. After arteriotomy a 2F Fogarty embolectomy catheter is introduced via the external carotid into the common carotid artery and advanced to the aortic arch. The balloon is inflated with physiologic saline and withdrawn with gentle resistance to remove the endothelium. After repeating this procedure three times, the balloon catheter is removed, the external carotid artery is ligated, blood flow in the common carotid artery is restored, and the neck wound is surgically closed. Animals are allowed to recover until sacrifice which is usually 14 days after injury. During this period animals are treated with test compounds orally, subcutaneously or intraperitoneally as single injections or as intraperitoneal infusion via osmotic minipumps. At sacrifice the injured vessels are excised and histologically processed for morphometric evaluation of lumen, neointima and media. The primary parameter is the cross-sectional neointimal area. (Lit.: C. Gerdes, V. Faber-Steinfeld, Ö. Yalkinoglu, S. Wohlfeil, Arteriosclerosis, Thrombosis, and Vascular Biology Vol 16, No 10, 1996, 1306–1311). The tests results of a selection of compounds are shown in Table 1 below.

TABLE 1

| Example | avb3 IC$_{50}$ | SMC IC$_{50}$ |
|---|---|---|
| 1.5 | 5 nM | 480 nM |
| 1.13 | 1.2 nM | 390 nM |
| 4.1 | 33 nM | 300 nM |
| 7.1 | 1.2 nM | |
| 8.1 | 48 nM | 300 nM |
| 1.73 | 2 nM | 3–40 nM |

TABLE 1-continued

| Example | avb3 IC$_{50}$ | SMC IC$_{50}$ |
|---|---|---|
| 18.1.3 | 9 nM | 35–80 nM |
| 19.1.2 | 1 nM | 80 nM |

Although the invention has been described and illustrated above with reference to certain embodiments and examples presently regarded as preferred, it is obvious to the person skilled in the art that numerous alterations, modifications and substitutions can be performed without departing from the spirit and scope of the present invention.

What is claimed is:

1. A compound of the formula (I):

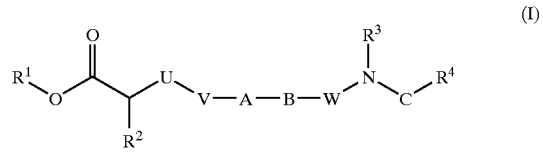

wherein $R^1$ is hydrogen, a substituted or unsubstituted alkyl or cycloalkyl residue, a substituted or unsubstituted aryl residue or a saturated or unsaturated, optionally substituted heterocyclic residue;

$R^2$ is a substituted or unsubstituted alkyl or cycloalkyl residue, a substituted or unsubstituted aryl residue or a saturated or unsaturated, optionally substituted heterocyclic residue, an optionally substituted alkenyl residue, an optionally substituted alkinyl residue, —NR$^{2'}$SO$_2$R$^{2''}$, —NR$^{2'}$COOR$^{2'}$, —NR$^{2'}$CONR$^{2'}_2$, or —NR$^{2'}$CSNR$^{2'}_2$;

$R^{2'}$ is hydrogen, a substituted or unsubstituted alkyl or cycloalkyl residue, a substituted or unsubstituted aryl residue or a saturated or unsaturated, optionally substituted heterocyclic residue;

$R^{2''}$ is hydrogen, a substituted or unsubstituted alkyl, alkenyl or cycloalkyl residue, a substituted or unsubstituted aryl residue or a saturated or unsaturated, optionally substituted heterocyclic residue;

U is a direct bond or a substituted or unsubstituted alkylene group;

V is a substituted or unsubstituted alkylene group;

A and B are each independently of one another a 1,3- or 1,4-bridging phenylene group each of which may optionally have additional substituents;

W is a direct bond or a substituted or unsubstituted alkylene group;

C is a direct bond or

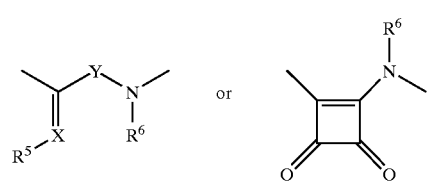

$R^3$ is hydrogen, a substituted or unsubstituted alkyl or cycloalkyl residue, a substituted or unsubstituted aryl residue or a saturated or unsaturated, optionally substituted heterocyclic residue, an alkylamine residue, an alkylamide residue or is connected to one of $R^4$, Y, $R^5$ or $R^6$, if present, with formation of an optionally substituted heterocyclic ring system which includes the nitrogen atom to which $R^3$ is bonded, and can be saturated or unsaturated and/or can contain further heteroatoms;

$R^4$ is hydrogen, a substituted or unsubstituted alkyl or cycloalkyl residue, a substituted or unsubstituted aryl residue or a saturated or unsaturated, optionally substituted heterocyclic residue, an alkylamine residue, an alkylamide residue or is connected to one of $R^3$, Y, $R^5$ or $R^6$, if present, with formation of an optionally substituted heterocyclic ring system which includes the nitrogen atom to which $R^4$ is bonded, and can be saturated or unsaturated and/or can contain further heteroatoms;

X is $CHNO_2$, CHCN, O, N or S;

Y is a direct bond or an optionally substituted alkylene or alkine group;

$R^5$ is absent, or is hydrogen, a substituted or unsubstituted alkyl or cycloalkyl residue, $-NO_2$, $-CN$, $-COR^{5'}$, $-COOR^{5'}$, or is connected to one of $R^3$, Y, $R^4$ or $R^6$, if present, with formation of an optionally substituted carbocyclic or heterocyclic ring system which includes X and can be saturated or unsaturated and/or can contain further heteroatoms;

$R^{5'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

$R^6$ is hydrogen, a substituted or unsubstituted alkyl or cycloalkyl residue, a substituted or unsubstituted aryl residue or arylcarbonyl residue, a saturated or unsaturated, optionally substituted heterocyclic residue, an alkylamine residue, an alkylamide residue or is connected to one of $R^3$, $R^4$, Y or $R^5$, if present, with formation of an optionally substituted heterocyclic ring system which includes the nitrogen atom to which $R^6$ is bonded, and can be saturated or unsaturated and/or can contain further heteroatoms;

with the proviso that if A is a phenylene group and V is $-NR^{2'}CO-$ or $-NR^{2'}SO_2-$, C is not a direct bond and X is not N;

or a physiologically acceptable salt and/or stereoisomer thereof; or wherein $R^1$ is hydrogen, a substituted or unsubstituted alkyl or cycloalkyl residue, a substituted or unsubstituted aryl residue or a saturated or unsaturated, optionally substituted heterocyclic residue;

$R^2$ is hydrogen, a substituted or unsubstituted alkyl or cycloalkyl residue, a substituted or unsubstituted aryl residue or a saturated or unsaturated, optionally substituted heterocyclic residue, an optionally substituted alkenyl residue, an optionally substituted alkinyl residue, $-NR^{2'}SO_2R^{2''}$, $-NR^{2'}COOR^{2'}$, $-NR^{2'}CONR^{2'}_2$, or $-NR^{2'}CSNR^{2'}_2$;

$R^{2'}$ is hydrogen, a substituted or unsubstituted alkyl or cycloalkyl residue, a substituted or unsubstituted aryl residue or a saturated or unsaturated, optionally substituted heterocyclic residue;

$R^{2''}$ is hydrogen, a substituted or unsubstituted alkyl, alkenyl or cycloalkyl residue, a substituted or unsubstituted aryl residue or a saturated or unsaturated, optionally substituted heterocyclic residue;

U is a direct bond or a substituted or unsubstituted alkylene group:

V is a $-NR2'CO-$ or $-NR2'SO2-$;

A and B are each independently of one another a 1,3- or 1,4-bridging phenylene group each of which may optionally have additional substituents;

W is a direct bond or a substituted or unsubstituted alkylene group;

C is a direct bond or

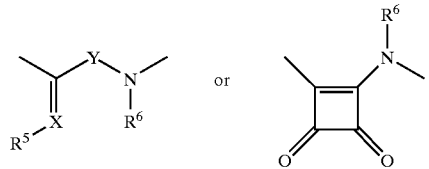

$R^3$ is hydrogen, a substituted or unsubstituted alkyl or cycloalkyl residue, a substituted or unsubstituted aryl residue or a saturated or unsaturated, optionally substituted heterocyclic residue, an alkylamine residue, an alkylamide residue or is connected to one of $R^4$, Y, $R^5$ or $R^6$, if present, with formation of an optionally substituted heterocyclic ring system which includes the nitrogen atom to which $R^3$ is bonded, and can be saturated or unsaturated and/or can contain further heteroatoms;

$R^4$ is hydrogen, a substituted or unsubstituted alkyl or cycloalkyl residue, a substituted or unsubstituted aryl residue or a saturated or unsaturated, optionally substituted heterocyclic residue, an alkylamine residue, an alkylamide residue or is connected to one of $R^3$, Y, $R^5$ or $R^6$, if present, with formation of an optionally substituted heterocyclic ring system which includes the nitrogen atom to which $R^4$ is bonded, and can be saturated or unsaturated and/or can contain further heteroatoms;

X is $CHNO_2$, CHCN, O, N or S;

Y is a direct bond or an optionally substituted alkylene or alkine group;

$R^5$ is absent, or is hydrogen, a substituted or unsubstituted alkyl or cycloalkyl residue, $-NO_2$, $-CN$, $-COR^{5'}$, $-COOR^{5'}$, or is connected to one of $R^3$, Y, $R^4$ $R^6$, if present, with formation of an optionally substituted carbocyclic or heterocyclic ring system which includes X and can be saturated or unsaturated and/or can contain further heteroatoms;

$R^{5'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

$R^6$ is hydrogen, a substituted or unsubstituted alkyl or cycloalkyl residue, a substituted or unsubstituted aryl residue or arylcarbonyl residue, a saturated or unsaturated, optionally substituted heterocyclic residue, an alkylamine residue, an alkylamide residue or is connected to one of $R^3$, $R^4$, Y or $R^5$, if present, with formation of an optionally substituted heterocyclic ring system which includes the nitrogen atom to which $R^6$ is bonded, and can be saturated or unsaturated and/or can contain further heteroatoms;

with the proviso that if A is a phenylene group and V is $-NR^{2'}CO-$ or $-NR^{2'}SO_2-$, C is not a direct bond and X is not N;

or a physiologically acceptable salt and/or stereoisomer thereof.

2. A compound as claimed in claim 1, wherein

R¹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, or tolyl;

R² is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, an optionally substituted alkinyl residue, $-NR^{2'}SO_2R^{2''}$, $-NR^{2'}COOR^{2'}$, $-NR^{2'}COR^{2'}$, $-NR^{2'}CONR^{2'}{}_2$ or $-NR^{2'}CSNR^{2'}{}_2$;

R²' is hydrogen, methyl, ethyl, propyl, isopropyl, butyl, isobutyl, t-butyl, pentyl, isopentyl, neopentyl, hexyl, cyclopropyl, cyclobutyl, cyclpentyl, cyclohexyl, phenyl, benzyl, tolyl, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, or 4-trifluoromethyl phenyl;

R²'' is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl, 4-ethylphenyl, $-C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluoro-phenyl, 2-trifluoromethoxy-4-bromo-phenyl, 2-fluoro-4-trifluoromethylphenyl, 8-quinolinyl or a group of the formula

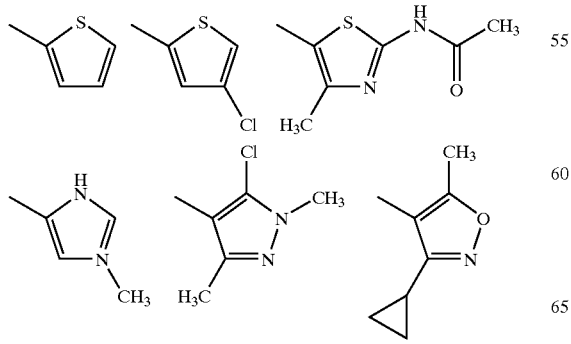

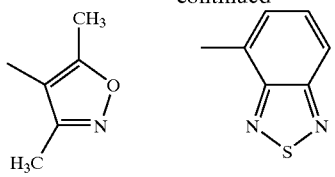

U is a direct bond,

V is an optionally substituted $C_{1-5}$-alkylene group;

A is a 1,3- or 1,4-bridging phenylene group which is unsubstituted or carries at least one alkoxy or halogeno residue;

B is a 1,3- or 1,4-bridging phenylene group which is unsubstituted or carries at least one alkyl residue;

W is a direct bond or an optionally substituted $C_{1-4}$-alkylene group;

C is a direct bond or

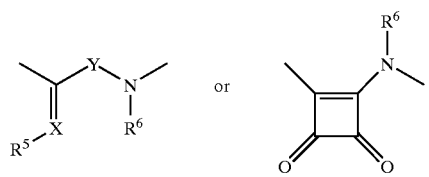

R³ is hydrogen, methyl, ethyl, propyl, isopropyl, butyl, 1-methylpropyl, isobutyl, t-butyl, pentyl, 2-methylbutyl, isopentyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl,

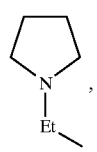  (a1)

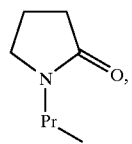  (a2)

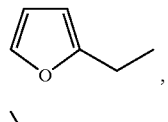  (a3)

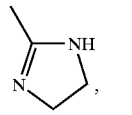  (a4)

461
-continued
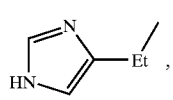 (a5)
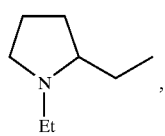 (a6)
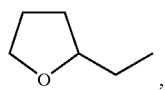 (a7)
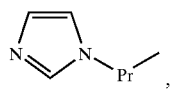 (a8)
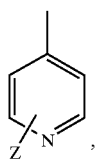 (a9)
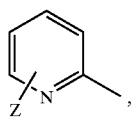 (a10)
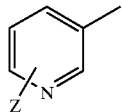 (a11)
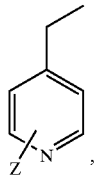 (a12)
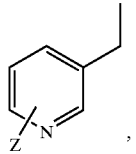 (a13)
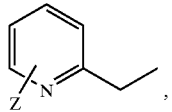 (a14)
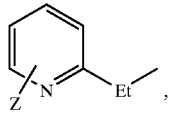 (a15)
462
-continued
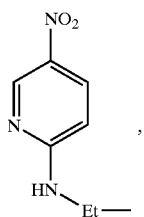 (a16)
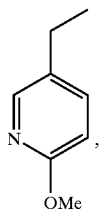 (a17)
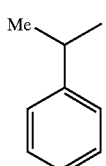 (a18)
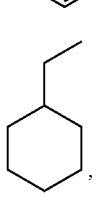 (a19)
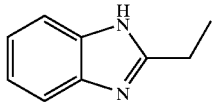 (a20)
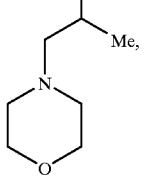 (a21)
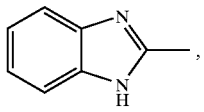 (a22)
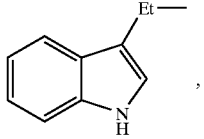 (a23)
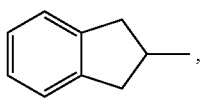 (a24)

-continued
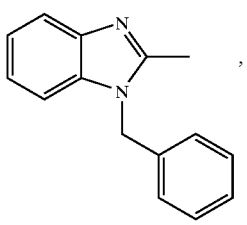
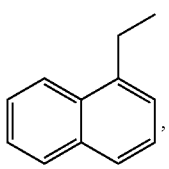
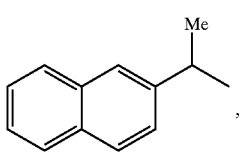
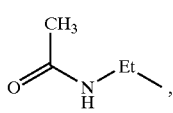
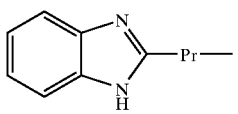
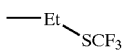
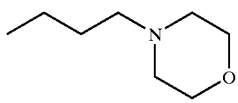
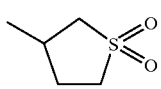
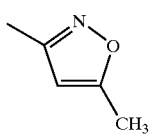
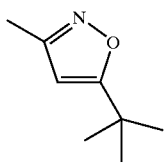
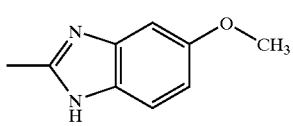
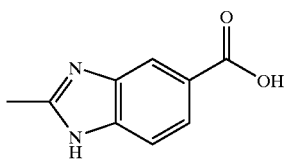
-continued
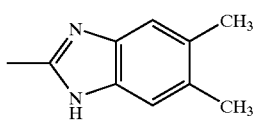 (a37)
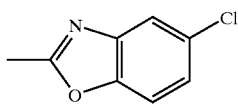 (a38)
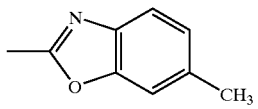 (a39)
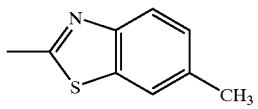 (a40)
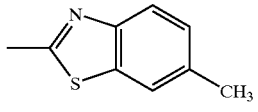 (a41)
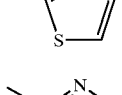 (a42)
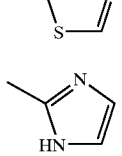 (a43)
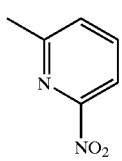 (a44)
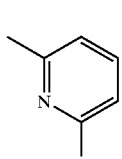 (a45)
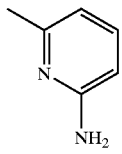 (a46)
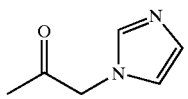 (a47)
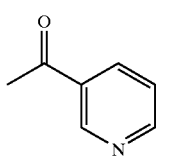 (a48)

(a49)

(a50)

(a51)

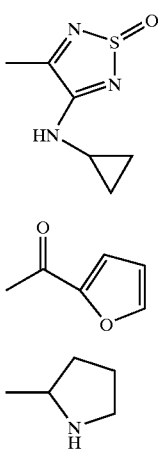

wherein

Z is hydrogen, —NO₂ or —NH₂, or

R³ is connected to one of R⁴, Y, R⁵ or R⁶, if present, with formation of an optionally substituted heterocyclic 4- to 6-membered ring system which includes the nitrogen atom to which R³ bonded and can be saturated or unsaturated and/or can contain further heteroatoms;

R⁴ is hydrogen, methyl, ethyl, propyl, isopropyl, butyl, 1-methyl-propyl, isobutyl, t-butyl, pentyl, 2-methyl-butyl, isopentyl, neopentyl, hexyl, C$_{1-4}$-perfluoralkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, C$_{1-4}$-alkylamino-C$_{1-4}$-alkyl, C$_{1-4}$-dialkylamino-C$_{1-4}$-alkyl, amino-C$_{1-4}$-alkyl, C$_{1-4}$-alkyloxy-C$_{1-4}$-alkyl, C$_{1-2}$-perfluoralkyl-C$_{1-4}$-alkyl, one of the residues (a1) to (a51) or is connected to one of R³, Y, R⁵ or R⁶, if present, with formation of an optionally substituted heterocyclic 4- to 6-membered ring system which includes the nitrogen atom to which R⁴ bonded and can be saturated or unsaturated and/or can contain further heteroatoms;

X is CHNO₂, CHCN, O, N or S;

Y is a direct bond or a substituted or unsubstituted methylene or methine group;

R⁵ is absent, or is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, —NO₂, —CN, —COR⁵', —COOR⁵' or is connected to one of R³, Y, R⁴ or R⁶, if present, with formation of an optionally substituted carbocyclic or heterocyclic 4- to 6-membered ring system which includes X and can be saturated or unsaturated and/or can contain further heteroatoms;

R⁵' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl;

R⁶ is hydrogen, methyl, ethyl, propyl, isopropyl, butyl, 1-methylpropyl, isobutyl, t-butyl, pentyl, isopentyl, 2-methylbutyl, neopentyl, hexyl, C$_{1-4}$-perfluoralkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, C$_{1-4}$-alkylamino-C$_{1-4}$-alkyl, C$_{1-4}$-dialkylamino-C$_{1-4}$-alkyl, amino-C$_{1-4}$-alkyl, C$_{1-4}$-alkyloxy-C$_{1-4}$-alkyl, C$_{1-2}$-perfluoroalkyl-C$_{1-4}$-alkyl, one of the residues (a1) to (a51) or is connected to one of R³, Y, R⁴ or R⁵, if present, with formation of an optionally substituted heterocyclic 4- to 6-membered ring system which includes the nitrogen atom to which R⁶ is bonded and can be saturated or unsaturated and/or can contain further heteroatoms.

3. A compound as claimed in claim 2, wherein

R² is —NR²'SO₂R²'', —NR²'COOR²', —NR²'COR²', —NR²'CONR²'₂ or —NR²'CSNR²'₂;

R²' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, or 4-trifluoromethyl phenyl;

R²'' is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl, 4-ethylphenyl, —C₆H₂(CH₃)₃, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluoro-phenyl, 2-trifluoromethoxy-4-bromo-phenyl, 2-fluoro-4-trifluoromethylphenyl, 8-quinolinyl or a group of the formula

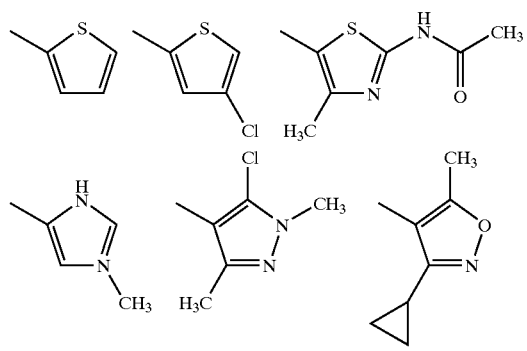

467

-continued

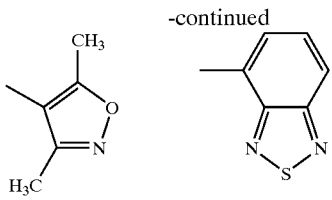

and the other substituents are as defined in claim 2.

4. A compound as claimed in claim 2, wherein, $R^2$ is —$NR^{2'}SO_2R^{2''}$ or —$NR^{2'}COOR^{2'}$;

$R^{2'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, or 4-trifluoromethyl phenyl;

$R^{2''}$ is methyl, ethyl, propyl, isopropyl, butyl, isobutyl, t-butyl, pentyl, isopentyl, neopentyl, hexyl, 1,1,1-trifluorobutyl, allyl, cyclopropyl, cyclobutyl, cyclopentyl, cyclohexyl, phenyl, benzyl, tolyl, 4-ethylphenyl, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,4-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilin-o, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, 4-chloro-2-trifluorphenyl, 2-trifluoromethoxy-4-bromo-phenyl, 2-fluoro-4-trifluoromethylphenyl, 8-quinolinyl, a group of the formula

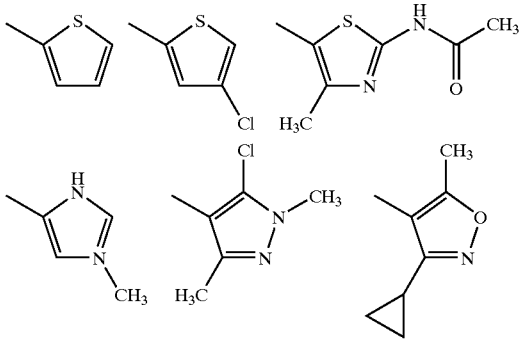

468

-continued

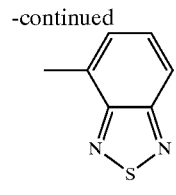

A is a 1,3- or 1,4-bridging phenylene group optionally substituted with a methoxy or up to 2 fluororesidues;

B is an optionally methyl-substituted 1,3- or 1,4-bridging phenylene group;

C is a direct bond or

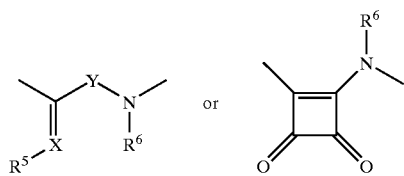

$R^5$ is absent, —$NO_2$, —CN, or is connected to one of $R^3$, Y, $R^4$ or $R^6$, if present, with formation of an optionally substituted carbocyclic or heterocyclic 4- to 6-membered ring system which includes X and can be saturated or unsaturated and/or can contain further heteroatoms;

and the other substituents are as defined in claim 2.

5. A compound as claimed in claim 2, wherein $R^2$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl residue, an optionally substituted alkinyl residue, U is a direct bond, V is —$CHR^7$— or —$CHR^7(CH_2)_{1-4}$;

$R^7$ is —$NR^{7'}SO_2R^{7''}$, —$NR^{7'}COOR^{7'}$, —$NR^{7'}COR^{7'}$, —$NR^{7'}CONR^{7'}_2$ or —$NR^{7'}CSNR^{7'}_2$;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, or 4-trifluoromethyl phenyl;

$R^{7''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butylphenyl, 2,5-dimethylphenyl, 2,6-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N- acetyl-6-methoxy)anilin-o, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, and the other substituents are as defined in claim 2.

6. A compound as claimed in claim 2, wherein $R^2$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, or an optionally substituted alkinyl residue, U is a direct bond;

V is —$CHR^7$—;

$R^7$ is —$NR^{7'}SO_2R^{7''}$ or —$NR^{7'}COOR^{7'}$;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, 2-chlorophenyl, 2-methoxyphenyl, 2,4,6-trimethylphenyl, 4-methoxyphenyl, 4-t-butylphenyl, 2,5-dichlorophenyl, 3-chlorophenyl, 4-chlorophenyl, or 4-trifluoromethyl phenyl;

$R^{7''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, —$C_6H_2(CH_3)_3$, 2-chlorophenyl, 4-chlorophenyl, 2,5-dichlorophenyl, 4-trifluoromethylphenyl, campher-10-yl, 4-methoxyphenyl, 4-t-butyphenyl, 2,5-dimethylphenyl, 2,6-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulfonylphenyl, 2-arylsulfonylphenyl, 3-(N-acetyl-6-methoxy)anilino, 2-methoxycarbonylphenyl, 4-N-acetylphenyl, 4-ethylphenyl, 3-chloro-4-fluorphenyl, 2-fluorophenyl, 3-fluorophenyl, 2,4-difluorophenyl, 2,6-difluorophenyl, 3,4-difluorophenyl, 1-naphthyl, 4-trifluoromethoxyphenyl, 2-trifluoromethoxyphenyl, or 8-quinolinyl, A is a 1,3- or 1,4-bridging phenylene group optionally substituted with a methoxy or up to 2 fluoro residnes;

B is an optionally methyl-substituted 1,3- or 1,4-bridging phenylene group;

C is a direct bond or

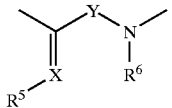

W is direct bond or a —$CH_2$-group

X is O or S

Y is a direct bond $R^5$ is absent and the other substituents are as defined in claim 2.

7. A compound as claimed in claim 2, wherein $R^2$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, an optionally substituted alkinyl residue, U is a direct bond, V is a $C_{1-5}$-alkylene group which is optionally substituted by one or more residues $R^7$ which are selected from the group consisting of hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, or a saturated or unsaturated, optionally substituted heterocyclic analog thereof, an optionally substituted alkenyl residue or an optionally substituted alkinyl residue;

and the other substituents are as defined in claim 2.

8. A compound as claimed in claim 2, wherein $R^2$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, an optionally substituted alkinyl residue, U is a direct bond, V is —$CHR^7$—;

$R^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, an optionally substituted alkinyl residue, A is a 1,3- or 1,4-bridging phenylene group optionally substituted with a methoxy or up to 2 fluoro residues B is an optionally methyl-substituted 1,3- or 1,4-bridging phenylene group;

C is a direct bond or

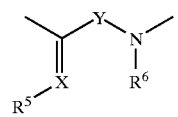

W is a direct bond or a —$CH_2$-group

X is O or S;

Y is a direct bond $R^5$ is absent and the other substituents are as defined in claim 2.

9. A compound as claimed in claim 1, wherein $R^1$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, or tolyl;

$R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, phenylethyl, or a saturated or unsaturated, optionally substituted heterocyclic analog thereof, an optionally substituted alkenyl residue, an optionally substituted alkinyl residue;

U is a direct bond or an optionally substituted $C_{1-3}$-alkylene group;

V is —$NR^8CO$— or —$NR^8SO_2$—;

$R^8$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl, phenylethyl, phenylpropyl, or phenoxyethyl;

A is a 1,3- or 1,4-bridging phenylene group or a 2,4- or 2,5-bridging thienylene group which are unsubstituted or have at least one alkoxy or halogeno residue;

B is a 1,3- or 1,4-bridging phenylene group which is unsubstituted or has at least one alkyl residue;

W is a direct bond or an optionally substituted $C_{1-3}$-alkylene group;

C is

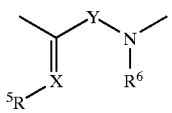

$R^3$ is hydrogen, methyl, ethyl, propyl, isopropyl, butyl, 1-methylpropyl, isobutyl, t-butyl, pentyl, 2-methylbutyl, isopentyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl, one of the residues (a1) to (a51) or is connected to one of $R^4$, Y or $R^6$, if present, with formation of an optionally substituted heterocyclic 4- to 6-membered ring system which includes the nitrogen atom to which $R^3$ is bonded and can be saturated or unsaturated and/or can contain further heteroatoms;

$R^4$ is hydrogen, methyl, ethyl, propyl, isopropyl, butyl, 1-methyl-propyl, isobutyl, t-butyl, pentyl, 2-methyl-butyl, isopentyl, neopentyl, hexyl, $C_{1-4}$-perfluoralkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoralkyl-$C_{1-4}$-alkyl, one of the residues (a1) to (a51) or is connected to one of $R^3$, Y or $R^6$, if present, with formation of an optionally substituted heterocyclic 4- to 6-membered ring system which includes the nitrogen atom to which $R^4$ is bonded and can be saturated or unsaturated and/or can contain further heteroatoms;

X is $CHNO_2$, CHCN, O or S; Y is a direct bond or a substituted or unsubstituted methylene or methine group;

$R^5$ is absent;

$R^6$ is hydrogen, methyl, ethyl, propyl, isopropyl, butyl, 1-methylpropyl, isobutyl, t-butyl, pentyl, isopentyl, 2-methylbutyl, neopentyl, hexyl, $C_{1-4}$-perfluoroalkyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, allyl, propinyl, phenyl, benzyl, tolyl, benzoyl, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, $C_{1-2}$-perfluoroalkyl-$C_{1-4}$-alkyl, one of the residues (a1) to (a51) or is connected to one of $R^3$, Y, $R^4$, if present, with formation of an optionally substituted heterocyclic 4- to 6-membered ring system which includes the nitrogen atom to which R is bonded and can be saturated or unsaturated and/or can contain further heteroatoms.

10. A compound as claimed in claim 9,

U is a direct bond or —$CHR^7$—, $R^7$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl, an optionally substituted alkenyl residue, an optionally substituted alkinyl residue or pyridyl;

A is a 1,3- or 1,4-bridging phenylene group optionally substituted with a methoxy group or up to 2 fluoro residues;

B is an optionally methyl-substituted 1,3- or 1,4-bridging phenylene group;

W is a direct bond or a —$CH_2$-group;

C is

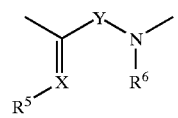

X is O or S

Y is a direct bond $R^5$ is absent and the other substituents are as defined in claim 9.

11. A pharmaceutical composition comprising at least one compound according to claim 1 and an inert, non-toxic, pharmaceutically acceptable excipient or solvent.

12. A method for inhibiting angiogenesis and/or for treating a disorder selected from the group consisting of osteolytic diseases, arteriosclerosis, restenosis after percutaneous transluminal angioplasty, rheumatoid arthritis and ophthalmia, said method comprising administering to said patient an effective amount therefor of at least one compound according to claim 1.

13. The method according to claim 12, which is for inhibiting angiogenesis.

14. The method according to claim 12, which is for treating osteolytic diseases.

15. The method according to claim 14, which is for treating osteoporosis.

16. The method according to claim 12, which is for treating arteriosclerosis.

17. The method according to claim 12, which is for treating restenosis after percutaneous transluminal angioplasty.

18. The method according to claim 12, which is for treating rheumatoid arthritis.

19. The method according to claim 12, which is for treating ophthalmia.

20. A process for the preparation of compounds as claimed in claim 1 having the general formula (1)

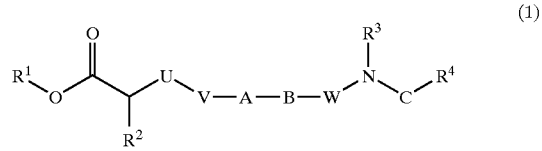

(1)

which comprises the steps a) reaction of a carboxylic acid derivative of the formula (2)

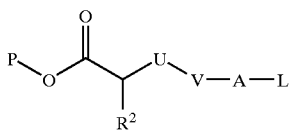
(2)

where
- P is a conventional protective group, a solid phase used for carrying out a solid-phase reaction or $R^1$ is as defined in claim 1;
- A is a phenylene group which is 1,3- or 1,4-substituted or a thienylene group which is 2,4- or 2,5-substituted with respect to V and L and optionally has additional residues;
- L is —H, —F, —Cl, —Br, —I, —SCN, —$N_2^+$ or an organometallic residue; and the other residues are as defined in claim 1;

with a phenyl compound of the formula (3)

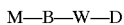
(3)

where
- M is —H, —I, —$N_2^+$, —COOCOBNO$_2$ or an organometallic residue;
- B is a phenylene group which is 1,3- or 1,4-substituted with respect to M and W—D and optionally has additional residues;
- W is as defined in claim 1;
- D is —NO$_2$, —NH$_2$ or —CHO;

to give a biphenyl or thienyl-phenyl compound of the formula (4)

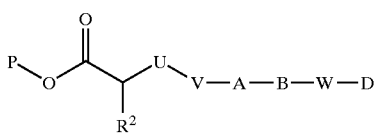
(4)

where the residues are as defined above;
b) conversion of the residue D into the corresponding amino group, if D is not —NH$_2$; and
c) if appropriate, derivatization of nitrogen atoms present at preferred times within the preparation process and/or the conversion of the compound obtained into the free acid and/or the conversion of the compound obtained into one of its physiologically acceptable salts by reaction with an inorganic or organic base or acid.

21. The process as claimed in claim 20, wherein all steps during the bonding of the carboxylic acid derivative of the formula (2) are carried out on a solid phase.

22. The process as claimed in claim 20, wherein
a carboxylic acid derivative of the formula (2), in which
L is —F, —Cl, —Br or —I
and the other residues are as defined in claim 20, is reacted with a phenyl compound of the formula (3), in which
M is an organometallic residue;
and the other residues are as defined in claim 20, in the presence of a palladium compound and of a phosphane.

23. The process as claimed in claim 20, wherein
the carboxylic acid derivative of the formula (2) contains a sulfonamide or carbamate group which was formed by reaction of an amino group of the corresponding precursor of the carboxylic acid derivative of the formula (2) with a sulfonyl halide or a carbamoyl halide.

24. The process as claimed in claim 20, wherein
if D is —NO$_2$ in the compound of the formula (4), the conversion of D into an amino group is carried out in the presence of a tin-(II) compound.

25. The process as claimed in claim 20, wherein
if D is —CHO in the compound of formula (4), the conversion of D into an amino group is carried out by reaction with an amine under reacting conditions.

26. The process as claimed in 20, wherein
the compound of formula (4) in which D is an amino group is converted into a urea or thiourea unit, where $R^4$ and $R^6$ are as defined in claim 20, by a reaction of this amino group with a carbonic acid derivative or thiocarbonic acid derivative and a subsequent reaction to this with an amine of the formula NHR$^4$R$^6$.

* * * * *

UNITED STATES PATENT AND TRADEMARK OFFICE
CERTIFICATE OF CORRECTION

PATENT NO. : 6,677,360 B2
DATED : January 13, 2004
INVENTOR(S) : Albers et al.

It is certified that error appears in the above-identified patent and that said Letters Patent is hereby corrected as shown below:

<u>Column 471,</u>
between lines 10 and 15, "$^5$R" should read -- $R^5$ --.
Line 65, "to which R is bonded" should read -- to which $R^6$ is bonded --.

Signed and Sealed this

Twentieth Day of July, 2004

JON W. DUDAS
*Acting Director of the United States Patent and Trademark Office*